United States Patent
Totoritis et al.

(10) Patent No.: US 10,450,379 B2
(45) Date of Patent: Oct. 22, 2019

(54) METHOD FOR TREATING JOINT DAMAGE

(71) Applicants: Genentech, Inc., South San Francisco, CA (US); F. Hoffmann-La Roche AG, Basel (CH); Biogen Inc., Cambridge, MA (US)

(72) Inventors: Mark Totoritis, Rancho Santa Fe, CA (US); Timothy Mark Shaw, Hertfordshire (GB); Sunil Agarwal, Corte Madera, CA (US); David Yocum, San Mateo, CA (US); Ariella Kelman, Hillsborough, CA (US)

(73) Assignees: Genetech, Inc., South San Francisco, CA (US); F. Hoffmann-La Roche AG, Basel (CH); Biogen Inc., Cambridge, MA (US)

(*) Notice: Subject to any disclaimer, the term of this patent is extended or adjusted under 35 U.S.C. 154(b) by 0 days.

(21) Appl. No.: 16/384,333

(22) Filed: Apr. 15, 2019

(65) Prior Publication Data
US 2019/0270824 A1 Sep. 5, 2019

Related U.S. Application Data

(60) Division of application No. 15/055,485, filed on Feb. 26, 2016, now abandoned, which is a continuation of application No. 11/665,525, filed as application No. PCT/US2006/044290 on Nov. 14, 2006, now abandoned.

(60) Provisional application No. 60/737,291, filed on Nov. 15, 2005, provisional application No. 60/864,463, filed on Nov. 6, 2006.

(51) Int. Cl.
| | |
|---|---|
| C07K 16/28 | (2006.01) |
| A61K 31/519 | (2006.01) |
| A61K 39/395 | (2006.01) |
| A61K 45/06 | (2006.01) |
| A61K 47/68 | (2017.01) |
| A61K 39/00 | (2006.01) |

(52) U.S. Cl.
CPC ........ C07K 16/2887 (2013.01); A61K 31/519 (2013.01); A61K 39/3955 (2013.01); A61K 45/06 (2013.01); A61K 47/6849 (2017.08); C07K 16/2896 (2013.01); A61K 2039/505 (2013.01); C07K 2317/24 (2013.01); C07K 2317/56 (2013.01); C07K 2317/565 (2013.01); C07K 2317/76 (2013.01)

(58) Field of Classification Search
None
See application file for complete search history.

(56) References Cited

U.S. PATENT DOCUMENTS

| | | |
|---|---|---|
| 4,120,649 A | 10/1978 | Schechter |
| 4,485,045 A | 11/1984 | Regen |
| 4,544,545 A | 10/1985 | Ryan et al. |
| 4,665,077 A | 5/1987 | Stringfellow et al. |
| 4,676,980 A | 6/1987 | Segal et al. |
| 4,816,567 A | 3/1989 | Cabilly et al. |
| 4,861,579 A | 8/1989 | Meyer, Jr. et al. |
| 5,013,556 A | 5/1991 | Woodle et al. |
| 5,114,721 A | 5/1992 | Cohen et al. |
| 5,500,362 A | 3/1996 | Robinson et al. |
| 5,545,807 A | 8/1996 | Surani et al. |
| 5,565,332 A | 10/1996 | Hoogenboom et al. |
| 5,571,894 A | 11/1996 | Wels et al. |
| 5,573,905 A | 11/1996 | Lerner et al. |
| 5,587,458 A | 12/1996 | King et al. |
| 5,589,369 A | 12/1996 | Seidman et al. |
| 5,591,669 A | 1/1997 | Krimpenfort et al. |
| 5,595,721 A | 1/1997 | Kaminski et al. |
| 5,641,870 A | 6/1997 | Rinderknecht et al. |
| 5,677,180 A | 10/1997 | Robinson et al. |
| 5,693,780 A | 12/1997 | Newman et al. |
| 5,721,108 A | 2/1998 | Robinson et al. |
| 5,731,168 A | 3/1998 | Carter et al. |
| 5,736,137 A | 4/1998 | Anderson et al. |
| 5,739,277 A | 4/1998 | Presta et al. |
| 5,776,456 A | 7/1998 | Anderson et al. |
| 5,821,337 A | 10/1998 | Carter et al. |
| 5,843,398 A | 12/1998 | Kaminski et al. |
| 5,843,439 A | 12/1998 | Anderson et al. |
| 5,849,898 A | 12/1998 | Seed et al. |
| 6,015,542 A | 1/2000 | Kaminski et al. |
| 6,090,365 A | 7/2000 | Kaminski et al. |
| 6,120,767 A | 9/2000 | Robinson et al. |

(Continued)

FOREIGN PATENT DOCUMENTS

| | | |
|---|---|---|
| CA | 2627886 | 11/2006 |
| CA | 2378574 | 1/2012 |

(Continued)

OTHER PUBLICATIONS

"A safety study of escalating doses of PRO70769 for subjects with moderate to severe Rheumatoid arthritis receiving stable doses of concomitant methotrexate", ClinicalTrials.gov, pp. 1-3, (2007).
American College of Rheumatology 2005 Annual Meeting, Abstract Supplement, Arthritis & Rheumatism, vol. 52, No. 9 Supplement, Nov. 12-17, 2005, 2 pgs.

(Continued)

*Primary Examiner* — Sharon X Wen
(74) *Attorney, Agent, or Firm* — Wendy M. Lee

(57) ABSTRACT

Methods of treating joint damage in a subject eligible for treatment are provided involving administering an antagonist that binds to a B-cell surface marker, such as CD20 antibody, to the subject in an amount effective to slow progression of the joint damage as measured by radiography. Further provided are articles of manufacture useful for such methods.

18 Claims, 31 Drawing Sheets

Specification includes a Sequence Listing.

(56) References Cited

U.S. PATENT DOCUMENTS

| | | |
|---|---|---|
| 6,171,586 B1 | 1/2001 | Lam et al. |
| 6,183,744 B1 | 2/2001 | Goldenberg |
| 6,194,551 B1 | 2/2001 | Idusogie et al. |
| 6,224,866 B1 | 5/2001 | Barbera-Guillem |
| 6,242,195 B1 | 6/2001 | Idusogie et al. |
| 6,267,958 B1 | 7/2001 | Andya et al. |
| 6,287,537 B1 | 9/2001 | Kaminski et al. |
| 6,306,393 B1 | 10/2001 | Goldenberg |
| 6,348,463 B1 | 2/2002 | Head et al. |
| 6,368,596 B1 | 4/2002 | Ghetie et al. |
| 6,369,229 B1 | 4/2002 | Head et al. |
| 6,399,061 B1 | 6/2002 | Anderson et al. |
| 6,410,391 B1 | 6/2002 | Zelsacher |
| 6,455,043 B1 | 9/2002 | Grillo-Lopez |
| 6,528,624 B1 | 3/2003 | Idusogie et al. |
| 6,538,124 B1 | 3/2003 | Idusogie et al. |
| 6,565,927 B1 | 5/2003 | Drzal et al. |
| 6,602,684 B1 | 8/2003 | Umana et al. |
| 6,652,852 B1 | 11/2003 | Robinson et al. |
| 6,677,339 B2 | 1/2004 | Head et al. |
| 6,682,734 B1 | 1/2004 | Anderson et al. |
| 6,737,056 B1 | 5/2004 | Presta |
| 6,846,476 B2 | 1/2005 | White |
| 6,893,625 B1 | 5/2005 | Robinson et al. |
| 6,896,885 B2 | 5/2005 | Hanna |
| 6,897,044 B1 | 5/2005 | Braslawsky et al. |
| 7,708,994 B2 | 5/2010 | Benyunes et al. |
| 7,976,838 B2 | 7/2011 | Benyunes |
| 2001/0018041 A1 | 8/2001 | Hanna et al. |
| 2001/0056066 A1 | 12/2001 | Bugelski et al. |
| 2002/0004587 A1 | 1/2002 | Miller et al. |
| 2002/0006404 A1 | 1/2002 | Hanna et al. |
| 2002/0009427 A1 | 1/2002 | Wolin et al. |
| 2002/0009444 A1 | 1/2002 | Grillo-Lopez |
| 2002/0012665 A1 | 1/2002 | Hanna |
| 2002/0041847 A1 | 4/2002 | Goldenberg |
| 2002/0042368 A1 | 4/2002 | Fanslow et al. |
| 2002/0058029 A1 | 5/2002 | Hanna |
| 2002/0128488 A1 | 9/2002 | Yamakawa et al. |
| 2002/0136719 A1 | 9/2002 | Shenoy et al. |
| 2002/0164328 A1 | 11/2002 | Shinkawa et al. |
| 2002/0197255 A1 | 12/2002 | Anderson et al. |
| 2002/0197256 A1 | 12/2002 | Grewal |
| 2003/0021781 A1 | 1/2003 | Anderson et al. |
| 2003/0026801 A1 | 2/2003 | George et al. |
| 2003/0068664 A1 | 4/2003 | Albitar et al. |
| 2003/0082172 A1 | 5/2003 | Anderson et al. |
| 2003/0095963 A1 | 5/2003 | Anderson et al. |
| 2003/0103971 A1 | 6/2003 | Hariharan et al. |
| 2003/0115614 A1 | 6/2003 | Kanda et al. |
| 2003/0133930 A1 | 7/2003 | Goldenberg et al. |
| 2003/0147885 A1 | 8/2003 | Anderson et al. |
| 2003/0157108 A1 | 8/2003 | Presta |
| 2003/0180292 A1 | 9/2003 | Hanna et al. |
| 2003/0185796 A1 | 10/2003 | Wolin et al. |
| 2003/0219433 A1 | 11/2003 | Hansen et al. |
| 2003/0219818 A1 | 11/2003 | Bohen et al. |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2004/0202658 A1 | 10/2004 | Benyunes et al. |
| 2004/0258682 A1 | 12/2004 | Leung et al. |
| 2005/0001862 A1 | 1/2005 | Kimura et al. |
| 2005/0025764 A1 | 2/2005 | Watkins et al. |
| 2005/0037000 A1 | 2/2005 | Stavenhage et al. |
| 2005/0069545 A1 | 3/2005 | Carr et al. |
| 2005/0079174 A1 | 4/2005 | Barbera-Guillem et al. |
| 2005/0106108 A1 | 5/2005 | Leung et al. |
| 2005/0112060 A1 | 5/2005 | White |
| 2005/0123540 A1 | 6/2005 | Hanna et al. |
| 2005/0123546 A1 | 6/2005 | Umana et al. |
| 2005/0180972 A1 | 8/2005 | Wahl et al. |
| 2005/0186216 A1 | 8/2005 | Ledbetter et al. |
| 2005/0191300 A1 | 9/2005 | Goldenberg et al. |
| 2005/0202023 A1 | 9/2005 | Ledbetter et al. |
| 2005/0202028 A1 | 9/2005 | Ledbetter et al. |
| 2005/0202534 A1 | 9/2005 | Ledbetter et al. |
| 2006/0069545 A1 | 3/2006 | Wu et al. |
| 2009/0238762 A1 | 9/2009 | Totoritis |
| 2011/0300136 A1 | 12/2011 | Benyunes et al. |

FOREIGN PATENT DOCUMENTS

| | | |
|---|---|---|
| CA | 2350064 | 5/2012 |
| CA | 2340091 | 2/2013 |
| CA | 2461714 | 3/2013 |
| CA | 2350058 | 10/2015 |
| CA | 2372603 | 11/2015 |
| CA | 2783210 | 10/2016 |
| CA | 2904259 | 11/2016 |
| EP | 0332865 | 9/1989 |
| EP | 0633945 | 1/1995 |
| EP | 0330191 | 10/1996 |
| EP | 0404097 | 8/1997 |
| EP | 0869180 | 7/1998 |
| EP | 1104244 | 6/2001 |
| EP | 1176981 | 2/2002 |
| EP | 1613350 | 1/2006 |
| EP | 1951304 | 8/2008 |
| EP | 2000149 | 12/2008 |
| EP | 2155169 | 2/2010 |
| EP | 1504035 | 3/2010 |
| EP | 1476120 | 9/2010 |
| WO | WO 1990/08187 | 7/1990 |
| WO | WO 1991/01133 | 2/1991 |
| WO | WO 1992/200373 | 1/1992 |
| WO | WO 1993/08829 | 5/1993 |
| WO | WO 1993/11161 | 6/1993 |
| WO | WO 1993/16185 | 8/1993 |
| WO | WO 1994/04690 | 3/1994 |
| WO | 1995/11026 | 5/1994 |
| WO | 1994/011026 | 8/1994 |
| WO | 1995/003770 | 2/1995 |
| WO | WO 1997/30087 | 8/1997 |
| WO | WO 1997/38731 | 10/1997 |
| WO | WO 1998/18921 | 5/1998 |
| WO | WO 1998/27114 | 6/1998 |
| WO | 1998/042378 | 10/1998 |
| WO | 1998/056418 | 12/1998 |
| WO | WO 1998/56418 | 12/1998 |
| WO | WO 1998/58964 | 12/1998 |
| WO | WO 1999/12964 | 3/1999 |
| WO | WO 1999/22764 | 5/1999 |
| WO | WO 1999/33980 | 7/1999 |
| WO | WO 1999/51642 | 10/1999 |
| WO | WO 2000/09160 | 2/2000 |
| WO | WO 2000/10460 | 3/2000 |
| WO | WO 2000/20864 | 4/2000 |
| WO | 2000/027428 | 5/2000 |
| WO | WO 2000/27428 | 5/2000 |
| WO | WO 2000/27433 | 5/2000 |
| WO | WO 2000/32575 | 6/2000 |
| WO | WO 2000/37444 | 6/2000 |
| WO | WO 2000/40716 | 7/2000 |
| WO | WO 2000/42072 | 7/2000 |
| WO | WO 2000/44788 | 8/2000 |
| WO | WO 2000/61739 | 10/2000 |
| WO | 2000/067796 | 11/2000 |
| WO | WO 2000/67795 | 11/2000 |
| WO | WO 2000/67796 | 11/2000 |
| WO | WO 2000/68378 | 11/2000 |
| WO | 2000/074718 | 12/2000 |
| WO | WO 2000/74718 | 12/2000 |
| WO | WO 2000/76542 | 12/2000 |
| WO | WO 2001/03734 | 1/2001 |
| WO | WO 2001/10461 | 2/2001 |
| WO | WO 2001/10462 | 2/2001 |
| WO | WO 2001/12812 | 2/2001 |
| WO | WO 2001/13945 | 3/2001 |
| WO | WO 2001/29246 | 4/2001 |
| WO | WO 2001/34194 | 5/2001 |
| WO | WO 2001/72333 | 10/2001 |

(56) References Cited

FOREIGN PATENT DOCUMENTS

| WO | WO 2001/74388 | 10/2001 |
|---|---|---|
| WO | WO 2001/77342 | 10/2001 |
| WO | WO 2001/79173 | 10/2001 |
| WO | WO 2001/80884 | 11/2001 |
| WO | WO 2001/97858 | 12/2001 |
| WO | WO 2002/02556 | 1/2002 |
| WO | 2002/22212 | 3/2002 |
| WO | WO 2002/28830 | 4/2002 |
| WO | WO 2002/34790 | 5/2002 |
| WO | WO 2002/56910 | 7/2002 |
| WO | WO 2002/060955 | 8/2002 |
| WO | WO 2002/079255 | 10/2002 |
| WO | WO 2002/092620 | 11/2002 |
| WO | WO 2002/096948 | 12/2002 |
| WO | WO 2002/102312 | 12/2002 |
| WO | WO 2003/002607 | 1/2003 |
| WO | WO 2003/10135 | 2/2003 |
| WO | WO 2003/011878 | 2/2003 |
| WO | WO 2003/014294 | 2/2003 |
| WO | WO 2003/049694 | 6/2003 |
| WO | WO 2003/53926 | 7/2003 |
| WO | WO 2003/061694 | 7/2003 |
| WO | WO 2003/068821 | 8/2003 |
| WO | WO 2003/68821 | 8/2003 |
| WO | WO 2003/68822 | 8/2003 |
| WO | WO 2003/70709 | 8/2003 |
| WO | WO 2003/084570 | 10/2003 |
| WO | WO 2003/085119 | 10/2003 |
| WO | WO 2003/89410 | 10/2003 |
| WO | WO 2004/032828 | 4/2004 |
| WO | WO2004/035607 | 4/2004 |
| WO | WO 2004/058298 | 7/2004 |
| WO | WO 2004/63351 | 7/2004 |
| WO | WO 2004/103404 | 12/2004 |
| WO | 2003/068821 | 1/2005 |
| WO | WO 2005/000901 | 1/2005 |
| WO | 2004/091657 | 2/2005 |
| WO | WO 2005/014618 | 2/2005 |
| WO | WO 2005/016969 | 2/2005 |
| WO | WO 2005/035586 | 4/2005 |
| WO | WO 2005/035778 | 4/2005 |
| WO | 2004/056312 | 5/2005 |
| WO | WO 2005/044859 | 5/2005 |
| WO | WO 2005/053742 | 6/2005 |
| WO | WO 2005/070963 | 8/2005 |
| WO | WO 2005/103081 | 11/2005 |
| WO | 2005/060999 | 9/2008 |

OTHER PUBLICATIONS

Anonymous, NCT00077870: "A Safety Study of Escalating Doses of Pro70769 for Subjects with Moderate to Severe Rheumatoid Arthritis Receiving Stable Doses of Comitant Methotrexate" Clinical. Gov, [Online] (Feb. 12, 2004), pp. 1-3, XP002425328.
Bathon, et al., "Highlights from the 2005 American College of Rheumatology National Scientific Meetings", The John Hopkins Arthritis Center, pp. 1-12, (2005).
Bathon: Rheumatoid Arthritis Treatments The John Hopkins Arthritis Center, 2005 American College of Rheumatology, [Online], (Nov. 17, 2005), pp. 1-12, XP002425337.
Communication pursuant to Article 94(3) EPC dated Jul. 15, 2013, in corresponding EP Patent Application No. 06837634.2.
Communication pursuant to Rule 114(2) EPC dated Dec. 12, 2012, in corresponding EP Patent Application No. 06837634.2.
Edwards, et al., "Efficacy of B-Cell-Targeted Therapy with Rituximab in Patients with Rheumatoid Arthritis." N Engl J Med 2004;350-2572-81.
Edwards, J.C.W., et al., "B Lymphocyte Depletion Therapy with Rituximab in Rheumatic Arthritis" Rheumatoid Diseases Clinics of North America, W.B. Saunders, Philadelphia, PA US., vol. 30, No. 2, 2004, pp. 393-403 XP008076293 ISSN: 0889-857X.

Fields, "Rituximab in the treatment of rheumatoid arthritis, systemic lupus, and other autoimmune diseases: past, present, and future", Hospital for Special Surgery, [Online] (Oct. 25, 2002), pp. 1-9 XP002425336.
Fields, "Rituximab in the treatment of rheumatoid arthritis, systemic lupus, and other autoimmune diseases: past, present, and future", Hospital for Special Surgery, pp. 1-7, (2002).
Hibble, et al., "Rheumatoid arthritis—MabThera provides lasting benefits", Medical News Today, Published Nov. 21, 2005.
Hibble: "Rheumatoid Arthritis—MabThera Provides Lasting Benefits" medical News Today, [Online] (Nov. 21, 2005), pp. 1-2 XP002425335.
Keystone et al., "Safety and Efficacy of Additional Courses of Rituximab in Patients with Active Rheumatoid Arthritis," Arthritis & Rheumatism, vol. 56, No. 12, Dec. 2007, pp. 3896-3908.
Rituximab Full Prescribing Information, revised Mar. 2012, 38 pgs.
Summary of product characteristics MabThera (Rituximab) from European Medicines Agency (EMA) website. www.ema.europa.eu/.../pl_PL/document_library/EPAR_-_Product_Information/human/000165/WC500025821.pdf.
Aggarwal et al. "Human tumor necrosis factor production, purification, and characterization", J Biological Chemistry 260:2345-2354, 1985.
Ahn et al. "Long-term remission from life-threatening hypercoagulable state associated with lupus anticoagulant (LA) following rituximab therapy", Am. J. Rheumatol. 78(2):127-129, 2005.
Alamanos et al. "Epidemiology of adult rheumatoid arthritis", Autoimmun. Rev. 4:130-136, 2005.
Alarcon et al. "Radiographic evidence of disease progression in methotrexate treated and nonmethotrexate disease modifying antirheumatic drug treated rheumatoid arthritis patients: a meta-analysis", J. Rheumatol., 19:1868-1873, 1992.
Albert et al. "Modeling therapeutic strategies in rheumatoid arthritis: use of decision analysis and Markov models", J. Rheumatol 27(3):644-652, 2000.
Anderson et al. "Expression of human B cell-associated antigens on leukemias and lymphomas: a model of human B cell differentiation", Blood, 63(6):1424-1433, 1984.
Arzoo et al. "Trearnent of refractory antibody mediated autoimmune disorders with an anti-CD20 monoclonal antibody (rituximab)", Annals of the Rheumatic Diseases 61(10):922-924, 2002.
Auner et al. "Flow cytometry and the study of cerebrospinal fluid in leukaemic patients: additional facts", British Journal Haematology 116:725-728, 2002.
Baker et al. "Generation arid characterization of LymphoStat-B, a human monoclonal antibody that antagonizes the bioactivities of B lymphocyte stimulator", Arthritis Rheum. 48:3253-3265, 2003.
Bathon et al. "A comparison of etanercept and methotrexate in patients with early rheumatoid arthritis", N. Engl. J. Med. 343(22):1586-1593, 2000.
Batten et al. "BAFF mediates survival of peripheral immature B lymphocytes", J. Exp. Med 192:1453-1466, 2000.
Bauduer "Spontaneous remission of juvenile idiopathic myelofibrosis", British Journal Haematology 112:1083-1090, 2001.
Berentsen et al. "Rituximab for primary chronic cold agglutinin disease: a prospective study of 37 course of therapy in 27 patients", Blood 103:2925-2928, 2004.
Berentsen et al. "Favourable response to therapy with the anti-CD20 monoclonal antibody rituximab in primary chronic cold agglutinin disease", Br. J. Haem2atol. 115(1):79-83, 2001.
Boers et al. "Randomised compaison of combined step-down prednisolone, methotrexate and sulphasalazine with sulphasalazine alone in early rheumatoid arthritis", Lancet 350:309-318, 1997.
Breedveld et al. "Association between baseline radiographic damage and improvement in physical function after treatment of patients with rheumatoid arthritis", Annals Rheumatic Diseases 64:52-55, 2005.
Brennan et al. "Preparation of bispecific antibodies by chemical recombination of monoclonal imunoglobulin G1 fragments", Science 229:81-83, 1985.
Bresnihan et al. "Treatment of rheumatoid arthritis with recombinant human interleukin-1 receptor antagonist", Arthritis Rheum. 41:2196-2204, 1998.

(56) References Cited

OTHER PUBLICATIONS

Brodeur et al., *Monoclonal Antibody Production Techniques and Applications*, pp. 51-64 (Marcel Dekker, Inc., New York, 1987).
Bruggerman et al. "Designer mice: the production of human antibody repertoires in transgenic animals", Year in Immunology 7:33-40, 1993.
Bukhari et al. "Rheumatoid factor is the major predictor of increasing severity of radiographic erosions in rheumatoid arthritis: results from the Norfolk Arthritis Register Study, a large inception cohort", Arthritis Rheum. 46:906-912, 2002.
Cambridge et al. "B lymphocyte depletion in patients with rheumatoid arthritis: serial studies of immunological parameters", Arthritis Rheum. Suppl.506 :1350, 2002.
Cambridge et al. "Serologic changes following B lymphocyte depletion therapy for rheumatoid arthritis", Arthritis Rheum., 48(8):2146-2154, 2003.
Campbell et al. "Severe inflammatory arthritis and lymphadenopathy in the absence of TNF", J. Clin. Invest, 107:1519-1527, 2001.
Caron et al, "Engineered humanized dimeric forms of IgG are more effective antibodies", J. Exp. Med. 176:1191-1195, 1992.
Carter et al. "High level *Escherichia coli* expression and production of a bivalent humanized antibody fragment", Biotechnology 10:163-167, 1992.
Carter et al. "Humanization of an anti-p185HER2 antibody for human cancer therapy", Proc. Natl. Acad. Sci. USA 89:4285-4289, 1992.
Cella et al. "Validation of the functional assessment of chronic illness therapy fatigue scale relative to other instrumentation in patients with rheumatoid arthritis", J. Rheumatology 32(5):811-819, 2005.
Chambers and Isenberg "Anti-B cell therapy (rituximab) in the treatment of autoimmune diseases", Lupus, 14(3):210-214, 2005.
Childs et al. "Efficacy of etanercept for wear debris-induced osteolysis", J. Bone Mineral Res. 16:338-347, 2001.
Chothia and Lesk "Canonical structures for the hypervariable regions of immunoglobulins", J. Mol. Biol.196:901-917, 1987.
Clackson et al. "Making antibody fragments using phage display libraries", Nature, 352:624-628, 1991.
Clark and Ledbetter "Structure, function, and genetics of human B cell-associated surface molecules", Adv. Cancer. Res. 52:81-149, 1989.
Clark et al. "Role of the Bp35 cell surface polypeptide in human B-cell activation", Proc. Natl. Acad. Sci.USA 82:1766-1770, 1985.
Clynes et al. "Fc receptors are required in passive and active immunity to melanoma", Proc. Natl. Acad. Sci. USA 95:652-656, 1998.
Coll et al. "Rituximab therapy for the type B syndrome of severe insulin resistance", N. Engl. J. Med.350:310-311, 2004.
Cragg et al. "Complement-mediated lysis by anti-CD20 mAb correlates with segregation into lipid rafts", Blood 101:1045-1052, 2003.
Cragg et al. "The biology of CD20 and its potential as a target for mAb therapy", Current Directions Autoimmun.8:140-174, 2005.
Cross et al. "Preliminary results from a phase 11 trial of rituximab in MS", Eighth Annual Meeting of the Americas Committee for Research and Treatment in Multiple Sclerosis, San Francisco, CA, USA, Oct. 19, 2003, pp. 20-21 (abstract).
Csuka et al. "Treatment of intractable rheumatoid arthritis with combined cyclophosphamide, azathioprine, and hydroxychloroquine", JAMA 255:2315-2319, 1986.
Cuchacovich et al. "Precision of the Larsen and the sharp methods of assessing radiologic change in patients with rheumatoid arthritis", Arthritis Rheum 35:736-739, 1992.
Cunningham and Wells "High-resolution epitope mapping of hGH-receptor interactions by alanine-scanning mutagenesis", Science 244:1081-1085, 1989.
D'Arena et al. "Late and long-lasting response in an adult chronic idiopathic thrombocytopenic purpura after extended course of rittiximab", Leuk. Lymphoma 44:561-562, 2003.
D'Cruz and Hughes "The treatment of lupus nephritis", BMJ 330:377-378, 2005.
Daëron, M. "Fc receptor biology", Annu. Rev. Immunol. 15:203-234, 1997.
Damiani et al. "Audit of laboratory investigation of antiphospholipid syndrome", British Journal Haematology 115:229-234, 2001.
De Haas et al. "Fc gamma receptors of phagocytes", J. Lab. Clin. Med 126:330-341, 1995.
Demidem et al. "Chimeric anti-CD20 (IDEC-C2B8) monoclonal antibody sensitizers a B cell lymphoma cell line to cell killing by cytotoxi drugs", Cancer Biother. Radiopharm. 12(3):177-186,1997.
DeVita et al. "Efficacy and safety of rituximab treatment in type II mixed cryoglobulinemia", Arthritis Rheumatism Abstract 469:S206, 2002.
Di Gaetano et al. "Complement activation determines the therapeutic activity of rituximab in vivo", J Immunology 171:1581-1587, 2003.
Doran et al. "Frequency of infection in patients with rheumatoid arthritis compared with controls: a population-based study", Arthritis Rheum.46:2287-2293, 2002.
Douni et al. "Transgenic and knockout analyses of the role of TNF in immune regulation and disease pathogenesis", J. Inflammation 42:27-38, 1996.
Drossaers-Bakker et al. "A comparison of three radiologic scoring systems for the long-term assessment of rheumatoid arthritis: findings of an ongoing prospective inception cohort study of 132 women followed up for a median of twelve years", Arthritis Rheum. 43:1465-1472, 2000.
Dupuy et al. "Treatment of refractory pemphigus vulgaris with rituximab (anti-CD20 monoclonal antibody)", Archives of Dermatology 140:91-96, 2004.
Durie et al. "Prevention of collagen-induced arthritis with an antibody to gp39, the ligand for CD40", Science 261:1328-1330,1993.
Edelbauer et al. "Rituximab in childhood systemic lupus erythematosus refractory to conventional immunosuppression: case report", Pediatr. Nephrol. 20(6):811-813, 2005.
Edmonds et al. "Antirheumatic drugs: a proposed new classification", Arthritis Rheumatism 36:336-340, 1993.
Edwards and Cambridge "Sustained improvement in rheumatoid arthritis following a protocol designed to deplete B lymphocytes", Rheumatology 40:205-211, 2001.
Edwards et al. "Do self-perpetuating B lymphocytes drive human autoimmune disease?", Immunology 97:188-196, 1999.
Edwards et al. "Efficacy and safety of rituximab, a B-cell targeted chimeric monoclonal antibody: A randomized, placebo-controlled trial in patients with rheumatoid arthritis", Arthritis & Rheumatism 446:(S197), Oct. 26, 2002.
Einfeld et al. "Molecular cloning of the human B cell CD20 receptor predicts a hydrophobic protein with multiple transmembrane domains", EMBO J.7(3):711-717, 1988.
Eisenberg, R. "SLE-rituximab in lupus", Arthritis Res. Ther 5:157-159, 2003.
Eisenberg, "Mechanisms of autoimmunity", Immunol. Res. 27:203-217, 2003.
Emery et al. "Sustained efficacy at 48 weeks after single treatment course of rituximab in patients with rheumatoid arthritis", Arthritis Rheum. 48 Supplement 9Abstract 1095: S439, 2003.
Emery et al. "Efficacy and safety of rituximab at 2 years following a single treatment in patients with active rheumatoid arthritis", Arthritis Rheumatisim (Abstrct #1762)50(S9):S659, 2004.
Emery et al. "[2005][OP0008] Primary analysis of a double-blind, placebo-controlled, dose-ranging trial of rituximab, an anti-CD20 monoclonal antibody, in patients with rheumatoid arthritis receiving methotrexate (DANCER TRIAL)", Ann Rheum Dis 2005; 64 (Suppl III):58.
Eppstein et al. "Biological activity of liposome-encapsulated murine interferon gamma is mediated by a cell membrane receptor", Proc. Natl. Acad. Sci. USA 82:3688-3692, 1985.
Eriksson, P. "Nine patients with anti-neutrophil cytoplasmic antibody-positive vasculitis successfully treated with rituximab", J. Internal Med., 257:540-548, 2005.

(56) References Cited

OTHER PUBLICATIONS

Eriksson, P. "Short-term outcome and safety in 5 patients with ANCA-positive vasculitis treated with rituximab", Kidney Blood Press. Res. 26:294, 2003.
Feldmann et al. "Rheumatoid arthritis", Cell 85(3):307-310,1996.
Felson et al. "American collage of rheumatology. Preliminary definition of improvement in rheumatoid arthritis", Arthritis Rheum. 38:727-735, 1995.
Fex et al. "Development of radiographic damage during the first 5-6 yr of rheumatoid arthritis. A prospective follow-up study of a Swedish cohort", British J. Rheumatology 35:1106-1115,1996.
Finck et al. "Treatment of murine lupus with CTLA4Ig", Science 265:1225-1227, 1994.
Forre. O. "Radiologic evidence of disease modification in rheumatoid arthritis patients treated with cyclosporine. Results of a 48-week muticenter study comparing low-dose cyclosporine with placebo. Norwegian arthritis study group", Arthritis Rheum. 37:1506-1512, 1994.
Fries et al. "Measurement of patient outcome in arthritis", Arthritis Rheum. 23:137-145, 1980.
Gazzano-Santoro et al. "A non-radioactive complement-dependent cytotoxicity assay for anti-CD20 monoclonal antibody", J. Immunology Methods 202:163-171, 1997.
Genant, H.K. "Methods of assessing radiographic change in rheumatoid arthritis", American Journal Medicine 30:35-47, 1983.
GenBank Accession No. AF136293 "*Homo sapiens* TNF and ApoL related ligand TALL-1 (TALL1) mRNA. complete cds".
Genovese et al. "Etanercept versus methotrexate in patients with early rheumatoid arthritis: two-year radiographic and clinical outcomes", Arthritis Rheum..46:1443-1450, 2002.
Ghetie et al. "Homodirnerization of tumor-reactive monoclonal antibodies markedly increases tehir ability to induce growth arrest or apoptosis of tumor cells", Proc. Natl. Acad. Sci.USA 94:7509-7514, 1997.
Glennie and van de Winkel "Renaissance of cancer therapeutic antibodies", Drug Discovery Today 8:503-510, 2003.
Goding, Monoclonal Antibodies: Principles and Practice, pp. 59-103 (Academic Press, 1986).
Goldring and Gravallese "Mechanisms of bone loss in inflammatory arthritis: diagnosis and therapeutic implications", Arthritis Res. 2(1):33-37, 2000.
Gong et al. "Importance of cellular microenvironment and circulatory dynamics in B cell immunotherapy", J. Immunol. 174:817-826, 2005.
Goodyear and Silverman "Death by a B cell superantigen: In vivo VH-targeted apoptotic supraclonal B cell deletion by a Staphylococcal toxin", J. Exp. Med. 197(9):1125-1139, 2003.
Gordon et al. "BAFF/BLyS receptor 3 comprises a minimal TNF receptor-like module that encodes a highly focused ligand-binding site", Biochemistry 42(20):5977-5983, 2003.
Gorman et al "Does B cell depletion have a role to play in the treatment of systemic lupus erythematosus?", Lupus 13:312-316, 2004.
Graudal et al. "Radiographic progression in rheumatoid arthritis: a long-term prospective study of 109 patients", Arthritis Rheum. 41:1470-1480, 1998.
Griffith et al. "Human anti-self antibodies with high specificity from phage display libraries", EMBO J. 12:725-734, 1993.
Gruber et al. "Efficient tumor cell lysis mediated by a bispecific single chain antibody expressed in *Escherichia coli*", J. Immunology 152:5368, 1994.
Guyer et al. "Immunoglobulin binding by mouse intestinal epithelial cell receptors", Journal Immunology 117:587-593, 1976.
Hainsworth et al. "Rituximab as first-line and maintenance therapy for patients with indolent non-hodgkin's lymphoma", J. Clinical Oncology 20:4261-4267, 2002.
Hainsworth et al. "Single-agent rituximab as first-line and maintenance treatment for patients with chronic lymphocytic leukemia or small lymphocytic lymphoma: a phase II trial of the minnie pearl cancer research network", J. Clinical Oncology 21:1746-1751, 2003.
Hamaguchi et al. "The peritoneal cavity provides a protective niche for B1 and conventional B lymphocytes during anti-CD20 immunotherapy in mice", J. Immunology174:4389-4399, 2005.
Hannonen et al. "Sulfasalazine in early rheumatoid arthritis, A 48-week double-blind, prospective, placebo-controlled study", Arthritis Rheum. 36:1501-1509, 1993.
Harris et al. "Reciprocal regulation of polarized cytokine production by effector B and T cells", Nature Immunology 1:475-482, 2000.
Heliovaara et al. "Rheumatoid factor, chronic arthritis and mortality", Ann. Rheum. Dis. 54: 811-814, 1995.
Higashida et al. "Treatment of DMARD-refractory rheumatoid arthritis with rituxirnab." Presented at the Annual Scientific Meeting of the American College of Rheumatology, Oct. 24-29, New Orleans, LA 2002.
Hochberg et al. "The American college of rheumatology 1991 revised criteria for the classification of global functional status in rheumatoid arthritis", Arthritis Rheumatism 35:498-502, 1992.
Hofbauer et al. "The roles of osteoprotegerin and osteoprotegerin ligand in the paracrine regulation of bone resorption", J. of Bone and Mineral Research 15(1):2-12, 2000.
Holliger et al. "Diabodies": small bivalent and bispecific antibody fragments. Proc. Natl. Acad. Sci, USA 90:6444-6448, 1993.
Hulsmans et al. "The course of radiologic damage during the first six years of rheumatoid arthritis", Arthritis Rheum.43:1927-1940, 2000.
Hwang et al. "Hepatic uptake and degradation of unilamellar sphingomyelin/cholesterol liposomes: a kinetic study", Proc. Natl. Acad. Sci. USA 77:4030-4034, 1980.
Jakobovits et al. "Germ-line transmission and expression of a human-derived yeast artificial chromosome", Nature 362:255-258, 1993.
Jakobovits et al. "Analysis of homozygous mutant chimeric mice: deletion of the immunoglobulin heavy-chain joining region blocks B-cell development and antibody production", Proc. Natl. Acad. Sci. USA 90:2551-2555, 1993.
Janeway et al. "The B cell is the initiating antigen-presenting cell in peripheral lymph nodes", J. Immunology 138:1051-1055, 1987.
Janeway, CA. "Immunotherpy by peptides", Nature 341:482-483, 1989.
Jayne et al. "B-cell depletion with rituximab for refractory vasculitis". Kidney Blood Press. Res. 26:294-295, 2003.
Jeurissen et al. "Influence of methotrexate and azathioprine on radiologic progression in rheumatoid arthritis. A randomized, double-blind study", Ann. Intern. Med. 114:999-1004, 1991.
Johnson et al. "Human antibody engineering", Current Opinion in Structural Biology 3:564-571, 1993.
Joint Committee of the Medical Research Council and Nuffield Foundation, "A comparison of prednisolone with aspirin or other analgesics in the treatment of rheumatoid arthritis",Ann. Rheum. Dis. 19:331-337, 1960.
Jones et al. "Replacing the complementarity-determining regions in a human antibody with those from a mouse", Nature, 321:522-525, 1986.
Kaarela et al. "Continous progression of radiological destruction in seropositive rheumatoid arthritis", J. Rheumatol. 24:1285-1287, 1997.
Kabat et al. Sequences of proteins of immunological interest, vol. 1, 5th Ed Public Health Service, National Institutes of Health, 1991.
Kane, "Rituximab a future challenge for anti-TNFs?" SCRIP News (Meeting in Vienna, Austria, Jun. 6-10, 2005) 3063:26 (Jun. 15, 2005).
Kayagaki et al. "BAFF/BLyS receptor 3 binds the B cell survival factor BAFF ligand through a discrete surface loop and promotes processing of NF-kappaB2", Immunity, 16:515-524, 2002.
Kazkaz and Isenberg, "Anti B cell therapy (rituximab) in the treatment of autoimmune diseases", Current Opinion in Pharmacology 4:398-402, 2004.
Kelley et al. "Engineering an APRIL-specific B cell maturation antigen", J. Biol. Chem. 279(16):16727-16735, 2004.

(56) References Cited

OTHER PUBLICATIONS

Keogh et al. "Rituximab for Remission Induction in Severe ANCA-Associated Vasculitis: Report of a Prospective Open-Label Pilot Trial in 10 Patients" American College of Rheumatology, Session No. 28.100, Session Title: Vasculitis, Session Type: ACR Concurrent Session, Primary Category: 28 Vasculitis Session 10/18/200.
Keogh et al. "Induction of remission by B lymphocyte depletion in eleven patients with refractory antineutrophil cytoplasmic antibody-associate vasculitis", Arthritis Rheum. 52:262-268, 2005.
Keogh et al. "Rituximab—a potential mechanistic-based therapy for treatment of refractory ANCA-associated vasculitis", Kidney Blood Press. Res (Abstract #032),26:293, 2003.
Keystone et al. "Adalimumab (D2E7), a fully human anti-TNF-monoclonal antibody, inhibits the progression of structural joint damage in patients with active RA despite concomitant methotrexate therapy", Arthritis Rheum. (4468), 46 (Suppl. 9):S205, 2002.
Keystone, EC. "B cells in rheumatoid arthritis: from hypothesis to the clinic", Rheumatology (Oxford) 44 Suppl. 2: ii8-ii12, 2005.
Kim et al. "Localization of the site of the murine lgG1 molecule that is involved in binding to the murine intestinal Fc receptor", Eur. J. Immunology 24:2429-2434, 1994.
Kirwan JR. "The effect of glucocorticoids on joint destruction in rheumatoid arthritis. The arthritis and rheumatism council low-dose glucocorticoid study group", N. Engl. J. Med. 333:142-146, 1995.
Klemmer et al. "Treatment of antibody mediated autoimmune disorders with a anti-CD20 monoclonal antibody Rituximab", Arthritis & Rheumatism 48(Suppl 9) abstract 1623:S624, 2003.
Kneitz et al. "Effective B cell depletion with rituximab in the treatment of autoimmune diseases", Immunobiology 206:519-527, 2002.
Kohler et al. "Continous cultures of fused cells secreting antibody of predifined specificity", Nature 256:495, 1975.
Kostelny et al. "Formation of a bispecific antibody by the use of leucine zippers", J. Immunology 148(5):1547-1553, 1992.
Kozbor et al. "A human hybrid myeloma for production of human monoclonal antibodies", J. Immunology 133:3001-3005, 1984.
Lake and Dionne, "Future Strategies in Immunotherapy" Burger's Medicinal Chemistry and Drug Discovery, Abraham, 6th edition, Hoboken:John Wiley & Sons, Inc., Chapter 6, vol. 5:223-247 (2003).
Landewe et al. "COBRA combination therapy in patients with early rheumatoid arthritis: long-term structural benefits of a brief intervention", Arthritis Rheum. 46:347-356, 2002.
Larsen et al. "Radiographic evaluation of rheumatoid arthritis and related conditions by standard reference films", Acta Radiology Diagnosis18:481-491, 1977.
Lassere et al. "Smallest detectable difference in radiological progression", J. Rheumatol, 26:731-739, 1999.
Layios et al. "Remission of severe cold agglutinin disease after Rituximab therapy", Leukemia 15:187-188, 2001.
Leandro et al. "Clinical outcome in 22 patients with rheumatoid arthritis treated with B lymphocyte depletion", Ann. Rheum Dis. 61:883-888, 2002.
Leandro et al. "B lymphocyte depletion in rheumatoid arthritis: early evidence for safety efficacy, and dose response", Arthritis & Rheumatism, 44(9):5370, abstract 1905, 2001.
Leandro et al. "An open study of B lymphocyte depletion in systemic lupus erythematosus", Arthritis Rheumatism 46:2673-2677, 2002.
Leandro et al. "B-cell repopulation occurs mainly from naïve B cells in patients with rheumatoid arthritis and systemic lupus erythematosus treated with rituximab", Arthritis Rheum. Suppl. 9, vol. 48, abstract 1160, S464, 2003.
Lehninger, "The amino acid building blocks of protein" Biochemistry (Figures 4.2-4.4), 2nd Edition edition, New York, NY:Worth Publishers, Inc. pp. 73-75 (1975).
Levine and Pestronk "IgM antibody-related polyneuropathies: B-cell depletion chemotherapy using Rituximab", Neurology 52:1701-1704, 1999.

Levine, TD. "A pilot study of rituximab therapy for refractory dermatomyositis", Arthritis Rheumatism 46 Suppl. 9:S1299 , 2002.
Liang and Tedder, *Wiley Encyclopedia of Molecular Medicine* "CD20 as an Immunotherapy Target", article online posting date: Jan. 15, 2002.
Lipsky et al. "Infliximab and methotrexate in the treatment of rheumatoid arthritis. Anti-tumor necrosis factor trial in rheumatoid arthritis with concomitant therapy study group", N. Engl. J. Med. 343:1594-1602, 2000.
Looney et al. "B cell depletion as a novel treatment for systemic lupus erythematosus: a phase I/II dose-escalation trial of rituximab", Arthritis Rheumatism 50:2580-2589, 2004.
Looney et al. "Treatment of SLE with anti-CD20 monoclonal antibody", Curr. Dir. Autoimmun. 8:193-205, 2005.
Looney, RJ. "Treating human autoimmune disease by depleting B cells", Ann. Rheum. Dis.61:863-866, 2002.
Looney, RJ. "B cell-targeted therapy in diseases other than rheumatoid arthritis", J. Rheumatology 32 Suppl.73:25-28, 2005.
Looney, RJ. "B cells as a therapeutic target in autoimmune diseases other than rheumatoid arthritis", Rheumatology (Oxford) 44 Suppl 2:ii13-ii17, 2005.
Lovell et al. "Etanercept in children with polyarticular juvenile rheumatoid arthritis, Pediatric rheumatology collaborative study group", N. Engl. J. Med. 342:763-769, 2000.
Mackay et al. "The role of BAFF in B-cell maturation, T-cell activation and autoimmunity", Trends in Immunology 23:113-115, 2002.
Maini et al. "Infliximab (chimeric anti-tumour necrosis factor alpha monoclonal antibody) versus placebo in rheumatoid arthritis patients receiving concomitant methotrexate: a randomised phase III trial. ATTRACT Study Group", Lancet 354:1932-1939, 1999.
Maloney et al. "The anti-tumor effect of monoclonal anti-CD20 antibody (mAb) therapy includes direct anti-proliferative activity and induction of apoptosis in CD20 positive non-hodgkin's lymphoma (NHL) cell lines", Blood 2535:637a, 1996.
Marks et al. "By-passing immunization: building high affinity human antibodies by chain shuffling", BioTechnology10:779-783, 1992.
Marks et al. "By-passing immunization. Human antibodies from V-gene libraries displayed on phage", J. Mol. Biol. 222:581-597, 1991.
Martin and Chan "Pathogenic roles of B cells in human autoimmunity; insights from the clinic", Immunity 20:517-527, 2004.
Martin et al. "Irreversible coupling of immunoglobulin fragments to preformed vesicles. An improved method for liposome targeting", J. Biol. Chem. 257:286-288, 1982.
Matthews, R. "Medical Heretics", New Scientist 34-37, 2001.
McCafferty et al. "Phage antibodies: filamentous phage displaying antibody variable domains", Nature 348:552-554, 1990.
Millstein et al. "Hybrid hybridomas and their use in immunohistochemistry", Nature 305:537-539, 1983.
Mohan et al. "Interaction between CD40 and its ligand gp39 in the development of murine lupus nephritis", J. Immunology 154:1470-1480, 1995.
Moore et al. "BLyS: member of the tumor necrosis factor family and B lymphocyte stimulator", Science, 285:260-263, 1999.
Moreland et al. "Etanercept therapy in rheumatoid arthritis. A randomized, controlled trial", Annals Internal Medicine 130:478-486, 1999.
Moreland et al. "Long-term safety and efficacy of etanercept in patients with rheumatoid arthritis", J. Rheumatol. 28:1238-1244, 2001.
Moreland et al. "Treatment of rheumatoid arthritis with a recombinant human tumor necrosis factor receptor (p75)-Fc fusion protein", N. Engl. J. Med. 337:141-147, 1997.
Morimoto et al. "Single-step purification of F(ab')2 fragments of mouse monoclonal antibodies (immunoglobulins G1) by hydrophobic interaction high performance liquid chromatography using TSKgel Phenyl-5PW", Journal of Biochemical and Biophysical Methods 24:107-117,1992.
Morrison et al. "Chimeric human antibody molecules: mouse antigen-binding domains with human constant region domains", Proc. Natl. Acad. Sci. USA 81:6851-6855,1984.

(56) References Cited

OTHER PUBLICATIONS

Mottonen et al. "Comparison of combination therapy with single-drug therapy in early rheumatoid arthritis: a randomised trial", Lancet 353:1658-1573,1999.
Mukhopadhyay et al. "Identification and characterization of a novel cytokine, THANK, a TNF homologue that activates apoptosis, nuclear factor-kappaB, and c-Jun NH2-terminal kinase", J. Biol. Chem. 274:15978-15981, 1999.
Munson et al. "Ligand: a versatile computerized approach for characterization of ligand-binding systems", Analytical Biochemistry 107:220-239, 1980.
O'Dell et al. "Treatment of rheumatoid arthritis with methotrexate alone, sulfasalazine and hydroxychloroquine, or a combination of all three medications", New Engl. J. Medicine 334:1287-1291,1996.
Offner et al. "T cell receptor peptide therapy triggers autoregulation of experimental encephalomyelitis", Science 251:430-432, 1991.
Okazaki et al. "Fucose depletion from Human lgG1 oligosaccharide enhances binding enthalpy and association rate between lgG1 and FcgammaRIIIa", J. Mol. Biol. 336:1239-1249, 2004.
Paulus et al. "Analysis of improvement in individual rheumatoid arthritis patients treated with disease-modifying antirheumatic drugs, based on the findings in patients treated with placebo. The Cooperative Systematic Studies of Rheumatic Diseases Group", Arthritis Rheum. 33:477-484, 1990.
Paulus et al. "Classifying structural joint damage in rheumatoid arthritis as progressive or nonprogressive using a composite definition of joint radiographic change: a preliminary proposal", Arthritis Rheum. 50:1083-1096, 2004.
Paulus et al. "Monitoring radiographic changes in early rheumatoid arthritis". J. Rheumatology 23:801-805, 1996.
Pavelka et al. "Improvement in patient reported outcomes with rituxiinab in patients with rheumatoid arthritis", Ann. Rheum. Dis 63(S1):289-290, 2004.
Penichet et al. "Antibody Engineering" Molecular Biology Institute 214-216, 2002.
Pennica et al. "Human tumour necrosis factor: precursor structure, expression and homology to lymphotoxin", Nature 312:724-729, 1984.
Perotta et al. "Response of chronic relapsing ITP of 10 years duration to rituximab", Blood (Abstract #3360)10(1)(Part 1-2):88B, 1998.
Perotta et al. "Rituxan in the treatment of chronic idiopathic thrombocytopenic", Blood (Abstract #49)94:4a (1999).
Pestronk et al. "Treatment of IgM antibody associated polyneuropathies using rituximab", J. Neurol. Neurosurg, Psychiatry 74:485-489, 2003.
Pincus et al. "Relative versus absolute goals of therapies for RA: ACR 20 or ACR 50 responses versus target values for "near remission" of DAS or single measures", Clin Exp Rheurnatol. 22 (Suppl. 35):S50-S56, 2004.
Plant et al. "Measurement and prediction of radiological progression in early rheumatoid arthritis", J. Rheumatology 21:1808-1813, 1994.
Plant et al. "Patterns of radiological progression in early rheumatoid arthritis: results of an 8 year prospective study", J. Rheumatology 25:417-426, 1998.
Plückthun, A "Mono-and bivalent antibody fragments produced in *Escherichia coli*: engineering, folding and antigen binding", Immunol. Rev. 130:151-188, 1992.
Plückthun, The Pharmacology of Monoclonal Antibodies, vol. 113, Rosenburg and Moore eds., Springer-Verlag, New York, pp. 269-315 (1994).
Pranzatelli et al. "CSF-B-cell over-expansion in paraneoplastic opsoclonus-myoclonus: Effect of rituximab, an anti-B cell monoclonal antibody", Neurology (Abstract#P05.128)60(5Suppl I): A395, 2003.
Press et al. "Monoclonal antibody 1F5(anti-CD20) Serotherapy of human B cell lymphomas", Blood 69(2):584-591,1987.
Presta et al. "Humanization of an antibody directed against lgE", J. Immunology 151:2623-2632,1993.

Presta, LG. "Antibody engineering", Current Opinion in Structural Biology 2:593-596, 1992.
Prevoo et al. "Modified disease activity scores that include twenty-eight-joint counts. Development and validation in a prospective longitudinal study patients with rheumatoid arthritis", Arthritis Rheum. 38:44-48, 1995.
Priolo et al. "Radiographic changes in the feet of patients with early rheumatoid arthritis. GRISAR(Gruppo Reumatologi Italiani Studio Artrite Reumatoide)", J. Rheumatol. 24:2113-2118, 1997.
Rastetter et al. "Rituximab: expanding role in therapy for lymphomas and autoimmune diseases", Annual Review Medicine 55:477-503, 2004.
Ratanatharathorn et al. "Anti-CD20 chimeric monoclonal antibody treatment of refractory immune-mediated thrombocytopenia in a patient with chronic graft-versus-host disease", Ann. Int. Med. 133:275-279, 2000.
Ravetch and Kinet "Fc receptors", Annu. Rev, Immunol. 9:457-492,1991.
Reff et al. "Depletion of B cells in vivo by a chimeric mouse human monoclonal antibody to CD20" Blood 83(2):435-445, 1994.
Remington's Pharmaceutical Sciences 16$^{th}$ edition (Osol, A, Ed. 1980) (a book—we are not providing a copy).
Riechman et al. "Reshaping human antibodies for therapy", Nature 332:323-327, 1988.
Riley and Sliwkowski "CD20: a gene in search of a function", Seminars in Oncology 27(12):17-24, 2000.
Ripka et al. "Two Chinese hamster ovary glycosylation mutants affected in the conversion of GDP-mannose to GDP-fucose", Arch. Biochem. Biophys. 249:533-545, 1986.
Rivera et al. "Role of B cells as antigen-presenting cells in vivo revisited: antigen-specific cells are essential for T cell expansion in lymph nodes and for systemic T cell responses to low antigent concentrations", International Immunology 13:1583-1593, 2001.
Saleh et al. "A pilot study of the anti-CD20 monoclonal antibody rituximab in patients with refractory immune thrombocytopenia", Seminars in Oncology 27(6 Suppl 12):99-103, 2000.
Schneider et al. "BAFF, a novel ligand of the tumor necrosis factor family, stimulates B cell growth", J. Exp. Med. 189:1747-1756, 1999.
Scott et al. "The links between joint damage and disability in rheumatoid arthritis", Rheumatology 29:122-132, 2000.
Scott, DL. "Radiological progression in established rheumatoid arthritis", J. Rheumatol 31(Suppl. 69):55-65, 2004 .
Sfikakis et al. "Remission of proliferative lupus nephritis following B cell depletion therapy is preceded by down-regulation of the T cell costimulatory molecule CD40 ligand: an open-label trial", Arthritis Rheum. 52(2):501-513, 2005.
Sharp et al. "Methods of scoring the progression of radiologic changes in rheumatoid arthritis. Correlation of radiologi, clinical and laboratory abnormalities", Arthritis Rheum.14:706-720,1971.
Sharp et al. "How many joints in the hands and wrists should be included in a score of radiologic abnormalities uses to assess rheumatoid arthritis", Arthritis Rheum.28:1326-1335, 1985.
Sharp et al. "Treatment with leflunomide slows radiographic progression of rheumatoid arthritis: results from three randomized controlled trials of leflunomide in patients with active rheumatoid arthritis. Leflunomide Rheumatoid Arthritis Investigators Group", Arthritis Rheum. 43:495-505, 2000.
Shopes, B. "A genetically engineered human lgG mutant with enhanced cytolytic activity", J. Immunol. 148:2918-2922, 1992.
Shu et al. "TALL-1 is a novel member of the TNF family that is down-regulated by mitogens", J. Leukoc. Biol. 65:680-683, 1999.
Silverman and Carson "Roles of B cells in rheumatoid arthritis", Arthritis Research Therapy 5 Suppl.4: S1-6, 2003.
Silverman and Weisman "Rituximab therapy and autoimmune disorders: prospects for anti-B cell therapy", Arthritis & Rheumatism 48:1484-1492, 2003.
Silverman "Anti-CD20 therapy in systemic lupus erythematosus", Arthritis Rheumatism 52(4):1342 , 2005.
Sims et al. "A humanized CD18 antibody can block function without cell destruction", J. Immunology 151:2296-2308,1993.
Skerra et al. "Bacterial expression of immunoglobulin fragments", Current Opinion in Immunology 5:256-262, 1993.

(56) References Cited

OTHER PUBLICATIONS

Smolen et al. "[SAT0031] Patients with early rheumatoid arthritis achieved a clinically meaningful and sustained improvement in physical function after treatment with infliximab", Annals Rheumatic Diseases 64 (Suppl III)::418, 2005.
Smolen et al. "Evidence of radiographic benefit of treatment with infliximab plus methotrexate in rheumatoid arthritis patients who had no clinical improvement: a detailed subanalysis of data from the anti-tumor necrosis factor trial in rheumatoid arthritis with concomitant therapy study", Arthritis Rheumatism 52:1020-1030, 2005.
Somer et al. "Improvement in Sjogren's syndrome following therapy with rituximab for marginal zone lymphoma", Arthritis Rheumatism 49:394-398, 2003.
Specks et al. "Response of Wegener's granulomatosis to anti-CD20 chimeric monoclonal antibody therapy", Arthritis Rheumatism 44:2836-2840, 2001.
Stahl et al. "Rituximab in RA: Efficacy and safety from a randomised, controlled trial", Ann. Rheum. Dis.(OP0004) 62 (Suppl. 1) (2003).
Stashenko et al. "Characterization of a human B lymphocyte-specific antigen", J. Immunology 125:1678-1685,1980.
Stasi et al. "Rituximab chimeric anti-CD20 monoclonal antibody treatment for adults with chronic idiopathic thrombocytopenic purpura", Blood 98:952-957, 2001.
Stockinger et al. "The CD system of leukocyte surface molecules", Current Protocols in Immunology A.4A.1 Suppl. 53:1A-4A, 2003.
Stone and Specks, "Rituximab Therapy for the Induction of Remission and Tolerance in ANCA-associated Vasculitis. Clinical Trial Research Summary of the 2002-2005 Immune Tolerance Network" American Society of Nephrology (11th International Vasculitis and ANCA workshop)(Poster 88) pp. 1-2 (retrieved May 27, 2008), http://www.immunetolerance.org/research/autoimmune/trials/stone.html.
Strand et al. "Treatment of active rheumatoid arthritis with leflunomide compared with placebo and methotrexate, Leflunomide Rheumatoid Arthritis Investigators Group", Arch. Internal Medicine 159:2542-2550, 1999.
Stuve et al. "Approved and future pharmacotherapy for multiple sclerosis", Neurology 8:290-301, 2002.
Suresh et al. "Bispecific monoclonal antibodies from hybrid hybridomas", Methods in Enzymology 121:210-228, 1986.
Szczepanski et al. "Safety data from 48 weeks follow-up of a randomised controlled trial of rituximab in patients with rheumatoid arthritis", Arthritis Rheumatism 48(9) abstract # 204:S121 (2003).
Tahir et al. "Humanized anti-CD20 monoclonal antibody in the treatment of severe resistant systemic lupus erythematosus in a patient with antibodies against rituximab", Rheumatology 44(4):561-562, 2005.
Takemura et al. "T cell activation in rheumatoid synovium is B cell dependent", J. Immunology 167:4710-4718, 2001.
Tedder et al. "The CD20 surface molecule of B lymphocytes functions as a calcium channel" J. Cell Biochem. 195 abstract # M023, 1990.
Tedder et al. "The B cell surface molecule B1 is functionally linked with B cell activation and differentiation", J. Immunology 135(2):973-979, 1985.
Teitelbaum, SL. "Bone resorption by oseteoclasts", Science 289:1504-1508, 2000.
The Leukoctye Antigen Facts Book $2^{nd}$ Edition. 1997, ed. Barclay et al. Academic Press, Harcourt Brace & Co., New York. (a book—we are not providing a copy).
Traunecker et al. "Bispecific single chain molecules (Janusins) target cytotoxic lymphocytes on HIV infected cells", EMBO J. 10:3655-3659, 1991.
Treon and Anderson "The use of rituximab in the treatment of malignant and nonmalignant plasma cell disorders", Seminars in Oncology 27:79-85, 2000.
Tugwell and Boers "OMERACT conference on outcome measure in rheumatoid arthritis clinical trials: introduction", J. Rheumatology 20:528-530, 1993.
Tuscano, "Successful treatment of infliximab-refractory rheumatoid arthritis with rituximab (Annual Scientific Meeting of the American College of Rheumatology, New Orleans, LA—Oct. 2002)" Arthritis and rheumatism (Presentation No. LB11) 46:3402 (2002).
Tutt et al. "Trispecific F(ab')3 derivatives that use cooperative signalling via the TCR/CD3 complex and CD2 to activate and redirect resting cytotoxic T cells", J. Immunology 147:60-69, 1991.
Uchida et al. "The innate mononuclear phagocyte network depletes B lymphocytes through Fc receptor-dependent mechanisms during anti-CD20 antibody immunotherapy", J. Exp. Med. 199: 1659-1669, 2004.
Valentine et al. "Phosphorylation of the CD20 phosphoprotein in resting B lymphocytes. Regulation by protein kinase C", J. Biol. Chem. 264(19):11282-11287, 1989.
Valentine et al. "Structure and funciton of the B-cell specific 35-37 kDa. CD20 protein", Leukoctye B3.9:440-443, 1987.
Van der Heijde et al. "Effect of infliximab and methotrexate on radiographic progression in patients with early rheumatoid arthritis", Annals Rheumatic Diseases 64:417-419, 2005.
Van der Heijde et al. "Biannual radiographic assessments of hands and feet in a three-year prospective followup of patients with early rheumatoid arthritis", Arthritis Rheumatism 35:26-44, 1992.
Van der Heijde et al. "Efficacy and safety of infliximab in patients with ankylosing spondylitis: results of a randomized, placebo-controlled trial (ASSERT)", Arthritis Rheumatism 5:582-591, 2005.
Van der Heijde et al. "How should treatment effect on spinal radiographic progression in patients with ankylosing spondylitis be measured?", Arthritis Rheumatism 52:1979-1985, 2005.
Van der Heijde et al. "Effects of hydroxychloroquine and sulphasalazine on progression of joint damage in rheumatoid arthritis", Lancet 1:1036-1038, 1989.
Van der Heijde, et al. "Plain X-rays in rheumatoid arthritis: overview of scoring methods, their reliability and applicability", Baillieres Clinical Rheumatology 10:435-433,1996.
Van der Heijde, D. "How to read radiographs according to the Sharp/van der Heijde method", J. Rheumatology 27:261-263, 2000.
Van Everdingen et al. "Low-dose prednisone therapy for patients with early active rheumatoid arthritis: clinical efficacy, disease-modifying properties, and side effects: a randomized, double-blind, placebo-controlled clinical trial"Ann. Intern. Med.136:1-12, 2002.
Van Vollenhoven et al. "[2005][SAT0072]Safety and tolerability of rituximab in patients with moderate to severe rheumatoid arthritis (RA): results from the dose-ranging assessment international clinical evaluation of rituximab in RA (DANCER) study", Ann Rheum Dis. 64(Suppl III):432, 2005.
Verhoeyen et al. "Reshaping human antibodies: grafting an antilysozyme activity", Science 239:1534-1536, 1988.
Virgolini and Marzocchi "Rituximab in autoimmune diseases", Biomedicine Pharmacotherapy 58:299-309, 2004.
Visvanathan et al. "[2005][FRI0209] Infiximab treatment of patients with ankylosing spondylitis leads to changes in markers of inflammation and bone turnover associated with clinical efficacy", Annals Rheumatic Diseases 64 (Suppl III):319 (2005).
Vugmeyster et al. "Depletion of B cells by a humanized anti-CD20 antibody PRO70769 in Macaca fascicularis", Immunother. 28:212-219, 2005.
Ware et al. "How to Score Version Two of the SF-36 Health Survey" (Lincoln, RI, Qualitymetric Incorporated, 2000) (we are not providing a copy of the book).
Wassenberg et al. "Low dose prenidnisolone therapy (LDPT) retards radiographically detectable destruction in early rheumatoid arthritis", Arthiritis Rheum. 42: :S243 (1999).
Waterhouse et al. "Combinatorial infection and in vivo recombination: a strategy for making large phage antibody repertoires", Nucleic Acids Res. 21:2265-2266, 1993.
Weide et al. "Successful long-term treatment of systemic lupus erythematosus with rituximab maintenance therapy", Lupus 12:779-782, 2003.
Weinblatt et al. "The effects of drug therapy on radiographic progression of rheumatoid arthritis. Results of a 36-week randomized trial comparing methotrexate and auranofin", Arthritis Rheum, 36:613-619, 1993.

(56) References Cited

OTHER PUBLICATIONS

Weinblatt et al. "A trial of etanercept, a recombinant tumor necrosis factor receptor: Fc fusion protein, in patients with rheumatoid arthritis receiving methotrexate", New England J. Medicine 240:253-259, 1999.
Wilson et al. "cDNA cloning of the B cell membrane protein CD22: a mediator of B-B cell interactions", J. Exp. Med. 173:137-146, 1991.
Wilson et al. "Genomic structure and chromosomal mapping of the human CD22 gene", J. Immunology 150:5013-5024, 1993.
Wolfe et al. "Radiographic outcome of recent-onset rheumatoid arthritis: a 19-year study of radiographic progression", Arthritis Rheum. 41:1571-1582, 1998.
Wolfe et al. "Radiographic progression predicts substantial income loss and work disability in rheumatoid arthritis" Arthritis Rheum. 43 (Suppl 9):S403, 2000.
Wolfe et al. "A core set of domains for longitudinal observation studies in rheumatic disorders: Consensus report from Omeract 4", Arthritis Rheum 41( Suppl 9):S204, 1998.
Wolff et al. "Monoclonal antibody homodimers: enhanced antitumor activity in nude mice", Cancer Research 53:2560-2565,1993.
Wylam et al. "Successful treatment of refractory myasthenia gravis using rituximab: a pediatric case report", J. Pediatric 143:674-677, 2003.
Yamane-Ohnuki et al. "Establishment of FUT8 knockout Chinese hamster ovary cells: an ideal host cell line for producing completely defucosylated antibodies with enhanced antibody-dependent cellular cytotoxicity", Biotechnol. Bioeng. 87:614-622, 2004.
Zaja at al. "B-cell depletion with rituximab as treatment for immune hemolytic anemia and chronic thrombocytopenia", Haematologica 87:189-195, 2002.
Zaja et al. "Efficacy and safety of rituximab in type II mixed", Blood 101:3827-3834, 2003.
Zaja et al. "Rituximab for myasthenia gravis developing after bone marrow transplant", Neurology 55:1062-1063, 2000.
Goronzy and Weyand et al., "B cells as a therapeutic target in autoimmune disease" Arthritis Res Ther 5(3):131-135 (Mar. 19, 2003).
Kelaidi et al., "Long-term remission of an EBV-positive B cell lymphoproliferative disorder associated with rheumatoid arthristis under methotrexate with anti-CD20 monoclonol antibody (Rituximab) monotherapy" Leukemia 16:2173-2174 ( 2002).
Pincus et al., Clinical and Experimental Rheumatology 21( Suppl 31):S179-S185 ( 2003).
Stewart et al., "Lymphoma in a patient with rheumatoid arthritis receiving methotrexate treatment: successful treatment with rituximab" Rheumatic Diseases 60:892-893 ( 2001).
Taylor, "Antibody therapy for rheumatoid arthritis" Curr Opin Pharmacol 3(3):323-328 ( 2003).
1997 Form 10-K405/A filed by IDEC Pharmaceuticals, United States Securities and Exchange Commission, 81 pages.
A Phase III, Randomized, Double-Blind, Placebo-Controlled, Multicenter Study of Retreatment With Rituximab in Subjects With Rheumatoid Arthritis Receiving Background Methotrexate, ClinicalTrials.gov, Identifier NCT00266227 (Mar. 9, 2006, downloaded on Jun. 22, 2015), 4 pages.
A Phase III, Randomized, Double-blind, Placebo-controlled, Multicenter Study of Retreatment with Rituximab in Subjects with Rheumatoid Arthritis Receiving Background Methotrexate, ClinicalTrials.gov, Identifier NCT00266227 (Oct. 27, 2006, downloaded on Jun. 22, 2015), 4 pages.
A Study to Evaluate the Efficacy and Safety of Mabthera Alone and in Combination with Either Cyclophosphamide or Methotrexate in Patients with Rheumatoid Arthritis, ClinicalTrials.gov, Study ID No. WA16291 (Feb. 23, 2016, downloaded on Jun. 1, 2018), 5 pages.
Affidavit of Christopher Butler, dated Jul. 20, 2016, 15 pages, IPR2017-01115 (U.S. Pat. No. 7,820,161).
Alarcon et al., "Methotrexate in rheumatoid arthritis: toxic effects as the major factor in limiting long-term treatment," Arthritis and Rheumatism 32:6 (1989), pp. 671-676.
Alzabin et al., "Incomplete response of inflammatory arthritis to TNFα blockade is associated with the Th17 pathway," Extended Report, Ann Rheum Dis 2012;71:1741-48.
Amlot et al., "A Phase I Study of an Anti-CD22-Deglycosylated Ricin A Chain Immunotoxin in the Treatment of B-cell Lymphomas Resistant to Conventional Therapy," Blood 82:9 (1993) pp. 2624-2633.
Amos et al., "Rheumatoid arthritis: relation of serum C-reactive protein and erythrocyte sedimentation rates to radiographic changes," British Medical Journal, 1 (1997) pp. 195-197.
An Open Label Study of the Efficacy and Safety of Retreatments with Rituximab (MabThera/Rituxan) in Patients with Active Rheumatoid Arthritis who Have had an Inadequate Response to Anti-TNFα Therapies, ClinicalTrials.gov, Identifier NCT02097745 (Nov. 6, 2014, downloaded on Jun. 1, 2018), 8 pages.
Appeal Decision by Appellate Trial Board of EPO (T0734/12-3.3.04) re EP1613350, dated Jul. 29, 2013, 43 pages.
Arnet et al., "The American Rheumatism Association 1987 Revised Criteria for the Classification of Rheumatoid Arthritis," Arthritis and Rheumatism 31:3 (1988) pp. 315-323.
Arthritis Foundation Statement on Rituximab for Rheumatoid Arthritis, dated Mar. 1, 2006, 2 pages.
Atkins, "Short Communication, Weighting Functions and Data Truncation in the Fitting of Multi-Exponential Functions," Biochem J (1974) 138, pp. 125-127.
Axtens et al., "Combination therapy with methotrexate and sulphasalazine in rheumatoid arthritis—tolerance of therapy," Ann Rheum Dis 53:703 (1994), 1 page.
Bathon et al., "A Comparison of Etanercept and Methotrexate in Patients with Early Rheumatoid Arthritis," 343(22) New England Journal of Medicine (2000), pp. 1586-1593.
Bender et al., "Body Surface Area (A Dictionary of Food and Nutrition)," (1995), 4 pages.
Bender et al., Oxford Paperback Reference (A Dictionary of Food and Nutrition), (1995), 5 pages.
Berczi et al., "Immune Modulating Agents" 75-120 (Thomas F. Kresina ed., 1998).
Berinstein et al., "Association of serum Rituximab (IDEC-C2B8) concentration and anti-tumor response in the treatment of recurrent low-grade or follicular non-Hodgkin's lymphoma," Annals of Oncology 9:995-1001 (1998).
Best Practices for Proving a Document is a Printed Publication, United States Patent and Trademark Office, (dated Dec. 7, 2017), 26 pages.
Bijlsma et al., "Glucocorticoids in the Treatment of Early and Late RA," Ann Rheum Dis 2003;62: pp. 1033-1037.
Biogen Idec and Genentech Announce FDA Acceptance of Supplemental Biologics License Application and Priority Review Designation for Rituxan in Rheumatoid Arthritis, Genentech Press Releases (Oct. 31, 2005, downloaded on Jun. 1, 2018), 3 pages.
Biogen Idec and Genentech Submit a Supplemental Biologics License Application for FDA Review of Rituxan for the Treatment of Rheumatoid Arthritis Genentech Press Releases ( Aug. 31, 2005, downloaded on Jun. 1, 2018), 5 pages.
Biogen Idec Inc., Annual Report (Form 10-K) (Dec. 31, 2003), 5 pages.
Biogen, Inc.'s Response to Petitioner's Additional Discovery, submitted Jul. 26, 2017, IPR2016-01614 (U.S. Pat. No. 7,820,161), 32 pages.
Boers et al., "Long acting Drug Combinations in Rheumatoid Arthritis: A Formal Overview," Journal of Rheumatology 18:3 (1991) pp. 316-324.
Boers et al., "Randomised Comparison of Combined Step-Down Prednisolone, Methotrexate and Sulphasalazine with Sulphasalazine Alone in Early Rheumatoid Arthritis," Lancet 350: 309-318 (1997).
Boers et al., "World Health Organization and International League of Associations for Rheumatology core endpoints for symptom modifying antirheumatic drugs in rheumatoid arthritis clinical trials," J Rheumatol 1994 (suppl 41) 21:86-89.

(56) References Cited

OTHER PUBLICATIONS

Boers, "Demonstration of response in rheumatoid arthritis patients who are nonresponders according to the American College of Rheumatology 20% criteria: the paradox of beneficial treatment effects in nonresponders in the ATTRACT trial," Arthritis & Rheumatism 44:11 (2001) pp. 2703-2704.
Bologna et al., "Association of Methotrexate (MTX) and Steroids in the Treatment of Rheumatoid Arthritis (RA) Patients," Arthritis & Rheumatism, Abstracts of Scientific Presentations, 1995 Regional Meetings of the American College of Rheumatology, Abstract No. 1280 (Jun. 1995), 1 page.
Breedveld et al., "Appropriate and effective management of rheumatoid arthritis," Ann Rheum Dis 2001;63:627-633.
Breedveld, "Therapeutic monoclonal antibodies," Lancet 2000; 355; 735-740.
Breker et al., "Therapeutic Antibodies for Human Diseases at the Dawn of the Twenty-First Century," Nature Reviews Drug Discovery 2003; 2: 52-62.
Bresnihan, "Anakinra as a new therapeutic option in rheumatoid arthritis: Clinical results and perspectives," Clin Exp Rheumatol 2002; 20 (Supple. 27): S32-S34.
Broeder et al., "A single dose, placebo controlled study of the fully human anti-tumor necrosis factor-alpha antibody adalimumab (D2E7) in patients with rheumatoid arthritis", The Journal of Rheumatology 29:11 (2002) pp. 2288-2298.
Buch et al., "Updated consensus statement on the use of rituximab in patients with rheumatoid arthritis," Ann Rheum Dis (2011); 70:909-920.
Bulpitt, "Biologic Therapies in Rheumatoid Arthritis," Current Rheumatology Reports 1999, 1:157-163.
Buske et al., "Monoclonal Antibody Therapy for B Cell Non-Hodgkin's Lymphomas: Emerging Concepts of a Tumor-targeted Strategy," European Journal of Cancer 35:4 (1999) pp. 549-557.
Callahan et al., "Mortality in the Rheumatic Diseases," Arthritis Care and Research 8:4 (1995) pp. 229-241.
Cambridge et al., "Response to Rituximab: Has the Original Hypothesis Been Confirmed?" Current Pharmaceutical Design (2015); 21:212-220.
Capps et al., "Body Surface Area as a Predictor of Aortic and Pulmonary Valve Diameter," The Journal of Thoracic and Cardiovascular Surgery 119:5 (2000) pp. 975-982.
Carson et al., "New Roles for Rheumatoid Factor," Journal of Clinical Investigation (1991); 87: pp. 379-383.
Carson et al., "Rheumatoid Factor and Immune Networks," Annual Review of Immunology (1987); 5: pp. 109-126.
Nepom, "Genetics of Rheumatoid Arthritis," Abstracts Presented at the Fourth International Synovitis Workshop, Dallas TX, Apr. 21-25, 1999, vol. 1, Suppl 1, Abstracts (Apr. 1999), 24 pages.
Celltrion and Pfizer against Biogen and Genentech IPR2016-01614 (U.S. Pat. No. 7,820,161), Deposition Transcript of Gregg Silverman, United States Patent and Trademark Office, dated Aug. 16, 2017, 171 pages.
*Celltrion and Pfizer v. Biogen and Genentech* Final Written Decision (FWD) in IPR2016-01614 (U.S. Pat. No. 7,820,161), United States Patent and Trademark Office, (dated Feb. 21, 2018), 25 pages.
*Celltrion and Pfizer v. Biogen and Genentech* Genentech's Response to Petitioner's Additional Discovery, United States Patent and Trademark Office, (dated Jul. 26, 2017), 27 pages, IPR2016-01614 (U.S. Pat. No. 7,820,161).
Centocor, Inc., "X-Ray Study Suggests Remicade(TM) Stops Progression of Rheumatoid Arthritis, PRNEWSWIRE," http://www.prnewswire.com/news-releases/x-ray-study-suggests-remicadetm-stops-progression-of-rheumatoid-arthritis-77215127.html (Nov. 16, 1999), downloaded on May 22, 2017, 9 pages.
Certificate of the Basel Register of Commerce, confirming the corporation details of F. Hoffmann-La Roche AG, and the use of alternative names F. Hoffmann-La Roche SA and F. Hoffmann-La Roche Ltd for the same corporation Handelsregisteramt des Kantons Basel-Stadt, (dated Feb. 11, 2014), 1 page.
Chabaud et al., "The Combination of Tumor Necrosis Factor α Blockade with Interluekin-1 and Interlukin-17 Blockade is More Effective for Controlling Synovial Inflammation and Bone Resorption in an Ex Vivo Model," Arthritis & Rheumatism 44:6 (2001) pp. 1293-1303.
Chiorazzi et al., "Synovial B Cells in Rheumatoid Arthritis: Clonal Expansion Diversification and Persistence," Arthritis Research vol. 1, Suppl 1, Abstracts, (1999), 1 page.
Choy et al., "Cytokine Pathways and Joint Inflammation in Rheumatoid Arthritis," 344(12) New England Journal of Medicine (2001), pp. 907-916.
Choy et al., "Monoclonal Antibody Therapy in Rheumatoid Arthritis," British Journal of Rheumatology 1998; 37:484-490.
Choy et al., "Therapeutic Benefit of Blocking Interleukin-6 Activity with an Anti-Interleukin-6 Receptor Monoclonal Antibody in Rheumatoid Arthritis," Arthritis & Rheumatism 46:12 (2002) pp. 3143-3150.
Chustecka, "Rituximab in RA: 'we should aim for permanent remission'" Medscape Medical News, (Jun. 16, 2004, downloaded on May 10, 2017), 4 pages.
Clinical Study Report relating to the REFLEX study (WA17042) by Biogen Idec and Roche Products, dated May 2008, 2 pages.
Cohen et al., "A Multicentre, Double Blind, Randomised, Placebo Controlled Trial of Anakinra (Kineret), A Recombinant Interleukin 1 Receptor Antagonist, in Patients with Rheumatoid Arthritis Treated with Background Methotrexate," Ann Rheum Dis 2004; 63:1062-1068.
Cohen et al., "Continued inhibition of structural damage over 2 years in patients with rheumatoid arthritis treated with rituximab in combination with methotrexate," Ann Rheum Dis 2010; 69:1158-1161.
Cohen et al., "Efficacy and Safety of Rituximab in Active RA Patients Who Experienced an Inadequate Response to One or More Anti-TNFα Therapies (REFLEX Study)," Arthritis & Rheumatism 52:9 (Suppl) (2005), Abstract 1830 (1 page).
Cohen et al., "Prolonged Efficacy of Rituximab in Rheumatoid Arthritis Patients with Inadequate Response to One or More TNF Inhibitors: 1-Year Follow-up of a Subset of Patients Receiving a Single Course in a Controlled Trial (REFLEX Study)," Ann Rheum Dis 2006; 65 (Suppl II): 183 (1 page).
Cohen et al., "Radiological Damage in Patients with Rheumatoid Arthritis on Sustained Remission," Ann Rheum Dis 2007; 66: pp. 358-363.
Cohen et al., "Rituximab for Rheumatoid Arthritis Refractory to Anti-Tumor Necrosis Factor Therapy: Results of a Multicenter, Randomized, Double-Blind, Placebo-Controlled, Phase III Trial Evaluating Primary Efficacy and Safety at Twenty-Four Weeks," Arthritis & Rheumatism 54:9 (2006) pp. 2793-2806.
Cronstein, "Low-Dose Methotrexate: A Mainstay in the Treatment of Rheumatoid Arthritis," Pharmacological Reviews 57:2 (2005) pp. 163-172.
Cutolo et al., "Anti-inflammatory Mechanisms of Mexotrexate in Rheumatoid Arthritis," Ann Rheum Dis 2001; 60: 729-735.
Davis et al., "Retreatments with Rituxan (Rituximab, Idec-C2B8) have significant efficacy, do not cause hama, and are a viable minimally toxic alternative in relapsed or refractory non-Hodgkin's lymphoma (NHL)," Blood 90:10 (Suppl 1) (1997), Abstract No. 328-IV, (1 page).
Davis et al., "Rituximab: First report of a phase II (PII) trial in NHL patients (PTS) with bulky disease," Blood 92:414a (1998), Abstract No. 1711, Poster Board#/Session: 383-III (1 page).
Davis et al., "Single-Agent Monoclonal Antibody Efficacy in Bulky Non-Hodgkin's Lymphoma: Results of a Phase II Trial of Rituximab," Journal of Clinical Oncology 17:6 (1999) pp. 1851-1857.
Davis et al., "Therapy of B-Cell Lymphoma with Anti-CD20 Antibodies Can Result in the Loss of CD20 Antigen Expression," Clinical Cancer Research 1999; 5:611-615.
De Clerck, "B Lymphocytes and Humoral Immune Responses in Rheumatoid Arthritis", Clinical Rheumatology 1995; 14 (Suppl 2) pp. 14-18.
De Vita et al., "Efficacy of Selective B Cell Blockade in the Treatment of Rheumatoid Arthritis", Arthritis & Rheumatism 46(8) (2002) pp. 2029-2033.

(56) References Cited

OTHER PUBLICATIONS

De Vita et al., "Pathogenetic Role of B Lymphocytes in Synovitis Arthritis: Selective B Cell Block Can Induce a Clinical Response in Patients With Refractory Rheumatoid Arthritis", Official Journal of the Italian Society of Rheumatology 53:3 (Suppl 4) (2001), (with certified translation dated Jul. 7, 2016), 2 pages.
De Vita et al., "Treatment of Rheumatoid Arthritis with Rituximab: An Update and Possible Indications", Autoimmunity Reviews 5 (2006) 443-448.
Decision by Opposition Board of EPO re revocation of EP 1613350, European Patent Office, dated Feb. 29, 2012, 20 pages.
Decision Denying Institution of Inter Partes Review, IPR2016-01667 (U.S. Pat. No. 7,976,838) United States Patent and Trademark Office, dated Mar. 2, 2017, 19 pages.
Decision Denying Institution of Inter Partes Review, IPR2017-02036 (U.S. Pat. No. 7,976838) United States Patent and Trademark Office, dated Mar. 4, 2018, 10 pages.
Decision Denying Institution of Inter Partes Review, IPR2017-02042 (U.S. Pat. No. 7,976,838) United States Patent and Trademark Office, dated Mar. 4, 2018, 13 pages.
Decision Denying Petitioner's Request for Rehearing in IPR2016-01667 (U.S. Pat. No. 7,976,838), United States Patent and Trademark Office, dated Aug. 18, 2017, 7 pages.
Decision for Dismissing Petitions and Terminating Proceedings in IPR2015-01733 (U.S. Pat. No. 7,976,838) and IPR2015-01744 (U.S. Pat. No. 7,820,161) United States Patent and Trademark Office, dated Oct. 6, 2015, 3 pages.
Decision for Institution of Inter Partes Review, Grant of Motion for Joinder, and Grant of Joint Motion to Dismiss Certain Challenges in the Petition in IPR2017-01115 (U.S. Pat. No. 7,820,161), United States Patent and Trademark Office, dated Jul. 18, 2017, 8 pages.
Decision for Institution of Inter Partes Review, IPR2015-00415 (U.S. Pat. No. 7,820,161) United States Patent and Trademark Office, dated Jul. 17, 2015, 31 pages.
Decision for Institution of Inter Partes Review, IPR2015-00417 (U.S. Pat. No. 7,976,838) United States Patent and Trademark Office, dated Jul. 14, 2015, 29 pages.
Decision for Institution of Inter Partes Review, IPR2016-01614 (U.S. Pat. No. 7,820,161) United States Patent and Trademark Office, dated Feb. 24, 2017, 14 pages.
Decision for Institution of Inter Partes Review, IPR2017-01923 (U.S. Pat. No. 7,976,838) United States Patent and Trademark Office, dated Apr. 4, 2018, 27 pages.
Decision of Opposition Division re revocation of EP 1176981, European Patent Office, dated Apr. 13, 2012, 17 pages.
Decision of the Board of Appeals (case No. T 0734/12) regarding EP 1613350, European Patent Office, dated Jul. 29, 2013, 43 pages.
Decision of the City Court of Prague of May 18, 2017 (PI proceedings), File No. 2Nc 1037/2017-44, English translation.
Decision of the Regional Court of Munich re EP 1951304, dated May 17, 2017, 18 pages (English translation).
Decision of the Technical Board of Appeal in the Opposition of EP 1179681, European Patent Office, dated Jun. 18, 2015, 17 pages.
Decision on Institution of Inter Partes Review IPR2015-00417 for U.S. Pat. No. 7,976,838 United States Patent and Trademark Office, dated Jul. 14, 2015, 29 pages.
Decision Revoking the European Patent No. 1613350, European Patent Office, dated Feb. 29, 2012, 64 pages.
Decision T1243/12 of the Technical Board of Appeal re revocation of EP 1176981, European Patent Office, dated Jun. 18, 2015, 18 pages.
Decision T734/12 of the Technical Board of Appeal re revocation of EP 1613350, European Patent Office, dated May 17, 2013, 39 pages.
Decisions Dismissing Petitions and Terminating Proceedings in IPR2015-001733 (U.S. Pat. No. 7,976,838) and 2015-01744 (U.S. Pat. No. 7,820,161), United States Patent and Trademark Office, dated Oct. 6, 2015, 3 pages.
Declaration and CV of Dr. Ferdinand Breedveld in Belgium Validity Attack (a/17/02930) re EP1951304, dated Apr. 4, 2017, 7 pages.

Declaration by Dr. Ronald F. Van Vollenhoven in EPO Opposition Proceedings (00 92 8991.9/1176981) re EP1176981, dated Jan. 9, 2012, 5 pages.
Declaration of Akiko Chai in the Second Instance at Patent Court, re KR1092171, dated Dec. 21, 2016, 12 pages.
Declaration of Antonio Grillo-Lopez and Lori Kunkel pursuant to 37 Cfr § 1.131, filed in U.S. Appl. No. 09/564,288 (now U.S. Pat. No. 7,820,161), United States Patent and Trademark Office, (dated May 21 2003), 19 pages.
Declaration of Dr. F.C. Breedveld Responsive to Dijkmans First Declaration (C39) (C/09/519083) re EP1951304, dated May 2, 2017, 3 pages, with appended CV (3 pages).
Declaration of Dr. F.C. Breedveld Responsive to Gaston Declaration (C38) and Dijkmans Declaration (C40) (C/09/519083) re EP1951304, dated May 2, 2017, 3 pages, with appended CV (3 pages).
Declaration of Dr. Jeffrey N. Siegel Before the Korean Intellectual Property Tribunal, Second Instance at Patent Court, re KR1092171, dated Apr. 5, 2016, 10 pages.
Declaration of Dr. Joseph M. Tuscano in opposition proceedings re RU 2358762, dated Apr. 4, 2017, 3 pages.
Declaration of Dr. Joseph M. Tuscano in Second Instance at Patent Court re KR1092171, dated Dec. 21, 2016, 3 pages.
Declaration of Dr. Marinus HJ van Oers filed during Technical Court Expertise (14750/2017) re EP1951304, dated Nov. 4, 2017, 5 pages.
Declaration of Dr. Mark C. Totoritis in Appeal Proceedings (200. 234.115/01) re EP1951304, dated Apr. 22, 2018, 2 pages.
Declaration of Elena M. Massarotti, M.D., (dated Aug. 28, 2017), 127 pages, from IPR2017-01923 (U.S. Pat. No. 7,976,838), with appended CV (36 pages).
Declaration of Elena Massarotti, M.D. (dated Mar. 24, 2017), 44 pages, IPR2017-01115 (U.S. Pat. No. 7,820,161), with appended CV (36 pages).
Declaration of Elizabeth Greenfield, J.D., M.L.I.S., (dated May 4, 2018), 249 pages, IPR2018-01019 (U.S. Pat. No. 7,976,838).
Declaration of Gregg Silverman, M.D., (dated Jun. 2, 2017), 89 pages, IPR2016-01614 (U.S. Pat. No. 7,820,161), with appended CV (29 pages).
Declaration of Jack Goldberg, M.D., FACP, (dated Jul. 30, 2016), 8 pages, IPR2016-01614 (U.S. Pat. No. 7,820,161), with appended CV (14 pages).
Declaration of Jack Goldberg, M.D., FACP, (dated Jul. 30, 2016), 8 pages, IPR2016-01667 (U.S. Pat. No. 7,976,838), with appended CV (14 pages).
Declaration of Jayesh Mehta, M.D., (dated May 3, 2018), 88 pages, IPR2018-01019 (U.S. Pat. No. 7,976,838).
Declaration of Joachim Kalden, M.D., (dated Dec. 8, 2014), 118 pages, IPR2015-01744 (U.S. Pat. No. 7,820,161).
Declaration of Joachim Kalden, M.D., (dated Dec. 8, 2014), 119 pages, IPR2015-01733 (U.S. Pat. No. 7,976,838).
Declaration of Joachim Kalden, M.D., (dated Dec. 8, 2014), 118 pages, IPR2015-00415 (U.S. Pat. No. 7,820,161).
Declaration of Joachim Kalden, M.D., (dated May 16, 2013), 119 pages, IPR2015-00417 (U.S. Pat. No. 7,976,838).
Declaration of Jonathan Charles Wright Edwards in EPO Opposition Proceedings re EP1176981, dated Feb. 27, 2008, 8 pages.
Declaration of Jonathan Charles Wright Edwards, (dated Aug. 22, 2008), 5 pages, IPR2016-01614 (U.S. Pat. No. 7,820,161).
Declaration of Jonathan Charles Wright Edwards, (dated Feb. 27, 2008), 8 pages, IPR2017-01115 (U.S. Pat. No. 7,820,161).
Declaration of Karen Sandrik in Supplementary Table of Documents Filed Apr. 2018 re EP1951304, dated Aug. 15, 2017, 15 pages, with appended CV (6 pages).
Declaration of Katherine Nolan-Stevaux, (dated Dec. 5, 2016), 16 pages, IPR2016-01667 (U.S. Pat. No. 7,976,838).
Declaration of M. Laurentius Marais, Ph.D., (dated Aug. 8, 2016), 17 pages, IPR2016-01667 (U.S. Pat. No. 7,976,838), with appended CV (6 pages).
Declaration of Maarten Boers, (dated Aug. 23, 2017), 14 pages, IPR2016-01614 (U.S. Pat. No. 7,820,161), with appended CV (48 pages).

(56) References Cited

OTHER PUBLICATIONS

Declaration of Maarten Boers, (dated Aug. 8, 2016), 59 pages, IPR2016-01667 (U.S. Pat. No. 7,976,838), with appended CV (48 pages).
Declaration of Maarten Boers, (dated Jul. 15, 2016), 44 pages, IPR2016-01614 (U.S. Pat. No. 7,820,161), with appended CV (48 pages).
Declaration of Maarten Boers, (dated May 3, 2018), 142 pages, IPR2018-01019 (U.S. Pat. No. 7,976,838), with appended CV (48 pages).
Declaration of Maarten Boers, (dated Sep. 14, 2017), 5 pages, IPR2016-01614 (U.S. Pat. No. 7,820,161), with appended CV (48 pages).
Declaration of Mark D. Janis in Appeal Proceedings (200.234.115/01) re EP1951304, dated Apr. 25, 2018, 25 pages, with appended CV (23 pages).
Declaration of Mark D. Janis in Appeal Proceedings (200.234.115/01) re EP1951304, dated Jun. 4, 2018, 7 pages, with appended CV (23 pages).
Declaration of Matthew Wolf (RK/16-1509) re EP1951304, dated Apr. 3, 2017, 9 pages.
Declaration of Megan Raymond, (dated Jan. 4, 2018), 6 pages, IPR2017-01923 (U.S. Pat. No. 7,976,838).
Declaration of Megan Raymond, (dated Jan. 4, 2018), 6 pages, IPR2017-02042 (U.S. Pat. No. 7,976,838).
Declaration of Michael L. Grossboard, M.D., (dated Aug. 28, 2017), 39 pages, IPR2017-01923 (U.S. Pat. No. 7,976,838).
Declaration of Mr. Roberto Ferraro in Validity Attack (A/17/02930) re EP 1951304, dated Apr. 25, 2018), 1 page.
Declaration of Philipp Groz in Opposition re EP1951304, dated Aug. 11, 2017, 4 pages.
Declaration of Professor Duncan Matthews in Opposition to EP1951304, dated Apr. 25, 2018, 6 pages, with appended CV (8 pages).
Declaration of Professor Hill Gaston, (dated Apr. 4, 2017), 11 pages, IPR2016-01614 (U.S. Pat. No. 7,820,161), with appended CV (23 pages).
Declaration of R. Polk Wagner in Belgium Validity Attack (A/17/02930) re 1951304, dated Jan. 11, 2018, 2 pages, with appended CV (12 pages).
Declaration of R. Polk Wagner in Opposition re EP1951304, dated May 3, 2017, 3 pages, with appended CV (12 pages).
Declaration of R. Polk Wagner in Opposition re EP1951304, dated Sep. 7, 2018, 14 pages, with appended CV (12 pages).
Declaration of Robert Ferraro (IPR2016-01667) re U.S. Pat. No. 7,976,838, dated Dec. 5, 2016, 12 pages.
Declaration of Robert Ferraro in Opposition re EP1951304, dated Apr. 25, 2018, 1 page.
Declaration of Robert V. Cerwinski in Dutch Proceedings (C/09/519083) re EP1951304, dated May 3, 2017, 55 pages.
Declaration of Ronald F. van Vollenhoven in Celltrion Exhibit List, Second Instance at Patent Court re KR101092171, dated Oct. 6, 2010, 11 pages.
Declaration of Ronald F. van Vollenhoven, (dated Oct. 15, 2010), 2 pages, IPR2015-00417 (U.S. Pat. No. 7,976,838).
Declaration of Ronald van Vollenhoven, (dated Jul. 30, 2007), 11 pages, IPR2015-01744 (U.S. Pat. No. 7,820,161).
Declaration of Rutger Kleemans, (dated Dec. 5, 2016), 3 pages, IPR2016-01667 (U.S. Pat. No. 7,976,838).
Declaration of Sarah Fink in Support of the Petition for Inter Partes Review of U.S. Pat. No. 7,820,161, United States Patent and Trademark Office, (dated Aug. 2, 2016), 4 pages, from IPR2016-01614 (U.S. Pat. No. 7,820,161).
Declaration of Sarah Fink in Support of the Petition for Inter Partes Review of U.S. Pat. No. 7,976,838, United States Patent and Trademark Office, (dated Aug. 23, 2016), 2 pages, from IPR2017-01667.
Declaration of Scott Bennett, Ph.D. Part 1, United States Patent and Trademark Office, (dated Aug. 24, 2017), 62 pages, from IPR2017-01923 (U.S. Pat. No. 7,976,838).
Declaration of Scott Bennett, Ph.D. Part 2, United States Patent and Trademark Office, (dated Aug. 24, 2017), 62 pages, from IPR2017-01923 (U.S. Pat. No. 7,976,838).
Declaration of Scott Bennett, Ph.D., Part 3, United States Patent and Trademark Office, (dated Aug. 24, 2017), 62 pages, from IPR2017-01923 (U.S. Pat. No. 7,976,838).
Declaration of Scott Bennett, Ph.D., Part 4, United States Patent and Trademark Office, (dated Aug. 24, 2017), 62 pages, from IPR2017-01923 (U.S. Pat. No. 7,976,838).
Declaration of Sebastian Moore in Croatian Validity Attack (P20150018) re EP1951304, dated Mar. 31, 2017, 4 pages.
Declaration of Sebastian Moore in Pfizer Opposition (RK/16-1509) re EP1951304, dated Mar. 31, 2017, 4 pages.
Declaration of Siegmund Gutman in Support of the Petition for Inter Partes Review of U.S. Pat. No. 7,976,838, (dated Aug. 31, 2017), 10 pages, from IPR2017-02036 (U.S. Pat. No. 7,976,838).
Declaration of Stacie Knight (redacted version), (dated Dec. 1, 2016), 6 pages, from IPR2016-01667 (U.S. Pat. No. 7,976,838).
Declaration of Stephanie Mendelsohn, (dated Dec. 2, 2016), 4 pages, from IPR2016-01667 (U.S. Pat. No. 7,976,838).
Declaration of Timothy Shaw in EP Opposition re EP1951304 (RK/16-1509), dated May 10, 2016, 1 page.
Declaration of Vibeke Strand, M.D., in Support of the Petition for Inter Partes Review of U.S. Pat. No. 7,820,161, United States Patent and Trademark Office, (dated Mar. 23, 2017), 6 pages, from IPR2016-01614 (U.S. Pat. No. 7,820,161).
Declaration of William J. Jusko, Ph.D., in Support of the Petition for Inter Partes Review of U.S. Pat. No. 7,976,838, United States Patent and Trademark Office, (dated Aug. 31, 2017), 19 pages, from IPR2017-02042 (U.S. Pat. No. 7,976,838).
Declaration of Yite John Lu, (dated Dec. 6, 2016), 7 pages, from IPR2016-01667 (U.S. Pat. No. 7,976,838).
Declaration of Yite John Lu, (dated Jun. 2, 2017), 4 pages, from IPR2016-01614 (U.S. Pat. No. 7,820,161).
Declaration of Zosia Chustecka, (dated Jun. 16, 2004), 4 pages, from IPR2015-00415 (U.S. Pat. No. 7,820,161).
Declaration on Aspects of Rheumatoid Arthritis Treatment by Prof. Dr. Ferdinand Breedveld in Opposition to EP1951304, dated Apr. 4, 2017, 6 pages, with appended CV (3 pages).
Delaware Secretary of State Certification of Biogen Inc. Company Registry Extract, (Mar. 23, 2015), 32 pages.
Demidem et al., "Chimeric anti-CD20(IDEC-C2B8) monoclonal antibody sensitizes a B cell lymphoma cell line to cell killing by cytotoxic drugs", Cancer Biotherapy & Radiopharmaceuticals 12:3 (1997) pp. 177-186.
Department of Rheumatology, "Patient Consent Form, Study of Treatment of Rheumatoid Arthritis by B Lymphocyte Depletion with a Monoclonal Anti-CD20 Antibody," University College London Hospitals, (dated Nov. 17, 1998), IPR2016-01614 (U.S. Pat. No. 7,820,161).
Deposition Transcript of Maarten Boers, M.D., United States Patent and Trademark Office, (May 10, 2017), 292 pages, from IPR2016-01614 (U.S. Pat. No. 7,820,161).
Dimasi et al., "Innovation in the pharmaceutical industry: new estimate of R&D costs", Journal of Health Economics 47 (2016) pp. 20-33.
Disposition of Claims, dated Mar. 17, 2010, p. 1-9, 9 pages, from IPR2015-00415 (U.S. Pat. No. 7,820,161).
Doan et al., "Rheumatoid Arthritis: An Overview of New and Emerging Therapies" J Clin Pharmacol (2005); 45: pp. 751-762.
Doan et al., "Rituximab" Drugs of Today (2005); 41:12, pp. 785-797.
Draft Guidance by the Arthritis Advisory Committee of the Food and Drug Administration, Center for Drug Evaluation and Research, (dated Aug. 7, 1998), 52 pages, from IPR2015-01744 (U.S. Pat. No. 7,820,161).
Drossaers-Bakker et al., "Long-Term Course and Outcome of Functional Capacity in Rheumatoid Arthritis", Arthritis & Rheumatism 42:9 (1999) pp. 1854-1860.
Drugs@FDA: FDA Approved Drug Products, Approval History for Rituxan, FDA Application No. (BLA) 103705, (Aug. 12, 2014, downloaded on Jul. 25, 2016), 7 pages.

(56) References Cited

OTHER PUBLICATIONS

Dwosh et al., "Plasmapheresis Therapy in Rheumatoid Arthritis: A Controlled, Double-blind, Crossover Trial", 308(18) New England Journal of Medicine (1983), pp. 1124-1129.
Edwards et al., "B-Lymphocyte Depletion Therapy in Rheumatoid Arthritis and Other Autoimmune Disorders", Biochemical Society Transactions 30:4 (2002) pp. 824-828.
Edwards et al., "Clinical Outcome in 22 Patients with Rheumatoid Arthritis Treated B Lymphocyte Depletion", Ann Rheum Dis 2002; 61:883-888.
Edwards et al., "Do Self-Perpetuating B Lymphocytes Drive Human Autoimmune Disease?", Immunology 1999; 97: 188-196.
Edwards et al., "Efficacy and Safety of Rituximab a B-Cell Targeted Chimeric Monoclonal Antibody: A Randomized, Placebo-controlled Trial in Patients with Rheumatoid Arthritis" Arthritis & Rheumatism 46:9 (Suppl) (2002), Abstract No. 446, 1 page.
Edwards et al., "Efficacy and Safety of Rituximab, a B-Cell Targeted Chimeric Monoclonal Antibody: A Randomized, Placebo-Controlled Trial in Patients with Rheumatoid Arthritis", dated May 29, 2002, 1 page.
Edwards et al., "Rheumatoid Arthritis: The Predictable Effect of Small Immune Complexes in Which Antibody is Also Antigen", British Journal of Rheumatology 1998; 37:126-130.
Edwards et al., "Sustained Improvement in Rheumatoid Arthritis Following a B Lymphocyte Depletion Protocol", Rheumatology 2000; 39 (Suppl 1), Abstract No. 89, 1 page.
Edwards et al., "Sustained improvement in rheumatoid arthritis following a protocol designed to deplete B lymphocytes" Rheumatology 2001; 40:205-211.
Edwards, "Adalimumab: A Fully Human Monoclonal Anti-Tumor Necrosis Factor-Alpha Antibody", Formulary, 38:5 (2003) pp. 272-289.
Edwards, "Can IgG Rheumatoid Factors Explain Everything?", Arthritis Research vol. 1 (Suppl 1) (1999), Abstracts, 1 page.
Edwards, "Can IgG Rheumatoid Factors Explain Everything?", presentation at the Fourth International Synovitis Workshop in Dallas, Texas, Harold C. Simmons Arthritis Research Center, (Apr. 22, 1999), 4 pages.
Efficacy and Safety Study of Rituximab in Combination With Methotrexate in Patients with Active Rheumatoid Arthritis, ClinicalTrials.gov, Identifier NCT00074438 (2005, downloaded on Jun. 1, 2018), 2 pages.
Eisenberg letter to Genentech Oncology & IDEC Pharmaceuticals Celltrion Ex. 1005, (dated May 29, 1998), 4 pages.
Elliot et al., "Treatment of Rheumatoid Arthritis With Chimeric Monoclonal Antibodies to Tumor Necrosis Factor α", Arthritis & Rheumatism 36:12 (1993) pp. 1681-1690.
Emery et al., "Efficacy and Safety of Different Doses and Retreatment of Rituximab: A Randomised, Placebo-Controlled Trial in Patients who Are Biological Naïve with Active Rheumatoid Arthritis and an Inadequate Response to Methotrexate (Study Evaluating Rituximab's Efficacy in MTX inadequate responders (SERENE)", Ann Rheum Dis 2010; 69: 1629-1635.
Emery et al., "Primary analysis of a double-blind, placebo-controlled, dose-ranging trial of rituximab, an anti-CD20 monoclonal antibody, in patients with rheumatoid arthritis receiving methotrexate (DANCER Trial)", Ann Rheum Dis 2005; 64 (Suppl III): 58 (Abstract No. OPO008), 1 page.
Emery et al., "Prolonged Efficacy of Rituximab in Rheumatoid Arthritis Patients with an Inadequate Response to Methotrexate: 1 Year Follow-up of Subset of Patients Receiving a Single Course in a Controlled Trial (DANCER Trial)", Ann Rheum Dis 2006; 65 (Suppl II): 190 (Abstract No. THU0240), 1 page.
Emery et al., "Retreatment with Rituximab (RTX) Based on a Treatment to Target (TT) Approach Provides Betters Disease Control than Treatment as Needed (PRN) in Patients (Pts) with Rheumatoid Arthritis (RA)", Abstract, Arthritis Rheum 2009; 60 Suppl 10: 2013 (1 page).
Emery et al., "Safety and Tolerability of Rituximab Retreatment in Patients with Active Rheumatoid Arthritis", Arthritis Rheum 2005; 52(9); S341, Abstract No. 860 (1 page).
Emery et al., "The Efficacy and Safety of Rituximab in Patients with Active Rheumatoid Arthritis despite the Methotrexate Treatment", Arthritis & Rheumatism 54:5 (2006) pp. 1390-1400.
Employee Proprietary Information and Inventions and Dispute Resolution Agreement between Biogen Idec Inc. and Dr. Mark Totoritis, (dated Mar. 15, 2004), 6 pages.
Employment Verification of Sini Ngobese, (dated Apr. 19, 2018), 1 page, filed in proceedings related to EP 1951304.
Employment Verification of Sini Ngobese, (dated Jan. 21, 2016), 1 page, filed in proceedings related to EP 1951304.
Epstein, "Expectation Bias in Rheumatoid Arthritis Clinical Trials", Arthritis & Rheumatism 39:11 (1996) pp. 1773-1780.
Event Program, Arthritis Research Center 4th International, Synovitis Workshop Program and Abstracts, The University of Texas Southwestern Medical Center (1999), 4 pages.
Excerpts from vols. 1 & 2 Kelley's Textbook of Rheumatology W.B. Saunders Company, (2001), pp. 275-290, 729-734, 899-912, 1001-1022.
Expert Declaration of Prof Hill Gaston in Dutch Proceedings (RK/16-1509) re EP1951304, dated Apr. 4, 2017, 11pages, with appended CV (23 pages).
Expert Declaration of Professor Vassiliki A. Boussiotis in Italian Infringement Proceedings (14750/2017) re EP1951304, dated Feb. 21, 2017, 7 pages.
Expert Declaration Professor Hill Gaston in Belgium Validity Attack (A/17/03987) re EP1951304, dated Apr. 4, 2017, 36 pages, with appended CV (23 pages).
Expert Report of Professor Dr. B.A.C. Dijkmans in IPR2017-01923 (U.S. Pat. No. 7,976,838), dated Feb. 28, 2017, 16 pages, with appended CV (2 pages).
FDA Drug Label for Enbrel, Immunex Corporation (Jul. 2005), 32 pages.
FDA Drug Label for Enbrel, Immunex Corporation, (Jan. 2002), 28 pages, IPR2017-02042 (U.S. Pat. No. 7,976,838).
Federal Register Notices, vol. 64, No. 31, Department of Health and Human Services, Food and Drug Administration, (Feb. 17, 1999), 2 pages.
Feldmann, "Development of anti-TNF Therapy for Rheumatoid Arthritis", Nature Reviews Immunology (2002), 2: pp. 364-371.
Felson et al., "Should improvement in rheumatoid arthritis clinical trials be defined as fifty percent or seventy percent improvement in core set measures, rather than twenty percent?" Arthritis & Rheumatism, Sep. 1998; 41(9): 1564-1570.
Felson et al., "American College of Rheumatology Preliminary Definition of Improvement in Rheumatoid Arthritis", Arthritis & Rheumatism 38:6 (1995) pp. 727-735.
Felson et al., "The comparative efficacy and toxicity of second-line drugs in rheumatoid arthritis", Arthritis & Rheumatism 33:10 (1990) pp. 1449-1461.
Felson et al., "The Efficacy and Toxicity of Combination Therapy in Rheumatoid Arthritis," Arthritis & Rheumatism 37:10 (1994) pp. 1487-1491.
Final Judgment of the Regional Court of Munich I (21 O 4325/17) re EP1951304, dated May 17, 2017, 17 pages (English translation).
Finckh et al., "Which Subgroup of Patients with Rheumatoid Arthritis Benefits from Switching to Rituximab Versus Alternative Anti-Tumor Necrosis Factor (TNF) Agents After Previous Failure of an Anti-TNF Agent?" Ann Rheum Dis 2010; 69: 387-393.
Firestein et al., "How important are T Cells in Chronic Rheumatoid Synovitis?", Arthritis and Rheumatism 33:6 (1990) pp. 768-773.
Fleischmann et al., "Preliminary Efficacy Results of Rituximab Retreatment in Patients with Active Rheumatoid Arthritis," Arthritis & Rheumatism, 52(9) (Supp) (2005) Abstract No. 264 (1 page).
Form 10-K Genentech, Inc. for the Period Ending Dec. 31, 2008 United States Securities and Exchange Commission, 141 pages.
Fransen et al., "The merits of monitoring: should we follow all our rheumatoid arthritis patients in daily practice?" 41 British Society for Rheumatology 601-604 (2002).

(56) References Cited

OTHER PUBLICATIONS

Furst et al., "Access to Disease Modifying Treatments for Rheumatoid Arthritis Patients," 58(Suppl I) Annals of the Rheumatic Diseases I129-I130 (1999).
Furst et al., "Building towards a consensus for the use of tumour necrosis factor blocking agents," 58 Annals of the Rheumatic Diseases 725-726 (1999).
Furst et al., "Increasing Methotrexate Effect with Increasing Dose in the Treatment of Resistant Rheumatoid Arthritis," 16(3) The Journal of Rheumatology, 313-320 (1989).
Furst et al., "Methotrexate in Rheumatoid Arthritis," 31(3) Arthritis & Rheumatism 305-314 (1988).
Furst et al., "Updated consensus statement on biologic agents for the treatment of rheumatic diseases," 65 Annals of the Rheumatic Diseases iii2-iii15 (2006), 14 pages.
Furst et al., "Updated consensus statement on biological agents for the treatment of rheumatoid arthritis and other rheumatic diseases," 61 Annals of the Rheumatic Diseases ii2-ii7 (2002), 6 pages.
Furst et al., "Updated consensus statement on biological agents the treatment of rheumatoid arthritis and other mediated inflammatory diseases," 62 Annals of the Rheumatic Diseases ii2-ii9 and 111-114 (2003), 13 pages.
Furst, "The Rational Use of Methotrexate in Rheumatoid Arthritis and Other Rheumatic Diseases," 36 British Journal of Rheumatology 1196, 1196-1204 (1997).
Fusconi et al., "B Lymphocyte Subsets in Patients with Rhinoscleroma" 144(5) Otolaryngology—Head and Neck Surgery Foundation Original Research—Sinonasal Disorders 809-814 (2010).
Gabriel, "The Epidemiology of Rheumatoid Arthritis," 81 27(2); 269-281 Rheumatic Disease Clinics of North America (2001).
Gaffney et al., "Azathioprine and Cyclophosphamide in the Treatment of Rheumatoid Arthritis," 37: 824-836 British Journal of Rheumatology 824-836 (1998).
Genant et al., "Assessment of Rheumatoid Arthritis Using a Modified Scoring Method on Digitized and Original Radiographs," 41(9): 1583-1590 Arthritis & Rheumatism (1998).
Genentech, Inc. SEC Form 10-K for Period Ending Dec. 31, 2008 United States Securities and Exchange Commission (Feb. 19, 2009, downloaded on Apr. 6, 2015), 141 pages, IPR2018-01019 (U.S. Pat. No. 7,976,838).
Genentech's Amendment No. 3 to Form S-3 Securities and Exchange Commission, (dated Jul. 16, 1999), 93 pages.
Genovese, "Biologic Therapies in Clinical Development for the Treatment of Rheumatoid Arthritis," 11(3): S45-S54 Journal of Clinical Rheumatology (2005).
Gioud-Paquet et al., "IgM rheumatoid (RF), IgA RF, IgE RF, and IgG RF detected by ELISA in rheumatoid arthritis," 46: 65-71 Annals of Rheumatic Diseases (1987).
Goekoop-Ruiterman et al., "Clinical and radiographic outcomes of four different treatment strategies in patients with early rheumatoid arthritis (the BeSt study): A randomised controlled trial," 52(11) Arthritis & Rheumatism (2005), pp. 3381-3390.
Goldblatt et al., "New Therapies for Rheumatoid Arthritis," 140: 195-204 Clinical and Experimental Immunology (2005).
Goldring et al., "Mechanisms of bone loss in inflammatory arthritis: diagnosis and therapeutic implications," 2: 33-37 Arthritis Research (2000).
Gopal et al., "Clinical applications of anti-CD20 antibodies," 134(5) Journal of Laboratory and Clinical Medicine 445-50 (1999).
Gorman et al., "B cell depletion in autoimmune disease," 5(Suppl. 4): S17-S21 Arthritis Research & Therapy (2003).
Gottenberg et al., "Tolerance and Short Term Efficacy of Rituximab in 43 Patients with Systemic Autoimmune Diseases," 64(6) Annals of the Rheumatic Diseases 913-920 (2005).
Gottlieb et al., "Anti-CD4 Monoclonal Antibody Treatment of Moderate to Severe Psoriasis Vulgaris: Results of a Pilot, multicenter, Multiple-dose, Placebo-controlled study," 43(4) Journal of the American Academy of Dermatology 595-604 (2000).
Gray, "Immunological memory: a function of antigen persistence," 1(2) Trends in Microbiology, 39-41 (1993).

Gremillion et al., "Rheumatoid Arthritis: Designing and Implementing a Treatment Plan," 103(2) Postgraduate Medicine 103-123 (2018).
Gremillion et al., "Tacrolimus (FK506) in the Treatment of Severe, Refractory Rheumatoid Arthritis: Initial Experience in 12 Patients," 26(11) The Journal of Rheumatology 2332-2336 (1999).
Grigo et al., "Effect of a treatment strategy of tight control for rheumatoid arthritis (the TICORA study): a single-blind randomised controlled trial," 364 The Lancet 263-269 (2004).
Grillo-Lopez et al., "Overview of the Clinical Development of Rituximab: First Monoclonal Antibody Approved for the Treatment of Lymphoma," 26(5) Seminars in Oncology 66-73 (1999).
Grossbard ML et al., "Anti-B4-blocked ricin: A Phase II Trial of 7 Day Continuous Infusion in Patients with Multiple Myeloma British," 102 Journal of Haematology 509-515, (1998).
Grounds for Appeal in the EPO, Appeal No. T0734/12-3.3.04 in Opposition to EP 1613350 MewburnEllis LLP, (dated May 10, 2012), 27 pages.
Gryn et al., "Clearance of Erythrocyte Allo-Antibodies Using Rituximab," 29 Bone Marrow Transplantation 631-632 (2002).
Guidance for Industry Clinical Development Programs for Drugs, Devices, and Biological Products for the Treatment of Rheumatoid Arthritis (RA) US Department of Health and Human Services Food and Drug Administration (Feb. 1999, downloaded on Jun. 1, 2018), 50 pages.
"Guidelines for the Management of Rheumatoid Arthritis, 2002 Update" American College of Rheumatology Subcommittee on Rheumatoid Arthritis Guidelines. Arthritis & Rheumatism 46:2 (2002), pp. 328-346 (Feb. 2002, downloaded on Jun. 1, 2018), 19 pages.
"Guidelines for the Management of Rheumatoid Arthritis," 39(5) Arthritis & Rheumatism 713-722 (1996).
Guinamard et al., "B Cell Antigen Receptor Engagement Inhibits Stromal Cell-derived Factor (SDF)-1 a Chemotaxis and Promotes Protein Kinase C (PKC)-induced Internalization of CXCR4," 189(9) Journal of Experimental Medicine 1461-1466 (1999).
Haagsma et al., "Combination of Sulphasalazine and Methotrexate Versus the Single Components in Early Rhuematoid Arthritis: A Randomized, Controlled, Double-blind, 52 Week Clinical Trial," 36 British Journal of Rheumatology 1082-1088 (1997).
Hall et al., "Corticosteroids in autoimmune disease," 22(1) Australian Prescriber 9-11 (1999).
Harris, "Treatment of Rheumatoid Arthritis: Textbook of Rheumatology," 933-937 ($5^{th}$ ed. 1997).
Higashida et al., "Safety and efficacy of rituximab in patients with rheumatoid arthritis refractory to disease modifying antirheumatic drugs and anti-tumor necrosis factor-alpha treatment," 32(11) Journal of Rheumatology 2009-2015 (2005).
Higashida et al., "Safety and efficacy of rituximab in the treatment of refractory rheumatoid arthritis," 102(11) Journal of the American Society of Hematology 288a (2003) (1 page).
Hitt, Medscape, "Adalimumab slows progression of structural joint damage," Medscape Medical American College of Rheumatology, Oct. 30, 2002. at 1-3.
Hoffman M., "Cladribine and Fludarabine for the Treatment of Lymphoproliferative Disorders," Cancer Investigation, 2-3 (1996).
Hueber et at., "Blood autoantibody and cytokine profiles predict response to anti-tumor necrosis factor therapy in rheumatoid arthritis," 11 Arthritis Research & Therapy, 1-13 (2009).
Hulmans et al., "The Course of Radiologic Damage During the First Six Years of Rheumatoid Arthritis," 43(9) Arthritis & Rheumatism, 1927-1940 (2002).
Humira FDA Drug Label US Department of Health and Human Services Food and Drug Administration, (dated Dec. 20, 2002), 16 pages.
Humira FDA label US Department of Health and Human Services Food and Drug Administration, (dated Sep. 27, 2005), 17 pages.
IDEC Pharmaceuticals Corp., Agreement and Plan of Merger between IDEC California and IDEC Delaware (Form 8-K) (Jun. 16, 1997), 4 pages.
Immunobiology, The Immune System in Health and Disease, 4th edition, (1999), 232 pages.

(56) References Cited

OTHER PUBLICATIONS

Infos für Ärzte, JournalMED, (Rheumatoide Arthritis: Neuartige B-Zell-Therapie mit Rituximab reduziert dauerhaft Symptome, JournalMED, Informationen fur Arzte, (Jul. 13, 2005), URL: http://www.journalmed.de/newsview.php?id=9311 (Accessed Jul. 20, 2015), (English translation of abstract), 1 page.
Introduction to antibodies by Prof. B.A.C. Dijkmans, Annex 9.1, from opposition to EP 1951304, 3 pages.
Janakiraman et al., "Rituximab: Correlation between effector cells and clinical activity in NHL", Blood 92:10 (Suppl 1) (1998), Abstract No. 1384, Poster Board #/Session: 56-III, 1 page.
JCW Edwards, "Is rheumatoid factor relevant?", Challenges in Rheumatoid Arthritis, (Bird HA and Snaith ML ed., ResearchGate), 3-24 (1999).
JCW Edwards. "The Case for Killing B Cells With Anti-CD20 in RA." Australian Rheumatology Association, May 26, 1998, University College London, London, United Kingdom, 4 pages.
Jenkins et al., "Biological Modifier Therapy for the Treatment of Rheumatoid Arthritis", The American Journal of the Medical Sciences 323:4 (2002) pp. 197-205.
Jonathan Charles Wright Edwards, Information for Patients Undergoing Treatment of Rheumatoid Arthritis by B Lymphocyte Depletion with an Anti-CD20 Monoclonal Antibody, University College London Hospitals Department of Rheumatology, 3 pages (no date).
Jonathan Charles Wright Edwards, Patient Records, Appendix H to Edwards Declaration pp. 2-17 (no date).
Jonathan Edwards Deposition Transcript (IPR2016-01614) re U.S. Pat. No. 7,820,161, dated Sep. 22, 2017, 171 pages.
Judgment by the President of the Dutch-speaking Commercial Court of Brussels (C/17/000047) re EP1951304 and EP 2055131, dated Dec. 19, 2017, 11 pages (English translation).
Judgment of the District Court of the Hague (C/09/517753 / HA ZA 16/1056) re EP1951304, dated Feb. 21, 2018, 22 pages.
Judgment of the District Court of the Hague (C/09/519083 / HA ZA 16/1117) re EP1951304, dated Sep. 27, 2017, 11 pages.
Kalden et al., "Biologic Agents in the Treatment of Inflammatory Rheumatic Diseases," 9 Current Opinion in Rheumatology 206-12 (1997).
Kalden et al., "The Efficacy and Safety of Leflunomide in Patients With Active Rheumatoid Arthritis", 48(6) Arthritis & Rheumatism 1513-1520 (2003).
Kalden, "Rescue of DMARD Failures by Means of Monoclonal Antibodies or Biological Agents", 15(17) Clinical and Experimental Rheumatology 91-98 (1997).
Kallerup., "IgG-, IgM- and IgA-Rheumatoid Factors in Healthy Adults and Rheumatoid Patients Determined by an Indirect Immunofluoroscence Method", 8 Scand J Rheumatology 1-9 (1979).
Kavanaugh et al., "Anti-TNF-α Monoclonal Antibody (mAb) Treatment of Rheumatoid Arthritis (RA) Patients with Active Disease on Methotrexate: Results of a Double-Blind Placebo Controlled Multicenter Trial [Abstract]," 39 Arthritis Rheumatology 575, (1996), 1 page.
Kavanaugh et al., "Repeat Treatment of Rheumatoid Arthritis Patients with a Murine Anti- Intercellular Adhesion Molecule 1 Monoclonal Antibody," 40(5) Arthritis & Rheumatism 849-853 (1997).
Keystone et al., "Long-Term Efficacy and Safety of a Repeat Treatment Course of Rituximab in Rheumatoid Arthritis Patients with an Inadequate Response to One or More TNF Inhibitors," 65 Ann. Rheum. Dis. 323, (2006), 1 page.
Keystone et al., "Prevention of joint structural damage at 1 year with rituximab in rheumatoid arthritis patients with an inadequate response to one or more TNF inhibitors (reflex study)," 65 Ann. Rheum. Dis 58, (2006), 2 pages.
Keystone et al., "Radiographic, Clinical, and Functional Outcomes of Treatment With Adalimumab (a Human Anti-Tumor Necrosis Factor Monoclonal Antibody) in Patients With Active Rheumatoid Arthritis Receiving Concomitant Methotrexate Therapy," 50 Arthritis & Rheumatism 1400-1411 (2004).

Keystone et al., "Rituximab Inhibits Structural Joint Damage in Patients with Rheumatoid Arthritis with an Inadequate Response to Tumour Necrosis Factor Inhibitor Therapies," Ann. Rheum. Dis., 68, 216-221 (2009).
Keystone, "Abandoned therapies and unpublished trials in rheumatoid arthritis," 15 Current Opinion in Rheumatology 253-258 (2003).
Keystone, "B Cells in Rheumatoid Arthritis: From Hypothesis to the Clinic," 44(Supple 2) Rheumatology ii8-ii12 (2005), 5 pages.
Keystone, "Clinical Implications of Understanding Radiographic Findings in Relation to Clinical Outcomes in Rheumatoid Arthritis," 82 J. of Rheumatology 11-16 (2009).
Keystone, "Treatments no longer in development for rheumatoid arthritis," 61(Suppl. II) Ann Rheum Dis ii43, ii43-ii45 (2002), 3 pages.
Kim et al., "B Cells in Rheumatoid Arthritis", Arthritis Res 2000, 2:126-131.
Kim et al., "Plasma Cell Development in Synovial Germinal Centers in Patients with Rheumatoid and Reactive Arthritis," 162(5) J. of Immunology 3053-3062 (1999).
King, "Applications and Engineering of Monoclonal Antibodies" 1-259 (Taylor & Francis, 1998).
Kirwan et al., "Rheumatoid Arthritis: Disease-modifying Antirheumatic Drugs," 9(3) Clinics in Rheumatic Diseases 581-599 (1983).
Kirwan et al., "The Effect of Glucocorticoids on Joint Destruction in Rheumatoid Arthritis," 333(3) The New Eng. J. Med. 142-146 (1995).
Kirwan, "The Relationship Between Synovitis and Erosions in Rheumatoid Arthritis", 36 British J. of Rheumatology 225-228 (1997).
Klareskog et al., "Therapeutic effect of the combination of etanercept and methotrexate compared with each treatment alone in patients with rheumatoid arthritis: double-blind randomised controlled trial," 363 The Lancet 675-681 (2004).
Klimiuk et al., "Tissue Cytokine Patterns Distinguish Variants of Rheumatoid Synovitis," 151 Am. J. Pathology 1311-1319 (1997).
Kneitz et al., "Improvement of Refractory Rheumatoid Arthritis After Depletion of B Cells," 33 Scandinavian J. of Rheumatology 82-86 (2004).
Koopman et al., "Do Nonimmunologically Mediated Pathways Play a Role in the Pathogenesis of Rheumatoid Arthritis?" 19(1) Controversies in Clinical Rheumatology 107-122 (1993).
Kremer and Lee, "The safety and efficacy of the use of methotrexate in long-term therapy for rheumatoid arthritis," 29 Arthritis Rheum 822-831 (1986).
Kremer et al., "Long-term prospective study of the use of methotrexate in the treatment of rheumatoid arthritis: update after a mean of 90 months," 35 Arthritis Rheum 138-145 (1992).
Kremer et al., "Methotrexate for Rheumatoid Arthritis, Suggested Guidelines for Monitoring Liver Toxicity," 37(3) Arthritis & Rheumatism 316-328 (1994).
Kremer et al., "Therapeutic strategies in rheumatoid arthritis over a 40 year period," 31 J. Rheumatology 2366-2373 (2004).
Kremer, "Combination Therapy with Biologic Agents in Rheumatoid Arthritis: Perils and Promise," 41(9) Arthritis & Rheumatism 1548-1551 (1998).
Kremer, "Methotrexate for Rheumatoid Arthritis," 37(3) Arthritis & Rheumatism 316-328 (1994).
Kremer, "Rational Use of New and Existing Disease-Modifying Agents in Rheumatoid Arthritis," 138(8) Ann. Internal Med. 695-706 (2001).
Kremer, "Safety, efficacy, and mortality in a long-term cohort of patients with rheumatoid arthritis taking methotrexate: follow up after a mean of 13.3 years," 40(5) Arthritis Rheum 984-983 (1997).
Kremer, "The Changing Face of Therapy for Rheumatoid Arthritis," 21(3) Rheumatic Disease Clinics of North America 845-852 (1995).
Landewe et al., "Cobra Combination Therapy in Patients with Early Rheumatoid Arthritis," 46(2) Arthritis & Rheumatism 347-356 (2002).
Lard et al., "Early versus Delayed Treatment in Patients with Recent-onset Rheumatoid Arthritis: Comparison of Two Cohorts Who Received Different Treatment Strategies," 111 The American J. of Medicine 446-451 (2001).

(56) References Cited

OTHER PUBLICATIONS

Leandro et al., "Clinical Outcome in 22 Patients with Rheumatoid Arthritis Treated with B Lymphocyte Depletion," 61 Ann Rheum Dis 883-888 (2002).
Lee et al., "Rituxan in the Treatment of Cold Agglutinin Disease", 92(9) Blood 3490-3491 (1998).
Leget et al., "Use of Rituximab, the new FDA-approved antibody," 10 Current Opinion in Oncology 548-550 (1998).
Letter from Alan Petronk, Principal Investigator, to Department of Neurology, (Oct. 12, 1998), 16 pages, IPR2016-01614 (U.S. Pat. No. 7,820,161).
Letter from Dr. F. D. Thompson to Professor J. Edwards regarding treatment of subjects with rheumatoid arthritis with a monoclonal anti-CD20 antibody, (dated Oct. 23, 1998), 1 page, IPR2016-01667 (U.S. Pat. No. 7,976,838).
Letter from Dr. F. D. Thompson, Chairman, University College London Hospitals, Joint UCL/UCLH Committees on the Ethics of Human Research, to Professor Edwards, Rheumatology Department of Arthur Stanley House (Oct. 23, 1998), 1 page.
Letter from Dr. Jeffrey Gryn, Assoc. Professor of Clinical Med., to Beth Parker at Cooper Cancer Institute (dated May 6, 1998), 7 pages.
Letter from Jide Aliu, Clinical Trials Unit, Medicines Control Agency, to J.C.W. Edwards, Professor of Connective Tissue Med. (Oct. 2, 1998), 1 page.
Letter from John Looney at University of Rochester Medical Center to Bonni Dutcher, Ph.D. at Medical Science Liaison University of Rochester Medical Center, dated Jan. 15, 1999, 9 pages.
Letter from Mansoor N. Saleh, Principal Investigator, Genentech, Inc., to Comprehensive Cancer Center (Oct. 1, 1998), 29 pages.
Letter from Norman Latov, Professor of Neurology, Columbia Presbyterian Medical Center, to Kathy Horvath, Senior Medical Science Liaison, Genentech, (Nov. 16, 1998), 31 pages.
Letter from Simon Robinson, Research & Development Directorate Manager, University College London Hospitals, to Professor Edwards, Rheumatology Department of Arthur Stanley House (Oct. 30, 1998) 1 page.
Letter from the Medicines Control Agency to Professor Edwards in Rheumatology, Arthur Stanley House, The Medicines (Exemption from Licenses)(Special Cases and Miscellaneous Provisions) Order 1972, Product: Mabthera (C2B8 Monoclonal anti-CD20), dated Oct. 2, 1998, 1 page.
Liew et al., "Use of Non-PBS Funded 'Off-Label' Rituximab in Rheumatology," 45 Internal Med. J., (2015), Abstract No. ARA17, 1 page.
Lipsky et al., "Infliximab and Methotrexate in the Treatment of Rheumatoid Arthritis," 343(22) New England Journal of Medicine (2000), pp. 1594-1602.
Lipsky, "Harrison's Principles of Internal Medicine," 1923-1937, (Eugene Braunwalk et al. eds., 15th ed. 2001).
Liu et al., "Production of a mouse-human chimeric monoclonal antibody to CD20 with potent Fc-dependent biologic activity," 139 J. Immunol 3521-3526 (1987).
Lloyd et al., Protein Engineering, 22 Design & Selection 159-168 (2009).
LoBuglio et al., "Mouse/human chimeric monoclonal antibody in man: Kinetics and immune response," 86 Proc. Natl. Acad. Sci. USA 4220-4224 (1989).
Looney, "B Cell-targeted Therapy for Rheumatoid Arthritis, An Update on the Evidence," 66(5) Drugs 625-639 (2006).
Looney, "Update on the Use of Rituximab for Intractable Rheumatoid Arthritis," 1 Open Access Rheumatology Research and Review 83-94 (2009).
Lopez-Olivio et al., "Rituximab for Rheumatoid Arthritis (Review)," 1(CD007356) Conchrane Database of Systematic Reviews 1-367 (2015).
Lorenz et al., "Biologic Agents in the Treatment of Inflammatory Rheumatic Diseases," 1(3) Current Opinion in Rheumatology 179-184 (1999).

Lorenz et al., "Biological Agents in Rheumatoid Arthritis: Which Ones Could be Used in Combination?" 9(4) BioDrugs 303-324 (1998).
Lowdell et al., "Less is More": The Role of Purging in Hematopoietic Stem Cell Transplantation, 2(4) The Oncologist 268-274 (1997).
Maarten Boers Dep. Transcript in IPR2016-01614 (U.S. Pat. No. 7,820,161), dated Sep. 21, 2017, 80 pages, IPR2016-01614 (U.S. Pat. No. 7,820,161).
Mackay, "The Autoimmune Diseases" 759-781,Noel R. Rose and Ian R. Mackay eds., 3rd ed. (1998).
Maini et al., "How Does Infliximab Work in Rheumatoid Arthritis?" Arthritis Res 2002, 4 (suppl 2); S22-S28.
Maini et al., "Infliximab (Chimeric Anti-tumor Necrosis Factor α Monoclonal Antibody) Versus Placebo in Rheumatoid Arthritis Patients Receiving Concomitant Methotrexate: A Randomised Phase III Trial," 354 Lancet 1932-1939 (1999).
Maini et al., "Therapeutic Efficacy of Multiple Intravenous Infusions of Anti-tumor Necrosis Factor α Monoclonal Antibody Combined with Low-dose Weekly Methotrexate in Rheumatoid Arthritis," 41(9) Arthritis & Rheumatism 1552-1563 (1998).
Maloney et al., "IDEC-C2B8 (rituximab) Anti-CD20 Monoclonal Antibody Therapy in Patients With Relapsed Low-Grade Non-Hodgkin's Lymphoma," 90(6) Blood 2188-2195 (1997).
Maloney et al., "IDEC-C2B8: Results of a Phase I Multiple-Dose Trial in Patients With Relapsed Non-Hodgkin's Lymphoma," 15(10) J. of Clinical Oncology 3266-3274 (1997).
Maloney et al., "Phase 1 Clinical Trial Using Escalating Single-Dose Infusion of Chimeric Anti-CD20 Monoclonal Antibody (IDEC-C2B8) in Patients With Recurrent B-Cell Lymphoma," 84(8) Blood, 2457-2466 (1994).
Manz et al., "Lifetime of Plasma Cells in the Bone Marrow," 388 Nature 133-134 (1997).
Manz et al., "Survival of Long-Lived Plasma Cells is Independent of Antigen," 10(1) International Immunology 1703-1711 (1998).
McLaughlin et al., "Clinical Status and Optimal Use of Rituximab for B-Cell Lymphomas," Oncology 12:12 (1998) pp. 1763-1781.
McLaughlin et al., "Efficacy controls in long-term follow-up of patients treated with rituximab for relapsed or refractory, low-grade or follicular NHL", University of Texas MD Anderson Cancer Center (1998), 2 pages.
McLaughlin et al., "Rituximab Chimeric Anti-CD20 Monoclonal Antibody Therapy for Relapsed Indolent Lymphoma: Half of Patients Respond to a Four-dose Treatment Program," 16(8) J. of Clinical Oncology 2825-2833 (1998).
Mease et al., "Efficacy and Safety of Retreatment in Patients with Rheumatoid Arthritis with Previous Inadequate Response to Tumor Necrosis Factor Inhibitors: Results from the SUNRISE Trial," 37(5) J, of Rheumatology 917-927 (2010).
Medical Economics Co, "Physicians' Desk Reference", Rituxan (Product Information) 1070-72 (1999), 2 pages.
Medical Economics Co., "Physicians' Desk Reference," Methotrexate and Cyclophosphamide (Product Information) 772-774 and 1397-1401 (1999), 9 pages.
Medical Economics Co., "Physicians' Desk Reference," Rituxan (Product Information) 131, 311, 317, 1070-1072, 1384-1386 (63rd ed. 2009), 8 pages.
Medical Economics Co., "Physicians' Desk Reference", Remicade (Product Information)927-30 (2000), 3 pages.
Medical Economics Co., "Physicians' Desk Reference," Enbrel (Product Information) 111, 1551-1554, 3370-3373, (55the ed. 2001), 10 pages.
Medical Economics Co., "Physicians' Desk Reference," Remicade (Product Information) 126, 310, 1085-1088 (55th ed. 2001), 5 pages.
Medical Economics Co., "Physicians' Desk Reference," Rituxan (Product Information), (53rd ed. 1999), 11 pages.
Medscape, "Rituximab in RA: DANCER study confirms efficacy," Medscape Med. News, (Jun. 14, 2005), http://www.medscape.com/viewarticle/538249_print., 5 pages.
Memorandum and Order for *Janssen Biotech, Inc.* v. *Celltrion Healthcare Co., Ltd.*, 2017 WL 4927666 (D. Mass. Oct. 31, 2017), 34 pages.

(56) References Cited

OTHER PUBLICATIONS

Moi et al., "Biological therapies for rheumatoid arthritis: non-TNF inhibitors," 13(1) Med. Today 59-63 (2012).
Moi et al., "Biological therapies for rheumatoid arthritis: TNF inhibitors," 12(10) Med. Today 87-92 (2011).
Moore et al., "A Phase II Study of Rituximab in Rheumatoid Arthritis Patients with Recurrent Disease Following Haematopoietic Stem Cell Transplantation," 34(3) Bone Marrow Transplantation 241-247 (2004).
Morand et al., "Life table analysis of 879 treatment episodes with slow acting antirheumatic drugs in community rheumatology practice," 19(5) J. Rheumatol May 704-708 (1992).
Morand, "Targets in RA Therapy," Centre for Inflammatory Diseases, Monash University, Melbourne, 1-49 (2001).
Moreland et al., "Double-Blind, Placebo-Controlled Multicenter Trial Using Chimeric Monoclonal Anti-CD4 Antibody, cM-T412, in Rheumatoid Arthritis Patients Receiving Concomitant Methotrexate," 38(11) Arthritis and Rheumatism 1581-1588 (1995).
Moreland et al., "Etanercept Therapy in Rheumatoid Arthritis a Randomized, Controlled Trial," 130 Ann Intern Med. 478-486 (1999).
Moreland, "Initial Experience Combining Methotrexate with Biologic Agents for Treating Rheumatoid Arthritis," 23(44) J. Rheum 78-83 (1996).
Moreland, "Rheumatology and Immunology Therapy: A to Z Essentials," 764-765 (Sandra Fabiani ed., Springer) (2004).
Moreland, "Rheumatology and Immunology Therapy: A to Z Essentials," 771-772 (Sandra Fabiani ed., Springer) (2004).
Morris et al., "HIV-1 Antigen-specific and -nonspecific B Cell Responses are Sensitive to Combination Antiretroviral Therapy," 188(2) J. Exp. Med. The Rockefeller University Press 233-245 (1988).
Möttönen et al., "Comparison of combination therapy with single-drug therapy in early rheumatoid arthritis: a randomised trial", 353 The Lancet 1568-1573 (1999).
Multani et al., "Monoclonal Antibody-Based Therapies for Hematologic Malignancies", 16(11) J. Clinical Oncology, 3691-3710 (1998).
Munich Court Final Decision (21 O 4325/17) re EP1951304, dated Apr. 2017, English translation, 8 pages.
Ng et al., "Population Pharmacokinetics of Rituximab (Anti-CD20 Monoclonal Antibody) in Rheumatoid Arthritis Patients During a Phase II Clinical Trial," 45 J. of Clinical Pharmacology 792, 792-801 (2005).
O'Dell, "Combination DMARD Therapy for Rheumatoid Arthritis: Apparent Universal Acceptance," 40(9) Arthritis & Rheumatism (Suppl), Abstract No. 119 (1997), 1 page.
O'Dell, "Conventional DMARD Options for Patients with a Suboptimal Response to Methotrexate", The Journal of Rheumatology (2001); 62; 21-26.
O'Dell, "Methotrexate Use in Arthritis", 23(4) Rheumatic Disease Clinics of North America 779-796 (1997).
O'Dell et al., "Methotrexate (M)-Sulfasalazine (S)-Hydroxychloroquine (H) Combination Therapy in Rheumatoid Arthritis (RA)," 39 Arthritis Rheumatology 578, (1996), 1 page.
O'Dell et al., "The treatment of rheumatoid arthritis in 1995: results of a survey," 38 Arthritis Rheum S366 (Abstract No. 1277), (1995), 1 page.
O'Dell et al., "Treatment of rheumatoid arthritis with methotrexate alone, sulfasalazine and hydroxychloroquine, or a combination of all three medications," 334(20) New England Journal of Medicine 1287-1291, (1996).
Olsen et al., "A Double-Blind, Placebo-Controlled Study of Anti-CD5 Immunoconjugate in Patients With Rheumatoid Arthritis," 39(7) Arthritis & Rheumatism 1102-1108 (1996).
Onrust et al., "ADIS New Drug Profile—Rituximab," 58(1) Drugs 79-88 (1999).
Order in the High Court of Justice, Chancery Division, Patents Court (Jul. 20, 2016) (where the revocation of the English part of EP 1951304 is enacted), 1 page.

Ory, "Interpreting Radiographic Data in Rheumatoid Arthritis," 62 Ann. Rheum. Dis. 597-604 (2003).
Overview of Publications of Prof Dr. B.A.C. Dijkmans (RK/16-1509) re EP1951304, (no date) 47 pages.
Panayi et al., T-Cell-dependent Pathways in Rheumatoid Arthritis, 9(3) Current Opinion in Rheumatology 236-240 (1997).
Panayi et al., "The Importance of the T Cell in Initiating and Maintaining the Chronic Synovitis of Rheumatoid Arthritis," 35(7) Arthritis and Rheumatism 729-735 (1992).
Pascual et al., "The Complete Nucleotide Sequences of the Heavy Chain Variable Regions of Six Monospecific Rheumatoid Factors Derived from Epstein-Barr Virus-transformed B Cells Isolated from the Synovial Tissue of Patients with Rheumatoid Arthritis," 86 J. Clin. Invest. 1320-1328 (1990).
Patel, "B Cell-Ablative Therapy for the Treatment of Autoimmune Diseases," 46(8) Arthritis & Rheumatism 1984-1985 (2002).
Patent Assignment Cover Sheet for U.S. Pat. No. 7,976,838, 3 pages, dated Jul. 13, 2016.
Patent Owner Preliminary Response (POPR) Under 37 CFR § 42.107 of Biogen Inc., submitted Apr. 15, 2015, IPR2015-00418 (U.S. Pat. No. 8,329,172), 69 pages.
Patent Owner Preliminary Response (POPR) Under 37 CFR § 42.107 of Genentech Inc., submitted Apr. 15, 2015, IPR2015-00417 (U.S. Pat. No. 7,976,838), 70 pages.
Patent Owner Preliminary Response (POPR) Under 37 CFR § 42.107 of Genentech Inc. and Biogen Inc., submitted Apr. 27, 2015, IPR2015-00415 (U.S. Pat. No. 7,820,161), 69 pages.
Patent Owner Preliminary Response (POPR) under 37 CFR § 42.107 of Genentech Inc. (redacted version), submitted Dec. 6, 2016, IPR2016-01667 (U.S. Pat. No. 7,976,838), 75 pages.
Patent Owner Response (POR) of Genentech Inc. and Biogen Inc. (redacted version), submitted Jun. 2, 2017, IPR2016-01614 (U.S. Pat. No. 7,820,161), 70 pages.
Patent Owner's Brief Requesting Rehearing/Modification of Supplemental Institution Decision, submitted May 18, 2018 by Genentech Inc., 16 pages, IPR2017-01923 (U.S. Pat. No. 7,976,838).
Patent Owners' Motion for Observations on Cross Examination under 37 CFR § 42.6, submitted Sep. 29, 2017 by Genentech Inc. and Biogen Inc., 17 pages, IPR2016-01614 (U.S. Pat. No. 7,820,161).
Patent Owner's Preliminary Response (POPR) under 37 CFR § 42.107 of Genentech Inc., submitted Jan. 5, 2018, IPR2017-01923 (U.S. Pat. No. 7,976,838), 75 pages.
Patent Owner's Preliminary Response (POPR) under 37 CFR § 42.107 of Genentech Inc., submitted Jan. 5, 2018, IPR2017-02036 (U.S. Pat. No. 7,976,838), 74 pages.
Patent Owner's Preliminary Response (POPR) under 37 CFR § 42.107 of Genentech Inc., submitted Jan. 5, 2018, IPR2017-02042 (U.S. Pat. No. 7,976,838), 74 pages.
Pavelka et al., "Efficacy and safety following repeated courses of rituximab in patients with active rheumatoid arthritis," 64 Ann. Rheum. Dis. 435, (2005), 1 page.
Penglis et al., "Abstracts Presented at the Annual Scientific Meeting of the Australian," Rheumatology Association, (May 1998), 2 pages.
Perlman, "Mouse models of human disease an evolutionary perspective," Evolution, Medicine, and Public Health 2016(1): 170-176.
Pestronk, "A study of Rituxan in the treatment of polyneuropathies associated with serum IgM autoantibodies," Washington University School of Medicine Department of Neurology, dated Oct. 12 1998, 16 pages.
Petition for Inter Partes Review of U.S. Pat. No. 7,976,838, United States Patent and Trademark Office, (dated Aug. 31, 2017), 81 pages, IPR2017-02042 (U.S. Pat. No. 7,976,838).
Petition for Inter Partes Review under 37 CFR §§ 42.6 and 42.105, submitted Aug. 31, 2017, 81 pages, IPR2017-02042 (U.S. Pat. No. 7,976,838).
Petition for Inter Partes Review under 37 CFR §§ 42.6 and 42.105, submitted Aug. 14, 2015, 71 pages, from IPR2016-01667 (U.S. Pat. No. 7,976,838).
Petition for Inter Partes Review under 37 CFR §§ 42.6 and 42.105, submitted Dec. 15, 2014, 73 pages, from IPR2016-01667 (U.S. Pat. No. 7,976,838).

(56) References Cited

OTHER PUBLICATIONS

Petition for Inter Partes Review under 37 CFR §§ 42.6 and 42.105, submitted Mar. 24, 2017, 58 pages, from IPR2017-01115 (U.S. Pat. No. 7,820,161).
Petition for Inter Partes Review under 37 CFR §§ 42.6 and 42.105, submitted May 4, 2018, 83 pages, from IPR2018-01019 (U.S. Pat. No. 7,976,838).
Petition for Inter Partes Review under 37 CFR §§ 42.6 and 42.105, submitted Aug. 24, 2016, 78 pages, from IPR2016-01667 (U.S. Pat. No. 7,976,838).
Petition for Inter Partes Review under 37 CFR §§ 42.6 and 42.105, submitted Aug. 14, 2015, 71 pages, from IPR2017-02036 (U.S. Pat. No. 7,976,838).
Petition for Inter Partes Review under 37 CFR §§ 42.6 and 42.105, submitted Aug. 29, 2017, 81 pages, from IPR2017-01923 (U.S. Pat. No. 7,976,838).
Petition for Inter Partes Review under 37 CFR §§ 42.6 and 42.105, submitted Aug. 15, 2016, 62 pages, from IPR2016-01614 (U.S. Pat. No. 7,820,161).
Petition for Inter Partes Review under 37 CFR §§ 42.6 and 42.105, submitted Aug. 31, 2017, 8 pages, from IPR2017-02036 (U.S. Pat. No. 7,976,838).
Petition for Inter Partes Review under 37 CFR §§ 42.6 and 42.105, submitted Aug. 17, 2015, 68 pages, from IPR2016-01614 (U.S. Pat. No. 7,820,161).
Petition for Inter Partes Review under 37 CFR §§ 42.6 and 42.105, submitted Aug. 15, 2016, 62 pages, from IPR2016-01667 (U.S. Pat. No. 7,976,838).
Petition of Inter Partes Review under 37 CFR §§ 42.6 and 42.105, submitted Dec. 15, 2014, 72 pages, from IPR2015-00415 (U.S. Pat. No. 7,820,161).
Petitioner Celltrion's Unopposed Motion to Dismiss Without Prejudice Its Petition under CFR § 42.6(e), submitted Oct. 2, 2015, 7 pages, from IPR2015-01744 (U.S. Pat. No. 7,820,161).
Petitioner's Authorized Opposition to Patent Owner's Request for Rehearing of the Board's May 4, 2018 Order under 37 CFR § 42.71(d), submitted May 18, 2018, 14 pages, from IPR2017-01923 (U.S. Pat. No. 7,976,838).
Petitioner's Authorized Reply to Patent Owner's Preliminary Response under 37 CFR §§ 42.6(e) and 42.105(a), submitted Jan. 26, 2018, 8 pages, from IPR2017-01923 (U.S. Pat. No. 7,976,838).
Petitioner's Authorized Reply to Patent Owner's Preliminary Response under 37 CFR § 314(a), submitted Feb. 2, 2018, 8 pages, from IPR2017-02036 (U.S. Pat. No. 7,976,838).
Petitioner's Authorized Reply to Patent Owner's Preliminary Response, submitted Feb. 2, 2018, 8 pages, from IPR2017-02042 (U.S. Pat. No. 7,976,838).
Petitioners' Motion for Additional Discovery under 37 CFR § 42.51(b)(2), submitted Jun. 16, 2017 by Celltrion, Inc., 16 pages, IPR2016-01614 (U.S. Pat. No. 7,820,161).
Petitioner's Motion for Additional Discovery under 37 CFR § 42.51(B)(2), submitted Jun. 9, 2017, 16 pages, from IPR2016-01614 (U.S. Pat. No. 7,820,161).
Petitioner's Motion for Joinder under 35 U.S.C. § 315(c), 37 CFR §§ 42.22 and 42.122(b), submitted May 4, 2018, 13 pages, from IPR2018-01019 (U.S. Pat. No. 7,976,838).
Petitioner's Motion to Exclude Evidence under 37 CFR § 42.6(e), submitted Sep. 29, 2017, 8 pages, from IPR2016-01614 (U.S. Pat. No. 7,820,161).
Petitioner's Reply to Patent Owners' Response under 37 CFR § 42.6(e), submitted Aug. 23, 2017, 28 pages, from IPR2016-01614 (U.S. Pat. No. 7,820,161).
Petitioner's Request for Rehearing under 37 CFR § 42.71(d), submitted Apr. 3, 2017, 16 pages, from IPR2016-01667 (U.S. Pat. No. 7,976,838).
Petitioner's Updated Mandatory Notices under 37 CFR § 42.6(e), submitted Oct. 24, 2016, 5 pages, from IPR2016-01614 (U.S. Pat. No. 7,820,161).
*Pfizer* v. *Biogen* Joint Motion to Dismiss Challenged Claims 1-12 in Grounds 2 and Challenged Claims 4, 8 and 12 in Grounds 2 and 3 in IPR2017-01115 (U.S. Pat. No. 7,820,161), United States Patent and Trademark Office, dated Jul. 10, 2017, 5 pages.
*Pfizer, Inc.* v. *Genentech, Inc.*, IPR2017-01923 (U.S. Pat. No. 7,976,838), Paper 11 (PTAB May 14, 2018), 4 pages.
*Pfizer, Inc.* v. *Genentech, Inc.*, IPR2017-01923 (U.S. Pat. No. 7,976,838), Paper 21 (PTAB May 4, 2018), 3 pages.
*Pfizer, Inc.* v. *Genentech, Inc.*, IPR2017-01923 (U.S. Pat. No. 7,976,838), Paper 22 (PTAB May 14, 2018), 3 pages.
Phase III Study Shows Rituxan Significantly Improves Symptoms in Patients with Rheumatoid Arthritis Who Inadequately Responded to Anti-TNF Therapies: Third Randomized Trial to Evaluate Efficacy and Safety of Rituxan in RA Genentech Press Releases (Apr. 5, 2005), downloaded on Jun. 1, 2018), 4 pages.
Pincus et al., "No Evidence of Disease" in Rheumatoid Arthritis Using Methotrexate in Combination with Other Drugs: A Contemporary Goal for Rheumatology Care?, Clinical and Experimental Rheumatology 1997; 15: 591-596.
Pincus et al., "Relative Versus Absolute Goals of Therapies for RA: ACR 20 or ACR 50 Responses Versus Target Values for "near remission" of DAS or Single Measures," (2004) Annex to DIO, Clin Exp Rheumatol 22(Suppl 35):S50-S56.
Pinkel, "The Use of Body Surface Area as a Criterion of Drug Dosage in Cancer Chemotherapy," 18 Cancer Res. 853-856 (1958).
Piro et al., "Extended Rituximab (anti-CD20 monoclonal Antibody) Therapy for Relapsed or Refractory Low-grade or Follicular Non-Hodgkin's Lymphoma," 10 Annals of Oncol 655-661 (1999).
Piro et al., "RITUXAN (rituximab, IDEC-C2B8): Interim analysis of a phase II study of once weekly times 8 dosing in patients with relapsed low-grade or follicular non-Hodgkin's lymphoma," 90 Blood 2272, (1997), 1 page.
Pollack, "IDEC to Merge With Biogen in $6.8 Billion Deal", N.Y. Times, Jun. 24, 2003, 5 pages.
Positive Data from Preliminary Phase II Study of Rituxan in Rheumatoid Arthritis Published in the New England Journal of Medicine: Data Highlight Potential of Selectively Targeting B-Cells Genentech Press Releases, (Jun. 16, 2004, downloaded on Jun. 1, 2018), 8 pages.
Predictors of response to anti-TNF alpha therapy among patients with rheumatoid arthritis: results from the British Society for Rheumatology Biologics Register Rheumatology, (May 16, 2006, downloaded on Apr. 19, 2018), 8 pages.
Preliminary Phase IIb Data Show Rituxan Improved Symptoms in Patients with Moderate-to-Severe Rheumatoid Arthritis, Genentech Press Releases, (Nov. 1, 2004, downloaded on Jun. 1, 2018), 4 pages.
Preliminary Phase IIb Study Showed Rituxan Improved Symptoms in Rheumatoid Arthritis Patients Who Failed One or More Disease-Modifying Anti-Rheumatic Drugs: Improvement Shown to be Independent of Administration of Corticosteroids, (Jun. 9, 2005, downloaded on Jun. 1, 2018), 5 pages.
Preliminary Positive Data from Investigational Randomized Phase II Trial Demonstrates Rituxan as Potential Treatment for Rheumatoid Arthritis: Study Presented at Plenary Session of American College of Rheumatology (ACR) Meeting Genentech, (Oct. 28, 2002, downloaded on Jun. 1, 2018), 6 pages.
Press OW et al., "Monoclonal Antibody 1F5 (anti-CD20) Serotherapy of Human B Cell Lymphomas," 69 Blood 584-591 (1987).
Press Release, F. Hoffmann-La Roche Ltd, New evidence shows MabThera inhibits joint damage in patients with rheumatoid arthritis, (Jun. 22, 2006) (available at http://www.roche.com/media/store/releases/med-cor-2006-06-22.htm), 5 pages.
Press Release, Mabthera, MabThera highly effective in treating rheumatoid arthritis, (Jun. 9, 2005) (available at www.news-medical.net), 1 page.
Press Release, PR Newswire UK, New Evidenced Shows MabThera Inhibits Joint Damage in Patients, (Jun. 22, 2006), 3 pages.
Press Release, Roche Holding Ltd., MabThera approved for use in rheumatoid in Europe (Jul. 11, 2006), 4 pages.
Prevoo et al., "Modified disease activity scores that include twenty-eight-joint counts," 38(1) Arthritis & Rheumatism 44-48 (1995).
Prevoo et al., "Remission in a prospective study of patients with rheumatoid arthritis. American rheumatism association preliminary

(56) References Cited

OTHER PUBLICATIONS remission criteria in relation to the disease activity score," 35 British J. of Rheumatology 1101-1105 (1996).
Proprietary Information and Inventions Agreement between Mark Totoritis and IDEC Pharmaceutical Corporation, (dated Jul. 14, 1997), 5 pages.
Proprietary Information and Inventions Agreement of Ariella Kelman with Genentech Inc., dated Jan. 2, 2006, 7 pages.
Proprietary Information and Inventions Agreement of David Yocum with Genentech Inc., dated Jul. 5, 2005, 7 pages.
Proprietary Information and Inventions Agreement of Mark Totoritis with Biogen Idec Inc., dated Mar. 2004, 6 pages.
Proprietary Information and Inventions Agreement of Mark Totoritis with Idec Pharmaceuticals Corporation dated Jul. 14, 1997, 5 pages.
Proprietary Information and Inventions Agreement of Sunil Agarwal with Genentech Inc., dated Sep. 2, 2003, 5 pages.
Protheroe et al., "Remission of Inflammatory Arthropathy in Association with Anti-CD20 Therapy for non-Hodgkin's Lymphoma," 38 Rheumatology 1150, (1999), 1 page.
Radoux et al., "A Conserved Human Germline Vk Gene Directly Encodes Rheumatoid Factor Light Chains," 164 J. Exp. Med 2119-2124 (1986).
Rajagopalan et al., "Interaction of Dihydrofolaten Reductase with Methotrexate: Ensemble and Single-molecule Kinetics," 99(21) PNAS 13481-13486 (2002).
Record of Oral Hearing in IPR2016-01614 (U.S. Pat. No. 7,820,161), dated Oct. 31, 2017, 57 pages.
Redacted Declaration of Mark Benyunes from IPR2016-01667 (U.S. Pat. No. 7,976,838), dated Dec. 2, 2016, 41 pages.
Redacted version of the Collaboration Agreement between Genentech and IDEC, dated Mar. 16, 1995, 87 pages.
Reff et al., "Depletion of B cells in vivo by a chimeric mouse human monoclonal antibody to CD20," 83 Blood 435, (1994), 1 page.
Reininger et al., "Cryoglobulinemia Induced by a Murine IgG3 Rheumatoid Factor: Skin Vasculitis and Glomerulonephritis Arise From Distinct Pathogenic Mechanisms," 87 Proc. Natl. Acad. Sci. USA 10038-10042 (1990).
Remicade® (infliximab) United States Prescribing Information (USPI), dated Jun. 2002, 23 pages.
Remicade® (infliximab) United States Prescribing Information (USPI), dated Sep. 2005, 21 pages.
Remicade® (infliximab) United States Prescribing Information (USPI), dated Feb. 2002, 23 pages.
Remicade® (infliximab) United States Prescribing Information (USPI), dated Aug. 1998, 12 pages.
Research and Development Agreement between Roche Products, Ltd. and F. Hoffmann-La Roche Ltd., dated Sep. 27, 1995, 4 pages.
Response to request for record from FDA, US Department of Health and Human Services, (dated Aug. 26, 2016), 3 pages.
Rituxan Warnings Change-pro Redline Comparison, dated Aug. 22, 2017, 2 pages.
Rituxan® (rituximab) United States Prescribing Information (USPI), dated Feb. 2010, 35 pages.
Rituxan® (rituximab) United States Prescribing Information (USPI), dated Nov. 1997, 2 pages.
Rituxan® (rituximab) United States Prescribing Information (USPI), dated Apr. 2016, 39 pages.
Rituxan® (rituximab) United States Prescribing Information (USPI), dated Dec. 2001, 20 pages.
Rituxan® (rituximab) United States Prescribing Information (USPI), dated Feb. 2006, 53 pages.
Rituxan® (rituximab) United States Prescribing Information (USPI), dated 2003, 2 pages.
Rituxan® (rituximab) United States Prescribing Information (USPI), dated Jul. 2016, 8 pages.
Rituxan® (rituximab) United States Prescribing Information (USPI), dated Sep. 29, 2006, 4 pages.
Rituxan® (rituximab) United States Prescribing Information (USPI), dated Jan. 2008, 16 pages.
Rituxan® Dosage and Administration Change-pro Redline Comparison, dated Aug. 22, 2017, 2 pages, IPR2016-01614 (U.S. Pat. No. 7,820,161).
Rituximab (IDEC-C2B8): Validation of a Sensitive Enzyme-Linked Immunoassay Applied to a Clinical Pharmacokinetic Study Therapeutic Drug Monitoring, (2000), downloaded on Jul. 20, 2017), 7 pages.
Robert A. Eisenberg, MD, "Investigator-sponsored Protocol Concept Worksheet," Genentech Oncology & IDEC Pharmaceuticals, dated May 29, 1998, 4 pages.
Roberton et al., "Use of Methylprednisolone as Prophylaxis for Immediate Adverse Infusion Reactions in Hypogammaglobulinaemic Patients Receiving Intraveneous Immunoglobulin: A controlled Trial," 24 Aust. Paediatr. J. 174-177 (1988).
Roche Holding Ltd, Basel, Roche Finance Report (2008), 144 pages, IPR2015-00415 (U.S. Pat. No. 7,820,161).
Roche Holding Ltd, Basel, Roche Finance Report (2009), 154 pages, IPR2015-00415 (U.S. Pat. No. 7,820,161).
Roche Holding Ltd, Basel, Roche Finance Report (2010), 166 pages, IPR2015-00415 (U.S. Pat. No. 7,820,161).
Roche Holding Ltd, Basel, Roche Finance Report (2011) 171 pages, IPR2015-00415 (U.S. Pat. No. 7,820,161).
Roche Holding Ltd, Basel, Roche Finance Report (2012) 171 pages, IPR2015-00415 (U.S. Pat. No. 7,820,161).
Roche Holding Ltd, Basel, Roche Finance Report (2013), 170 pages, IPR2015-00415 (U.S. Pat. No. 7,820,161).
Roche Holding Ltd, Basel, Roche Finance Report (2014), 153 pages, IPR2015-00415 (U.S. Pat. No. 7,820,161).
Roche, MabThera (rituximab) Research Report No. 1005599 (redacted version), dated Nov. 2003, 114 pages.
Rodriguez, Fludarabine phosphate, 12 Investigational New Drugs, 75 (1994), 18 pages.
Rouziere et al., "Regeneration of the Immunoglobulin Heavy-chain Repertoire After Transient B-cell Depletion with an Anti-CD20 Antibody," 7(4) Arthritis Research & Therapy R714-724 (2005).
Rubbert-Roth et al., "Treatment Options in Patients with Rheumatoid Arthritis Failing Initial TNF Inhibitor Therapy: A Critical Review," 11 Arthritis Research and Therapy Suppl 1 (2009), 12 pages.
Safety and Efficacy of Rituximab in Combination With Methotrexate in Patients With Active Rheumatoid Arthritis Who Respond Poorly to Anti-TNF' Therapies (REFLEX), ClinicalTrials.gov, Identifier NCT0046546 (2010, downloaded on Jun. 1, 2018), 4 pages.
Safety and Efficacy of Rituximab in Combination With Methotrexate in Patients With Active Rheumatoid Arthritis Who Respond Poorly to Anti-TNFα Therapies, ClinicalTrials.gov, Identifier NCT00468546, (May 1, 2007, downloaded on Jun. 1, 2018), 4 pages.
Sany, "Novel Biologic Approaches to the Treatment of Rheumatoid Arthritis," 66(11) Revue Du Rhumatisme (English Edition) 548-559 (1999).
Schulze-Koops et al., "Where is Biological Therapy Going?," 2 Arthritis Res. 337-341, http://arthritis-research.com/content/2/5/337 (Jun. 29, 2000).
Schwieterman, "Immunosuppression in Combination with Monoclonal Antibodies," Biologic Agents in Autoimmune Disease, 291-298 (1995).
Scott et al., "Joint Damage in Rheumatoid Arthritis: Radiological Assessments and the Effects of Anti-Rheumatic Drugs," 5 Rheumatology International 193-199 (1985).
Scott et al., "The links between joint damage and disability in rheumatoid arthritis," 39 British Society of Rheumatology 122-132 (2000).
Scott, DL, "Prognosis and Clinical Course," in Rheumatoid Arthritis (E. William St. Clair ed.), pp. 26-41 (2004).
Second Declaration of Dr. Ronald Van Vollenhoven (IPR2015-00415) re U.S. Pat. No.7,820,161, dated Jan. 19, 2010, 6 pages.
Second Declaration of Dr. Ronald van Vollenhoven in EPO proceedings related to EP 1613350 (dated Dec. 13, 2011), 4 pages.
Second Declaration, Dr. Andri Hess in Opposition of EP 1951304, dated Apr. 26, 2018, 4 pages.

(56) References Cited

OTHER PUBLICATIONS

Second Declaration, Professor Mark D. Janis in Opposition to EP 1951304, dated May 30, 2018, 11 pages, with appended CV (23 pages).
Second Declaration, Timothy Mark Shaw in Opposition to EP 1951304, dated Apr. 25, 2018, with Exhibits A, B and C, dated Apr. 25, 2018, 4 pages.
Second Expert Declaration, Prof Hill Gaston in Opposition to EP 1951304, dated May 4, 2017, 4 pages, with appended CV (23 pages).
Second Expert Report, Prof. Dr. Bac Dijkmans (C/09/519083) re EP1951304, dated Apr. 5, 2017, 7 pages, with appended CV (2 pages).
Seymor et al., "Anti-TNF agents for rheumatoid arthritis," 51(3) Br. J. Clin. Pharmacol (2001), pp. 201-208.
Shanthi et al., "Effect of Immuno Suppressant (Methylprednisolone) and its Biochemical Changes in Rheumatoid Arthritis," 2(1) Int. J. of Medical Sciences (2009), pp. 24-27.
Sharpe et al., "Methods of scoring the progression of radiologic changes in rheumatoid arthritis," 14(6) Arthritis and Rheumatism (1971), pp. 706-720.
Shaw et al., "B cell therapy for rheumatoid arthritis: the rituximab (anti-CD20) experience," 62 Ann Rheum Dis (2003), pp. ii55-ii59.
Silman et al., "Epidemiology and genetics of rheumatoid arthritis," 4 Arthritis Res (2002), pp. S265-S272.
Silverman et al., "Rituximab Therapy and Autoimmune Disorders," 48 Arthritis & Rheumatism 1484-1492 (2003).
Silverman et al., "Roles of B cells in rheumatoid arthritis," 5 Arthritis Res Ther. S1-S6 (2003).
Simsek, "Predictors of Response to TNF Inhibitors in Rheumatoid Arthritis, Do We Have New Tools for Personalized Medicine?," 70(3) Bulletin of the NYU Hospital for Joint Disease 187-190 (2012).
Sing et al., "Biologics for rheumatoid arthritis: an overview of Cochrane reviews," 4 Cochrane Database of Systematic Reviews 309-310 (2009).
Slikfa et al., "Humoral Immunity Due to Long-lived Plasma Cells", 8 Immunity 363-372 (1998).
Smolen et al., "Are Autoantibodies Active Players or Epiphenomena?," 10 Current Opinion in Rheumatology 201-206 (1998).
Smolen et al., "Consensus statement on the initiation and continuation of tumor necrosis factor blocking therapies in rheumatoid arthritis," 59 Ann Rheum Dis 504-505 (2000).
Smolen et al., "EULAR recommendations for the management of rheumatoid arthritis with synthetic and biological disease modifying drugs: 2013 update," 73 Ann Rheum Dis 492-509 (2014).
Smolen et al., "Leflunomide, a new disease-modifying antirheumatic drug and the never ending rheumatoid arthritis story," 39 Rheumatology 689-699 (2000).
Smolen et al., "Rheumatoid Arthritis," 388 The Lancet 2023-2038 (2016).
Smyth et al., "Cyclophosphamide Therapy for Rheumatoid Arthritis," 135 Arch. Intern. Med. 789-793 (1975).
St. Clair et al., "Combination of Infliximab and Methotrexate Therapy for Early Rheumatoid Arthritis," 50(11) Arthritis & Rheumatism 3432-3443 (2004).
St. Clair et al., "Treatment of Rheumatoid Arthritis with a DR4/1 Peptide," 27(8) The J. of Rheumatology 1855-1863 (2000).
Stenger et al., "Early effective suppression of inflammation in rheumatoid arthritis reduces radiographic progression," 37 British Journal of Rheumatology 1157-1163 (1998).
Storz, "How approval history is reflected by a corresponding patent filing strategy," 6(4) mAbs 820-837 (2014).
Strand et al., "Biologic therapies in rheumatology: lessons learned, future directions," 6 Nature Reviews Drug Discovery 75-92 (2017).
Strand et al., "Differential patterns of response in patients with rheumatoid arthritis following administration of an anti-CD5 immunoconjugate," 11 Clin. Exper. Rheum. S161, (1993), 3 pages.
Strand et al., "Randomized controlled trial design in rheumatoid arthritis: the past decade," 11 Arthritis Research & Therapy 205, (2009), 11 pages.
Strand et al., "Treatment of Active Rheumatoid Arthritis with Leflunomide Compared with Placebo and Methotrexate," 159(21) Arch. Intern. Med. 2542-2550 (1999).
Summerhayes, "Rituximab: A New Modality in Lymphoma Treatment," 5(3) European Hospital Pharmacy 126-135 (1999).
Supplemental Declaration of Karen Sandrik in Opposition re EP1951304, dated Jun. 5, 2018, 6 pages, with appended CV (6 pages).
Tak et al., "Sustained inhibition of progressive joint damage with rituximab plus methotrexate in early active rheumatoid arthritis: 2-year results from the randomised controlled trial Image," 71 Ann. Rheum. Dis. 351-357 (2012).
Takahashi et al., "In Situ Studies of the Primary Immune Response to (4-Hydroxy-3-Nitrophenyl) Acetyl. V. Affinity Maturation Develops in Two Stages of Clonal Selection," 187(6) J. Exp. Med., (1998) pp. 885-895.
Takemura et al., "T Cell Activation in Rheumatoid Synovium is B Cell Dependent," 167 J. Immunology 4710-4718 (2001).
Ten Wolde et al., "Randomised placebo-controlled study of stopping second-line drugs in rheumatoid arthritis," 347 Lancet 347-352 (1996).
Termination of European Opposition Proceedings related to EP 1613350, dated Jul. 29, 2013, 2 pages.
Termination of Opposition Proceedings of EP 1613350 Revocation, dated Aug. 22, 2013, 2 pages.
Textbook of the Autoimmune Disease (Robert G. Lahita et al. eds., 2000), Table of Contents and Preface, 7 pages.
The Pharma Letter, "Roche's Rituxan/MabThera Warning in European Union," Pharma Letter (Jan. 12, 1998), 1 page.
Theoharis C. Theorharides et al., "Essentials of Pharmacology (Chapter 7: Control of Pain and Inflammation)" 217-258 (Theoharis C. Theoharides eds., 2d ed. 1996).
Third Declaration of Ronald F. Van Vollenhoven submitted to the EPO in opposition proceedings against EP 1613350, (dated May 10, 2012), 7 pages.
Tich et al. "Textbook of Rheumatology" 241-249 Willliam N. Kelly et al. eds., 5th ed. (1997).
Tobinai et al., "Feasibility and pharmacokinetic study of a chimeric anti CD20 monoclonal antibody (IDEC-C2B8, rituximab) in relapsed B-cell lymphoma," 9 Annals. of Oncology 527, (1998) pp. 527-534.
Totoritis, "Phase III Study Design", Presentation at Advisory Meeting (2002), 15 pages.
Tr. Testimony of Jonathan Edwards, Day 2 in Chancery High Court, Claim No. HP-2015-000053, 93-275, Jan. 17, 2017, 182 pages.
Transcript of Proceedings, Department of Health and Human Services, Food and Drug Administration, Center for Biological Evaluation and Research, (dated Jul. 25, 1997), 201 pages.
Truckenbrodt et al., "Methotrexate Therapy in Juvenile Rheumatoid Arthritis: A Retrospective Study," 29(6) Arthritis and Rheumatism 801-807 (1986).
Tugwell et al., "Combination therapy with cyclosporine and methotrexate in severe rheumatoid arthritis," 333 New England Journal of Medicine (1995), pp. 137-141.
Turgeon, "Clinical hematology: theory and procedures," 211 Hagerstown, M. & Lippincott Williams & Wilkins. eds. (2005), p. 221.
Tuscano et al., "Successful treatment of infliximab-refractory rheumatoid arthritis with rituximab," 46(1) Arthritis & Rheumatism 3420, (2002) (Abstract No. LB11), 1 page.
U.S. Department of Health and Human Services, Food and Drug Administration, Center for Drug Evaluation and Research (CDER), "Guidance for Industry: Estimating the Maximum Safe Starting Dose in Initial Clinical Trials for Therapeutics in Adult Healthy Volunteers," (2005), 30 pages.
UK Consent Order revoking the UK portion of EP 1951304, dated Feb. 19, 2016, 2 pages.
Ulfgren et al., "Systemic Anti-Tumor Necrosis Factor α Therapy in Rheumatoid Arthritis Down-Regulates Synovial Tumor Necrosis Factor α Synthesis," 43(11) Arthritis & Rheumatism 2391-2396 (2000).

(56) References Cited

OTHER PUBLICATIONS

United States Food and Drug Administration, "Guidance for Industry, Clinical Development Programs for Drugs, Devices, and Biological Products for the Treatment of Rheumatoid Arthritis (RA)," Feb. 1999, 25 pages.
US Copyright Catalog, "Blood: The Journal of the American Society of Hematology (1998)", Catalog of Copyright entries (accessed Nov. 3, 2018), 2 pages.
US Department of Health and Human Services, Food and Drug Administration, Center for Drug Evaluation and Research (CDER), "Guidance for Industry: Estimating the Maximum Safe Starting Dose in Initial Clinical Trials for Therapeutics in Adult Healthy Volunteers," pp. 1-27 (2005).
Van de Veerdonk et al., "The Anti-CD20 Antibody Rituximab Reduces the Th17 Cell Response," 63(6) Arthritis & Rheumatism 1507-1516 (2011).
Van den Bosch et al., "rHuIL-4 in Subjects With Active Rheumatoid Arthritis (RA): A Phase I Dose Escalating Safety Study," 41(9) Arthritis & Rheumatism Abstract 144 Suppl (1998) National Scientific Meeting S56, Abstract No. 144, 1 page.
Van der Heijde et al., "Biannual radiographic assessments of hands and feet in a three-year prospective follow-up of patients with early rheumatoid arthritis," 35(1) Arthritis & Rheumatism 26-34 (1992).
Van der Heijde et al., "Effects of Hydroxychloroquine and Sulphasalazine on Progression of Joint Damage in Rheumatoid Arthritis", The Lancet, 1036-1038 (1989).
Van der Heijde, "How to Read Radiographs According to the Sharp / van der Heijde Method," 27(1) J. of Rheumatology 261-263 (2000).
Van der Lubbe et al., "A Randomized, Double-Blind, Placebo-Controlled Study of CD4 Monoclonal Antibody Therapy in Early Rheumatoid Arthritis," 38(8) Arthritis & Rheumatism 1097-1106 (1995).
Van Gestel at al., "ACR and EULAR Improvement Criteria Have Comparable Validity in Rheumatoid Arthritis Trials," 26(3) J. of Rheumatology 705-711 (1999).
Van Gestel et al., "Development and validation of the European League Against Rheumatism response criteria for rheumatoid arthritis," 39(1) Arthritis & Rheumatism 34-40 (1996).
Van Gestel et al., "Validation of rheumatoid arthritis improvement criteria that include simplified joint counts," 41(10) Arthritis & Rheumatism 1845-1850 (1998).
Van Jaarsveld et al., "Aggressive treatment in early rheumatoid arthritis: a randomised controlled trial," 59 Ann. Rheum. Dis. 468-477 (2000).
Van Leeuwen et al., "Interrelationship of outcome measures and process variables in early rheumatoid arthritis. A comparison of radiologic damage, physical disability, joint counts, and acute phase reactants," 21 J. Rheumatology 425-429 (1994).
Van Vollenhoven et al., "Response to rituximab in patients with rheumatoid arthritis is maintained by repeat therapy: results of an open-label trial," 65 Ann. Rheum. Dis. 510, (2006), Abstract No. SAT0197, 1 page.
Van Vollenhoven et al., "Treatment with Infliximab (Remicade) when Etnercept (Enbrel) has Failed or Vice Versa: Data from the STURE Registry Showing that Switching Tumor Necrosis Factor α Blockers can Make Sense," 62 Ann. Rheum. 1195-1198 (2003).
Vandenbroucke et al., "Survival and Cause of Death in Rheumatoid Arthritis: A 25-year Prospective Follow-up," 11(2) J. Rheum. 158-161 (1984).
Verhoeven et al., "Combination Therapy in Rheumatoid Arthritis: Updated Systematic Review," 37 British J. of Rheumatology 612-619 (1998).
Vose et al., "Phase II study of Rituximab in combination with CHOP chemotherapy in patients with previously untreated intermediate or high-grade non-Hodgkin's lymphoma (NHL)," Blood 94:10 (1999), Abstract No. 195, 1 page.
Waldman et al., "Emerging Therapies: Spectrum of Applications of Monoclonal Antibody Therapy," American Society of Hematology Education Program Book, 2000(1), 394-408.
Weinblatt et al., "A trial of etanercept, a recombinant tumor necrosis factor receptor:Fc fusion protein, in patients with rheumatoid arthritis receiving methotrexate," 340(4) New England Journal of Medicine 253-259 (1999).
Weinblatt et al., "Efficacy of Low-Dose Methotrexate in Rheumatoid Arthritis", 312(13) New England Journal of Medicine 818-822 (1985).
Weinblatt et al., "Leflunomide plus methotrexate in refractory rheumatoid arthritis: a pilot study," 40 Arthritis & Rheumatism 5193 Suppl, (1997), Abstract No. 974, 1 page.
Weinblatt et al., "The Effects of Drug Therapy on Radiographic Progression of Rheumatoid Arthritis," 36(5) Arthritis & Rheumatism 613-619 (1993).
Weinblatt et al., "Campath-1H, A Humanized Monoclonal Antibody, in Refractory Rheumatoid Arthritis," 38(11) Arthritis & Rheumatism 1589-1594 (1995).
Weisman et al., "A Dose Escalation Study Designed to Demonstrate the Safety, Tolerability and Efficacy of the Fully Human Anti-TNF Antibody, D2E7, Given in Combination with Methotrexate (MTX) in Patients with Active RA," 43(9) Arthritis & Rheumatism Suppl (2000), Abstract No. 1948, 1 page.
Wendler et al., "Rituximab in patients with rheumatoid arthritis in routine practice (GERINIS): six-year results from a prospective, multicentre, non-interventional study in 2,484 patients," 16 Arthritis Research & Therapy 2014, 16:R80, 9 pages.
Wendling et al., "Randomized, Double-Blind, Placebo-Controlled Multicenter Trail of Murine Anti-CD4 Monoclonal Antibody Therapy in Rheumatoid Arthritis," American College of Rheumatology 60th National Scientific Meeting (1996), Abstract No. 1303, 1 page.
Weyand et al., "Cell-Cell Interactions in Synovitis: Interactions Between T Cells and B Cells in Rheumatoid Arthritis," 2(6) Arthritis Research 457-463 (2000).
White et al., "IDEC-C2B8-induced B cell depletion is not associated with significant immune suppression or infection," 33 European J. Cancer S266, (1997), 1 page.
Wijnands et al., "Long-term second-line treatment: a prospective drug survival study," 31 British Journal of Rheumatology 253-258 (1992).
Wilkens et al., "Comparison of Azathioprine, Methotrexate and the Combination of the Two in the Treatment of Rheumatoid Arthritis," 38(12) Arthritis & Rheumatism 1799-1806 (1995).
Williams et al., "B cell memory and the long-lived plasma cell," 11(2) Current Opinion in Immunology 172-179 (1999).
Williams et al., "Comparison of Auranofin , Methotrexate and the Combination of Both in the Treatment of Rheumatoid Arthritis," 35(3) Arthritis and Rheumatism 259-269 (1992).
Williams, "Autoimmunity on Rheumatoid Arthritis," 3 Rheumatology 1-16 (1994).
Willkens et al., "Comparison of azathioprine, methotrexate, and the combination of both in the treatment of rheumatoid arthritis: a controlled clinical trial," 35 Arthritis & Rheumatism 849-856 (1992).
Wolfe et al., "A Core Set of Domains for longitudinal observational studies in rheumatic disorders: Consensus Report from OMERACT 4," 41 Arthritis Rheum. S204, (1998), 1 page.
Wolfe et al., "Radiographic Outcome of Recent-Onset Rheumatoid Arthritis," 41 Arthritis & Rheumatism 1571-1582 (1998).
Woodcock et al., "Development of Novel Combination Therapies," 364(11) New England Journal of Medicine (2011), pp. 985-987.
Yuen, "Central European Oncology Congress," 10 Annals of Oncology S19-S22 (1999).
Zhang, "Body Surface Area," 1 Encyclopedia of Global Health 273-274 (2008).
Zheng et al., "Immunosenescence and germinal center reaction," 160 Immunological Reviews 63-77 (1997).

All observed radiographic data. No imputation for missing values

Mean % Change in ACR Core Set
Parameters at Week 24 (ITT)

|  | Placebo (N=201) | Rituximab (N=298) | p-value |
|---|---|---|---|
| Swollen Joint Count (%) | -3.8 | -41.1 | <0.0001 |
| Tender Joint Count (%) | 8.4 | -39.9 | <0.0001 |
| Patient's Global Assessment (%) | -5.0 | -28.4 | 0.0048 |
| Physician's Global Assessment (%) | -3.2 | -38.4 | <0.0001 |
| HAQ (%) | -6.9 | -27.0 | <0.0001 |
| Pain (%) | 1.7 | -25.3 | 0.0045 |
| CRP (mg/dL - %) | 89.7 | -27.1 | <0.0001 |
| ESR (mm/h - %) | 11.7 | -29.5 | <0.0001 |

Percentages are ANCOVA-adjusted
P values are from ANCOVA

*Most commonly reported Adverse Event*
*(Safety Pop)*

|  | Placebo<br>(n=209) | Rituximab<br>2 x 1000 mg<br>(n=308) |
|---|---|---|
| All Events | 183 (88%) | 261 (85%) |
| Rheumatoid Arthritis | 87 (42%) | 65 (21%) |
| Headache | 19 (9%) | 26 (8%) |
| URTI | 14 (7%) | 24 (8%) |
| Nasopharyngitis | 12 (6%) | 23 (7%) |
| Diarrhoea | 16 (8%) | 18 (6%) |
| Fatigue | 12 (6%) | 21 (7%) |
| Hypertension | 11 (5%) | 21 (7%) |
| Arthralgia | 10 (5%) | 17 (6%) |
| Nausea | 5 (2%) | 22 (7%) |
| UTI | 16 (8%) | 10 (3%) |

Number of patients (%)

FIG. 20

*Adverse Events Leading to Withdrawal*

|  | Placebo<br>(n=209) | Rituximab<br>2 x 1000 mg<br>(n=308) |
|---|---|---|
| All Events | 2 (<1%) | 8 (3%) |
| Cough* | - | 1 (<1%) |
| Hoarseness* | - | 1 (1<1%) |
| Laryngeal Oedema* | - | 1 (<1%) |
| Urticaria* | - | 2 (<1%) |
| Cardiac Tamponade | - | 1 (<1%) |
| Anaphylactic Reaction* | - | 1 (<1%) |
| Rheumatoid Arthritis | - | 1 (<1%) |
| Gastric Cancer | 1 (<1%) | - |
| Abortion (spontaneous) | - | 1 (<1%) |

Number of patients (%) *Associated with infusion

FIG. 21

*Events occurring during/within 24h of Infusions* 
|  | First Infusion | | Second Infusion | |
|---|---|---|---|---|
|  | Placebo (n=209) | Rituximab (n=308) | Placebo (n=209) | Rituxmab (n=308) |
| All Events | 49 (23%) | 88 (29%) | 29 (14%) | 35 (11%) |
| Headache | 10 (5%) | 15 (5%) | 2 (<1%) | 3 (<1%) |
| Hypertension | 4 (2%) | 9 (3%) | 4 (2%) | 7 (2%) |
| Nausea | 2 (<1%) | 8 (3%) | - | 2 (<1%) |
| Pruritus | 2 (<1%) | 7 (2%) | - | - |
| Urticaria | 1 (<1%) | 7 (2%) | - | - |
| Insomnia | 2 (<1%) | 6 (2%) | - | - |
| Flushing | 2 (<1%) | 5 (2%) | 1 (<1%) | 2 (<1%) |
| Pyrexia | 1 (<1%) | 5 (2%) | 2 (<1%) | - |
| Throat irritation | - | 4 (1%) | - | 1 (<1%) |
| Tachycardia | 7 (3%) | 3 (<1%) | - | 2 (<1%) |
Number of patients (%)
*FIG. 22*
Acute Infusion Reactions 
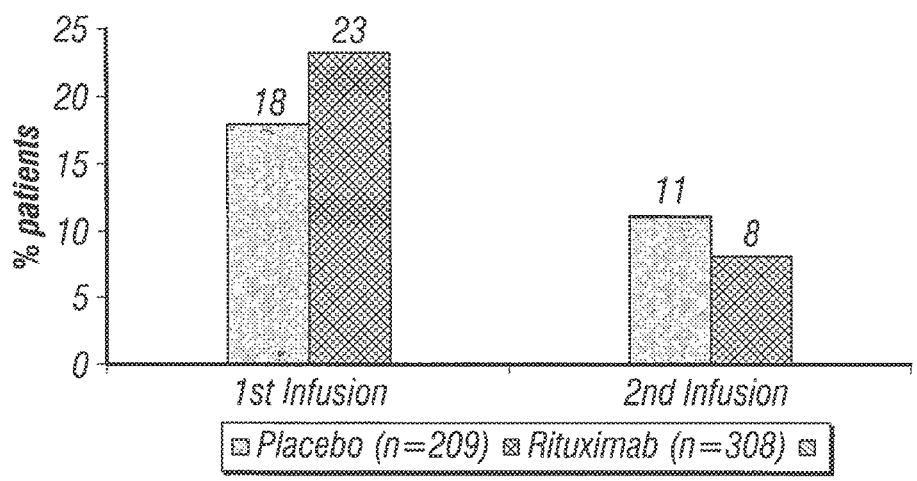
*FIG. 23*

Serious Adverse Events Occurring during/within 24h of infusion

|  | Placebo (n=209) | Rituximab 2 x 1000 mg (n=308) |
|---|---|---|
| First Infusion |  |  |
| All Events | 1 (<1%) | 1 (<1%) |
| Anaphylactic Reaction | - | 1 (<1%) |
| Diabetes Mellitus | 1 (<1%) | - |
|  |  |  |
| Second Infusion |  |  |
| All Events | 2 (<1%) | 1 (<1%) |
| Chest Pain | 1 (<1%) | - |
| Intestinal Abscess | 1 (<1%) | - |
| Hypertension | - | 1 (<1%) |

Number of patients (%)

FIG. 24

System Organ Class (Safety Pop.) Infections & Infestations

|  | Placebo (n=209) | Rituximab 2 x 1000 mg (n=308) |
|---|---|---|
| All Events | 79 (38%) | 127 (41%) |
| URTI | 17 (7%) | 24 (8%) |
| Nasopharyngitis | 12 (6%) | 23 (7%) |
| UTI | 16 (8%) | 10 (3%) |
| Bronchitis | 12 (6%) | 13 (4%) |
| Sinusitis | 11 (5%) | 10 (3%) |
| Rhinitis | 4 (2%) | 8 (3%) |
| Herpes simplex | 6 (3%) | 4 (1%) |
| Influenza | 3 (1%) | 4 (1%) |
| Gastroenteritis | 2 (<1%) | 4 (1%) |
| Cystitis | 1 (<1%) | 4 (1%) |

Number of patients (%)

FIG. 25

*Serious Infections* 

|  | Placebo (n=209) | Rituximab 2 x 1000 mg (n=308) |
|---|---|---|
| All Serious Infections | 2 (<1%) | 6 (2%) |
| Intestinal Abscess | 1 (<1%) | - |
| Gangrenous Cellulitis | - | 1 (<1%) |
| Central line infection | 1 (<1%) | - |
| Gastroenteritis | - | 1 (<1%) |
| Hepatitis B (de novo) | - | 1 (<1%) |
| Infection | - | 1 (<1%) |
| Influenza | - | 1 (<1%) |
| Pyelonephritis | - | 1 (<1%) |
| Zoonosis | - | 1 (<1%) |

Number of patients (%)

FIG. 26

*Infection Rate* 

|  | Placebo (n=209) | Rituximab 2 x 1000 mg (n=308) |
|---|---|---|
|  | Events per 100 Patient years | |
| All Infections | 155 | 138 |
| Clinically significant Infections* | 3.65 | 5.2 |

*Serious and/or those requiring i.v. antibiotics

FIG. 27

HACA (ITT) 
|  | Placebo (n=201) | Rituximab 2 x 1000 mg (n=298) |
| --- | --- | --- |
| Positive at week 24 | 0/197 (0%) | 12/287 (4%) |
FIG. 28
IgG (Safety population) 
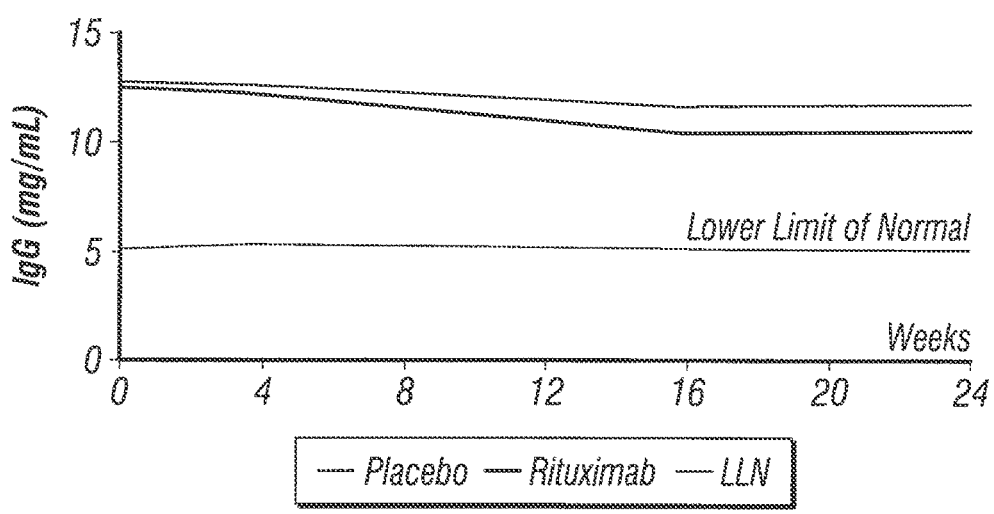
FIG. 29

```
              |————————— FR1 —————————|      CDR1      |——————
                  10        20             30              40
2H7         QIVLSQSPAILSASPGEKVTMTC  [RASSSVS-YMH]  WYQQKP
            *  *         *  **    * hu2H7.v16   DIQMTQSPSSLSASVGDRVTITC  [RASSSVS-YMH]  WYQQKP
                                        *  *  * ** hum KI      DIQMTQSPSSLSASVGDRVTITC  [RASQSISNYLA]  WYQQKP

FR2 ————|    CDR2     |————————— FR3 ——————————
                  50             60           70           80
2H7         GSSPKPWIY  [APSNLAS]  GVPARFSGSGSGTSYSLTISRVEA
              **   *                    *         *    ** hu2H7.v16   GKAPKPLIY  [APSNLAS]  GVPSRFSGSGSGTDFTLTISSLQP
                  *     *  *  * hum KI      GKAPKLLIY  [AASSLES]  GVPSRFSGSGSGTDFTLTISSLQP

——————————|  CDR3    |———FR4———|
                  90          100
2H7         EDAATYYC  [QQWSFNPPT]  FGAGTKLELKR
              *                     *    *  * hu2H7.v16   EDFATYYC  [QQWSFNPPT]  FGQGTKVEIKR
                       **** * hum KI      EDFATYYC  [QQYNSLPWT]  FGQGTKVEIKR
```

*FIG. 32A*

```
              |——————— FR1 ———————|    CDR1       |——
                  10        20         30            40
2H7         QAYLQQSGAELVRPGASVKMSCKAS [GYTFTSYNMH] WVKQT
            *   **   *  * ***  *                *  * hu2H7.v16   EVQLVESGGGLVQPGGSLRLSCAAS [GYTPTSYNMH] WVRQA
                                          *   *  * * hum III     EVQLVESGGGLVQPGGSLRLSCAAS [GPTFSSYAMS] WVRQA

——— FR2 —|    CDR2            |——— FR3 ———
                  50  a       60              70         80
2H7         PRQGLEWIG [AIYPGNGDTSYNQKFKG] KATLTVDKSSSTAYM
             **       *                         ** * * hu2H7.v16   PGKGLEWVG [AIYPGNGDTSYNQKFKG] RFTISVDKSKNTLYL
              *   * **** * * ****              * * hum III     PGKGLEWVA [VISGDGGSTYYADSVKG] RFTISRDNSKNTLTL

|———————————————|  CDR3          |—— FR4 ——|
                  abc    90        100abcde       110
2H7         QLSSLTSEDSAVYFCAR [VVYYSNSYWYFDY] WGTGTTVTVSS.
                 *    *                    *  * hu2H7.v16   QMNSLRASDTAVYYCAR [VVYYSNSYWYFDV] WGQGTLVTVSS
                                ***** * * hum III     QMNSLRAEDTAVYYCAR [GRVGYSLY===DY] WGQGTLVTVSS
```

*FIG. 32B*

DIQMTQSPSSLSASVGDRVTITCRASSSVSYMHWYQQKPGKAPKPLIYAPSNLASGVPSRFSG
SGSGTDFTLTISSLQPEDFATYYCQQWSFNPPTFGQGTKVEIKRTVAAPSVFIFPPSDEQLKS
GTASVVCLLNNFYPREAKVQWKVDNALQSGNSQESVTEQDSKDSTYSLSSTLTLSKADYEKHK
VYACEVTHQGLSSPVTKSFNRGEC (SEQ ID NO:13)

FIG. 33

EVQLVESGGGLVQPGGSLRLSCAASGYTFTSYNMHWVRQAPGKGLEWVGAIYPGNGDTSYNQK
FKGRFTISVDKSKNTLYLQMNSLRAEDTAVYYCARVVYYSNSYWYFDVWGQGTLVTVSSASTK
GPSVFPLAPSSKSTSGGTAALGCLVKDYFPEPVTVSWNSGALTSGVHTFPAVLQSSGLYSLSS
VVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSREEMTKNQVSLTCLVKGFY
PSDIAVEWESNGQPENNYKTTPPVLDSDGSFFLYSKLTVDKSRWQQGNVFSCSVMHEALHNHY
TQKSLSLSPGK (SEQ ID NO:14)

FIG. 34

EVQLVESGGGLVQPGGSLRLSCAASGYTFTSYNMHWVRQAPGKGLEWVGAIYPGNGDTSYNQK
FKGRFTISVDKSKNTLYLQMNSLRAEDTAVYYCARVVYYSNSYWYFDVWGQGTLVTVSSASTK
GPSVFPLAPSSKSTSGGTAALGCLVKDYFPEPVTVSWNSGALTSGVHTFPAVLQSSGLYSLSS
VVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYNATYRVVSVLTVLH
QDWLNGKEYKCKVSNKALPAPIAATISKAKGQPREPQVYTLPPSREEMTKNQVSLTCLVKGFY
PSDIAVEWESNGQPENNYKTTPPVLDSDGSFFLYSKLTVDKSRWQQGNVFSCSVMHEALHNHY
TQKSLSLSPGK (SEQ ID NO:15)

*FIG. 35*

```
hu2H7.v16.light   DIQMTQSPSSLSASVGDRVTITCRASSSVSYMHWYQQKPGKAPKPLIYAP
                  **************************************************
hu2H7.v138.light  DIQMTQSPSSLSASVGDRVTITCRASSSVSYLHWYQQKPGKAPKPLIYAP
                           10        20        30        40        50 hu2H7.v16.light   SNLASGVPSRFSGSGSGTDFTLTISSLQPEDFATYYCQQWSFNPPTFGQG
                  **********************************. *********
hu2H7.v138.light  SNLASGVPSRFSGSGSGTDFTLTISSLQPEDFATYYCQQWAFNPPTFGQG
                           60        70        80        90       100 hu2H7.v16.light   TKVEIKRTVAAPSVFIFPPSDEQLKSGTASVVCLLNNFYPREAKVQWKVD
                  **************************************************
hu2H7.v138.light  TKVEIKRTVAAPSVFIFPPSDEQLKSGTASVVCLLNNFYPREAKVQWKVD
                          110       120       130       140       150 hu2H7.v16.light   NALQSGNSQESVTEQDSKDSTYSLSSTLTLSKADYEKHKVYACEVTHQGL
                  **************************************************
hu2H7.v138.light  NALQSGNSQESVTEQDSKDSTYSLSSTLTLSKADYEKHKVYACEVTHQGL
                          160       170       180       190       200 hu2H7.v16.light   SSPVTKSFNRGEC
                  *************
hu2H7.v138.light  SSPVTKSFNRGEC
                          210
```

FIG. 36

```
hu2H7.v16.heavy   EVQLVESGGGLVQPGGSLRLSCAASGYTFTSYNMHWVRQAPGKGLEWVGA
hu2H7.v138.heavy  EVQLVESGGGLVQPGGSLRLSCAASGYTFTSYNMHWVRQAPGKGLEWVGA
                  **************************************************
                           10        20        30        40        50 hu2H7.v16.heavy   IYPGNGDTSYNQKFKGRFTISVDKSKNTLYLQMNSLRAEDTAVYYCARVV
hu2H7.v138.heavy  IYPGNGATSYNQKFKGRFTISVDKSKNTLYLQMNSLRAEDTAVYYCARVV
                  ******.*******************************************
                           60        70        80        90       100 hu2H7.v16.heavy   YYSNSYWYFDVWGQGTLVTVSSASTKGPSVFPLAPSSKSTSGGTAALGCL
hu2H7.v138.heavy  YYSASYWYFDVWGQGTLVTVSSASTKGPSVFPLAPSSKSTSGGTAALGCL
                  ***.**********************************************
                          110       120       130       140       150 hu2H7.v16.heavy   VKDYFPEPVTVSWNSGALTSGVHTFPAVLQSSGLYSLSSVVTVPSSSLGT
hu2H7.v138.heavy  VKDYFPEPVTVSWNSGALTSGVHTFPAVLQSSGLYSLSSVVTVPSSSLGT
                  **************************************************
                          160       170       180       190       200 hu2H7.v16.heavy   QTYICNVNHKPSNTKVDKKVEPKSCDKTHTCPPCPAPELLGGPSVFLFPP
hu2H7.v138.heavy  QTYICNVNHKPSNTKVDKKVEPKSCDKTHTCPPCPAPELLGGPSVFLFPP
                  **************************************************
                          210       220       230       240       250
```

FIG. 37

```
hu2H7.v16.heavy   KPKDTLMISRTPEVTCVVVDVSHEDPEVKFNWYVDGVEVHNAKTKPREEQ
                         260       270       280       290       300
hu2H7.v138.heavy  KPKDTLMISRTPEVTCVVVDVSHEDPEVKFNWYVDGVEVHNAKTKPREEQ
                         260       270       280       290       300 hu2H7.v16.heavy   YNSTYRVVSVLTVLHQDWLNGKEYKCKVSNKALPAPIEKTISKAKGQPRE
                         310       320       330       340       350
hu2H7.v138.heavy  YNATYRVVSVLTVLHQDWLNGKEYKCKVSNAALPAPIAATISKAKGQPRE
                         310       320       330       340       350 hu2H7.v16.heavy   PQVYTLPPSREEMTKNQVSLTCLVKGFYPSDIAVEWESNGQPENNYKTTP
                         360       370       380       390       400
hu2H7.v138.heavy  PQVYTLPPSREEMTKNQVSLTCLVKGFYPSDIAVEWESNGQPENNYKTTP
                         360       370       380       390       400 hu2H7.v16.heavy   PVLDSDGSFFLYSKLTVDKSRWQQGNVFSCSVMHEALHNHYTQKSLSLSPGK
                         410       420       430       440       450
hu2H7.v138.heavy  PVLDSDGSFFLYSKLTVDKSRWQQGNVFSCSVMHEALHNHYTQKSLSLSPGK
                         410       420       430       440       450
```

*FIG. 37 (Cont'd)*

```
     1
hu2H7.v16    DIQMTQSPSSLSASVGDRVTITCRASSSVSYMHWYQQKPGKAPKPLIYAP
hu2H7.v511   DIQMTQSPSSLSASVGDRVTITCRASSSVSYLHWYQQKPGKAPKPLIYAP 52
hu2H7.v16    SNLASGVPSRFSGSGSGTDFTLTISSLQPEDFATYYCQQWSFNPPTFGQG
hu2H7.v511   SNLASGVPSRFSGSGSGTDFTLTISSLQPEDFATYYCQQWAFNPPTFGQG 102
hu2H7.v16    TKVEIKRTVAAPSVFIFPPSDEQLKSGTASVVCLLNNFYPREAKVQWKVD
hu2H7.v511   TKVEIKRTVAAPSVFIFPPSDEQLKSGTASVVCLLNNFYPREAKVQWKVD 152
hu2H7.v16    NALQSGNSQESVTEQDSKDSTYSLSSTLTLSKADYEKHKVYACEVTHQGL
hu2H7.v511   NALQSGNSQESVTEQDSKDSTYSLSSTLTLSKADYEKHKVYACEVTHQGL 202      214
hu2H7.v16    SSPVTKSFNRGEC
hu2H7.v511   SSPVTKSFNRGEC
```

FIG. 38

```
hu2H7.v16    1   EVQLVESGGGLVQPGGSLRLSCAASGYTFTSYNMHW
hu2H7.v511       ************************************

82abc
hu2H7.v16   37   VRQAPGKGLEWVGAIYPGNGDTSYNQKFKGRFTISVDKSKNTLYLQMNSL
hu2H7.v511       ******       *************************************
                       52a hu2H7.v16        VRQAPGKGLEWVGAIYPGNGATSYNQKFKGRFTISVDKSKNTLYLQMNSL 100abcde        113
hu2H7.v16   83   RAEDTAVYYCARVVYYSNSYWYFDVWGQGTLVTVSS
hu2H7.v511       ***********       ******************
hu2H7.v16        RAEDTAVYYCARVVYSYRYWYFDVWGQGTLVTVSS hu2H7.v16   118  ASTKGPSVFPLAPS
hu2H7.v511       **************
hu2H7.v16        ASTKGPSVFPLAPS hu2H7.v16   132  SKSTSGGTAALGCLVKDYFPEPVTVSWNSGALTSGVHTFPAVLQSSGLYS
hu2H7.v511       **************************************************
hu2H7.v16        SKSTSGGTAALGCLVKDYFPEPVTVSWNSGALTSGVHTFPAVLQSSGLYS hu2H7.v16   182  LSSVVTVPSSSLGTQTYICNVNHKPSNTKVDKKVEPKSCDKTHTCPPCPA
hu2H7.v511       **************************************************
hu2H7.v16        LSSVVTVPSSSLGTQTYICNVNHKPSNTKVDKKVEPKSCDKTHTCPPCPA
```

*FIG. 39*

```
hu2H7.v16   232 PELLGGPSVFLFPPKPKDTLMISRTPEVTCVVVDVSHEDPEVKFNWYVDG
                ************************************************** 
hu2H7.v511      PELLGGPSVFLFPPKPKDTLMISRTPEVTCVVVDVSHEDPEVKFNWYVDG hu2H7.v16   282 VEVHNAKTKPREEQYNSTYRVVSVLTVLHQDWLNGKEYKCKVSNKALPAP
                ************* ****************** ******** 
hu2H7.v511      VEVHNAKTKPREEQYNATYRVVSVLTVLHQDWLNGKEYKCKVSNAALPAP hu2H7.v16   332 IEKTISKAKGQPREPQVYTLPPSREEMTKNQVSLTCLVKGFYPSDIAVEW
                * ************************************************ 
hu2H7.v511      IAATISKAKGQPREPQVYTLPPSREEMTKNQVSLTCLVKGFYPSDIAVEW hu2H7.v16   382 ESNGQPENNYKTTPPVLDSDGSFFLYSKLTVDKSRWQQGNVFSCSVMHEA
                ************************************************** 
hu2H7.v511      ESNGQPENNYKTTPPVLDSDGSFFLYSKLTVDKSRWQQGNVFSCSVMHEA hu2H7.v16   432 LHNHYTQKSLSLSPGK 447
                **************** 
hu2H7.v511      LHNHYTQKSLSLSPGK
```

*FIG. 39 (Cont'd)*

Humanized 2H7.v114 Variable Light-Chain Domain:

DIQMTQSPSSLSASVGDRVTITCRASSSVSYLHWYQQKPGKAPKPLIYAPSNLASGVPSRFSGSGSG
TDFTLTISSLQPEDFATYYCQQWAFNPPTFGQGTKVEIKR

*FIG. 40A*

Humanized 2H7.v114 Variable Heavy-Chain Domain:

EVQLVESGGGLVQPGGSLRLSCAASGYTFTSYNMHWVRQAPGKGLEWVGAIYPGNGATSYNQK
FKGRFTISVDKSKNTLYLQMNSLRAEDTAVYYCARVVYYSASYWYFDVWGQGTLVTVSS

*FIG. 40B*

Humanized 2H7.v114 Full-Length Heavy Chain:

EVQLVESGGGLVQPGGSLRLSCAASGYTFTSYNMHWVRQAPGKGLEWVGAIYPGNG
ATSYNQKFKGRFTISVDKSKNTLYLQMNSLRAEDTAVYYCARVVYYSASYWYFDVWGQG
TLVTVSSASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCPPCP
APELLGGPSVFLFPPKPKDTLMISRTPEVTCVVVDVSHEDPEVKFNWYVDGVEVHNAKTKP
REEQYNATYRVVSVLTVLHQDWLNGKEYKCKVSNKALPAPIAATISKAKGQPREPQVYTL
PPSREEMTKNQVSLTCLVKGFYPSDIAVEWESNGQPENNYKTTPPVLDSDGSFFLYSKLT
VDKSRWQQGNVFSCSVMHEALHNHYTQKSLSLSPG

*FIG. 40C*

*Cumulative distribution of change in total Sharp-Genant score*

*Sensitivity analyses: change in total Sharp-Genant score*

|  | Placebo + MTX | Rituximab + MTX | p-value |
|---|---|---|---|
| Median imputation for missing values | 1.63 (n=184) | 0.62 (n=273) | <0.0001 |
| All radiographs, linear extrapolation for missing values | 2.17 (n=186) | 0.92 (n=277) | 0.0094 |
| All radiographs, completer analysis | 2.17 (n=156) | 0.88 (n=242) | 0.0090 |

SEQUENCE LISTING

```
<160> NUMBER OF SEQ ID NOS: 47

<210> SEQ ID NO 1
<211> LENGTH: 107
<212> TYPE: PRT
<213> ORGANISM: Mus musculus

<400> SEQUENCE: 1

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Pro Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Ala Gly Thr Lys Leu Glu Leu Lys Arg
            100                 105

<210> SEQ ID NO 2
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Pro Leu Ile Tyr
        35                  40                  45

Ala Pro Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Phe Asn Pro Pro Thr
                85                  90                  95

Phe Gly Gln Gly Thr Lys Val Glu Ile Lys Arg Thr Val Ala Ala Pro
            100                 105                 110
```

```
Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
        210

<210> SEQ ID NO 3
<211> LENGTH: 108
<212> TYPE: PRT
<213> ORGANISM: Homo sapiens

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Leu Pro Trp
                85                  90                  95

Thr Phe Gly Gln Gly Thr Lys Val Glu Ile Lys Arg
            100                 105

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Arg Ala Ser Ser Ser Val Ser Tyr Met His
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Pro Ser Asn Leu Ala Ser
1               5
```

-continued

```
<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Gln Trp Ser Phe Asn Pro Pro Thr
1               5

<210> SEQ ID NO 7
<211> LENGTH: 122
<212> TYPE: PRT
<213> ORGANISM: Mus musculus

<400> SEQUENCE: 7

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Val Val Tyr Tyr Ser Asn Ser Tyr Trp Tyr Phe Asp Val Trp
            100                 105                 110

Gly Thr Gly Thr Thr Val Thr Val Ser Ser
        115                 120

<210> SEQ ID NO 8
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
        35                  40                  45

Gly Ala Ile Tyr Pro Gly Asn Gly Asp Thr Ser Tyr Asn Gln Lys Phe
    50                  55                  60

Lys Gly Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Val Tyr Tyr Ser Asn Ser Tyr Trp Tyr Phe Asp Val Trp
            100                 105                 110

Gly Gln Gly Thr Leu Val Thr Val Ser Ser Ala Ser Thr Lys Gly Pro
        115                 120                 125
```

```
Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
                275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Glu Glu Met Thr Lys Asn Gln Val
                355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
    435                 440                 445

Ser Pro Gly Lys
    450

<210> SEQ ID NO 9
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
                20                  25                  30
Ala Met Ser Trp Val Arg Gln Ala Pro Gly Lys Gly Leu Glu Trp Val
            35                  40                  45

Ala Val Ile Ser Gly Asp Gly Ser Thr Tyr Tyr Ala Asp Ser Val
        50                  55                  60

Lys Gly Arg Phe Thr Ile Ser Arg Asp Asn Ser Lys Asn Thr Leu Thr
65                  70                  75                  80

Leu Gln Met Asn Ser Leu Arg Ala Glu Asp Thr Ala Val Tyr Tyr Cys
                85                  90                  95

Ala Arg Gly Arg Val Gly Tyr Ser Leu Tyr Asp Tyr Trp Gly Gln Gly
            100                 105                 110

Thr Leu Val Thr Val Ser Ser
        115

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Tyr Thr Phe Thr Ser Tyr Asn Met His
1               5                   10

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Ile Tyr Pro Gly Asn Gly Asp Thr Ser Tyr Asn Gln Lys Phe Lys
1               5                   10                  15

Gly

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Val Tyr Tyr Ser Asn Ser Tyr Trp Tyr Phe Asp Val
1               5                   10

<210> SEQ ID NO 13
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
```

```
                  20                  25                  30
His Trp Tyr Gln Gln Lys Pro Gly Lys Ala Pro Lys Pro Leu Ile Tyr
            35                  40                  45
Ala Pro Ser Asn Leu Ala Ser Gly Val Pro Ser Arg Phe Ser Gly Ser
        50                  55                  60
Gly Ser Gly Thr Asp Phe Thr Leu Thr Ile Ser Ser Leu Gln Pro Glu
65                  70                  75                  80
Asp Phe Ala Thr Tyr Tyr Cys Gln Gln Trp Ser Phe Asn Pro Pro Thr
                85                  90                  95
Phe Gly Gln Gly Thr Lys Val Glu Ile Lys Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210

<210> SEQ ID NO 14
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Val Gln Leu Val Glu Ser Gly Gly Gly Leu Val Gln Pro Gly Gly
1               5                   10                  15
Ser Leu Arg Leu Ser Cys Ala Ala Ser Gly Tyr Thr Phe Thr Ser Tyr
            20                  25                  30
Asn Met His Trp Val Arg Gln Ala Pro Gly Lys Gly Leu Glu Trp Val
        35                  40                  45
Gly Ala Ile Tyr Pro Gly Asn Gly Asp Thr Ser Tyr Asn Gln Lys Phe
    50                  55                  60
Lys Gly Arg Phe Thr Ile Ser Val Asp Lys Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Val Val Tyr Tyr Ser Asn Ser Tyr Trp Tyr Phe Asp Val Trp
            100                 105                 110
Gly Gln Gly Thr Leu Val Thr Val Ser Ser Ala Ser Thr Lys Gly Pro
        115                 120                 125
Ser Val Phe Pro Leu Ala Pro Ser Ser Lys Ser Thr Ser Gly Gly Thr
    130                 135                 140
Ala Ala Leu Gly Cys Leu Val Lys Asp Tyr Phe Pro Glu Pro Val Thr
145                 150                 155                 160
```

Val Ser Trp Asn Ser Gly Ala Leu Thr Ser Gly Val His Thr Phe Pro
              165                 170                 175

Ala Val Leu Gln Ser Ser Gly Leu Tyr Ser Leu Ser Ser Val Val Thr
          180                 185                 190

Val Pro Ser Ser Ser Leu Gly Thr Gln Thr Tyr Ile Cys Asn Val Asn
      195                 200                 205

His Lys Pro Ser Asn Thr Lys Val Asp Lys Lys Val Glu Pro Lys Ser
  210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
              245                 250                 255

Met Ile Ser Arg Thr Pro Glu Val Thr Cys Val Val Val Asp Val Ser
          260                 265                 270

His Glu Asp Pro Glu Val Lys Phe Asn Trp Tyr Val Asp Gly Val Glu
      275                 280                 285

Val His Asn Ala Lys Thr Lys Pro Arg Glu Glu Gln Tyr Asn Ser Thr
  290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
              325                 330                 335

Ile Glu Lys Thr Ile Ser Lys Ala Lys Gly Gln Pro Arg Glu Pro Gln
          340                 345                 350

Val Tyr Thr Leu Pro Pro Ser Arg Glu Glu Met Thr Lys Asn Gln Val
      355                 360                 365

Ser Leu Thr Cys Leu Val Lys Gly Phe Tyr Pro Ser Asp Ile Ala Val
  370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
              405                 410                 415

Val Asp Lys Ser Arg Trp Gln Gln Gly Asn Val Phe Ser Cys Ser Val
          420                 425                 430

Met His Glu Ala Leu His Asn His Tyr Thr Gln Lys Ser Leu Ser Leu
      435                 440                 445

Ser Pro Gly Lys
      450

<210> SEQ ID NO 15
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
          20                  25                  30

Asn Met His Trp Val Arg Gln Ala Pro Gly Lys Gly Leu Glu Trp Val
      35                  40                  45

Gly Ala Ile Tyr Pro Gly Asn Gly Asp Thr Ser Tyr Asn Gln Lys Phe
  50                  55                  60

Lys Gly Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Val Val Tyr Tyr Ser Asn Ser Tyr Trp Tyr Phe Asp Val Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Val Glu Pro Lys Ser
            210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ala Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Ala Ala Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
450

<210> SEQ ID NO 16
<211> LENGTH: 285

```
<212> TYPE: PRT
<213> ORGANISM: Homo sapiens

<400> SEQUENCE: 16

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Val Thr Gln
    130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
        195                 200                 205

Gly His Leu Ile Gln Arg Lys Lys Val His Val Phe Gly Asp Glu Leu
    210                 215                 220

Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
                245                 250                 255

Asp Glu Leu Gln Leu Ala Ile Pro Arg Glu Asn Ala Gln Ile Ser Leu
            260                 265                 270

Asp Gly Asp Val Thr Phe Phe Gly Ala Leu Lys Leu Leu
        275                 280                 285

<210> SEQ ID NO 17
<211> LENGTH: 309
<212> TYPE: PRT
<213> ORGANISM: Mus musculus

<400> SEQUENCE: 17

Met Asp Glu Ser Ala Lys Thr Leu Pro Pro Cys Leu Cys Phe Cys
1               5                   10                  15

Ser Glu Lys Gly Glu Asp Met Lys Val Gly Tyr Asp Pro Ile Thr Pro
            20                  25                  30

Gln Lys Glu Glu Gly Ala Trp Phe Gly Ile Cys Arg Asp Gly Arg Leu
        35                  40                  45

Leu Ala Ala Thr Leu Leu Leu Ala Leu Leu Ser Ser Ser Phe Thr Ala
    50                  55                  60
```

```
Met Ser Leu Tyr Gln Leu Ala Ala Leu Gln Ala Asp Leu Met Asn Leu
 65                  70                  75                  80

Arg Met Glu Leu Gln Ser Tyr Arg Gly Ser Ala Thr Pro Ala Ala Ala
                 85                  90                  95

Gly Ala Pro Glu Leu Thr Ala Gly Val Lys Leu Leu Thr Pro Ala Ala
            100                 105                 110

Pro Arg Pro His Asn Ser Ser Arg Gly His Arg Asn Arg Arg Ala Phe
        115                 120                 125

Gln Gly Pro Glu Glu Thr Glu Gln Asp Val Asp Leu Ser Ala Pro Pro
    130                 135                 140

Ala Pro Cys Leu Pro Gly Cys Arg His Ser Gln His Asp Asp Asn Gly
145                 150                 155                 160

Met Asn Leu Arg Asn Ile Ile Gln Asp Cys Leu Gln Leu Ile Ala Asp
                165                 170                 175

Ser Asp Thr Pro Thr Ile Arg Lys Gly Thr Tyr Thr Phe Val Pro Trp
                180                 185                 190

Leu Leu Ser Phe Lys Arg Gly Asn Ala Leu Glu Glu Lys Glu Asn Lys
            195                 200                 205

Ile Val Val Arg Gln Thr Gly Tyr Phe Phe Ile Tyr Ser Gln Val Leu
    210                 215                 220

Tyr Thr Asp Pro Ile Phe Ala Met Gly His Val Ile Gln Arg Lys Lys
225                 230                 235                 240

Val His Val Phe Gly Asp Glu Leu Ser Leu Val Thr Leu Phe Arg Cys
                245                 250                 255

Ile Gln Asn Met Pro Lys Thr Leu Pro Asn Asn Ser Cys Tyr Ser Ala
                260                 265                 270

Gly Ile Ala Arg Leu Glu Glu Gly Asp Glu Ile Gln Leu Ala Ile Pro
            275                 280                 285

Arg Glu Asn Ala Gln Ile Ser Arg Asn Gly Asp Asp Thr Phe Phe Gly
    290                 295                 300

Ala Leu Lys Leu Leu
305

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid except Cys
<220> FEATURE:
<221> NAME/KEY: MOD_RES
<222> LOCATION: (3)..(3)
<223> OTHER INFORMATION: Any amino acid except Cys
<220> FEATURE:
<221> NAME/KEY: MOD_RES
<222> LOCATION: (5)..(5)
<223> OTHER INFORMATION: Any amino acid except Cys
<220> FEATURE:
<221> NAME/KEY: MOD_RES
<222> LOCATION: (7)..(12)
<223> OTHER INFORMATION: Any amino acid except Cys
<220> FEATURE:
<221> NAME/KEY: MOD_RES
<222> LOCATION: (14)..(15)
<223> OTHER INFORMATION: Any amino acid except Cys
<220> FEATURE:
<221> NAME/KEY: MOD_RES
<222> LOCATION: (16)..(16)
```

```
<223> OTHER INFORMATION: Leu, Phe, Ile or Val
<220> FEATURE:
<221> NAME/KEY: MOD_RES
<222> LOCATION: (17)..(17)
<223> OTHER INFORMATION: Any amino acid except Cys
<220> FEATURE:
<223> OTHER INFORMATION: see specification as filed for detailed
      description of substitutions and preferred embodiments

<400> SEQUENCE: 18

Xaa Cys Xaa Asp Xaa Leu Xaa Xaa Xaa Xaa Xaa Xaa Cys Xaa Xaa Xaa
1               5                   10                  15

Xaa

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Glu Cys Phe Asp Leu Leu Val Arg Ala Trp Val Pro Cys Ser Val Leu
1               5                   10                  15

Lys

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Glu Cys Phe Asp Leu Leu Val Arg His Trp Val Pro Cys Gly Leu Leu
1               5                   10                  15

Arg

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Glu Cys Phe Asp Leu Leu Val Arg Arg Trp Val Pro Cys Glu Met Leu
1               5                   10                  15

Gly

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Glu Cys Phe Asp Leu Leu Val Arg Ser Trp Val Pro Cys His Met Leu
1               5                   10                  15

Arg
```

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Glu Cys Phe Asp Leu Leu Val Arg His Trp Val Ala Cys Gly Leu Leu
1               5                   10                  15

Arg

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Cys Phe Asp Arg Leu Asn Ala Trp Val Pro Cys Ser Val Leu Lys
1               5                   10                  15

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid except Cys
<220> FEATURE:
<221> NAME/KEY: MOD_RES
<222> LOCATION: (3)..(3)
<223> OTHER INFORMATION: Any amino acid except Cys
<220> FEATURE:
<221> NAME/KEY: MOD_RES
<222> LOCATION: (5)..(5)
<223> OTHER INFORMATION: Any amino acid except Cys
<220> FEATURE:
<221> NAME/KEY: MOD_RES
<222> LOCATION: (8)..(9)
<223> OTHER INFORMATION: Any amino acid except Cys
<220> FEATURE:
<221> NAME/KEY: MOD_RES
<222> LOCATION: (14)..(15)
<223> OTHER INFORMATION: Any amino acid except Cys
<220> FEATURE:
<221> NAME/KEY: MOD_RES
<222> LOCATION: (17)..(17)
<223> OTHER INFORMATION: Any amino acid except Cys
<220> FEATURE:
<223> OTHER INFORMATION: see specification as filed for detailed
      description of substitutions and preferred embodiments

<400> SEQUENCE: 25

Xaa Cys Xaa Asp Xaa Leu Val Xaa Xaa Trp Val Pro Cys Xaa Xaa Leu
1               5                   10                  15

Xaa

<210> SEQ ID NO 26
<211> LENGTH: 184
<212> TYPE: PRT
<213> ORGANISM: Homo sapiens

<400> SEQUENCE: 26

Met Arg Arg Gly Pro Arg Ser Leu Arg Gly Arg Asp Ala Pro Ala Pro
1               5                   10                  15

Thr Pro Cys Val Pro Ala Glu Cys Phe Asp Leu Leu Val Arg His Cys
            20                  25                  30

Val Ala Cys Gly Leu Leu Arg Thr Pro Arg Pro Lys Pro Ala Gly Ala
        35                  40                  45

Ser Ser Pro Ala Pro Arg Thr Ala Leu Gln Pro Gln Glu Ser Val Gly
    50                  55                  60

Ala Gly Ala Gly Glu Ala Ala Leu Pro Leu Pro Gly Leu Leu Phe Gly
65                  70                  75                  80

Ala Pro Ala Leu Leu Gly Leu Ala Leu Val Leu Ala Leu Val Leu Val
                85                  90                  95

Gly Leu Val Ser Trp Arg Arg Gln Arg Arg Leu Arg Gly Ala Ser
                100                 105                 110

Ser Ala Glu Ala Pro Asp Gly Asp Lys Asp Ala Pro Glu Pro Leu Asp
            115                 120                 125

Lys Val Ile Ile Leu Ser Pro Gly Ile Ser Asp Ala Thr Ala Pro Ala
130                 135                 140

Trp Pro Pro Gly Glu Asp Pro Gly Thr Thr Pro Pro Gly His Ser
145             150                 155                 160

Val Pro Val Pro Ala Thr Glu Leu Gly Ser Thr Glu Leu Val Thr Thr
                165                 170                 175

Lys Thr Ala Gly Pro Glu Gln Gln
            180

<210> SEQ ID NO 27
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Pro Cys Val Pro Ala Glu Cys Phe Asp Leu Leu Val Arg His Cys
1               5                   10                  15

Val Ala Cys Gly Leu Leu Arg Thr Pro Arg
            20                  25

<210> SEQ ID NO 28
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Leu
            20                  25                  30

His Trp Tyr Gln Gln Lys Pro Gly Lys Ala Pro Lys Pro Leu Ile Tyr
        35                  40                  45

Ala Pro Ser Asn Leu Ala Ser Gly Val Pro Ser Arg Phe Ser Gly Ser
    50                  55                  60

```
Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Ala Phe Asn Pro Pro Thr
                 85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 29
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Val Glu Ser Gly Gly Gly Leu Val Gln Pro Gly Gly
  1               5                  10                  15

Ser Leu Arg Leu Ser Cys Ala Ala Ser Gly Tyr Thr Phe Thr Ser Tyr
             20                  25                  30

Asn Met His Trp Val Arg Gln Ala Pro Gly Lys Gly Leu Glu Trp Val
         35                  40                  45

Gly Ala Ile Tyr Pro Gly Asn Gly Ala Thr Ser Tyr Asn Gln Lys Phe
 50                  55                  60

Lys Gly Arg Phe Thr Ile Ser Val Asp Lys Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Val Val Tyr Tyr Ser Ala Ser Tyr Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205
```

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
        260                 265                 270

His Glu Asp Pro Glu Val Lys Phe Asn Trp Tyr Val Asp Gly Val Glu
    275                 280                 285

Val His Asn Ala Lys Thr Lys Pro Arg Glu Glu Gln Tyr Asn Ala Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Ala Ala Leu Pro Ala Pro
            325                 330                 335

Ile Ala Ala Thr Ile Ser Lys Ala Lys Gly Gln Pro Arg Glu Pro Gln
        340                 345                 350

Val Tyr Thr Leu Pro Pro Ser Arg Glu Glu Met Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro Gly Lys
    450

<210> SEQ ID NO 30
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Leu
            20                  25                  30

His Trp Tyr Gln Gln Lys Pro Gly Lys Ala Pro Lys Pro Leu Ile Tyr
        35                  40                  45

Ala Pro Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ala Phe Asn Pro Pro Thr
            85                  90                  95

Phe Gly Gln Gly Thr Lys Val Glu Ile Lys Arg Thr Val Ala Ala Pro

```
            100                 105                 110
Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
        210

<210> SEQ ID NO 31
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
        35                  40                  45

Gly Ala Ile Tyr Pro Gly Asn Gly Ala Thr Ser Tyr Asn Gln Lys Phe
    50                  55                  60

Lys Gly Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Val Tyr Tyr Ser Tyr Arg Tyr Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240
```

```
Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ala Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Ala Ala Leu Pro Ala Pro
                325                 330                 335

Ile Ala Ala Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 32
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Leu
            20                  25                  30

His Trp Tyr Gln Gln Lys Pro Gly Lys Ala Pro Lys Pro Leu Ile Tyr
        35                  40                  45

Ala Pro Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ala Phe Asn Pro Pro Thr
                85                  90                  95

Phe Gly Gln Gly Thr Lys Val Glu Ile Lys Arg
            100                 105

<210> SEQ ID NO 33
<211> LENGTH: 122
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
        35                  40                  45

Gly Ala Ile Tyr Pro Gly Asn Gly Ala Thr Ser Tyr Asn Gln Lys Phe
    50                  55                  60

Lys Gly Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Val Tyr Tyr Ser Ala Ser Tyr Trp Tyr Phe Asp Val Trp
            100                 105                 110

Gly Gln Gly Thr Leu Val Thr Val Ser Ser
        115                 120

<210> SEQ ID NO 34
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
        35                  40                  45

Gly Ala Ile Tyr Pro Gly Asn Gly Ala Thr Ser Tyr Asn Gln Lys Phe
    50                  55                  60

Lys Gly Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Val Tyr Tyr Ser Ala Ser Tyr Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Ser Leu Gly Thr Gln Thr Tyr Ile Cys Asn Val Asn
    195                 200                 205
```

His Lys Pro Ser Asn Thr Lys Val Asp Lys Lys Val Glu Pro Lys Ser
        210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
                260                 265                 270
His Glu Asp Pro Glu Val Lys Phe Asn Trp Tyr Val Asp Gly Val Glu
            275                 280                 285
Val His Asn Ala Lys Thr Lys Pro Arg Glu Glu Gln Tyr Asn Ala Thr
        290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Ala Ala Thr Ile Ser Lys Ala Lys Gly Gln Pro Arg Glu Pro Gln
                340                 345                 350
Val Tyr Thr Leu Pro Pro Ser Arg Glu Glu Met Thr Lys Asn Gln Val
            355                 360                 365
Ser Leu Thr Cys Leu Val Lys Gly Phe Tyr Pro Ser Asp Ile Ala Val
        370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
Ser Pro Gly
    450

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Met or Leu

<400> SEQUENCE: 35

Arg Ala Ser Ser Ser Val Ser Tyr Xaa His
1               5                   10

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ser or Ala

```
<400> SEQUENCE: 36

Gln Gln Trp Xaa Phe Asn Pro Pro Thr
1               5

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Asp or Ala

<400> SEQUENCE: 37

Ala Ile Tyr Pro Gly Asn Gly Xaa Thr Ser Tyr Asn Gln Lys Phe Lys
1               5                   10                  15

Gly

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Asn, Ala, Tyr, Trp or Asp
<220> FEATURE:
<221> NAME/KEY: MOD_RES
<222> LOCATION: (7)..(7)
<223> OTHER INFORMATION: Ser or Arg

<400> SEQUENCE: 38

Val Val Tyr Tyr Ser Xaa Xaa Tyr Trp Tyr Phe Asp Val
1               5                   10

<210> SEQ ID NO 39
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Leu
            20                  25                  30

His Trp Tyr Gln Gln Lys Pro Gly Lys Ala Pro Lys Pro Leu Ile Tyr
        35                  40                  45

Ala Pro Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ala Phe Asn Pro Pro Thr
                85                  90                  95

Phe Gly Gln Gly Thr Lys Val Glu Ile Lys Arg
            100                 105
```

<210> SEQ ID NO 40
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
        35                  40                  45

Gly Ala Ile Tyr Pro Gly Asn Gly Ala Thr Ser Tyr Asn Gln Lys Phe
    50                  55                  60

Lys Gly Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Val Tyr Tyr Ser Tyr Arg Tyr Trp Tyr Phe Asp Val Trp
            100                 105                 110

Gly Gln Gly Thr Leu Val Thr Val Ser Ser
        115                 120

<210> SEQ ID NO 41
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
        35                  40                  45

Gly Ala Ile Tyr Pro Gly Asn Gly Ala Thr Ser Tyr Asn Gln Lys Phe
    50                  55                  60

Lys Gly Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Val Tyr Tyr Ser Tyr Arg Tyr Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

```
Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ala Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Ala Ala Leu Pro Ala Pro
                325                 330                 335

Ile Ala Ala Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 42
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
        35                  40                  45

Gly Ala Ile Tyr Pro Gly Asn Gly Asp Thr Ser Tyr Asn Gln Lys Phe
    50                  55                  60

Lys Gly Arg Phe Thr Ile Ser Val Asp Lys Ser Lys Asn Thr Leu Tyr
```

```
            65                  70                  75                  80
Leu Gln Met Asn Ser Leu Arg Ala Glu Asp Thr Ala Val Tyr Tyr Cys
                    85                  90                  95

Ala Arg Val Val Tyr Ser Asn Ser Tyr Trp Tyr Phe Asp Val Trp
                100                 105                 110

Gly Gln Gly Thr Leu Val Thr Val Ser Ser Ala Ser Thr Lys Gly Pro
                    115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Lys Val Glu Pro Lys Ser
            210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ala Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Ala Ala Thr Ile Ser Lys Ala Lys Gly Gln Pro Arg Glu Pro Gln
                340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
            435                 440                 445

Ser Pro Gly
        450

<210> SEQ ID NO 43
<211> LENGTH: 451
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
        35                  40                  45

Gly Ala Ile Tyr Pro Gly Asn Gly Ala Thr Ser Tyr Asn Gln Lys Phe
    50                  55                  60

Lys Gly Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Val Tyr Tyr Ser Tyr Arg Tyr Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ala Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Ala Ala Leu Pro Ala Pro
                325                 330                 335

Ile Ala Ala Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
```

```
385                 390                 395                 400
Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly
        450

<210> SEQ ID NO 44
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Pro Leu Ile Tyr
        35                  40                  45

Ala Pro Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Phe Asn Pro Pro Thr
                85                  90                  95

Phe Gly Gln Gly Thr Lys Val Glu Ile Lys Arg
            100                 105

<210> SEQ ID NO 45
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
        35                  40                  45

Gly Ala Ile Tyr Pro Gly Asn Gly Asp Thr Ser Tyr Asn Gln Lys Phe
    50                  55                  60

Lys Gly Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Val Tyr Tyr Ser Asn Ser Tyr Trp Tyr Phe Asp Val Trp
            100                 105                 110

Gly Gln Gly Thr Leu Val Thr Val Ser Ser
```

115            120

<210> SEQ ID NO 46
<211> LENGTH: 356
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
        35                  40                  45

Gly Ala Ile Tyr Pro Gly Asn Gly Ala Thr Ser Tyr Asn Gln Lys Phe
    50                  55                  60

Lys Gly Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Val Tyr Tyr Ser Ala Ser Tyr Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ala Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Ala Ala Thr Ile Ser Lys Ala Lys Gly Gln Pro Arg Glu Pro Gln
            340                 345                 350

Val Tyr Thr Leu
          355

<210> SEQ ID NO 47
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
        35                  40                  45

Gly Ala Ile Tyr Pro Gly Asn Gly Asp Thr Ser Tyr Asn Gln Lys Phe
    50                  55                  60

Lys Gly Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Val Tyr Tyr Ser Asn Ser Tyr Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

```
Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370             375                 380

Glu Trp Glu Ser Asn Gly Gln Pro Glu Asn Asn Tyr Lys Thr Thr Pro
385             390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450
```

METHOD FOR TREATING JOINT DAMAGE

CROSS REFERENCE TO RELATED APPLICATIONS

This application is a divisional of U.S. application Ser. No. 15/055,485, filed Feb. 26, 2016, which is a continuation of U.S. application Ser. No. 11/665,525, filed Jun. 4, 2009, which is a national stage application filed under 35 USC § 371 of PCT Application No. PCT/US2006/044290, filed Nov. 14, 2006, which claims the benefit of priority under 35 USC § 119(e) of provisional application Nos. 60/864,463, filed Nov. 6, 2006 and 60/737,291, filed Nov. 15, 2005. The entire contents of each application are herein incorporated by reference.

FIELD OF THE INVENTION

The present invention concerns methods for treating joint damage in subjects suffering therefrom.

BACKGROUND OF THE INVENTION

Joint Destruction and Damage

Inflammatory arthritis is a prominent clinical manifestation in diverse autoimmune disorders including rheumatoid arthritis (RA), psoriatic arthritis (PsA), systemic lupus erythematosus (SLE), Sjögren's syndrome and polymyositis. Most of these patients develop joint deformities on physical examination but typically only RA and PsA patients manifest bone erosions on imaging studies.

RA is a chronic inflammatory disease that affects approximately 0.5 to 1% of the adult population in northern Europe and North America, and a slightly lower proportion in other parts of the world. Alamonosa and Drosos, *Autoimmun. Rev.*, 4: 130-136 (2005). It is a systemic inflammatory disease characterized by chronic inflammation in the synovial membrane of affected joints, which ultimately leads to loss of daily function due to chronic pain and fatigue. The majority of patients also experience progressive deterioration of cartilage and bone in the affected joints, which may eventually lead to permanent disability. The long-term prognosis of RA is poor, with approximately 50% of patients experiencing significant functional disability within 10 years from the time of diagnosis. Keystone, *Rheumatology*, 44 (Suppl. 2): ii8-ii12 (2005). Life expectancy is reduced by an average of 3-10 years. Alamanos and Rosos, supra. Patients with a high titer of rheumatoid factor (RF) (approximately 80% of patients) have more aggressive disease (Bukhari et al., *Arthritis Rheum.* 46: 906-912 (2002)), with a worse long-term outcome and increased mortality over those who are RF negative. Heliovaara et al., *Ann. Rheum. Dis.* 54: 811-814 (1995)).

The pathogenesis of chronic inflammatory bone diseases, such as RA, is not fully elucidated. Such diseases are accompanied by bone loss around affected joints due to increased osteoclastic resorption. This process is mediated largely by increased local production of pro-inflammatory cytokines. Teitelbaum *Science*, 289:1504-1508 (2000); Goldring and Gravallese *Arthritis Res.* 2(1):33-37 (2000). These cytokines can act directly on cells in the osteoclast lineage or indirectly by affecting the production of the essential osteoclast differentiation factor, receptor activator of NF<B ligand (RANKL), I and/or its soluble decoy receptor, osteoprotegerin (OPG), by osteoblast/stromal cells. Hossbauer et al. *J. Bone Miner. Res.* 15(1): 2-12 (2000). TNF-alpha is a major mediator of inflammation, whose importance in the pathogenesis of various forms of bone loss is supported by several lines of experimental and clinical evidence (Feldmann et al. *Cell* 85(3):307-310 (1996). However, TNF-alpha is not essential for osteoclastogenesis (Douni et al. *J. Inflamm.* 47:27-38 (1996)), erosive arthritis (Campbell et al. *J. Clin. Invest.* 107(12):1519-1527 (2001)), or osteolysis (Childs et al. *J. Bon. Min. Res.* 16:338-347 (2001)), as these can occur in the absence of TNF-alpha.

In RA specifically, an immune response is thought to be initiated/perpetuated by one or several antigens presenting in the synovial compartment, producing an influx of acute inflammatory cells and lymphocytes into the joint. Successive waves of inflammation lead to the formation of an invasive and erosive tissue called pannus. This contains proliferating fibroblast-like synoviocytes and macrophages that produce proinflammatory cytokines such as tumor necrosis factor-alpha (TNF-alpha) and interleukin-1 (IL-1). Local release of proteolytic enzymes, various inflammatory mediators, and osteoclast activation contribute to much of the tissue damage. There is loss of articular cartilage and the formation of bony erosions. Surrounding tendons and bursa may become affected by the inflammatory process. Ultimately, the integrity of the joint structure is compromised, producing disability.

The precise contributions of B cells to the immunopathogenesis of RA are not completely characterized. However, there are several possible mechanisms by which B cells may participate in the disease process. Silverman and Carson, *Arthritis Res. Ther.*, 5 Suppl. 4: S1-6 (2003).

Historically, B cells were thought to contribute to the disease process in RA predominantly by serving as the precursors of autoantibody-producing cells. A number of autoantibody specificities have been identified including antibodies to Type II collagen, and proteoglycans, as well as rheumatoid factors. The generation of large quantities of antibody leads to immune complex formation and the activation of the complement cascade. This in turn amplifies the immune response and may culminate in local cell lysis. Increased RF synthesis and complement consumption has been correlated with disease activity. The presence of RF itself is associated with a more severe form of RA and the presence of extra-articular features.

Recent evidence (Janeway and Katz, *J. Immunol.*, 138: 1051 (1998); Rivera et al., *Int. Immunol.*, 13: 1583-1593 (2001)) shows that B cells are highly efficient antigen-presenting cells (APC). RF-positive B cells may be particularly potent APCs, since their surface immunoglobulin would readily allow capture of any immune complexes regardless of the antigens present within them. Many antigens may thus be processed for presentation to T cells. In addition, it has been recently suggested that this may also allow RF-positive B cells to self-perpetuate. Edwards et al., *Immunology*, 97: 188-196 (1999).

For activation of T cells, two signals need to be delivered to the cell; one via the T-cell receptor (TCR), which recognizes the processed peptide in the presence of major histocompatibility complex (MHC) antigen, and a second, via co-stimulatory molecules. When activated, B cells express co-stimulatory molecules on their surface and can thus provide the second signal for T-cell activation and the generation of effector cells.

B cells may promote their own function as well as that of other cells by producing cytokines. Harris et al., *Nat. Immunol.*, 1: 475-482 (2000). TNF-alpha and IL-1, lymphotoxin-alpha, IL-6, and IL-10 are amongst some of the cytokines that B cells may produce in the RA synovium.

Although T-cell activation is considered to be a key component in the pathogenesis of RA, recent work using human synovium explants in severe combined immunodeficiency disorders (SCID) mice has demonstrated that T-cell activation and retention within the joint is critically dependent on the presence of B cells. Takemura et al., *J. Immunol.*, 167: 4710-4718 (2001). The precise role of B cells in this is unclear, since other APCs did not appear to have the same effect on T cells.

Structural damage to joints is an important consequence of chronic synovial inflammation. Between 60% and 95% of patients with rheumatoid arthritis (RA) develop at least one radiographic erosion within 3-8 years of disease onset (Paulus et al., *J. Rheumatol.*, 23: 801-805 (1996); Hulsmans et al., *Arthritis Rheum.* 43: 1927-1940 (2000)). In early RA, the correlation between radiographic damage scores and functional capacity is weak, but after 8 years of disease, correlation coefficients can reach as high as 0.68 (Scott et al., *Rheumatology*, 39: 122-132 (2000)). In 1,007 patients younger than age 60 years who had RA for at least four years, Wolfe et al. (*Arthritis Rheum*, 43 Suppl. 9:S403 (2000)) found a significant association between the rate of progression of the Larsen radiographic damage score (Larsen et al., *Acta Radiol. Diagn.* 18: 481-491 (1977)), increasing social security disability status, and decreasing family income.

Prevention or retardation of radiographic damage is one of the goals of RA treatment (Edmonds et al., *Arthritis Rheum.* 36: 336-340 (1993)). Controlled clinical trials of 6 or 12 months' duration have documented that the progression of radiographic damage scores was more rapid in the placebo group than in groups that received methotrexate (MTX) (Sharp et al., *Arthritis Rheum.* 43: 495-505 (2000)), leflunomide (Sharp et al., supra), sulfasalazine (SSZ) (Sharp et al., supra), prednisolone (Kirwan et al., *N. Engl. J. Med.*, 333: 142-146 (1995); Wassenburg et al., *Arthritis Rheum*, 42: Suppl 9:S243 (1999)), interleukin-1 receptor antagonist (Bresnihan et al., *Arthritis Rheum*, 41: 2196-2204 (1998)), or an infliximab/MTX combination (Lipsky et al., *N. Eng. J. Med.*, 343: 1594-1604 (2000)), and that radiographic progression following treatment with etanercept was less rapid than that following treatment with MTX (Bathon et al., *N. Engl. J. Med.*, 343: 1586-1593 (2000)). Other studies have evaluated radiographic progression in patients treated with corticosteroids (Joint Committee of the Medical Research Council and Nuffield Foundation, *Ann Rheum. Dis.* 19: 331-337 (1960); Van Everdingen et al., *Ann. Intern. Med.*, 136: 1-12 (2002)), cyclosporin A (Pasero et al., *J. Rheumatol.*, 24: 2113-2118 (1997); Forre, *Arthritis Rheum.*, 37: 1506-1512 (1994)), MTX versus azathioprine (Jeurissen et al., *Ann. Intern. Med.*, 114: 999-1004 (1991)), MTX versus auranofin (Weinblatt et al., *Arthritis Rheum.*, 36: 613-619 (1993)), MTX (meta-analysis) (Alarcon et al., *J. Rheumatol.*, 19: 1868-1873 (1992)), hydroxychloroquine (HCQ) versus SSZ (Van der Heijde et al., Lancet, 1: 1036-1038), SSZ (Hannonen et al., *Arthritis Rheum.* 36: 1501-1509 (1993)), the COBRA (Combinatietherapei Bij Reumatoide Artritis) combination of prednisolone, MTX, and SSZ (Boers et al., *Lancet*, 350: 309-318 (1997); Landewe et al., *Arthritis Rheum.*, 46: 347-356 (2002)), combinations of MTX, SSZ, and HCQ (O'Dell et al., *N. Engl. J. Med.*, 334: 1287-1291 (1996); Mottonen et al., *Lancet*, 353: 1568-1573 (1999)), the combination of cyclophosphamide, azathioprine, and HCQ (Csuka et al., *JAMA*, 255: 2115-2119 (1986)), and the combination of adalimumab with MTX (Keystone et al., *Arthritis Rheum.*, 46 Suppl. 9:S205 (2002)).

The FDA has now approved labeling claims that certain medications, e.g., leflunomide, etanercept, and infliximab, slow the progression of radiographic joint damage. These claims are based on the statistically significant differences in progression rates observed between randomly assigned treatment groups and control groups. However, the progression rates in individuals within the treatment and control groups overlap to a considerable extent; therefore, despite significant differences between treatment groups, these data cannot be used to estimate the probability that a patient who is starting a treatment will have a favorable outcome with respect to progression of radiographic damage. Various methods have been suggested to categorize paired radiographs from individual patients as not progressive, e.g., damage scores of 0 at both time points, no increase in damage scores, no new joints with erosions, and a change in score not exceeding the smallest detectable difference (i.e., 95% confidence interval for the difference between repeated readings of the same radiograph) (Lassere et al., *J. Rheumatol.*, 26: 731-739 (1999)).

Determining whether there has been increased structural damage in an individual patient during the interval between paired radiographs obtained at the beginning and end of a 6- or 12-month clinical trial has been difficult, for several reasons. The rate of radiographic damage is not uniform within a population of RA patients; a few patients may have rapidly progressing damage, but many may have little or no progression, especially if the tie interval is relatively short. The methods for scoring radiographic damage, e.g., Sharp (Sharp et al., *Arthritis Rheum.*, 14: 706-720 (1971); Sharp et al., *Arthritis Rheum.*, 28: 1326-1335 (1985)), Larsen (Larsen et al., *Acta Radiol. Diagn.*, 18: 481-491 (1977)), and modifications of these methods (Van der Heijde, *J. Rheumatol.*, 27: 261-263 (2000)), depend on the judgment and the interpretation of the reader as to whether an apparent interruption of the subchondral cortical plate is real, or whether a decrease in the distance between the cortices on opposite sides of a joint is real or is due to a slight change in the position of the joint relative to the film and the radiographic beam, to a change in radiographic exposure, or to some other technical factor.

Therefore, the recorded score is an approximation of the true damage, and for many subjects, the smallest detectable difference between repeat scores of the same radiographs is larger than the actual change that has occurred during the interval between the baseline and final radiographs. If the reader is blinded to the temporal sequence of the films, these unavoidable scoring errors may be in either direction, leading to apparent "healing" when the score decreases or to apparent rapid progression when reading error increases the difference between films. When the study involves a sufficiently large population of patients who have been randomly assigned to receive an effective treatment as compared with placebo, the positive and negative reading errors offset each other, and small but real differences between treatment groups can be detected.

The imprecision of the clinical measures that are used to quantitate RA disease activity has caused a similar problem; statistically significant differences between certain outcome measures from clinical trials were not useful for estimating the probability of improvement for an individual who was starting the treatment (Paulus et al., *Arthritis Rheum.*, 33: 477-484 (1990)). Attribution of individual improvement became practical with the creation of the American College of Rheumatology (ACR) 20% composite criteria for improvement (ACR20), which designated a patient as improved if there was 20% improvement in the tender and swollen joint counts and 20% improvement in at least 3 of 5 additional measures (pain, physical function, patient global health assessment, physician global health assessment, and acute-phase reactant levels) (Felson et al., *Arthritis Rheum.*, 38: 727-735 (1995)). All of these measures have large values for the smallest detectable difference, but by requiring simultaneous improvement in 5 of the 7 aspects of the same process (disease activity), the randomness of the 7 measurement errors is constrained and it is easier to attribute real improvement to the individual.

In RA, joint damage is a prominent feature. Radiologic parameters of joint destruction are seen as a key outcome measure in descriptions of disease outcome. In the recent OMERACT (Outcome Measures in Rheumatology Clinical Trials) consensus meeting, radiology was chosen as part of the core set of outcome measures for longitudinal observational studies (Wolfe et al., *Arthritis Rheum.*, 41 Supp 9: 5204 (1998) abstract). Radiology is also part of the WHO/ILAR (World Health Organization/International League of Associations for Rheumatology) required core set of measures for long-term clinical trials (Tugwell and Boers, *J. Rheumatol.*, 20: 528-530 (1993)).

Available data on the outcome of radiologic damage in RA have been obtained in both short-term and long-term studies. In short-term studies of RA patients with recent-onset disease, radiographs obtained every 6 months showed that after an initial rapid progression, there was diminution of the progression rate of radiologic damage in the hands and feet after 2-3 years (Van der Heijde et al., *Arthritis Rheum.*, 35: 26-34 (1992); Fex et al., *Br. J. Rheumatol.*, 35: 1106-1055 (1996)). In long-term studies with radiographs taken less frequently, a constant rate of progression was found, with relentless deterioration of damage up to 25 years of disease duration (Wolfe and Sharp, *Arthritis Rheum.*, 41: 1571-1582 (1998); Graudal et al., *Arthritis Rheum.*, 41: 1470-1480 (1998); Plant et al., *J. Rheumatol.*, 25: 417-426 (1998); Kaarela and Kautiainen, *J. Rheumatol.*, 24: 1285-1287 (1997)). Whether these differences in radiographic progression pattern are due to differences in the scoring techniques is not clear.

The scoring systems used differ in the number of joints being scored, the presence of independent scores for erosions (ERO) and joint space narrowing (JSN), the maximum score per joint, and the weighing of a radiologic abnormality. As yet, there is no consensus on the scoring method of preference. During the first 3 years of follow-up in a cohort study of patients with early arthritis, JSN and ERO were found to differ in their contribution to the measured progression in radiologic damage of the hands and feet (Van der Heijde et al., *Arthritis Rheum.*, 35: 26-34 (1992)). Furthermore, methods that independently score ERO and JSN, such as the Sharp and Kellgren scores, were found to be more sensitive to change in early RA than methods using an overall measure, such as the Larsen score (Plant et al., *J. Rheumatol.*, 21: 1808-1813 (1994); Cuchacovich et al., *Arthritis Rheum.*, 35: 736-739 (1992)). The Sharp score is a very labor-intensive method (Van der Heijde, *Baillieres Clin. Rheumatol.*, 10: 435-533 (1996)). In late or destructive RA, the Sharp and the Larsen methods were found to provide similar information. However, the sensitivity to change of the various scoring methods late in the disease has not yet been investigated and it can be argued that the scoring methods that independently measure ERO and JSN provide useful information (Pincus et al., *J. Rheumatol.*, 24: 2106-2122 (1997)). See also Drossaers-Bakker et al., *Arthritis Rheum.*, 43: 1465-1472 (2000), which compared the three radiologic scoring systems for the long-term assessment of RA.

Paulus et al., *Arthritis Rheum.*, 50: 1083-1096 (2004) categorized radiographic joint damage as progressive or non-progressive in individuals with RA participating in clinical trials, and concluded that RA joint damage in an observational cohort can be classified as progressive or non-progressive with the use of a composite definition that includes a number of imprecise and related, but distinct, measures of structural joint damage. It appears that in day-to-day clinical management of an RA patient, an interval change between a pair of radiographs of at least five Sharp radiographic damage score units should be present before one considers the structural change to be real and uses it as the basis for a treatment decision.

Over the past 10 years there have been major advances in the treatment of RA. Combination use of existing disease-modifying anti-rheumatic drugs (DMARDs), together with new biologic agents, have provided higher levels of efficacy in a larger proportion of patients, while the early diagnosis and treatment of the disease has also improved outcomes.

Etanercept is a fully human fusion protein that inhibits tumor necrosis factor (TNF) and the subsubsequent inflammatory cytokine cascade. Etanercept has been shown to be safe and effective in rapidly reducing disease activity in adults with RA and in sustaining that improvement (Bathon et al., *N. Eng. J. Med.*, 343: 1586-1593 (2000); Moreland et al., *N. Engl. J. Med.*, 337: 141-147 (1997); Moreland et al., *Ann. Intern. Med.*, 130: 478-486 (1999); Weinblatt et al., *N. Engl. J. Med.*, 340: 253-259 (1999); Moreland et al., *J. Rheumatol.*, 28: 1238-1244 (2001)). It is equally effective in children with polyarticular juvenile RA (Lovell et al., *N. Engl. J. Med.*, 342: 763-769 (2000)). Etanercept is approved for use as monotherapy, as well as combination therapy with MTX, for the treatment of RA.

Loss of function and radiographic change occur early in the course of the disease. These changes can be delayed or prevented with the use of certain DMARDs. Although several DMARDs are initially clinically effective and well tolerated, many of these drugs become less effective or exhibit increased toxicity over time. Based on its efficacy and tolerability, MTX has become the standard therapy by which other treatments are measured (Bathon et al., *N. Eng. J. Med.*, 343: 1586-1593 (2000); Albert et al., *J. Rheumatol.*, 27: 644-652 (2000)).

Recent studies have examined radiographic progression in patients with late-stage RA who have taken leflunomide, MTX, or placebo (Strand et al., *Arch. Intern. Med.*, 159: 2542-2550 (1999)) as well as patients who have taken infliximab plus MTX or placebo plus MTX following a partial response to MTX (Lipsky et al., *N. Engl. J. Med.*, 343: 1594-1602 (2000); Maini et al., *Lancet*, 354: 1932-1939 (1999)). In the first year of the Enbrel ERA (early RA) trial, etanercept was shown to be significantly more effective than MTX in improving signs and symptoms of disease and in inhibiting radiographic progression (Bathon et al., *N. Eng. J. Med.*, 343: 1586-1593 (2000)). Genovese et al., *Arthritis Rheum.* 46: 1443-1450 (2002) reports results from the second year of the study, concluding that etanercept as monotherapy was safe and superior to MTX in reducing disease activity, arresting structural damage, and decreasing disability over 2 years in patients with early, aggressive RA.

Further, reduction in radiographic progression in the hands and feet was observed in patients with early rheumatoid arthritis after receiving infliximab in combination with methotrexate (Van der Heijde et al., *Annals Rheumatic*

Diseases 64: 418-419 (2005)). Patients with early rheumatoid arthritis achieved a clinically meaningful and sustained improvement in physical function after treatment with infliximab (Smolen et al., *Annals Rheumatic Diseases* 64: 418 (2005)). The effect of infliximab and methotrexate on radiographic progression in patients with early rheumatoid arthritis is reported in Van der Heijde et al., *Annals Rheumatic Diseases* 64: 417 (2005). Infliximab treatment of patients with ankylosing spondylitis leads to changes in markers of inflammation and bone turnover associated with clinical efficacy (Visvanathan et al., *Annals Rheumatic Diseases* 64: 319 (2005)).

The effect of infliximab therapy on bone mineral density in patients with ankylosing spondylitis (AS) resulting from a randomized, placebo-controlled trial named ASSERT) is reported by Van der Heijde et al., *Annals Rheumatic Diseases* 64: 319 (2005). Infliximab was found to improve fatigue and pain in patients with AS, in results from ASSERT (Van der Heijde et al., *Annals Rheumatic Diseases* 64: 318-319 (2005)). Further, the efficacy and safety of infliximab in patients with AS as a result of ASSERT are described by van der Heijde et al., *Arthritis Rheum.* 5:582-591 (2005). The authors conclude that infliximab was well tolerated and effective in a large cohort of patients with AS during a 24-week study period. In addition, the effect of infliximab therapy on spinal inflammation was assessed by magnetic resonance imaging in a randomized, placebo-controlled trial of 279 patients with AS (Van der Heijde et al., *Annals Rheumatic Diseases* 64: 317 (2005)). The manner in which the treatment effect on spinal radiographic progression in patients with AS should be measured is addressed by van der Heijde et al., *Arthritis Rheum.* 52: 1979-1985 (2005).

The results of radiographic analyses of the infliximab multinational psoriatic arthritis controlled trial (IMPACT) after one year are reported by Antoni et al., *Annals Rheumatic Diseases* 64: 107 (2005). Evidence of radiographic benefit of treatment with infliximab plus MTX in rheumatoid arthritis patients who had no clinical improvement, with a detailed subanalysis of data from the anti-tumor necrosis factor trial in rheumatoid arthritis with concomitant therapy study, is reported by Smolen et al., *Arthritis Rheum.* 52:1020-1030 (2005). Radiographic progression as measured by mean change in modified Sharp/van derHeijde score) was much greater in patients receiving MTX plus placebo than in patients receiving infliximab plus MTX. The authors conclude that even in patients without clinical improvement, treatment with infliximab plus MTX provided significant benefit with regard to the destructive process, suggesting that in such patients these 2 measures of disease are dissociated. The association between baseline radiographic damage and improvement in physical function after treatment of patients having rheumatoid arthritis with infliximab is described by Breedveld et al., *Annals Rheumatic Diseases* 64:52-55 (2005). Structural damage was assessed using the van der Heijde modification of the Sharp score. The authors conclude that greater joint damage at baseline was associated with poorer physical function at baseline and less improvement in physical function after treatment, underlining the importance of early intervention to slow the progression of joint destruction.

CD20 Antibodies and Therapy Therewith

Lymphocytes are one of many types of white blood cells produced in the bone marrow during the process of hematopoiesis. There are two major populations of lymphocytes: B lymphocytes (B cells) and T lymphocytes (T cells). The lymphocytes of particular interest herein are B cells.

B cells mature within the bone marrow and leave the marrow expressing an antigen-binding antibody on their cell surface. When a naive B cell first encounters the antigen for which its membrane-bound antibody is specific, the cell begins to divide rapidly and its progeny differentiate into memory B cells and effector cells called "plasma cells". Memory B cells have a longer life span and continue to express membrane-bound antibody with the same specificity as the original parent cell. Plasma cells do not produce membrane-bound antibody, but instead produce the antibody in a form that can be secreted. Secreted antibodies are the major effector molecules of humoral immunity.

The CD20 antigen (also called human B-lymphocyte-restricted differentiation antigen, Bp35, or B1) is a four-pass, glycosylated integral membrane protein with a molecular weight of approximately 35 kD located on pre-B and mature B lymphocytes. Valentine et al., *J. Biol. Chem.* 264(19): 11282-11287 (1989) and Einfeld et al., *EMBO J.* 7(3):711-717 (1988). The antigen is also expressed on greater than 90% of B-cell non-Hodgkin's lymphomas (NHL) (Anderson et al. *Blood* 63(6):1424-1433 (1984)), but is not found on hematopoietic stem cells, pro-B cells, normal plasma cells, or other normal tissues (Tedder et al. *J. Immunol.* 135(2): 973-979 (1985)). CD20 regulates an early step(s) in the activation process for cell-cycle initiation and differentiation (Tedder et al., supra), and possibly functions as a calcium-ion channel Tedder et al., *J. Cell. Biochem.* 14D:195 (1990). CD20 undergoes phosphorylation in activated B cells (Riley and Sliwkowski *Semin Oncol,* 27(12), 17-24 (2000)). CD20 appears on the surface of B-lymphocytes at the pre-B-cell stage and is found on mature and memory B cells, but not plasma cells (Stashenko et al. *J Immunol* 1980; 125:1678-1685 (1980)); Clark and Ledbetter *Adv Cancer Res* 52, 81-149 (1989)). CD20 has calcium-channel activity and may have a role in the development of B cells. The relationship between lysis of peripheral $CD20^+$ B cells in vitro and rituximab activity in vivo is unclear. Rituximab displays antibody-dependent cellular cytotoxicity (ADCC) in vitro (Reff et al. *Blood* 83:435-445 (1994)). Potent complement-dependent cytotoxic (CDC) activity has also been observed for rituximab on lymphoma cells and cell lines (Reff et al., supra, 1994) and in certain mouse xenograft models (Di Gaetano et al. *J Immunol* 171:1581-1587 (2003)). Several anti-CD20 antibodies, including rituximab, have been shown to induce apoptosis in vitro when crosslinked by a secondary antibody or by other means (Ghetie et al. *Proc Natl Acad Sci.* 94, 7509-7514 (1997)).

Given the expression of CD20 in B-cell lymphomas, this antigen can serve as a candidate for "targeting" of such lymphomas. In essence, such targeting can be generalized as follows: antibodies specific to the CD20 surface antigen of B cells are administered to a patient. These anti-CD20 antibodies specifically bind to the CD20 antigen of (ostensibly) both normal and malignant B cells; the antibody bound to the CD20 surface antigen may lead to the destruction and depletion of neoplastic B cells. Additionally, chemical agents or radioactive labels having the potential to destroy the tumor can be conjugated to the anti-CD20 antibody such that the agent is specifically "delivered" to the neoplastic B cells. Irrespective of the approach, a primary goal is to destroy the tumor; the specific approach can be determined by the particular anti-CD20 antibody that is utilized, and thus, the available approaches to targeting the CD20 antigen can vary considerably.

The rituximab (RITUXAN®) antibody is a genetically engineered chimeric murine/human monoclonal antibody directed against the CD20 antigen. Rituximab is the antibody called "C2B8" in U.S. Pat. No. 5,736,137 issued Apr. 7, 1998 (Anderson et al.). Rituximab is indicated for the treatment of patients with relapsed or refractory low-grade or follicular, CD20-positive, B-cell non-Hodgkin's lymphoma. In vitro mechanism-of-action studies have demonstrated that rituximab binds human complement and lyses lymphoid B-cell lines through CDC. Reff et al., *Blood* 83(2):435-445 (1994). Additionally, it has significant activity in assays for ADCC. More recently, rituximab has been shown to have anti-proliferative effects in tritiated thymidine-incorporation assays and to induce apoptosis directly, while other anti-CD19 and anti-CD20 antibodies do not. Maloney et al. *Blood* 88(10):637a (1996). Synergy between rituximab and chemotherapies and toxins has also been observed experimentally. In particular, rituximab sensitizes drug-resistant human B-cell lymphoma cell lines to the cytotoxic effects of doxorubicin, CDDP, VP-16, diphtheria toxin, and ricin (Demidem et al., *Cancer Chemotherapy & Radiopharmaceuticals* 12(3):177-186 (1997)). In vivo preclinical studies have shown that rituximab depletes B cells from the peripheral blood, lymph nodes, and bone marrow of cynomolgus monkeys, presumably through complement- and cell-mediated processes. Reff et al., *Blood* 83:435-445 (1994).

Rituximab was approved in the United States in November 1997 for the treatment of patients with relapsed or refractory low-grade or follicular CD20$^+$ B-cell NHL at a dose of 375 mg/m$^2$ weekly for four doses. In April 2001, the Food and Drug Administration (FDA) approved additional claims for the treatment of low-grade NHL: re-treatment (weekly for four doses) and an additional dosing regimen (weekly for eight doses). There have been more than 300,000 patient exposures to rituximab either as monotherapy or in combination with immunosuppressant or chemotherapeutic drugs. Patients have also been treated with rituximab as maintenance therapy for up to 2 years. Hainsworth et al., *J. Clin. Oncol.* 21:1746-1751 (2003); Hainsworth et al., *J. Clin. Oncol.* 20:4261-4267 (2002). Also, rituximab has been used in the treatment of malignant and nonmalignant plasma cell disorders. Treon and Anderson, *Semin. Oncol.* 27: 79-85 (2000).

Rituximab has also been studied in a variety of nonmalignant autoimmune disorders, in which B cells and autoantibodies appear to play a role in disease pathophysiology. Edwards et al., *Biochem Soc. Trans.* 30:824-828 (2002). Rituximab has been reported to potentially relieve signs and symptoms of, for example, rheumatoid arthritis (RA) (Leandro et al., *Ann. Rheum. Dis.* 61:883-888 (2002); Edwards et al., *Arthritis Rheum.*, 46 (Suppl. 9): S46 (2002); Stahl et al., *Ann. Rheum. Dis.*, 62 (Suppl. 1): OP004 (2003); Emery et al., *Arthritis Rheum.* 48(9): 5439 (2003)), lupus (Eisenberg, *Arthritis. Res. Ther.* 5:157-159 (2003); Leandro et al. *Arthritis Rheum.* 46: 2673-2677 (2002); Gorman et al., *Lupus*, 13: 312-316 (2004)), immune thrombocytopenic purpura (D'Arena et al., *Leuk. Lymphoma* 44:561-562 (2003); Stasi et al., *Blood*, 98: 952-957 (2001); Saleh et al., *Semin. Oncol.*, 27 (Supp 12):99-103 (2000); Zaia et al., *Haematolgica*, 87: 189-195 (2002); Ratanatharathorn et al., *Ann. Int. Med.*, 133: 275-279 (2000)), pure red cell aplasia (Auner et al., *Br. J. Haematol.*, 116: 725-728 (2002)); autoimmune anemia (Zaja et al., *Haematologica* 87:189-195 (2002) (erratum appears in *Haematologica* 87:336 (2002)), cold agglutinin disease (Layios et al., *Leukemia*, 15: 187-8 (2001); Berentsen et al., *Blood*, 103: 2925-2928 (2004); Berentsen et al., *Br. J. Haematol.*, 115: 79-83 (2001); Bauduer, *Br. J. Haematol.*, 112: 1083-1090 (2001); Damiani et al., *Br. J. Haematol.*, 114: 229-234 (2001)), type B syndrome of severe insulin resistance (Coll et al., *N. Engl. J. Med.*, 350: 310-311 (2004), mixed cryoglobulinemia (DeVita et al., *Arthritis Rheum.* 46 Suppl. 9:S206/S469 (2002)), myasthenia gravis (Zaja et al., *Neurology*, 55: 1062-63 (2000); Wylam et al., *J. Pediatr.*, 143: 674-677 (2003)), Wegener's granulomatosis (Specks et al., *Arthritis & Rheumatism* 44: 2836-2840 (2001)), refractory pemphigus vulgaris (Dupuy et al., *Arch Dermatol.*, 140:91-96 (2004)), dermatomyositis (Levine, *Arthritis Rheum.*, 46 (Suppl. 9):51299 (2002)), Sjögren's syndrome (Somer et al., *Arthritis & Rheumatism*, 49: 394-398 (2003)), active type-II mixed cryoglobulinemia (Zaja et al., *Blood*, 101: 3827-3834 (2003)), pemphigus vulgaris (Dupay et al., *Arch. Dermatol.*, 140: 91-95 (2004)), autoimmune neuropathy (Pestronk et al., *J. Neurol. Neurosurg. Psychiatry* 74:485-489 (2003)), paraneoplastic opsoclonus-myoclonus syndrome (Pranzatelli et al. *Neurology* 60 (Suppl. 1) PO5.128:A395 (2003)), and relapsing-remitting multiple sclerosis (RRMS). Cross et al. (abstract) "Preliminary Results from a Phase II Trial of Rituximab in MS" Eighth Annual Meeting of the Americas Committees for Research and Treatment in Multiple Sclerosis, 20-21 (2003).

A Phase II study (WA16291) has been conducted in patients with rheumatoid arthritis (RA), providing 48-week follow-up data on safety and efficacy of Rituximab. Emery et al. *Arthritis Rheum* 48(9):5439 (2003); Szczepanski et al. *Arthritis Rheum* 48(9):5121 (2003). A total of 161 patients were evenly randomized to four treatment arms: methotrexate, rituximab alone, rituximab plus methotrexate, and rituximab plus cyclophosphamide (CTX). The treatment regimen of rituximab was one gram administered intravenously on days 1 and 15. Infusions of rituximab in most patients with RA were well tolerated by most patients, with 36% of patients experiencing at least one adverse event during their first infusion (compared with 30% of patients receiving placebo). Overall, the majority of adverse events was considered to be mild to moderate in severity and was well balanced across all treatment groups. There were a total of 19 serious adverse events across the four arms over the 48 weeks, which were slightly more frequent in the rituximab/CTX group. The incidence of infections was well balanced across all groups. The mean rate of serious infection in this RA patient population was 4.66 per 100 patient-years, which is lower than the rate of infections requiring hospital admission in RA patients (9.57 per 100 patient-years) reported in a community-based epidemiologic study. Doran et al., *Arthritis Rheum.* 46:2287-2293 (2002).

The reported safety profile of rituximab in a small number of patients with neurologic disorders, including autoimmune neuropathy (Pestronk et al., supra), opsoclonus-myoclonus syndrome (Pranzatelli et al., supra), and RRMS (Cross et al., supra), was similar to that reported in oncology or RA. In an ongoing investigator-sponsored trial (IST) of rituximab in combination with interferon-beta (IFN-β) or glatiramer acetate in patients with RRMS (Cross et al., supra), 1 of 10 treated patients was admitted to the hospital for overnight observation after experiencing moderate fever and rigors following the first infusion of rituximab, while the other 9 patients completed the four-infusion regimen without any reported adverse events.

Patents and patent publications concerning CD20 antibodies and CD20-binding molecules include U.S. Pat. Nos. 5,776,456, 5,736,137, 5,843,439, 6,399,061, and 6,682,734, as well as US 2002/0197255, US 2003/0021781, US 2003/

0082172, US 2003/0095963, US 2003/0147885 (Anderson et al.); U.S. Pat. No. 6,455,043 and WO 2000/09160 (Grillo-Lopez, A.); WO 2000/27428 (Grillo-Lopez and White); WO 2000/27433 (Grillo-Lopez and Leonard); WO 2000/44788 (Braslawsky et al.); WO 2001/10462 (Rastetter, W.); WO 2001/10461 (Rastetter and White); WO 2001/10460 (White and Grillo-Lopez); US 2001/0018041, US 2003/0180292, WO 2001/34194 (Hanna and Hariharan); US 2002/0006404 and WO 2002/04021 (Hanna and Hariharan); US 2002/0012665, WO 2001/74388 and 6,896,885B5 (Hanna, N.); US 2002/0058029 (Hanna, N.); US 2003/0103971 (Hariharan and Hanna); US 2005/0123540 (Hanna et al.); US 2002/0009444 and WO 2001/80884 (Grillo-Lopez, A.); WO 2001/97858; US 2005/0112060, and U.S. Pat. No. 6,846,476 (White, C.); US 2002/0128488 and WO 2002/34790 (Reff, M.); WO 2002/060955 (Braslawsky et al.); WO 2002/096948 (Braslawsky et al.); WO 2002/079255 (Reff and Davies); U.S. Pat. No. 6,171,586 and WO 1998/56418 (Lam et al.); WO 1998/58964 (Raju, S.); WO 1999/22764 (Raju, S.); WO 1999/51642, U.S. Pat. Nos. 6,194,551, 6,242,195, 6,528,624 and U.S. Pat. No. 6,538,124 (Idusogie et al.); WO 2000/42072 (Presta, L.); WO 2000/67796 (Curd et al.); WO 2001/03734 (Grillo-Lopez et al.); US 2002/0004587 and WO 2001/77342 (Miller and Presta); US 2002/0197256 (Grewal, I.); US 2003/0157108 (Presta, L.); U.S. Pat. Nos. 6,565,827, 6,090,365, 6,287,537, 6,015,542, 5,843,398, and 5,595,721, (Kaminski et al.); U.S. Pat. Nos. 5,500,362, 5,677,180, 5,721,108, 6,120,767, 6,652,852, 6,893,625 (Robinson et al.); U.S. Pat. No. 6,410,391 (Raubitschek et al.); U.S. Pat. No. 6,224,866 and WO00/20864 (Barbera-Guillem, E.); WO 2001/13945 (Barbera-Guillem, E.); WO 2000/67795 (Goldenberg); US 2003/0133930; WO 2000/74718 and US 2005/0191300A1 (Goldenberg and Hansen); US 2003/0219433 and WO 2003/68821 (Hansen et al.); WO 2004/058298 (Goldenberg and Hansen); WO 2000/76542 (Golay et al.); WO 2001/72333 (Wolin and Rosenblatt); U.S. Pat. No. 6,368,596 (Ghetie et al.); U.S. Pat. No. 6,306,393 and US 2002/0041847 (Goldenberg, D.); US 2003/0026801 (Weiner and Hartmann); WO 2002/102312 (Engleman, E.); US 2003/0068664 (Albitar et al.); WO 2003/002607 (Leung, S.); WO 2003/049694, US 2002/0009427, and US 2003/0185796 (Wolin et al.); WO 2003/061694 (Sing and Siegall); US 2003/0219818 (Bohen et al.); US 2003/0219433 and WO 2003/068821 (Hansen et al.); US 2003/0219818 (Bohen et al.); US 2002/0136719 (Shenoy et al.); WO 2004/032828 and US 2005/0180972 (Wahl et al.); and WO 2002/56910 (Hayden-Ledbetter). See also U.S. Pat. No. 5,849,898 and EP 330,191 (Seed et al.); EP332,865A2 (Meyer and Weiss); U.S. Pat. No. 4,861,579 (Meyer et al.); US 2001/0056066 (Bugelski et al.); WO 1995/03770 (Bhat et al.); US 2003/0219433 A1 (Hansen et al.); WO 2004/035607 (Teeling et al.); WO 2005/103081 (Teeling et al.); WO 2004/056312 (Lowman et al.); US 2004/0093621 (shitara et al.); WO 2004/103404 (Watkins et al.); WO 2005/000901 (Tedder et al.); US 2005/0025764 (Watkins et al.); WO 2005/016969 (Carr et al.); US 2005/0069545 (Carr et al.); WO 2005/014618 (Chang et al.); US 2005/0079174 (Barbera-Guillem and Nelson); US 2005/0106108 (Leung and Hansen); WO 2005/044859 and US 2005/0123546 (Umana et al.); WO 2005/070963 (Allan et al.); US 2005/0186216 (Ledbetter and Hayden-Ledbetter); US 2005/0202534 (Hayden-Ledbetter and Ledbetter); US 2005/0202028 (Hayden-Ledbetter and Ledbetter); US 2005/0202023 (Hayden-Ledbetter and Ledbetter); U.S. Pat. No. 6,183,744 (Goldenberg); and U.S. Pat. No. 6,897,044 (Braslawski et al.).

Publications concerning treatment with rituximab include: Perotta and Abuel, "Response of chronic relapsing ITP of 10 years duration to rituximab" Abstract #3360 *Blood* 10(1)(part 1-2): p. 88B (1998); Perotta et al., "Rituxan in the treatment of chronic idiopathic thrombocytopaenic purpura (ITP)", *Blood,* 94: 49 (abstract) (1999); Matthews, R., "Medical Heretics" New Scientist (7 Apr. 2001); Leandro et al., "Clinical outcome in 22 patients with rheumatoid arthritis treated with B lymphocyte depletion" *Ann Rheum Dis,* supra; Leandro et al., "Lymphocyte depletion in rheumatoid arthritis: early evidence for safety, efficacy and dose response" *Arthritis and Rheumatism* 44(9): 5370 (2001); Leandro et al., "An open study of B lymphocyte depletion in systemic lupus erythematosus", *Arthritis and Rheumatism,* 46:2673-2677 (2002), wherein during a 2-week period, each patient received two 500-mg infusions of rituximab, two 750-mg infusions of cyclophosphamide, and high-dose oral corticosteroids, and wherein two of the patients treated relapsed at 7 and 8 months, respectively, and have been retreated, although with different protocols; "Successful long-term treatment of systemic lupus erythematosus with rituximab maintenance therapy" Weide et al., *Lupus,* 12: 779-782 (2003), wherein a patient was treated with rituximab (375 mg/m$^2$×4, repeated at weekly intervals) and further rituximab applications were delivered every 5-6 months and then maintenance therapy was received with rituximab 375 mg/m$^2$ every three months, and a second patient with refractory SLE was treated successfully with rituximab and is receiving maintenance therapy every three months, with both patients responding well to rituximab therapy; Edwards and Cambridge, "Sustained improvement in rheumatoid arthritis following a protocol designed to deplete B lymphocytes" Rheumatology 40:205-211 (2001); Cambridge et al., "B lymphocyte depletion in patients with rheumatoid arthritis: serial studies of immunological parameters" *Arthritis Rheum.,* 46 (Suppl. 9): 51350 (2002); Cambridge et al., "Serologic changes following B lymphocyte depletion therapy for rheumatoid arthritis" *Arthritis Rheum.,* 48: 2146-2154 (2003); Edwards et al., "B-lymphocyte depletion therapy in rheumatoid arthritis and other autoimmune disorders" *Biochem Soc. Trans.,* supra; Edwards et al., "Efficacy and safety of rituximab, a B-cell targeted chimeric monoclonal antibody: A randomized, placebo controlled trial in patients with rheumatoid arthritis. Arthritis and Rheumatism 46(9): 5197 (2002); Edwards et al., "*Efficacy of B-cell—targeted therapy with rituximab in patients with rheumatoid arthritis*" *N Engl. J. Med.* 350:2572-2582 (2004); Pavelka et al., *Ann. Rheum. Dis.* 63: (S1):289-290 (2004); Emery et al., *Arthritis Rheum.* 50 (59):5659 (2004); Levine and Pestronk, "IgM antibody-related polyneuropathies: B-cell depletion chemotherapy using rituximab" *Neurology* 52: 1701-1704 (1999); Uchida et al., "The innate mononuclear phagocyte network depletes B lymphocytes through Fc receptor-dependent mechanisms during anti-CD20 antibody immunotherapy" *J. Exp. Med.* 199: 1659-1669 (2004); Gong et al., "Importance of cellular microenvironment and circulatory dynamics in B cell immunotherapy" *J. Immunol.* 174: 817-826 (2005); Hamaguchi et al., "The peritoneal cavity provides a protective niche for B1 and conventional B lymphocytes during anti-CD20 immunotherapy in mice" *J. Immunol.* 174: 4389-4399 (2005); Cragg et al. "The biology of CD20 and its potential as a target for mAb therapy" *Curr. Dir. Autoimmun.* 8:140-174 (2005); Eisenberg, "Mechanisms of autoimmunity" *Immunol. Res.* 27: 203-218 (2003); DeVita et al., "Efficacy of selective B cell blockade in the treatment of rheumatoid arthritis" *Arthritis & Rheum* 46:2029-2033 (2002);

Hidashida et al. "Treatment of DMARD-refractory rheumatoid arthritis with rituximab." *Presented at the Annual Scientific Meeting of the American College of Rheumatology*; October 24-29; New Orleans, La. 2002; Tuscano, J. "Successful treatment of infliximab-refractory rheumatoid arthritis with rituximab" *Presented at the Annual Scientific Meeting of the American College of Rheumatology*; October 24-29; New Orleans, La. 2002 and published Tuscano, *Arthritis Rheum.* 46: 3420 (2002); "Pathogenic roles of B cells in human autoimmunity; insights from the clinic" Martin and Chan, *Immunity* 20:517-527 (2004); Silverman and Weisman, "Rituximab therapy and autoimmune disorders, prospects for anti-B cell therapy", *Arthritis and Rheumatism*, 48: 1484-1492 (2003); Kazkaz and Isenberg, "Anti B cell therapy (rituximab) in the treatment of autoimmune diseases", *Current opinion in pharmacology*, 4: 398-402 (2004); Virgolini and Vanda, "Rituximab in autoimmune diseases", *Biomedicine & pharmacotherapy*, 58: 299-309 (2004); Klemmer et al., "Treatment of antibody mediated autoimmune disorders with a AntiCD20 monoclonal antibody Rituximab", *Arthritis And Rheumatism*, 48: (9) 9,S (SEP), page: S624-S624 (2003); Kneitz et al., "Effective B cell depletion with rituximab in the treatment of autoimmune diseases", *Immunobiology*, 206: 519-527 (2002); Arzoo et al., "Treatment of refractory antibody mediated autoimmune disorders with an anti-CD20 monoclonal antibody (rituximab)" *Annals of the Rheumatic Diseases*, 61 (10), p 922-924 (2002) Comment in Ann Rheum Dis. 61: 863-866 (2002); "Future strategies in immunotherapy" by Lake and Dionne, in *Burger's Medicinal Chemistry and Drug Discovery* (2003 by John Wiley & Sons, Inc.) Article Online Posting Date: Jan. 15, 2003 (Chapter 2 "Antibody-Directed Immunotherapy"); Liang and Tedder, *Wiley Encyclopedia of Molecular Medicine*, Section: CD20 as an Immunotherapy Target, article online posting date: 15 Jan. 2002 entitled "CD20"; Appendix 4A entitled "Monoclonal Antibodies to Human Cell Surface Antigens" by Stockinger et al., eds: Coligan et al., in *Current Protocols in Immunology* (2003 John Wiley & Sons, Inc) Online Posting Date: May, 2003; Print Publication Date: February, 2003; Penichet and Morrison, "CD Antibodies/molecules: Definition; Antibody Engineering" in *Wiley Encyclopedia of Molecular Medicine* Section: Chimeric, Humanized and Human Antibodies; posted online 15 Jan. 2002.

Further, see Looney "B cells as a therapeutic target in autoimmune diseases other than rheumatoid arthritis" *Rheumatology*, 44 Suppl 2: ii13-ii17 (2005); Chambers and Isenberg, "Anti-B cell therapy (rituximab) in the treatment of autoimmune diseases" *Lupus* 14(3): 210-214 (2005); Looney et al., "B-cell depletion as a novel treatment for systemic lupus erythematosus: a phase I/II dose-escalating trial of rituximab" *Arthritis Rheum.* 50: 2580-2589 (2004); Looney, "Treating human autoimmune disease by depleting B cells" *Ann Rheum. Dis.* 61: 863-866 (2002); Edelbauer et al., "Rituximab in childhood systemic lupus erythematosus refractory to conventional immunosuppression Case report" *Pediatr. Nephrol.* 20(6): 811-813 (2005); D'Cruz and Hughes, "The treatment of lupus nephritis" *BMJ* 330(7488): 377-378 (2005); Looney, "B cell-targeted therapy in diseases other than rheumatoid arthritis" *J. Rheumatol. Suppl.* 73: 25-28; discussion 29-30 (2005); Sfikakis et al., "Remission of proliferative lupus nephritis following B cell depletion therapy is preceded by down-regulation of the T cell costimulatory molecule CD40 ligand: an open-label trial" *Arthritis Rheum.* 52(2): 501-513 (2005); Rastetter et al., "Rituximab: expanding role in therapy for lymphomas and autoimmune diseases" *Annu. Rev. Med.* 55: 477-503 (2004); Silverman, "Anti-CD20 therapy in systemic lupus erythematosus: a step closer to the clinic" *Arthritis Rheum.* 52(2): 371-7 (2005), Erratum in: *Arthritis Rheum.* 52(4): 1342 (2005); Ahn et al., "Long-term remission from life-threatening hypercoagulable state associated with lupus anticoagulant (LA) following rituximab therapy" *Am. J. Hematol.* 78(2): 127-129 (2005); Tahir et al., "Humanized anti-CD20 monoclonal antibody in the treatment of severe resistant systemic lupus erythematosus in a patient with antibodies against rituximab" *Rheumatology*, 44(4): 561-562 (2005), Epub 2005 January 11; Looney et al., "Treatment of SLE with anti-CD20 monoclonal antibody" *Curr. Dir. Autoimmun.* 8: 193-205 (2005); Cragg et al., "The biology of CD20 and its potential as a target for mAb therapy" *Curr. Dir. Autoimmun.* 8: 140-174 (2005); Gottenberg et al., "Tolerance and short term efficacy of rituximab in 43 patients with systemic autoimmune diseases" *Ann. Rheum. Dis.* 64(6): 913-920 (2005) Epub 2004 November 18; Tokunaga et al., "Down-regulation of CD40 and CD80 on B cells in patients with life-threatening systemic lupus erythematosus after successful treatment with rituximab" *Rheumatology* 44(2): 176-182 (2005), Epub 2004 Oct. 19. See also Leandro et al., "B cell repopulation occurs mainly from naïve B cells in patient with rheumatoid arthritis and systemic lupus erythematosus" *Arthritis Rheum.*, 48 (Suppl 9): 51160 (2003).

Specks et al. "Response of Wegener's granulomatosis to anti-CD20 chimeric monoclonal antibody therapy" *Arthritis & Rheumatism* 44(12):2836-2840 (2001) discloses successful use of four infusions of 375 mg/m$^2$ of rituximab and high-dose glucocorticoids to treat Wegener's granulomatosis. The therapy was repeated after 11 months when the cANCA recurred, but therapy was without glucocorticoids. At 8 months after the second course of rituximab, the patients' disease remained in complete remission. Further, in another study, rituximab was found to be a well-tolerated, effective remission induction agent for severe ANCA-associated vasculitis, when used in a dose of 375 mg/m$^2$×4 along with oral prednisone 1 mg/kg/day, which was reduced by week 4 to 40 mg/day, and to complete discontinuation over the following 16 weeks. Four patients were re-treated with rituximab alone for recurring/rising ANCA titers. Other than glucocorticoids, no additional immunosuppressive agents seem to be necessary for remission induction and maintenance of sustained remission (6 months or longer). See online abstract submission and invitation Keogh et al., "Rituximab for Remission Induction in Severe ANCA-Associated Vasculitis: Report of a Prospective Open-Label Pilot Trial in 10 Patients", American College of Rheumatology, Session Number: 28-100, Session Title: Vasculitis, Session Type: ACR Concurrent Session, Primary Category: 28 Vasculitis, Session Oct. 18, 2004 (<www.abstractsonline.com/viewer/SearchResults.asp>). See also Keogh et al., *Kidney Blood Press. Res.* 26:293 (2003), wherein it is reported that eleven patients with refractory ANCA-associated vasculitis were treated with four weekly doses of 375 mg/m$^2$ of rituximab and high-dose glucocortoicoids, resulting in remission.

Patients with refractory ANCA-associated vasculitis were administered rituximab along with immunosuppressive medicaments such as intravenous cyclophosphamide, mycophenolate mofetil, azathioprine, or leflunomide, with apparent efficacy. Eriksson, "Short-term outcome and safety in 5 patients with ANCA-positive vasculitis treated with rituximab", *Kidney and Blood Pressure Research*, 26: 294 (2003) (five patients with ANCA-associated vasculitis treated with rituximab 375 mg/m$^2$ once a week for 4 weeks responded to the treatment); Jayne et al., "B-cell depletion with rituximab for refractory vasculitis" *Kidney and Blood Pressure Research,* 26: 294-295 (2003) (six patients with refractory vasculitis receiving four weekly infusions of rituximab at 375 mg/m² with cyclophosphamide along with background immunosuppression and prednisolone experienced major falls in vasculitic activity). A further report of using rituximab along with intravenous cyclophosphamide at 375 mg/m² per dose in 4 doses for administering to patients with refractory systemic vasculitis is provided in Jayne, poster 88 (11th International Vasculitis and ANCA workshop), 2003 American Society of Nephrology. See also Stone and Specks, "Rituximab Therapy for the Induction of Remission and Tolerance in ANCA-associated Vasculitis", in the Clinical Trial Research Summary of the 2002-2003 Immune Tolerance Network, http://www.immunetolerance.org/research/autoimmune/trials/stone.html, in which a trial of rituximab in ANCA-associated vasculitis is proposed for a total length of 18 months. See also Eriksson, *J. Internal Med.,* 257: 540-548 (2005) regarding nine patients with ANCA-positive vasculitis who were successfully treated with two or four weekly doses of 500 mg of rituximab, as well as Keogh et al., *Arthritis and Rheumatism,* 52: 262-268 (2005), who reported that in 11 patients with refractory ANCA-associated vasculitis, treatment or re-treatment with four weekly doses of 375 mg/m² of rituximab induced remission by B lymphocyte depletion, the study being conducted between January 2000 and September 2002.

As to the activity of a humanized anti-CD20 antibody, see, for example, Vugmeyster et al., "Depletion of B cells by a humanized anti-CD20 antibody PRO70769 in Macaca fascicularis" *J. Immunother.* 28: 212-219 (2005). For discussion of a human monoclonal antibody, see Baker et al., "Generation and characterization of LymphoStat-B, a human monoclonal antibody that antagonizes the bioactivities of B lymphocyte stimulator" *Arthritis Rheum.* 48: 3253-3265 (2003).

The findings of study WA17043, a phase IIb, randomized, double-blind, dose-ranging study in rheumatoid arthritis patients who have had an inadequate response to DMARDs (including anti-TNF agents) (Emery et al., *European League against Rheumatism (EULAR)* (June 2005) OP0008; Van Vollenhoven et al., *EULAR* (June 2005) SAT0072), indicate that the combination of rituximab with MTX is associated with a clinically and statistically significant improvement in disease symptoms. This study identified doses of rituximab in combination with MTX that require further investigation and confirmation within the setting of a phase III clinical study. See also World Pharmaceutical News, www.scrippharma.com Scrip article dated 13 Jun. 2005, entitled "Rituximab a future challenge for anti-TNFs?" describing the EULAR studies and speculating whether x-ray data from Phase III REFLEX study would show if rituximab can slow joint damage. In addition, WO 2004/091657 published Oct. 28, 2004 discloses treating patients having rheumatoid arthritis who exhibit an inadequate response to TNFα-inhibitor therapies with CD20 antibodies, wherein the patients may have radiographic evidence of at least one joint with definite erosion attributable to rheumatoid arthritis, as determined by the central reading site (any joint of the hands, wrists or feet with the exception of the DIP joints of the hands). A potential secondary endpoint includes change in modified Sharp radiographic total score, erosion score, and joint space narrowing score, which may be analyzed using continuous or categorical methodology, as appropriate. Exploratory endpoints and analysis may involve radiographic analyses including the proportion of patients with no erosive progression, which may be assessed at weeks 24 and beyond. See also US 2005/00001862 published Aug. 25, 2005 equivalent to WO 2005/060999 published Jul. 7, 2005 regarding treatment of patients having rheumatoid arthritis with rituximab wherein the potential secondary endpoint and exploratory endpoints and analyses include those in WO 2004/091657, supra.

Despite the advances in treatment of joint disease, a significant number of patients do not qualify for, are intolerant of, or experience an insufficient response to current treatments. Therefore, new treatment options, particularly those that may target different aspects of the pathology of the disease and offer similar or better levels of clinical benefit, are needed.

SUMMARY OF THE INVENTION

The present invention involves administration of a CD20 antagonist that provides a safe and active treatment regimen in subjects with joint damage, including selection of an efficacious dosing regimen and scheduled or unscheduled re-treatment. This antagonist is effective both in initial therapy and in the management of refractory disease.

Accordingly, the invention is as claimed. In a first aspect, the present invention concerns a method for treating joint damage in a subject comprising administering a CD20 antibody to the subject and giving the subject, at least about one month after the administration, a radiographic test that measures a reduction in the joint damage as compared to baseline prior to the administration, wherein the amount of CD20 antibody administered is effective in achieving a reduction in the joint damage.

In another aspect, the invention relates to a method of monitoring the treatment of joint damage in a subject comprising administering an effective amount of a CD20 antibody to the subject and measuring by radiography after at least about one month from the administration whether the joint damage has been reduced over baseline prior to the administration, wherein a decrease versus baseline in the subject after treatment indicates the CD20 antibody is having an effect on the joint damage. In a preferred embodiment, the degree of reduction versus baseline is measured a second time after the administration of the CD20 antibody.

In a further aspect, the invention provides a method of determining whether to continue administering a CD20 antibody to a subject with joint damage comprising measuring by radiography reduction in joint damage in the subject after administration of the CD20 antibody a first time, measuring by radiography reduction in joint damage in the subject after administration of the CD20 antibody a second time, comparing the radiography scores in the subject at the first time and at the second time, and if the score is less at the second time than at the first time, continuing administration of the CD20 antibody.

In yet another aspect, the invention is directed to an article of manufacture comprising:

(a) a container comprising a CD20 antibody; and (b) a package insert with instructions for treating joint damage in a subject, wherein the instructions indicate that the subject is administered the CD20 antibody and is then subjected, at least one about month after the administration, to a radiographic test that measures a reduction in the joint damage as compared to baseline prior to the administration, wherein the amount of CD20 antibody administered is effective in achieving a reduction in the joint damage.

In a preferred aspect, the article further comprises a container comprising a second medicament, wherein the CD20 antibody is a first medicament, further comprising instructions on the package insert for treating the subject with an effective amount of the second medicament.

In another embodiment of the invention, a method is provided for treating joint damage in a subject comprising administering a CD20 antibody to the subject, and giving the subject, at least about 52 weeks after the administration, a radiographic test that measures a reduction in the joint damage as compared to baseline prior to the administration, wherein the amount of CD20 antibody administered is effective in achieving a reduction in the joint damage.

In a still further embodiment, the invention provides a method of monitoring the treatment of joint damage in a subject comprising administering an effective amount of a CD20 antibody to the subject and measuring by radiography after at least about 52 weeks from the administration whether the joint damage has been reduced over baseline prior to the administration, wherein a decrease versus baseline in the subject after treatment indicates the CD20 antibody is having an effect on the joint damage.

Further, the invention provides an article of manufacture comprising:

(a) a container comprising a CD20 antibody; and (b) a package insert with instructions for treating joint damage in a subject, wherein the instructions indicate that the subject is administered the CD20 antibody and is then subjected, at least about 52 weeks after the administration, to a radiographic test that measures a reduction in the joint damage as compared to baseline prior to the administration, wherein the amount of CD20 antibody administered is effective in achieving a reduction in the joint damage.

In a further aspect, the invention provides a method for the treatment of joint damage in a subject, wherein (a) the subject has exhibited an inadequate response to one or more anti-tumor necrosis factor (TNF) inhibitors; (b) the subject received at least one prior course of treatment with a CD20 antibody, and (c) the treatment comprises administering at least one further course of treatment with a CD20 antibody.

These and further aspects will be apparent from the rest of the disclosure, including the examples and the appended claims.

BRIEF DESCRIPTION OF THE DRAWINGS

FIG. 20 shows the most commonly reported adverse events in the study of RA patients over six months, wherein the patients are treated with control or with rituximab (1000 mg×2) plus MTX.

FIG. 21 shows adverse events leading to withdrawal in the study of RA patients over six months, wherein the patients are treated with control or with rituximab (1000 mg×2) plus MTX.

FIG. 22 shows events occurring during/within 24 hours of infusions in the study of RA patients over six months, wherein the patients are treated with control or with rituximab (1000 mg×2) plus MTX.

FIG. 23 shows acute infusion reactions in the study of RA patients over six months, wherein the patients are treated with control or with rituximab (1000 mg×2) plus MTX.

FIG. 24 shows serious adverse events occurring during/within 24 hours of infusions in the study of RA patients over six months, wherein the patients are treated with control or with rituximab (1000 mg×2) plus MTX.

FIG. 25 shows system organ class—infections and infestations in the study of RA patients over six months, wherein the patients are treated with control or with rituximab (1000 mg×2) plus MTX.

FIG. 26 shows serious infections in the study of RA patients over six months, wherein the patients are treated with control or with rituximab (1000 mg×2) plus MTX.

FIG. 27 shows the infection rate in the study of RA patients over six months, wherein the patients are treated with control or with rituximab (1000 mg×2) plus MTX.

FIG. 28 shows HACA in the study of RA patients over six months, wherein the patients are treated with control or with rituximab (1000 mg×2) plus MTX.

FIG. 29 shows IgG levels over six months in RA patients treated with control or with rituximab (1000 mg×2) plus MTX.

FIG. 32A is a sequence alignment comparing the amino acid sequences of the light chain variable domain ($V_L$) of each of murine 2H7 (SEQ ID NO:1), humanized 2H7.v16 variant (SEQ ID NO:2), and the human kappa light chain subgroup I (SEQ ID NO:3). The CDRs of $V_L$ of 2H7 and hu2H7.v16 are as follows: CDR1 (SEQ ID NO:4), CDR2 (SEQ ID NO:5), and CDR3 (SEQ ID NO:6).

FIG. 32B is a sequence alignment comparing the amino acid sequences of the heavy chain variable domain ($V_H$) of each of murine 2H7 (SEQ ID NO:7), humanized 2H7.v16 variant (SEQ ID NO:8), and the human consensus sequence of the heavy chain subgroup III (SEQ ID NO:9). The CDRs of $V_H$ of 2H7 and hu2H7.v16 are as follows: CDR1 (SEQ ID NO:10), CDR2 (SEQ ID NO:11), and CDR3 (SEQ ID NO:12).

In FIG. 32A and FIG. 32B, the CDR1, CDR2 and CDR3 in each chain are enclosed within brackets, flanked by the framework regions, FR1-FR4, as indicated. 2H7 refers to the murine 2H7 antibody. The asterisks in between two rows of sequences indicate the positions that are different between the two sequences. Residue numbering is according to Kabat et al. *Sequences of Immunological Interest,* 5th Ed. Public Health Service, National Institutes of Health, Bethesda, Md. (1991), with insertions shown as a, b, c, d, and e.

FIG. 33 shows the amino acid sequence of the mature 2H7.v16 L chain (SEQ ID NO:13)

FIG. 34 shows the amino acid sequence of the mature 2H7.v16 H chain (SEQ ID NO:14).

FIG. 35 shows the amino acid sequence of the mature 2H7.v31 H chain (SEQ ID NO:15). The L chain of 2H7.v31 is the same as for 2H7.v16.

FIG. 36 is a sequence alignment comparing the light-chain amino acid sequences of the humanized 2H7.v16 variant (SEQ ID NO:2) and humanized 2H7.v138 variant (SEQ ID NO:28).

FIG. 37 is a sequence alignment comparing the heavy-chain amino acid sequences of the humanized 2H7.v16 variant (SEQ ID NO:8) and humanized 2H7.v138 variant (SEQ ID NO:29).

FIG. 38 shows an alignment of the mature 2H7.v16 and 2H7.v511 light chains (SEQ ID NOS: 13 and 30, respectively), with Kabat variable-domain residue numbering and Eu constant-domain residue numbering.

FIG. 39 shows an alignment of the mature 2H7.v16 and 2H7.v511 heavy chains (SEQ ID NOS:14 and 31, respectively), with Kabat variable-domain residue numbering and Eu constant-domain residue numbering.

FIG. 40A shows the sequence of the humanized 2H7.v114 variable light-chain domain (SEQ ID NO:32); FIG. 40B shows the sequence of the humanized 2H7.v114 variable heavy-chain domain (SEQ ID NO:33); and FIG. 40C shows the sequence of the humanized 2H7.v114 full-length heavy chain (SEQ ID NO:34), with Kabat variable-domain residue numbering and Eu constant-domain residue numbering.

DETAILED DESCRIPTION OF THE PREFERRED EMBODIMENTS

I. Definitions

Figure 1:
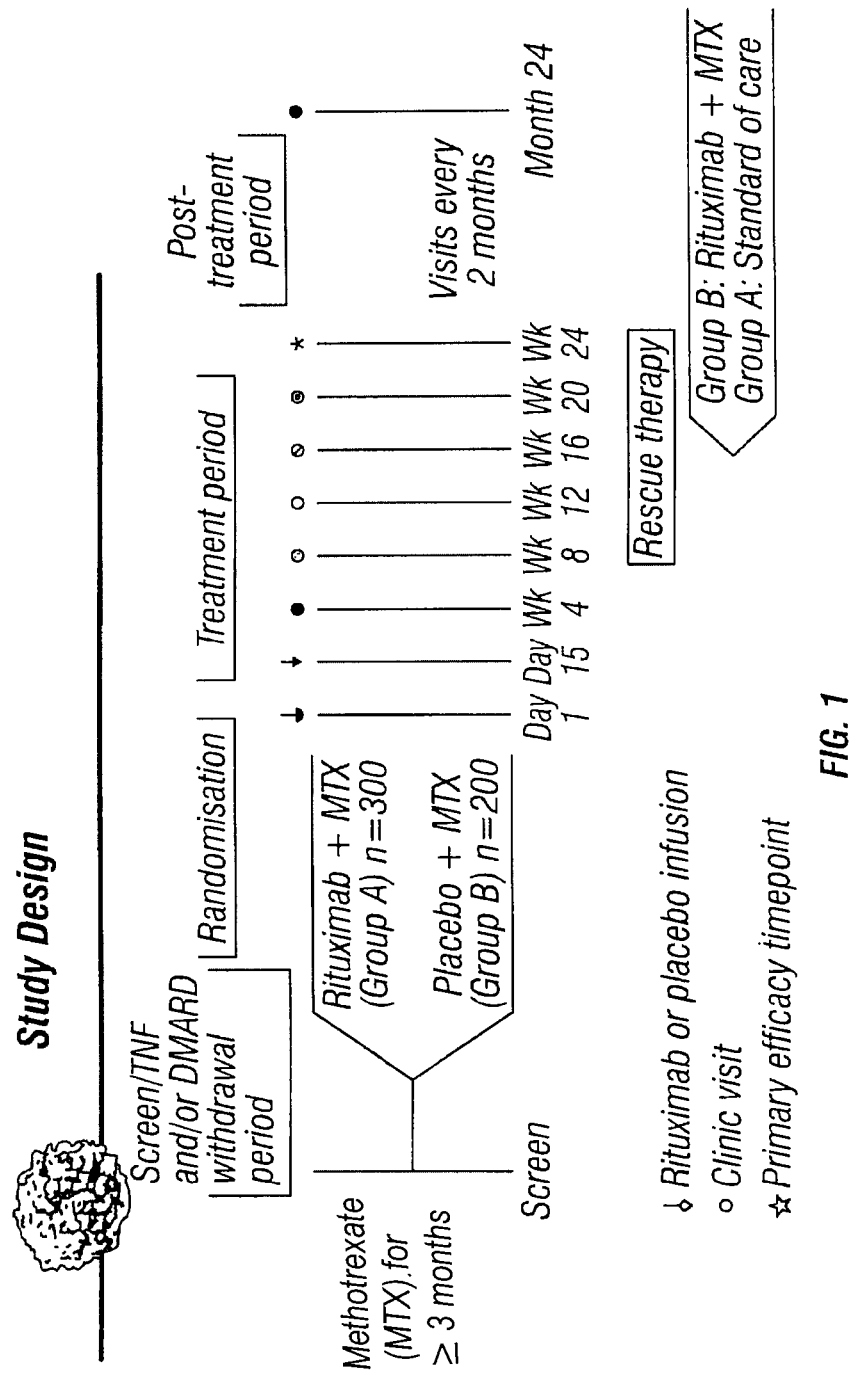
FIG. 1 shows the study design to treat RA patients with control (placebo plus MTX) or rituximab (1000 mg×2) plus MTX (Example 1 herein).
Figure 2:
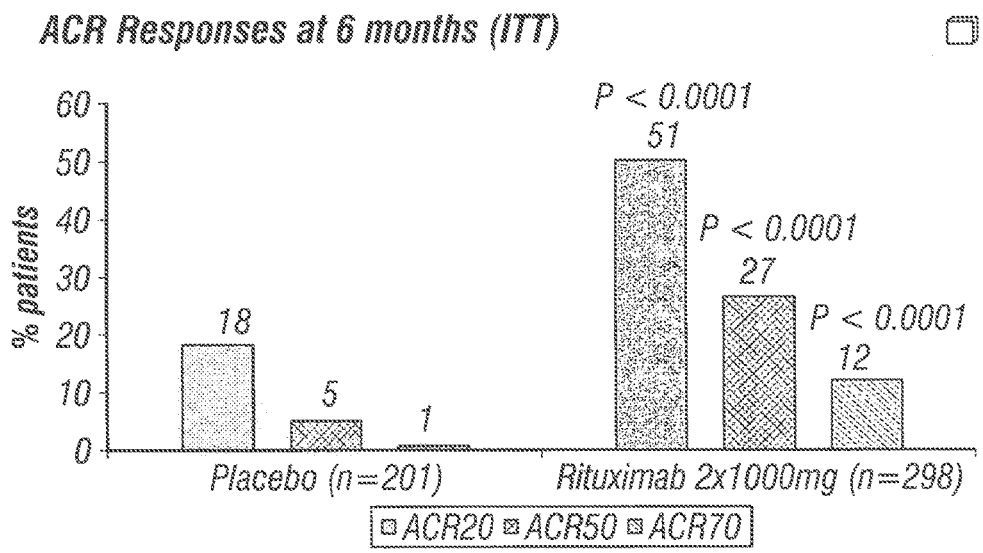
FIG. 2 shows the ACR responses at six months of RA patients treated with control or with rituximab (1000 mg×2) plus MTX.
Figure 3:
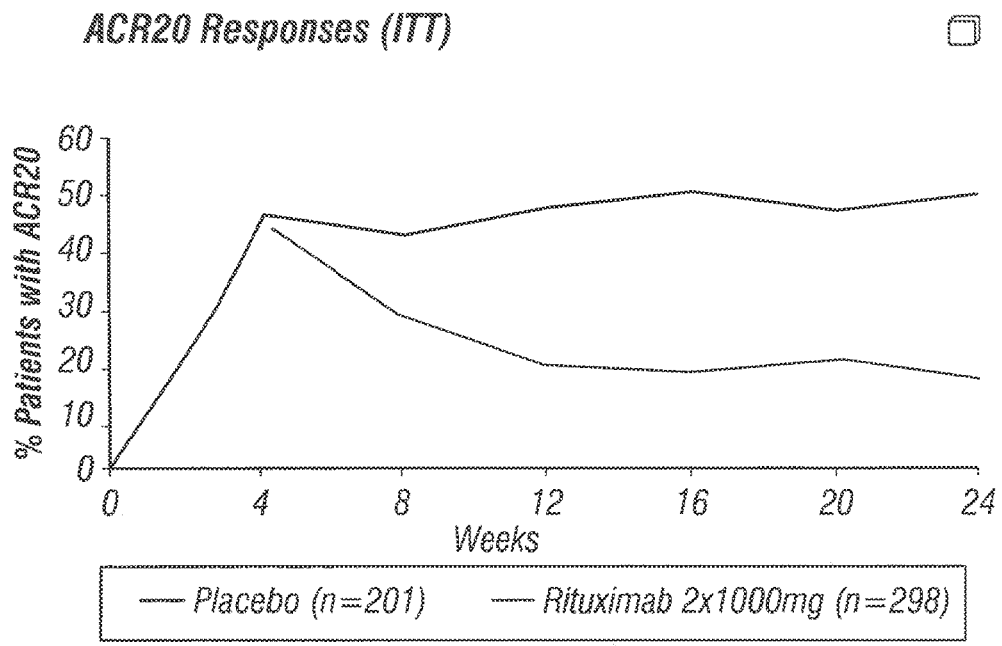
FIG. 3 shows the ACR20 responses over six months of RA patients treated with control or with rituximab (1000 mg×2) plus MTX.
Figure 4:
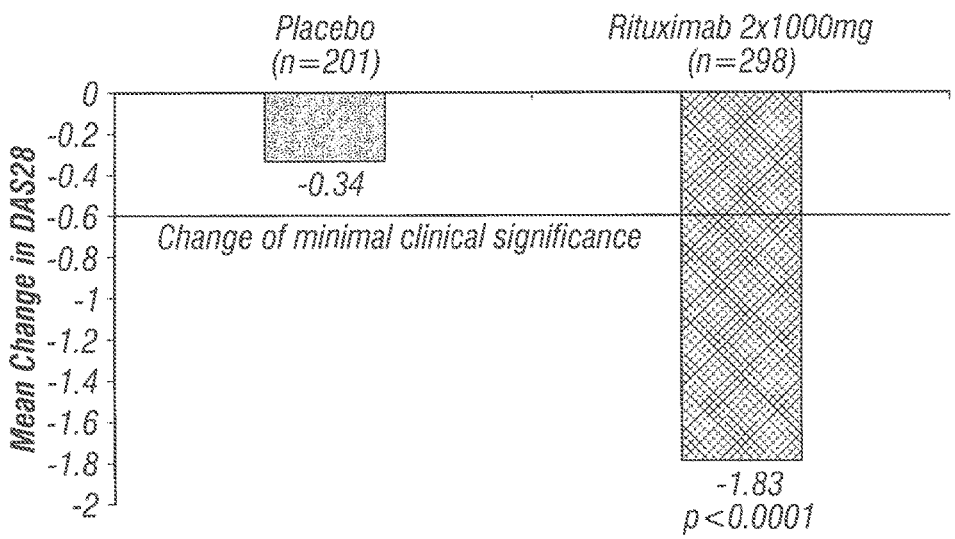
FIG. 4 shows the changes in 328DS at six months of RA patients treated with control or with rituximab (1000 mg×2) plus MTX.
Figure 5:
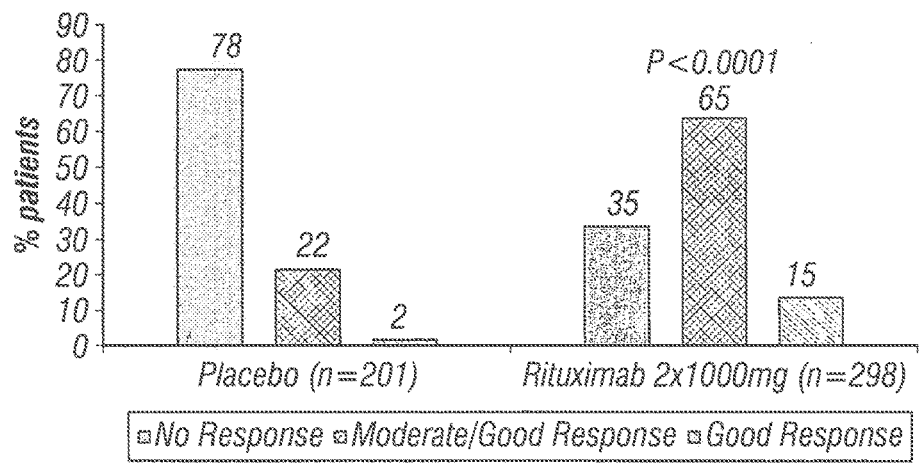
FIG. 5 shows EULAR responses at six months of RA patients treated with control or with rituximab (1000 mg×2) plus MTX.
Figure 6:
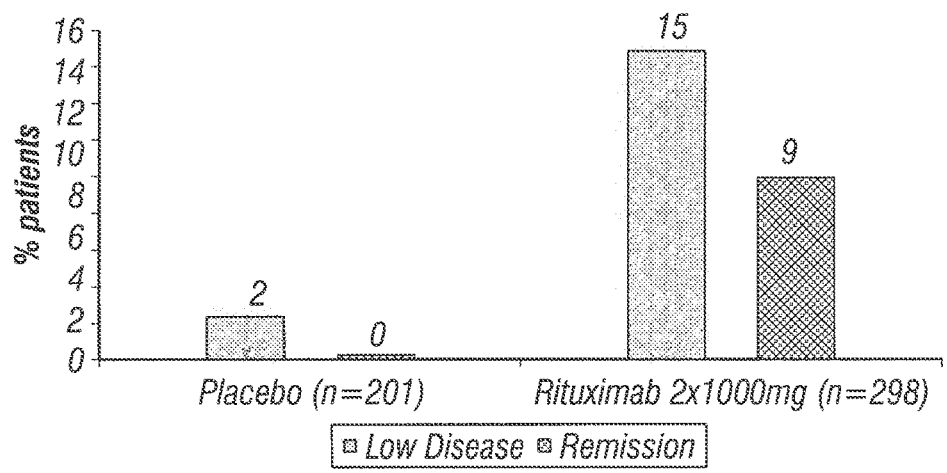
FIG. 6 shows EULAR remission or low disease at six months of RA patients treated with control or with rituximab (1000 mg×2) plus MTX.
Figure 7:
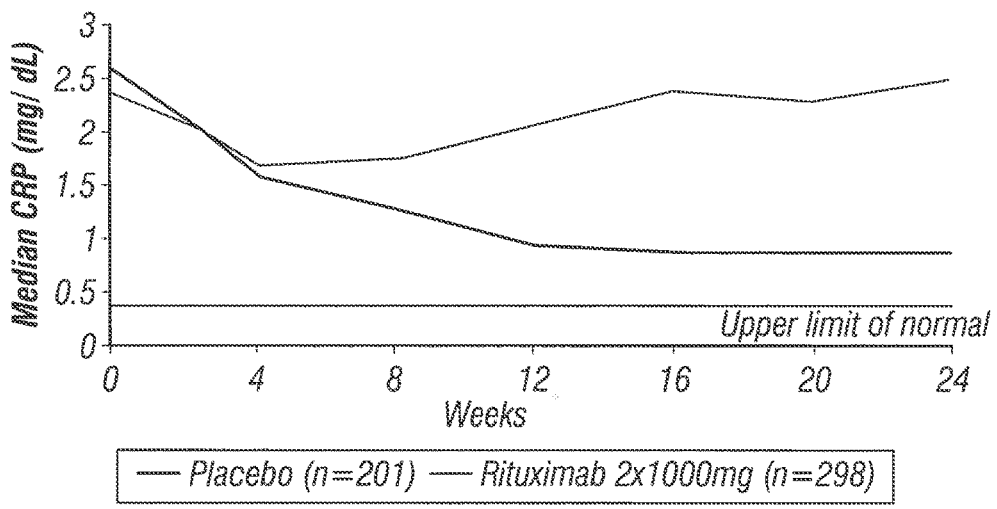
FIG. 7 shows the median C-reactive protein (CRP) over six months of RA patients treated with control or with rituximab (1000 mg×2) plus MTX.
Figure 8:
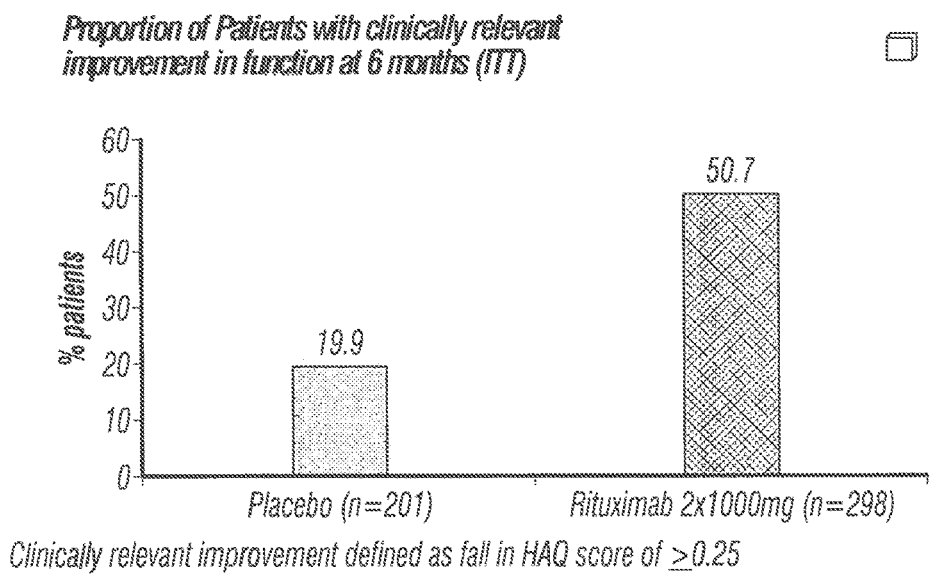
FIG. 8 shows the proportion of RA patients with clinically relevant improvement in function at six months, wherein the patients are treated with control or with rituximab (1000 mg×2) plus MTX.
Figure 9:
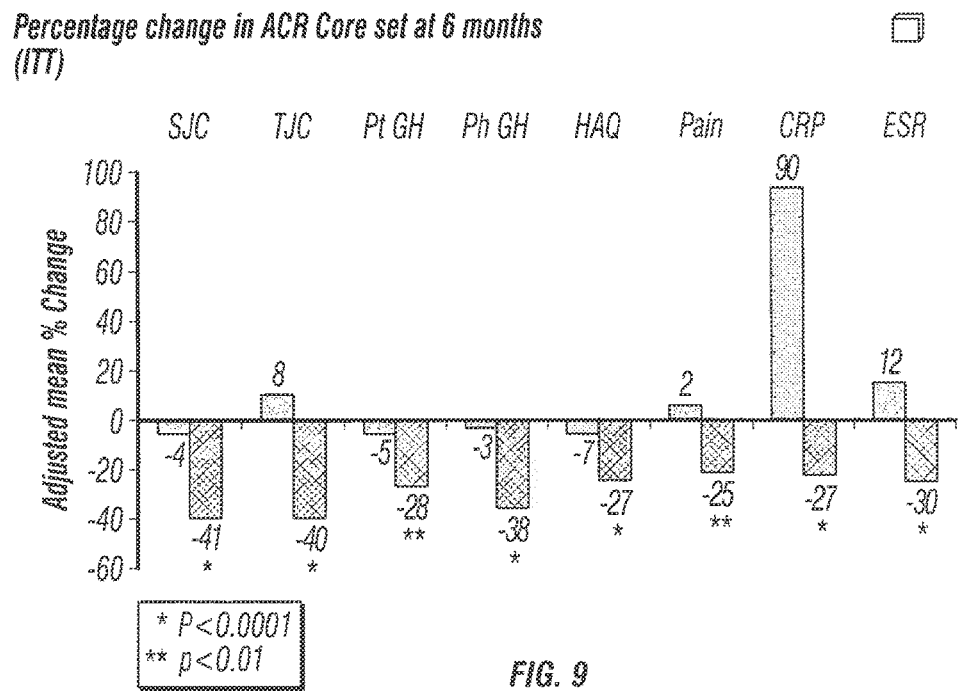
FIG. 9 shows the percentage change in ACR score set at six months of RA patients treated with control or with rituximab (1000 mg×2) plus MTX.
Figure 10:
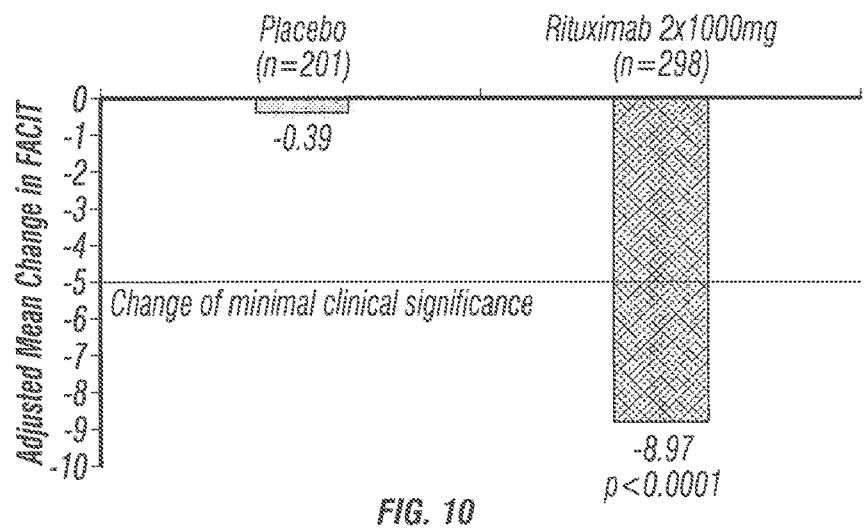
FIG. 10 shows the change in FACIT-F at six months of RA patients treated with control or with rituximab (1000 mg×2) plus MTX.
Figure 11:
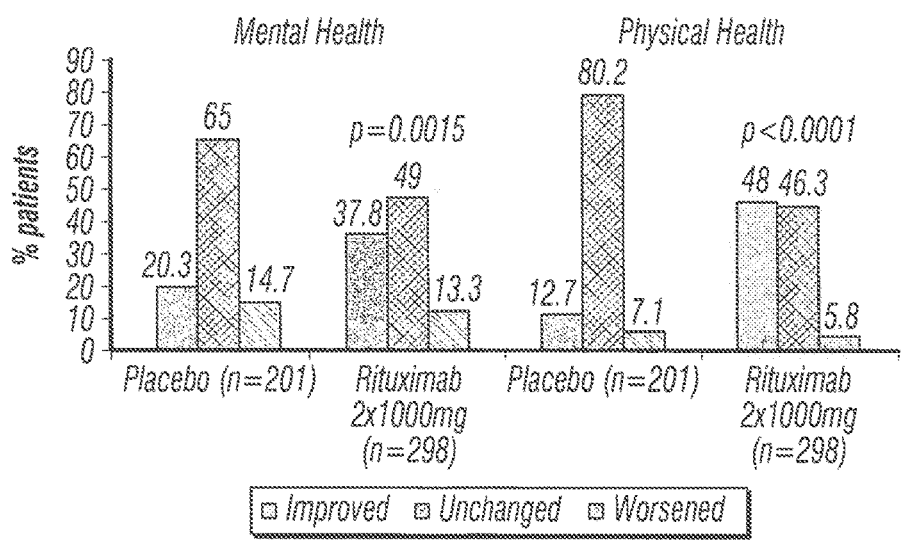
FIG. 11 shows the changes in SF-36 categories (mental and physical health) at six months of RA patients treated with control or with rituximab (1000 mg×2) plus MTX.
Figure 12:
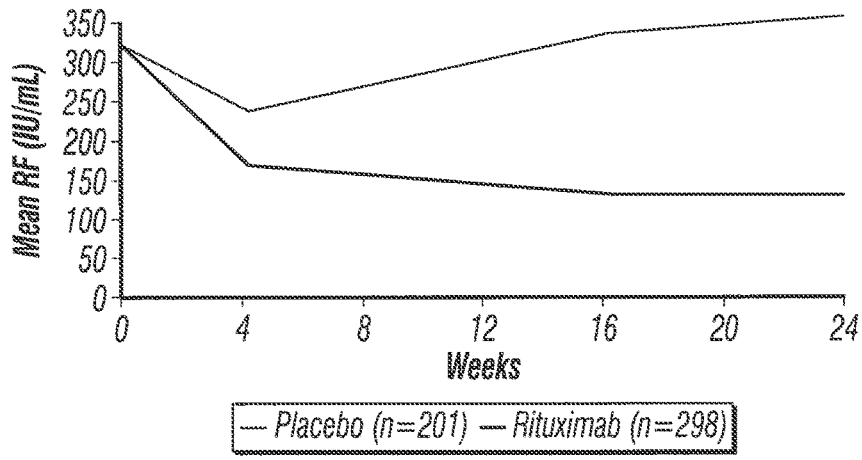
FIG. 12 shows the total rheumatoid factor at six months of RA patients treated with control or with rituximab (1000 mg×2) plus MTX.
Figure 13:
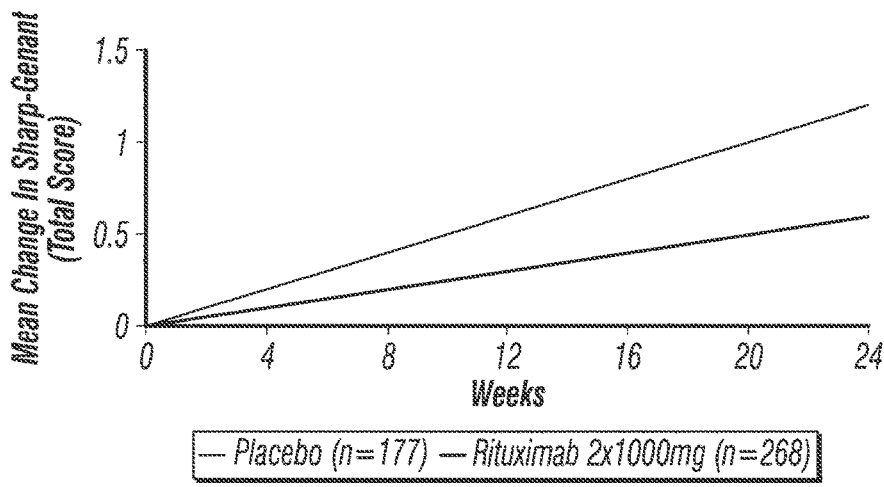
FIG. 13 shows the mean change in Sharp-Genant total score at six months of RA patients treated with control or with rituximab (1000 mg×2) plus MTX.
Figure 14:
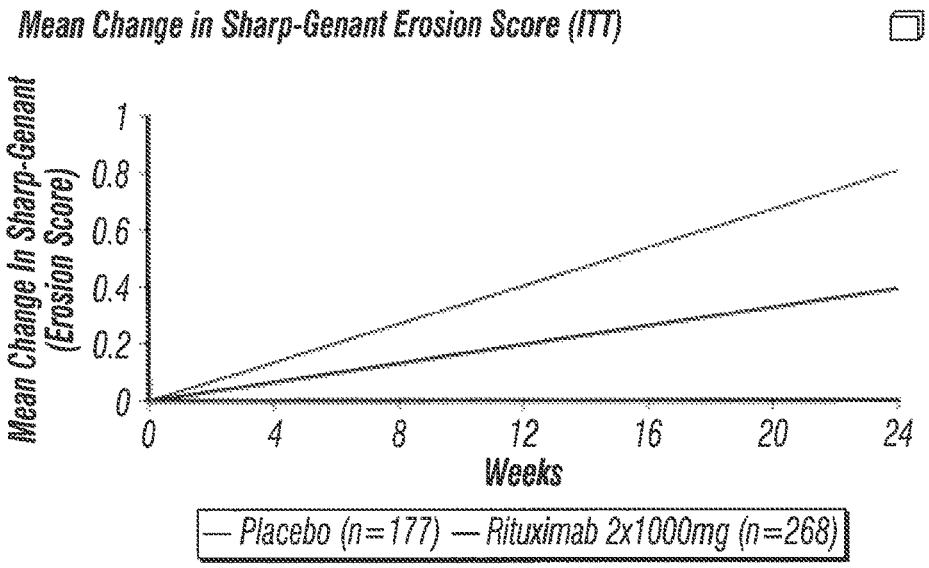
FIG. 14 shows the mean change in Sharp-Genant erosion score at six months of RA patients treated with control or with rituximab (1000 mg×2) plus MTX.
Figure 15:
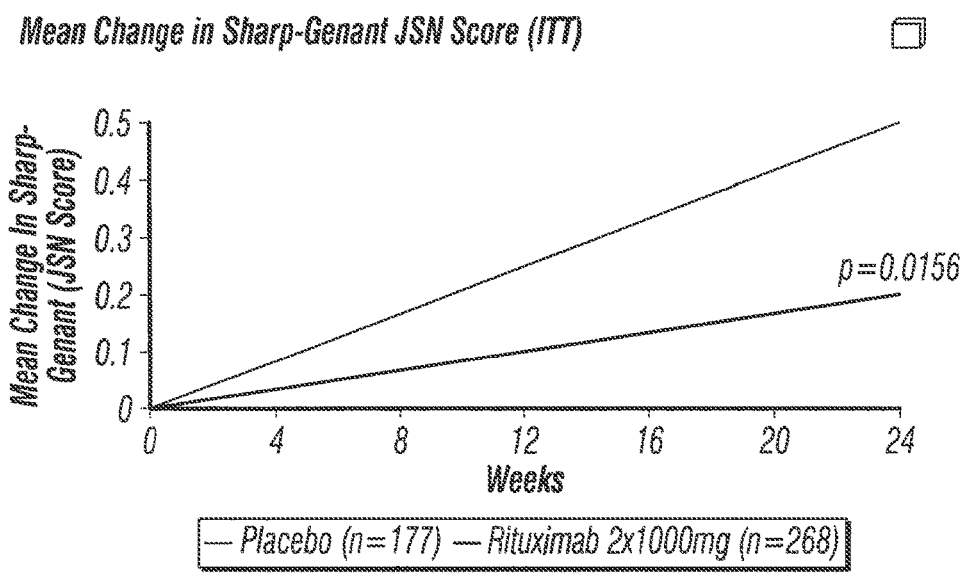
FIG. 15 shows the mean change in Sharp-Genant joint space narrowing (JSN) score at six months of RA patients treated with control or with rituximab (1000 mg×2) plus MTX.
Figure 16:
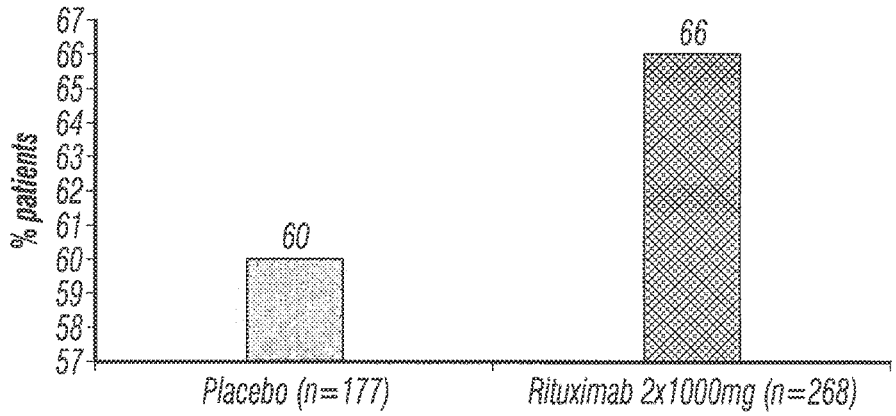
FIG. 16 shows the proportion of RA patients with no change in erosion score at six months, wherein the patients are treated with control or with rituximab (1000 mg×2) plus MTX.
Figure 17:
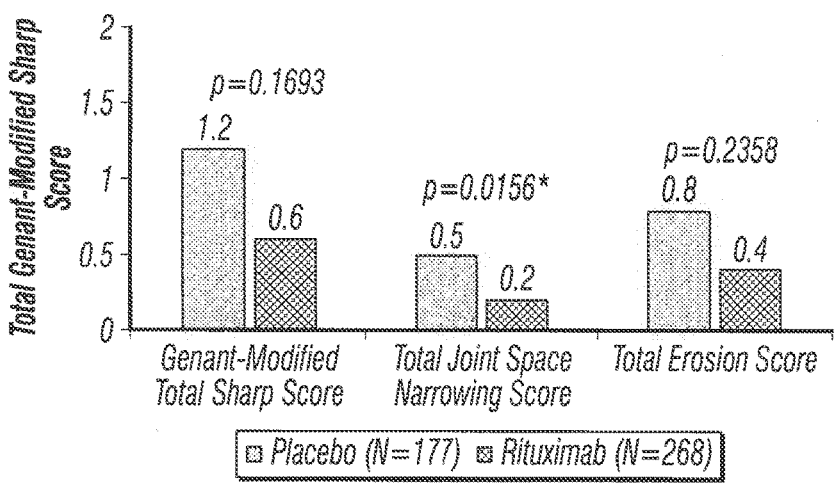
FIG. 17 shows the change in radiographic endpoints at week 24 (exploratory endpoint) for RA patients treated with control or with rituximab (1000 mg×2) plus MTX.

A "B cell" is a lymphocyte that matures within the bone marrow, and includes a naive B cell, memory B cell, or effector B cell (plasma cells). The B cell herein is a normal or non-malignant B cell.

A "B-cell surface marker" or "B-cell surface antigen" herein is an antigen expressed on the surface of a B cell that can be targeted with an antagonist that binds thereto. Exemplary B-cell surface markers include the CD10, CD19, CD20, CD21, CD22, CD23, CD24, CD37, CD40, CD53, CD72, CD73, CD74, CDw75, CDw76, CD77, CDw78, CD79a, CD79b, CD80, CD81, CD82, CD83, CDw84, CD85 and CD86 leukocyte surface markers (for descriptions, see The Leukocyte Antigen Facts Book, $2^{nd}$ Edition. 1997, ed. Barclay et al. Academic Press, Harcourt Brace & Co., New York). Other B-cell surface markers include RP105, FcRH2, B-cell CR2, CCR6, P2X5, HLA-DOB, CXCR5, FCER2, BR3, Btig, NAG14, SLGC16270, FcRH1, IRTA2, ATWD578, FcRH3, IRTA1, FcRH6, BCMA, and 239287. The B-cell surface marker of particular interest is preferentially expressed on B cells compared to other non-B-cell tissues of a mammal and may be expressed on both precursor B cells and mature B cells. The preferred B-cell surface markers herein are CD20 and CD22.

The "CD20" antigen, or "CD20," is an about 35-kDa, non-glycosylated phosphoprotein found on the surface of greater than 90% of B cells from peripheral blood or lymphoid organs. CD20 is present on both normal B cells as well as malignant B cells, but is not expressed on stem cells. Other names for CD20 in the literature include "B-lymphocyte-restricted antigen" and "Bp35". The CD20 antigen is described in Clark et al., *Proc. Natl. Acad. Sci.* (USA) 82:1766 (1985), for example.

The "CD22" antigen, or "CD22," also known as BL-CAM or Lyb8, is a type 1 integral membrane glycoprotein with molecular weight of about 130 (reduced) to 140kD (unreduced). It is expressed in both the cytoplasm and cell membrane of B-lymphocytes. CD22 antigen appears early in B-cell lymphocyte differentiation at approximately the same stage as the CD19 antigen. Unlike other B-cell markers, CD22 membrane expression is limited to the late differentiation stages comprised between mature B cells (CD22+) and plasma cells (CD22−). The CD22 antigen is described, for example, in Wilson et al., *J. Exp. Med.* 173:137 (1991) and Wilson et al., *J. Immunol.* 150:5013 (1993).

An "antagonist" is a molecule that, upon binding to CD20 on B cells, destroys or depletes B cells in a mammal and/or interferes with one or more B-cell functions, e.g. by reducing or preventing a humoral response elicited by the B cell. The antagonist preferably is able to deplete B cells (i.e. reduce circulating B-cell levels) in a mammal treated therewith. Such depletion may be achieved via various mechanisms such as ADCC and/or CDC, inhibition of B-cell proliferation and/or induction of B-cell death (e.g. via apoptosis). Antagonists included within the scope of the present invention include antibodies, synthetic or native-sequence peptides, immunoadhesins, and small-molecule antagonists that bind to CD20, optionally conjugated with or fused to another molecule. The preferred antagonist comprises an antibody.

An "antibody antagonist" herein is an antibody that, upon binding to a B-cell surface marker on B cells, destroys or depletes B cells in a mammal and/or interferes with one or more B-cell functions, e.g., by reducing or preventing a humoral response elicited by the B cell. The antibody antagonist preferably is able to deplete B cells (i.e., reduce circulating B-cell levels) in a mammal treated therewith. Such depletion may be achieved via various mechanisms such as ADCC and/or CDC, inhibition of B-cell proliferation and/or induction of B-cell death (e.g., via apoptosis).

The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity.

"Antibody fragments" comprise a portion of an intact antibody, preferably comprising the antigen binding region thereof. Examples of antibody fragments include Fab, Fab', F(ab')$_2$, and Fv fragments; diabodies; linear antibodies; single-chain antibody molecules; and multispecific antibodies formed from antibody fragments.

For the purposes herein, an "intact antibody" is one comprising heavy and light variable domains as well as an Fc region.

An "antibody that binds to a B-cell surface marker" is a molecule that, upon binding to a B-cell surface marker, destroys or depletes B cells in a mammal and/or interferes with one or more B-cell functions, e.g. by reducing or preventing a humoral response elicited by the B cell. The antibody preferably is able to deplete B cells (i.e. reduce circulating B-cell levels) in a mammal treated therewith. Such depletion may be achieved via various mechanisms such as ADCC and/or CDC, inhibition of B-cell proliferation and/or induction of B-cell death (e.g. via apoptosis). In one preferred embodiment, the B-cell surface marker is CD20 or CD22, so that the antibody that binds to a B-cell surface marker is an antibody that binds to CD20 or CD22, respectively, or a "CD20 antibody" or "CD22 antibody," respectively. Examples of CD22 antibodies include the ones described in EP 1,476,120 (Tedder and Tuscano), EP 1,485, 130 (Tedder), and EP 1,504,035 (Popplewell et al.), as well as those described in US 2004/0258682 (Leung et al.). In a still more preferred embodiment, the antibody is a CD20 antibody. A particularly preferred embodiment is a CD20 or CD22 antibody, preferably a CD20 antibody.

Examples of CD20 antibodies include: "C2B8," which is now called "rituximab" ("RITUXAN®/MABTHERA®") (U.S. Pat. No. 5,736,137); the yttrium-[90]-labelled 2B8 murine antibody designated "Y2B8" or "Ibritumomab Tiuxetan" (ZEVALIN®) commercially available from Biogen Idec, Inc. (e.g., U.S. Pat. No. 5,736,137; 2B8 deposited with ATCC under accession no. HB11388 on Jun. 22, 1993); murine IgG2a "B1," also called "Tositumomab," optionally labelled with $^{131}$I to generate the "131I-B1" or "iodine I131 tositumomab" antibody (BEXXAR™) commercially available from Corixa (see, also, e.g., U.S. Pat. No. 5,595,721); murine monoclonal antibody "1F5" (e.g., Press et al. *Blood* 69(2):584-591 (1987) and variants thereof including "framework patched" or humanized 1F5 (e.g., WO 2003/002607, Leung, S.; ATCC deposit HB-96450); murine 2H7 and chimeric 2H7 antibody (e.g., U.S. Pat. No. 5,677,180); a humanized 2H7 (e.g., WO 2004/056312 (Lowman et al.) and as set forth below); HUMAX-CD20™ fully human, high-affinity antibody targeted at the CD20 molecule in the cell membrane of B-cells (Genmab, Denmark; see, for example, Glennie and van de Winkel, *Drug Discovery Today* 8: 503-510 (2003) and Cragg et al., *Blood* 101: 1045-1052 (2003)); the human monoclonal antibodies set forth in WO 2004/035607 and WO 2005/103081 (Teeling et al., GenMab/Medarex); the antibodies having complex N-glycoside-linked sugar chains bound to the Fc region described in US 2004/0093621 (shitara et al.); monoclonal antibodies and antigen-binding fragments binding to CD20 (e.g., WO 2005/000901, Tedder et al.) such as HB20-3, HB20-4, HB20-25, and MB20-11; single-chain proteins binding to CD20 (e.g., US 2005/0186216 (Ledbetter and Hayden-Ledbetter); US 2005/0202534 (Hayden-Ledbetter and Ledbetter); US 2005/0202028 (Hayden-Ledbetter and Ledbetter); US 2005/0202023 (Hayden-Ledbetter and Ledbetter)—Trubion Pharm Inc.); CD20-binding molecules such as the AME series of antibodies, e.g., AME-33™ antibodies as set forth, for example, in WO 2004/103404 and US 2005/0025764 (Watkins et al., Applied Molecular Evolution, Inc.) and the CD20 antibodies with Fc mutations as set forth, for example, in WO 2005/070963 (Allan et al., Applied Molecular Evolution, Inc.); CD20-binding molecules such as those described in WO 2005/016969 and US 2005/0069545 (Carr et al.); bispecific antibodies as set forth, for example, in WO 2005/014618 (Chang et al.); humanized LL2 monoclonal antibodies as described, for example, in US 2005/0106108 (Leung and Hansen; Immunomedics); chimeric or humanized B-Ly1 antibodies to CD20 as described, for example, in WO2005/044859 and US 2005/0123546 (Umana et al.; GlycArt Biotechnology AG); A20 antibody or variants thereof such as chimeric or humanized A20 antibody (cA20, hA20, respectively) and IMMUN-106 (e.g., US 2003/0219433, Immunomedics); and monoclonal antibodies L27, G28-2, 93-1B3, B-C1 or NU-B2 available from the International Leukocyte Typing Workshop (e.g., Valentine et al., In: *Leukocyte Typing III* (McMichael, Ed., p. 440, Oxford University Press (1987)). The preferred CD20 antibodies herein are chimeric, humanized, or human CD20 antibodies, more preferably rituximab, a humanized 2H7, chimeric or humanized A20 antibody (Immunomedics), HUMAX-CD20™ human CD20 antibody (Genmab), and immunoglobulins/proteins binding to CD20 (Trubion Pharm Inc.).

The terms "rituximab" or "RITUXAN®" herein refer to the genetically engineered chimeric murine/human monoclonal antibody directed against the CD20 antigen and designated "C2B8" in U.S. Pat. No. 5,736,137, including fragments thereof which retain the ability to bind CD20.

Purely for the purposes herein and unless indicated otherwise, a "humanized 2H7" refers to a humanized CD20 antibody, or an antigen-binding fragment thereof, comprising one, two, three, four, five, or six of the following CDR sequences:
CDR L1 sequence RASSSVSYXH wherein X is M or L (SEQ ID NO:35), for example, SEQ ID NO:4 (FIG. 32A), CDR L2 sequence of SEQ ID NO:5 (FIG. 32A), CDR L3 sequence QQWXFNPPT wherein X is S or A (SEQ ID NO:36), for example, SEQ ID NO:6 (FIG. 32A),
CDR H1 sequence of SEQ ID NO:10 (FIG. 32B),
CDR H2 sequence of AIYPGNGXTSYNQKFKG wherein X is D or A (SEQ ID NO:37), for example, SEQ ID NO:11 (FIG. 32B), and
CDR H3 sequence of VVYYSXXYWYFDV wherein the X at position 6 is N, A, Y, W, or D, and the X at position 7 is S or R (SEQ ID NO:38), for example, SEQ ID NO:12 (FIG. 32B).

The humanized 2H7 antibodies herein include those with heavy-chain amino acid sequences containing a C-terminal lysine and those without. The CDR sequences above are generally present within human variable light- and variable heavy-framework sequences, such as substantially the human consensus FR residues of human light-chain kappa subgroup I (V$_L$6I), and substantially the human consensus FR residues of human heavy-chain subgroup III (V$_H$III). See also WO 2004/056312 (Lowman et al.).

The variable heavy region may be joined to a human IgG chain constant region, wherein the region may be, for example, IgG1 or IgG3, including native-sequence and non-native-sequence constant regions.

In a preferred embodiment, such antibody comprises the variable heavy-domain sequence of SEQ ID NO:8 (v16, as shown in FIG. 32B), optionally also comprising the variable light-domain sequence of SEQ ID NO:2 (v16, as shown in FIG. 32A), which optionally comprises one or more amino acid substitution(s) at positions 56, 100, and/or 100a, e.g., D56A, N100A, or N100Y, and/or S100aR in the variable heavy domain and one or more amino acid substitution(s) at positions 32 and/or 92, e.g. M32L and/or S92A, in the variable light domain. Preferably, the antibody is an intact antibody comprising the light-chain amino acid sequence of SEQ ID NO:13 or 30, and heavy-chain amino acid sequence of SEQ ID NO:14, 15, 29, 31, 34, or 39, the sequence of SEQ ID NO:39 being given below.

A preferred humanized 2H7 antibody is ocrelizumab (Genentech, Inc.).

The antibody herein may further comprise at least one amino acid substitution in the Fc region that improves ADCC activity, such as one wherein the amino acid substitutions are at positions 298, 333, and 334, preferably S298A, E333A, and K334A, using Eu numbering of heavy-chain residues. See also U.S. Pat. No. 6,737,056, L. Presta.

Any of these antibodies may comprise at least one substitution in the Fc region that improves FcRn binding or serum half-life, for example, a substitution at heavy-chain position 434, such as N434W. See also U.S. Pat. No. 6,737,056, L. Presta.

Any of these antibodies may further comprise at least one amino acid substitution in the Fc region that increases CDC activity, for example, comprising at least a substitution at position 326, preferably K326A or K326W. See also U.S. Pat. No. 6,528,624, Idusogie et al.

Some preferred humanized 2H7 variants are those comprising the variable light domain of SEQ ID NO:2 and the variable heavy domain of SEQ ID NO:8, including those with or without substitutions in an Fc region (if present), and those comprising a variable heavy domain with alteration in SEQ ID NO:8 of N100A; or D56A and N100A; or D56A, N100Y, and S100aR; and a variable light domain with alteration in SEQ ID NO:2 of M32L; or S92A; or M32L and S92A.

M34 in the variable heavy domain of 2H7.v16 has been identified as a potential source of antibody stability and is another potential candidate for substitution.

In a summary of some various preferred embodiments of the invention, the variable region of variants based on 2H7.v16 comprise the amino acid sequences of v16 except at the positions of amino acid substitutions that are indicated in the table below. Unless otherwise indicated, the 2H7 variants will have the same light chain as that of v16.

| | Exemplary Humanized 2H7 Antibody Variants | | |
|---|---|---|---|
| 2H7 Version | Heavy chain (V$_H$) changes | Light chain (V$_L$) changes | Fc changes |
| 16 for reference | — | — | — |
| 31 | — | — | S298A, E333A, K334A |
| 73 | N100A | M32L | |
| 75 | N100A | M32L | S298A, E333A, K334A |
| 96 | D56A, N100A | S92A | |
| 114 | D56A, N100A | M32L, S92A | S298A, E333A, K334A |
| 115 | D56A, N100A | M32L, S92A | S298A, E333A, K334A, E356D, M358L |
| 116 | D56A, N100A | M32L, S92A | S298A, K322A, K334A, |
| 138 | D56A, N100A | M32L, S92A | S298A, K326A, E333A, K334A, |
| 477 | D56A, N100A | M32L, S92A | S298A, K326A, E333A, K334A, N434W |
| 375 | — | — | K334L |
| 588 | — | — | S298A, K326A, E333A, K334A |
| 511 | D56A, N100Y, S100aR | M32L, S92A | S298A, K326A, E333A, K334A |

One preferred humanized 2H7 comprises 2H7.v16 variable light-domain sequence:

(SEQ ID NO: 2)
DIQMTQSPSSLSASVGDRVTITCRASSSVSYMHWYQQKPGKAPKPLIYAP

SNLASGVPSRFSGSGSGTDFTLTISSLQPEDFATYYCQQWSFNPPTFGQG

TKVEIKR;

and 2H7.v16 variable heavy-domain sequence:

(SEQ ID NO: 8)
EVQLVESGGGLVQPGGSLRLSCAASGYTFTSYNMHWVRQAPGKGLEWVGA

IYPGNGDTSYNQKFKGRFTISVDKSKNTLYLQMNSLRAEDTAVYYCARVV

YYSNSYWYFDVWGQGTLVTVSS.

Where the humanized 2H7.v16 antibody is an intact antibody, it may comprise the light-chain amino acid sequence:

(SEQ ID NO: 13)
DIQMTQSPSSLSASVGDRVTITCRASSSVSYMHWYQQKPGKAPKPLIYAP

SNLASGVPSRFSGSGSGTDFTLTISSLQPEDFATYYCQQWSFNPPTFGQG

TKVEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC;

and the heavy-chain amino acid sequence of SEQ ID NO:14 or:

(SEQ ID NO: 15)
EVQLVESGGGLVQPGGSLRLSCAASGYTFTSYNMHWVRQAPGKGLEWVGA

IYPGNGDTSYNQKFKGRFTISVDKSKNTLYLQMNSLRAEDTAVYYCARVV

YYSNSYWYFDVWGQGTLVTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPRE

PQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLSLSP

G.

Another preferred humanized 2H7 antibody comprises 2H7.v511 variable light-domain sequence:

(SEQ ID NO: 39)
DIQMTQSPSSLSASVGDRVTITCRASSSVSYLHWYQQKPGKAPKPLIYAP

SNLASGVPSRFSGSGSGTDFTLTISSLQPEDFATYYCQQWAFNPPTFGQG

TKVEIKR and 2H7.v511 variable heavy-domain sequence:

(SEQ ID NO: 40)
EVQLVESGGGLVQPGGSLRLSCAASGYTFTSYNMHWVRQAPGKGLEWVGA

IYPGNGATSYNQKFKGRFTISVDKSKNTLYLQMNSLRAEDTAVYYCARVV

YYSYRYWYFDVWGQGTLVTVSS.

Where the humanized 2H7.v511 antibody is an intact antibody, it may comprise the light-chain amino acid sequence:

(SEQ ID NO: 30)
DIQMTQSPSSLSASVGDRVTITCRASSSVSYLHWYQQKPGKAPKPLIYAP

SNLASGVPSRFSGSGSGTDFTLTISSLQPEDFATYYCQQWAFNPPTFGQG

TKVEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC and the heavy-chain amino acid sequence of SEQ ID NO:31 or:

(SEQ ID NO: 41)
EVQLVESGGGLVQPGGSLRLSCAASGYTFTSYNMHWVRQAPGKGLEWVGA

IYPGNGATSYNQKFKGRFTISVDKSKNTLYLQMNSLRAEDTAVYYCARVV

YYSYRYWYFDVWGQGTLVTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREEQ

YNATYRVVSVLTVLHQDWLNGKEYKCKVSNAALPAPIAATISKAKGQPRE

PQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLSLSP

G.

See FIGS. 38 and 39, which align the mature light and heavy chains, respectively, of humanized 2H7.v511 with humanized 2H7.v16 using the C-terminal lysine sequence for the heavy chain.

Where the humanized 2H7.v31 antibody is an intact antibody, it may comprise the light-chain amino acid sequence:

(SEQ ID NO: 13)
DIQMTQSPSSLSASVGDRVTITCRASSSVSYLHWYQQKPGKAPKPLIYAP

SNLASGVPSRFSGSGSGTDFTLTISSLQPEDFATYYCQQWAFNPPTFGQG

TKVEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC and the heavy-chain amino acid sequence of SEQ ID NO:15 or:

(SEQ ID NO: 42)
EVQLVESGGGLVQPGGSLRLSCAASGYTFTSYNMHWVRQAPGKGLEWVGA

IYPGNGDTSYNQKFKGRFTISVDKSKNTLYLQMNSLRAEDTAVYYCARVV

YYSNSYWYFDVWGQGTLVTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREEQ

YNATYRVVSVLTVLHQDWLNGKEYKCKVSNKALPAPIAATISKAKGQPRE

PQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLSLSP

G or:

(SEQ ID NO: 43)
EVQLVESGGGLVQPGGSLRLSCAASGYTFTSYNMHWVRQAPGKGLEWVGA

IYPGNGATSYNQKFKGRFTISVDKSKNTLYLQMNSLRAEDTAVYYCARVV

YYSYRYWYFDVWGQGTLVTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREEQ

YNATYRVVSVLTVLHQDWLNGKEYKCKVSNAALPAPIAATISKAKGQPRE

PQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLSLSP

G.

A preferred embodiment herein is where the antibody is humanized 2H7 comprising the variable domain sequences in SEQ ID NOS:2 and 8 (version 16). Another preferred embodiment herein is where the antibody is humanized 2H7 comprising the variable domain sequences in SEQ ID NOS: 39 and 40 (version 511). Further preferred is where the antibody is humanized 2H7 comprising the variable domain sequences in SEQ ID NOS:32 and 33 (see FIG. 40 re version 114), such as one comprising the variable light-chain domain in SEQ ID NO:32 and the heavy-chain amino acid sequence of SEQ ID NO:34. Further preferred is wherein the antibody is humanized 2H7 comprising a variable heavy-chain domain with alteration N100A, or D56A and N100A, or D56A, N100Y, and S100aR in SEQ ID NO:8 and a variable light-chain domain with alteration M32L, or S92A, or M32L and S92A in SEQ ID NO:2.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, Annu. Rev. Immunol. 9:457-492 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998).

"Human effector cells" are leukocytes that express one or more FcRs and perform effector functions. Preferably, the cells express at least FcγRIII and carry out ADCC effector function. Examples of human leukocytes that mediate ADCC include peripheral blood mononuclear cells (PBMC), natural killer (NK) cells, monocytes, cytotoxic T cells and neutrophils; with PBMCs and NK cells being preferred.

The terms "Fc receptor" or "FcR" are used to describe a receptor that binds to the Fc region of an antibody. The preferred FcR is a native-sequence human FcR. Moreover, a preferred FcR is one that binds an IgG antibody (a gamma receptor) and includes receptors of the FcγRI, FcγRII, and Fcγ RIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see Daëron, Annu. Rev. Immunol. 15:203-234 (1997)). FcRs are reviewed in Ravetch and Kinet, Annu. Rev. Immunol 9:457-492 (1991); Capel et al., Immunomethods 4:25-34 (1994); and de Haas et al., J. Lab. Clin. Med. 126:330-341 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

"Complement-dependent cytotoxicity" or "CDC" refers to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., J. Immunol. Methods 202:163 (1996), may be performed.

"Growth-inhibitory" antibodies are those that prevent or reduce proliferation of a cell expressing an antigen to which the antibody binds. For example, the antibody may prevent or reduce proliferation of B cells in vitro and/or in vivo.

Antibodies that "induce apoptosis" are those that induce programmed cell death, e.g. of a B cell, as determined by standard apoptosis assays, such as binding of annexin V, fragmentation of DNA, cell shrinkage, dilation of endoplasmic reticulum, cell fragmentation, and/or formation of membrane vesicles (called apoptotic bodies).

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain Particular amino acid residues are believed to form an interface between the light chain and heavy chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in ADCC.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-binding sites and is still capable of cross-linking antigen.

"Fv" is the minimum antibody fragment that contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. $F(ab')_2$ antibody fragments originally were produced as pairs of Fab' fragments that have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy chain constant domains that correspond to the different classes of antibodies are called α, δ, ε, γ, and μ, respectively. The subunit structures and three-dimensional configurations of different classes of immunoglobulins are well known.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains that enables the scFv to form the desired structure for antigen binding. For a review of scFv see Plückthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA,* 90:6444-6448 (1993).

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature,* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature,* 352:624-628 (1991) and Marks et al., *J. Mol. Biol.,* 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA,* 81:6851-6855 (1984)). Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences (U.S. Pat. No. 5,693,780).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence, except for FR substitution(s) as noted above. The humanized antibody optionally also will comprise at least a portion of an immunoglobulin constant region, typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

The term "hypervariable region" when used herein refers to the amino acid residues of an antibody that are responsible for antigen binding. The hypervariable region comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101

(H3) in the heavy chain variable domain; Chothia and Lesk *J. Mol. Biol.* 196:901-917 (1987)). "Framework" or "FR" residues are those variable domain residues other than the hypervariable region residues as herein defined.

A "naked antibody" is an antibody (as herein defined) that is not conjugated to a heterologous molecule, such as a cytotoxic moiety, polymer, or radiolabel.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

"Joint damage" is used in the broadest sense and refers to damage or partial or complete destruction to any part of one or more joints, including the connective tissue and cartilage, where damage includes structural and/or functional damage of any cause, and may or may not cause joint pain/arthalgia. It includes, without limitation, joint damage associated with or resulting from inflammatory joint disease as well as non-inflammatory joint disease. This damage may be caused by any condition, such as an autoimmune disease such as lupus (e.g., systemic lupus erythematosus), arthritis (e.g., acute and chronic arthritis, rheumatoid arthritis including juvenile-onset rheumatoid arthritis, juvenile idiopathic arthritis (JIA), or juvenile RA (JRA), and stages such as rheumatoid synovitis, gout or gouty arthritis, acute immunological arthritis, chronic inflammatory arthritis, degenerative arthritis, type II collagen-induced arthritis, infectious arthritis, septic arthritis, Lyme arthritis, proliferative arthritis, psoriatic arthritis, Still's disease, vertebral arthritis, osteoarthritis, arthritis chronica progrediente, arthritis deformans, polyarthritis chronica primaria, reactive arthritis, menopausal arthritis, estrogen-depletion arthritis, and ankylosing spondylitis/rheumatoid spondylitis), rheumatic autoimmune disease other than RA, significant systemic involvement secondary to RA (including but not limited to vasculitis, pulmonary fibrosis or Felty's syndrome), Sjögren's syndrome, particular secondary such syndrome, secondary limited cutaneous vasculitis with RA, seronegative spondyloarthropathy, Lyme disease, inflammatory bowel disease, scleroderma, inflammatory myopathy, mixed connective tissue disease, any overlap syndrome, bursitis, tendonitis, osteomyelitis, infectious diseases, including influenza, measles (rubeola), rheumatic fever, Epstein-Barr viral syndrome, hepatitis, mumps, rebella (German measles), and varicella (chickenpox), Chondromalacia patellae, collagenous colitis, autoimmune disorders associated with collagen disease, joint inflammation, unusual exertion or overuse such as sprains or strains, injury including fracture, gout, especially found in the big toe, as well as caused by neurological disorders, hemophilic disorders (for example, hemophilic arthropathy), muscular disorders, progressive disorders, bone disorders, cartilage disorders, and vascular disorders. For purposes herein, joints are points of contact between elements of a skeleton (of a vertebrate such as an animal) with the parts that surround and support it and include, but are not limited to, for example, hips, joints between the vertebrae of the spine, joints between the spine and pelvis (sacroiliac joints), joints where the tendons and ligaments attach to bones, joints between the ribs and spine, shoulders, knees, feet, elbows, hands, fingers, ankles and toes, but especially joints in the hands and feet.

A "subject" herein is a human subject, including a patient, eligible for treatment who is experiencing or has experienced one or more signs, symptoms, or other indicators of joint damage, has been diagnosed with joint damage, whether, for example, newly diagnosed or previously diagnosed and now experiencing a recurrence or relapse, or is at risk for developing joint damage, no matter the cause. The subject may have been previously treated with CD20 antibody or not so treated. A subject eligible for treatment of joint damage may optionally be identified as one who has been screened, as in the blood, for elevated levels of infiltrating CD20 cells or is screened using an assay to detect auto-antibodies, wherein autoantibody production is assessed qualitatively, and preferably quantitatively. The subject may be naïve to a second medicament being used when the treatment is started, i.e., the subject has not been previously treated with, for example, an immunosuppressive agent such as methotrexate at "baseline" (i.e., at a set point in time before the administration of a first dose of CD20 antibody in the treatment method herein, such as the day of screening the subject before treatment is commenced). Such subjects are generally considered to be candidates for treatment with such second medicament.

"Treatment" of a subject herein refers to both therapeutic treatment and prophylactic or preventative measures. Those in need of treatment include those already with joint damage as well as those in which the joint damage or the progress of joint damage is to be prevented. Hence, the subject may have been diagnosed as having the joint damage or may be predisposed or susceptible to the joint damage, or may have limited joint damage, which is likely to progress in the absence of treatment. Treatment is successful herein if the joint damage is alleviated or healed, or progression of joint or structural damage is halted or slowed down as compared to prior to administration. Successful treatment further includes complete or partial prevention of the development of joint damage. For purposes herein, slowing down or reducing joint damage or the progression of joint damage is the same as arrest, decrease, or reversal in the joint damage.

"Clinical improvement" refers to prevention of further progress of joint damage or any improvement in joint damage as a result of treatment, as determined by other than radiographic testing. Thus, clinical improvement may, for example, be determined by assessing the number of tender or swollen joints, the Psoriasis Assessment Severity Index, a global clinical assessment of the subject, assessing erythrocyte sedimentation rate, or assessing the amount of C-reactive protein level.

For purposes herein, a subject is in "remission" if he/she has no symptoms of active joint damage, such as those detectable by the methods disclosed herein, and has had no progression of joint damage as assessed at baseline or at a certain point of time during treatment. Those who are not in remission include, for example, those experiencing a worsening or progression of joint damage. Such subjects experiencing a return of symptoms, including active joint damage, are those who have "relapsed" or had a "recurrence."

A "symptom" of joint damage is any morbid phenomenon or departure from the normal in structure, function, or sensation, experienced by the subject and indicative of joint damage, such as those noted above, including tender or swollen joints.

The expression "effective amount" refers to an amount of the antibody or antagonist that is effective for treating joint damage, including an amount that is effective in achieving a reduction in joint damage as compared to baseline prior to administration of such amount as determined by radiographic testing. An effective amount of other medicaments such as second medicaments is an amount of such medicament effective to treat joint damage or other undesirable effects, including side-effects or symptoms or other conditions accompanying joint damage, including an underlying disease or disorder.

"Total modified Sharp score" means a score obtained for assessment of radiographs using the method according to Sharp, as modified by Genant, *Am. J. Med.,* 30: 35-47 (1983). The primary assessment will be the change in the total Sharp-Genant score from screening. The Sharp-Genant score combines an erosion score and a joint space narrowing score of both hands and feet. Joint damage is measured in this test scoring by a mean change of less than the score at baseline (when patient is screened or tested before first administration of CD20 antagonist herein).

As used herein, "rheumatoid arthritis" refers to a recognized disease state which may be diagnosed according to the 2000 revised American Rheumatoid Association criteria for the classification of rheumatoid arthritis, or any similar criteria. Physiological indicators of RA include, symmetric joint swelling which is characteristic though not invariable in rheumatoid arthritis. Fusiform swelling of the proximal interphalangeal (PIP) joints of the hands as well as metacarpophalangeal (MCP), wrists, elbows, knees, ankles and metatarsophalangeal (MTP) joints are commonly affected and swelling is easily detected. Pain on passive motion is the most sensitive test for joint inflammation, and inflammation and structural deformity often limits the range of motion for the affected joint. Typical visible changes include ulnar deviation of the fingers at the MCP joints, hyperextension or hyperflexion of the MCP and PIP joints, flexion contractures of the elbows, and subluxation of the carpal bones and toes. The subject with rheumatoid arthritis may be resistant to DMARDs, in that the DMARDs are not effective or fully effective in treating symptoms. Further, candidates for therapy according to this invention include those who have experienced an inadequate response to previous or current treatment with TNF inhibitors such as etanercept, infliximab and/or adalimumab because of toxicity or inadequate efficacy (for example, etanercept for 3 months at 25 mg twice a week or at least 4 infusions of infliximab at 3 mg/kg). A patient with "active rheumatoid arthritis" means a patient with active and not latent symptoms of rheumatoid arthritis. Subjects with "early active rheumatoid arthritis" are those subjects with active rheumatoid arthritis diagnosed for at least 8 weeks but no longer than four years, according to the revised 1987 ACR criteria for the classification of RA.

Psoriatic arthritis (PsA) is an inflammatory joint disease characterized by extensive bone resorption. Also disclosed herein, blood samples from PsA patients, particularly those with bone erosions on plain radiographs, exhibit a marked increase in osteoclast precursors (OCP) compared to healthy controls.

"Antibody exposure" refers to contact with or exposure to the antibody herein in one or more doses administered over a period of time of about 1 day to about 5 weeks. The doses may be given at one time or at a fixed or at irregular time intervals over this period of exposure, such as, for example, one dose weekly for four weeks or two doses separated by a time interval of about 13-17 days. Initial and later antibody exposures are separated in time from each other as described in detail herein.

An exposure not being administered or provided until a certain time "from the initial exposure" or from any prior exposure means that the time for the second or later exposure is measured from the time any of the doses from the prior exposure were administered, if more than one dose was administered in that exposure. For example, when two doses are administered in an initial exposure, the second exposure is not given until at least about 16-54 weeks as measured from the time the first or the second dose was administered within that prior exposure. Similarly, when three doses are administered, the second exposure may be measured from the time of the first, second, or third dose within the prior exposure. Preferably, "from the initial exposure" or from any prior disclosure is measured from the time of the first dose.

The term "immunosuppressive agent" as used herein for adjunct therapy refers to substances that act to suppress or mask the immune system of the mammal being treated herein. This would include substances that suppress cytokine production, down-regulate or suppress self-antigen expression, or mask the MHC antigens. Examples of such agents include 2-amino-6-aryl-5-substituted pyrimidines (see U.S. Pat. No. 4,665,077); non-steroidal anti-inflammatory drugs (NSAIDs); ganciclovir, tacrolimus, glucocorticoids such as cortisol or aldosterone, anti-inflammatory agents such as a cyclooxygenase inhibitor, a 5-lipoxygenase inhibitor, or a leukotriene receptor antagonist; purine antagonists such as azathioprine or mycophenolate mofetil (MMF); alkylating agents such as cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporin A; steroids such as corticosteroids or glucocorticosteroids or glucocorticoid analogs, e.g., prednisone, methylprednisolone, including SOLU-MEDROL® methylprednisolone sodium succinate, and dexamethasone; dihydrofolate reductase inhibitors such as methotrexate (oral or subcutaneous); anti-malarial agents such as chloroquine and hydroxychloroquine; sulfasalazine; leflunomide; cytokine antagonists such as cytokine antibodies or cytokine receptor antibodies including anti-interferon-alpha, -beta, or -gamma antibodies, anti-tumor necrosis factor (TNF)-alpha antibodies (infliximab (REMICADE®) or adalimumab), anti-TNF-alpha immunoadhesin (etanercept), anti-TNF-beta antibodies, anti-interleukin-2 (IL-2) antibodies and anti-IL-2 receptor antibodies, and anti-interleukin-6 (IL-6) receptor antibodies and antagonists; anti-LFA-1 antibodies, including anti-CD11a and anti-CD18 antibodies; anti-L3T4 antibodies; heterologous anti-lymphocyte globulin; pan-T antibodies, preferably anti-CD3 or anti-CD4/CD4a antibodies; soluble peptide containing a LFA-3 binding domain (WO 90/08187 published Jul. 26, 1990); streptokinase; transforming growth factor-beta (TGF-beta); streptodornase; RNA or DNA from the host; FK506; RS-61443; chlorambucil; deoxyspergualin; rapamycin; T-cell receptor (Cohen et al., U.S. Pat. No. 5,114,721); T-cell receptor fragments (Officer et al., *Science,* 251: 430-432 (1991); WO 90/11294; Ianeway, *Nature,* 341: 482 (1989); and WO 91/01133); BAFF antagonists such as BAFF antibodies and BR3 antibodies and zTNF4 antagonists (for review, see Mackay and Mackay, *Trends Immunol.,* 23:113-5 (2002)); biologic agents that interfere with T cell helper signals, such as anti-CD40 receptor or anti-CD40 ligand (CD154), including blocking antibodies to CD4O-CD40 ligand (e.g., Durie et al., *Science,* 261: 1328-30 (1993); Mohan et al., *J. Immunol.,* 154: 1470-80 (1995)) and CTLA4-Ig (Finck et al., *Science,* 265: 1225-7 (1994)); and T-cell receptor antibodies (EP 340,109) such as T10B9. Some immunosuppressive agents herein are also DMARDs, such as methotrexate. Examples of preferred immunosuppressive agents herein include cyclophosphamide, chlorambucil, azathioprine, leflunomide, MMF, or methotrexate.

The term "cytokine" is a generic term for proteins released by one cell population that act on another cell as intercellular mediators. Examples of such cytokines are lymphokines, monokines; interleukins (ILs) such as IL-1, IL-1α, IL-2, IL-3, IL-4, IL-5, IL-6, IL-7, IL-8, IL-9, IL-11, IL-12, IL-15, including PROLEUKIN® rIL-2; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native-sequence cytokines, including synthetically produced small-molecule entities and pharmaceutically acceptable derivatives and salts thereof. A "cytokine antagonist" is a molecule that inhibits or antagonizes such cytokines by any mechanism, including, for example, antibodies to the cytokine, antibodies to the cytokine receptor, and immunoadhesins.

The term "hormone" refers to polypeptide hormones, which are generally secreted by glandular organs with ducts. Included among the hormones are, for example, growth hormone such as human growth hormone, N-methionyl human growth hormone, and bovine growth hormone; parathyroid hormone; thyroxine; insulin; proinsulin; relaxin; estradiol; hormone-replacement therapy; androgens such as calusterone, dromostanolone propionate, epitiostanol, mepitiostane, or testolactone; prorelaxin; glycoprotein hormones such as follicle stimulating hormone (FSH), thyroid stimulating hormone (TSH), and luteinizing hormone (LH); prolactin, placental lactogen, mouse gonadotropin-associated peptide, gonadotropin-releasing hormone; inhibin; activin; mullerian-inhibiting substance; and thrombopoietin. As used herein, the term hormone includes proteins from natural sources or from recombinant cell culture and biologically active equivalents of the native-sequence hormone, including synthetically produced small-molecule entities and pharmaceutically acceptable derivatives and salts thereof.

The term "growth factor" refers to proteins that promote growth, and include, for example, hepatic growth factor; fibroblast growth factor; vascular endothelial growth factor; nerve growth factors such as NGF-β; platelet-derived growth factor; transforming growth factors (TGFs) such as TGF-α and TGF-β; insulin-like growth factor-I and -II; erythropoietin (EPO); osteoinductive factors; interferons such as interferon-α, -β, and -γ; and colony stimulating factors (CSFs) such as macrophage-CSF (M-CSF); granulocyte-macrophage-CSF (GM-CSF); and granulocyte-CSF (G-CSF). As used herein, the term growth factor includes proteins from natural sources or from recombinant cell culture and biologically active equivalents of the native-sequence growth factor, including synthetically produced small-molecule entities and pharmaceutically acceptable derivatives and salts thereof.

The term "integrin" refers to a receptor protein that allows cells both to bind to and to respond to the extracellular matrix and is involved in a variety of cellular functions such as wound healing, cell differentiation, homing of tumor cells and apoptosis. They are part of a large family of cell adhesion receptors that are involved in cell-extracellular matrix and cell-cell interactions. Functional integrins consist of two transmembrane glycoprotein subunits, called alpha and beta, that are non-covalently bound. The alpha subunits all share some homology to each other, as do the beta subunits. The receptors always contain one alpha chain and one beta chain Examples include Alpha6beta1, Alpha3beta1, Alpha7beta1, LFA-1 etc. As used herein, the term "integrin" includes proteins from natural sources or from recombinant cell culture and biologically active equivalents of the native-sequence integrin, including synthetically produced small-molecule entities and pharmaceutically acceptable derivatives and salts thereof.

For the purposes herein, "tumor necrosis factor alpha (TNF-alpha)" refers to a human TNF-alpha molecule comprising the amino acid sequence as described in Pennica et al., *Nature,* 312:721 (1984) or Aggarwal et al., *JBC,* 260: 2345 (1985). A "TNF-alpha inhibitor" herein is an agent that inhibits, to some extent, a biological function of TNF-alpha, generally through binding to TNF-alpha and neutralizing its activity. Examples of TNF inhibitors specifically contemplated herein are etanercept (ENBREL®), infliximab (REMICADE®), and adalimumab (HUMIRA™).

Examples of "disease-modifying anti-rheumatic drugs" or "DMARDs" include hydroxycloroquine, sulfasalazine, methotrexate, leflunomide, etanercept, infliximab (plus oral and subcutaneous methotrexate), azathioprine, D-penicillamine, gold salts (oral), gold salts (intramuscular), minocycline, cyclosporine including cyclosporine A and topical cyclosporine, staphylococcal protein A (Goodyear and Silverman, *J. Exp. Med.,* 197, (9), p 1125-39 (2003)), including salts and derivatives thereof, etc. A preferred DMARD herein is methotrexate.

Examples of "non-steroidal anti-inflammatory drugs" or "NSAIDs" include aspirin, acetylsalicylic acid, ibuprofen, flurbiprofen, naproxen, indomethacin, sulindac, tolmetin, phenylbutazone, diclofenac, ketoprofen, benorylate, mefenamic acid, methotrexate, fenbufen, azapropazone; COX-2 inhibitors such as celecoxib (CELEBREX®; 4-(5-(4-methylphenyl)-3-(trifluoromethyl)-1H-pyrazol-1-yl) benzenesulfonamide, valdecoxib (BEXTRA®), meloxicam (MOBIC®), GR 253035 (Glaxo Wellcome); and MK966 (Merck Sharp & Dohme), including salts and derivatives thereof, etc. Preferably, they are aspirin, naproxen, ibuprofen, indomethacin, or tolmetin.

Examples of "integrin antagonists or antibodies" herein include an LFA-1 antibody, such as efalizumab (RAPTIVA®) commercially available from Genentech, or an alpha 4 integrin antibody such as natalizumab (ANTEGREN®) available from Biogen, or diazacyclic phenylalanine derivatives (WO 2003/89410), phenylalanine derivatives (WO 2003/70709, WO 2002/28830, WO 2002/16329 and WO 2003/53926), phenylpropionic acid derivatives (WO 2003/10135), enamine derivatives (WO 2001/79173), propanoic acid derivatives (WO 2000/37444), alkanoic acid derivatives (WO 2000/32575), substituted phenyl derivatives (U.S. Pat. Nos. 6,677,339 and 6,348,463), aromatic amine derivatives (U.S. Pat. No. 6,369,229), ADAM disintegrin domain polypeptides (US2002/0042368), antibodies to alphavbeta3 integrin (EP 633945), aza-bridged bicyclic amino acid derivatives (WO 2002/02556), etc.

"Corticosteroid" refers to any one of several synthetic or naturally occurring substances with the general chemical structure of steroids that mimic or augment the effects of the naturally occurring corticosteroids. Examples of synthetic corticosteroids include prednisone, prednisolone (including methylprednisolone, such as SOLU-MEDROL® methylprednisolone sodium succinate), dexamethasone or dexamethasone triamcinolone, hydrocortisone, and betamethasone. The preferred corticosteroids herein are prednisone, methylprednisolone, hydrocortisone, or dexamethasone.

The terms "BAFF," "BAFF polypeptide," "TALL-1" or "TALL-1 polypeptide," and "BLyS" when used herein encompass "native-sequence BAFF polypeptides" and "BAFF variants". "BAFF" is a designation given to those polypeptides that have any one of the amino acid sequences shown below:

Human BAFF sequence (SEQ ID NO:16):

```
  1  MDDSTEREQSRLTSCLKKREEMKLKECVSILPRKESPSVRSSKDGKLLAATLLLALLSCC

61  LTVVSFYQVAALQGDLASLRAELQGHHAEKLPAGAGAPKAGLEEAPAVTAGLKIFEPPAP

121  GEGNSSQNSRNKRAVQGPEETVTQDCLQLIADSETPTIQKGSYTFVPWLLSFKRGSALEE

181  KENKILVKETGYFFIYGQVLYTDKTYAMGHLIQRKKVHVFGDELSLVTLFRCIQNMPETL

241  PNNSCYSAGIAKLEEGDELQLAIPRENAQISLDGDVTFFGALKLL
```

Mouse BAFF sequence (SEQ ID NO:17):

```
  1  MDESAKTLPPPCLCFCSEKGEDMKVGYDPITPQKEEGAWFGICRDGRLLAATLLLALLSS

61  SFTAMSLYQLAALQADLMNLRMELQSYRGSATPAAAGAPELTAGVKLLTPAAPRPHNSSR

121  GHRNRRAFQGPEETEQDVDLSAPPAPCLPGCRHSQHDDNGMNLRNIIQDCLQLIADSDTP

181  TIRKGTYTFVPWLLSFKRGNALEEKENKIVVRQTGYFFIYSQVLYTDPIFAMGHVIQRKK

241  VHVFGDELSLVTLFRCIQNMPKTLPNNSCYSAGIARLEEGDEIQLAIPRENAQISRNGDD

301  TFFGALKLL
``` and homologs and fragments and variants thereof, which have the biological activity of the native BAFF. A biological activity of BAFF can be selected from the group consisting of promoting B-cell survival, promoting B-cell maturation and binding to BR3. Variants of BAFF will preferably have at least 80% or any successive integer up to 100% including, more preferably, at least 90%, and even more preferably, at least 95% amino acid sequence identity with a native sequence of a BAFF polypeptide.

A "native-sequence" BAFF polypeptide comprises a polypeptide having the same amino acid sequence as the corresponding BAFF polypeptide derived from nature. For example, BAFF exists in a soluble form following cleavage from the cell surface by furin-type proteases. Such native-sequence BAFF polypeptides can be isolated from nature or can be produced by recombinant and/or synthetic means.

The term "native-sequence BAFF polypeptide" or "native BAFF" specifically encompasses naturally occurring truncated or secreted forms (e.g., an extracellular domain sequence), naturally occurring variant forms (e.g., alternatively spliced forms), and naturally occurring allelic variants of the polypeptide. The term "BAFF" includes those polypeptides described in Shu et al., *J. Leukocyte Biol.*, 65:680 (1999); GenBank Accession No. AF136293; WO 1998/18921 published May 7, 1998; EP 869,180 published Oct. 7, 1998; WO 1998/27114 published Jun. 25, 1998; WO 1999/12964 published Mar. 18, 1999; WO 1999/33980 published Jul. 8, 1999; Moore et al., *Science,* 285:260-263 (1999); Schneider et al., *J. Exp. Med.*, 189:1747-1756 (1999) and Mukhopadhyay et al., *J. Biol. Chem.*, 274:15978-15981 (1999).

The term "BAFF antagonist" as used herein is used in the broadest sense, and includes any molecule that (1) binds a native-sequence BAFF polypeptide or binds a native-sequence of BR3 to partially or fully block BR3 interaction with BAFF polypeptide, and (2) partially or fully blocks, inhibits, or neutralizes native-sequence BAFF activity. In one preferred embodiment the BAFF receptor to be blocked is the BR3 receptor. Native BAFF activity promotes, among other things, B-cell survival and/or B-cell maturation. In one embodiment, the inhibition, blockage or neutralization of BAFF activity results in a reduction in the number of B cells. A BAFF antagonist according to this invention will partially or fully block, inhibit, or neutralize one or more biological activities of a BAFF polypeptide, in vitro and/or in vivo. In one embodiment, a biologically active BAFF potentiates any one or a combination of the following events in vitro and/or in vivo: an increased survival of B cells, an increased level of IgG and/or IgM, an increased numbers of plasma cells, and processing of NF-κb2/100 to p52 NF-κb in splenic B cells (e.g., Batten et al., *J. Exp. Med.* 192:1453-1465 (2000); Moore et al., *Science* 285:260-263 (1999); Kayagaki et al. *Immunity* 17:515-524 (2002)).

As mentioned above, a BAFF antagonist can function in a direct or indirect manner to partially or fully block, inhibit or neutralize BAFF signaling, in vitro or in vivo. For instance, the BAFF antagonist can directly bind BAFF. For example, BAFF antibodies that bind within a region of human BAFF comprising residues 162-275 and/or a neighboring residue of a residue selected from the group consisting of 162, 163, 206, 211, 231, 233, 264 and 265 of human BAFF such that the antibody sterically hinders BAFF binding to BR3 are contemplated, where such residue numbers refer to SEQ ID NO:16. In another example, a direct binder is a polypeptide comprising any portion of a BAFF receptor that binds BAFF such as an extracellular domain of a BAFF receptor, or fragments and variants thereof that bind native BAFF. In another example, BAFF antagonists include the polypeptides having a sequence of a polypeptide comprising the sequence of Formula I: $X_1$-C-$X_3$-D-$X_5$-L-$X_7$-$X_8$-$X_9$-$X_{10}$-$X_{11}$-$X_{12}$-C-$X_{14}$-$X_{15}$-$X_{16}$-$X_{17}$ (Formula I) (SEQ ID NO:18) wherein $X_1$, $X_3$, $X_5$, $X_7$, $X_8$, $X_9$, $X_{10}$, $X_{11}$, $X_{12}$, $X_{14}$, $X_{15}$ and $X_{17}$ are any amino acid except cysteine; and wherein $X_{16}$ is an amino acid selected from the group consisting of L, F, I and V; and wherein the polypeptide does not comprise a cysteine within seven amino acid residues N-terminal to the most N-terminal cysteine C and C-terminal to the most C-terminal cysteine C of Formula I.

In one embodiment, a polypeptide comprising the sequence of Formula I has the two Cs joined by disulfide bonding; $X_5LX_7X_8$ forming the conformation of a type I beta turn structure with the center of the turn between L and $X_7$; and has a positive value for the dihedral angle phi of $X_8$. In one embodiment, $X_{10}$ is selected from the group consisting of W, F, V, L, I, Y, M and a non-polar amino amino acid. In another embodiment, $X_{10}$ is W. In another embodiment, $X_3$ is an amino acid selected from the group consisting of M, V, L, I, Y, F, W and a non-polar amino acid. In another embodiment, $X_5$ is selected from the group consisting of V, L, P, S, I, A and R. In another embodiment, $X_7$ is selected from the group consisting of V, T, I and L. In another embodiment, $X_8$ is selected from the group consisting of R, K, G, N, H and a D-amino acid. In another embodiment, $X_9$ is selected from the group consisting of H, K, A, R and Q. In another embodiment, $X_{11}$ is I or V. In another embodiment, $X_{12}$ is selected from the group consisting of P, A, D, E and S. In another embodiment, $X_{16}$ is L. In one specific embodiment, the sequence of Formula I is a sequence selected from the group consisting of ECFDLL-VRAWVPCSVLK (SEQ ID NO:19), ECFDLLVRHWVP-CGLLR (SEQ ID NO:20), ECFDLLVRRWVPCEMLG (SEQ ID NO:21), ECFDLLVRSWVPCHMLR (SEQ ID NO:22), ECFDLLVRHWVACGLLR (SEQ ID NO:23), and QCFDRLNAWVPCSVLK (SEQ ID NO:24). In a preferred embodiment, the BAFF antagonist comprises any one of the amino acid sequences selected from the group consisting of SEQ ID NO:19, 20, 21, 22, and 23.

In still another example, BAFF antagonists include the polypeptides having a sequence of a polypeptide comprising the sequence of Formula II: $X_1$-C-$X_3$-D-$X_5$-L-V-$X_8$-$X_9$-W-V-P-C-$X_{14}$-$X_{15}$-L-$X_{17}$ (Formula II) (SEQ ID NO:25)

wherein $X_1$, $X_3$, $X_5$, $X_8$, $X_9$, $X_{14}$, $X_{15}$ and $X_{17}$ are any amino acid, except cysteine; and wherein the polypeptide does not comprise a cysteine within seven amino acid residues N-terminal to the most N-terminal cysteine C and C-terminal to the most C-terminal cysteine C of Formula II.

In one embodiment, a polypeptide comprising the sequence of Formula II has a disulfide bond between the two Cs and has the conformation of $X_5LX_7X_8$ forming a type I beta turn structure with the center of the turn between L and $X_7$; and has a positive value for the dihedral angle phi of $X_8$. In another embodiment of Formula II, $X_3$ is an amino acid selected from the group consisting of M, A, V, L, I, Y, F, W and a non-polar amino acid. In another embodiment of Formula II, $X_5$ is selected from the group consisting of V, L, P, S, I, A and R. In another embodiment of Formula II, $X_8$ is selected from the group consisting of R, K, G, N, H and D-amino acid. In another embodiment of Formula II, $X_9$ is selected from the group consisting of H, K, A, R and Q.

In a further embodiment, the BAFF receptor from which the extracellular domain or BAFF-binding fragment or BAFF-binding variant thereof is derived is TACI, BR3 or BCMA. Alternatively, the BAFF antagonist can bind an extracellular domain of a native-sequence BR3 at its BAFF binding region to partially or fully block, inhibit or neutralize BAFF binding to BR3 in vitro, in situ, or in vivo. For example, such indirect antagonist is an anti-BR3 antibody that binds in a region of BR3 comprising residues 23-38 of human BR3 as defined below (SEQ ID NO:26) or a neighboring region of those residues such that binding of human BR3 to BAFF is sterically hindered.

In some embodiments, a BAFF antagonist according to this invention includes BAFF antibodies and immunoadhesins comprising an extracellular domain of a BAFF receptor, or fragments and variants thereof that bind native BAFF. In a further embodiment, the BAFF receptor from which the extracellular domain or BAFF-binding fragment or BAFF-binding variant thereof is derived is TACI, BR3 or BCMA. In a still another embodiment, the immunoadhesin comprises an amino acid sequence of that of Formula I or Formula II as set forth above, including an amino acid sequence selected from any one of the group consisting of SEQ ID NOS: 19, 20, 21, 22, 23, and 24.

According to one embodiment, the BAFF antagonist binds to a BAFF polypeptide or a BR3 polypeptide with a binding affinity of 100 nM or less. According to another embodiment, the BAFF antagonist binds to a BAFF polypeptide or a BR3 polypeptide with a binding affinity of 10 nM or less. According to yet another embodiment, the BAFF antagonist binds to a BAFF polypeptide or a BR3 polypeptide with a binding affinity of 1 nM or less.

The terms "BR3", "BR3 polypeptide" or "BR3 receptor" when used herein encompass "native-sequence BR3 polypeptides" and "BR3 variants" (which are further defined herein). "BR3" is a designation given to those polypeptides comprising the following amino acid sequence and homologs thereof, and variants or fragments thereof that bind native BAFF: Human BR3 sequence (SEQ ID NO:26):

```
  1 MRRGPRSLRGRDAPAPTPCVPAECFDLLVRHCVACGLLRTPRPKPAGASSPAPRTALQPQ

61 ESVGAGAGEAALPLPGLLFGAPALLGLALVLALVLVGLVSWRRRQRRLRGASSAEAPDGD

121 KDAPEPLDKVIILSPGISDATAPAWPPPGEDPGTTPPGHSVPVPATELGSTELVTTKTAG

181 PEQQ.
```

The BR3 polypeptides of the invention can be isolated from a variety of sources, such as from human tissue types or from another source, or prepared by recombinant and/or synthetic methods. The term BR3 includes the BR3 polypeptides described in WO 2002/24909 and WO 2003/14294.

A "native-sequence" BR3 polypeptide or "native BR3" comprises a polypeptide having the same amino acid sequence as the corresponding BR3 polypeptide derived from nature. Such native-sequence BR3 polypeptides can be isolated from nature or can be produced by recombinant and/or synthetic means. The term "native-sequence BR3 polypeptide" specifically encompasses naturally occurring truncated, soluble or secreted forms (e.g., an extracellular domain sequence), naturally occurring variant forms (e.g., alternatively spliced forms) and naturally occurring allelic variants of the polypeptide. The BR3 polypeptides of the invention include the BR3 polypeptide comprising or consisting of the contiguous sequence of amino acid residues 1 to 184 of a human BR3 (SEQ ID NO:26).

A BR3 "extracellular domain" or "ECD" refers to a form of the BR3 polypeptide that is essentially free of the transmembrane and cytoplasmic domains. ECD forms of BR3 include a polypeptide comprising any one of the amino acid sequences selected from the group consisting of amino acids 1-77, 2-62, 2-71, 1-61, 7-71, 23-38 and 2-63 of human BR3. The invention contemplates BAFF antagonists that are polypeptides comprising any one of the above-mentioned ECD forms of human BR3 and variants and fragments thereof that bind a native BAFF.

Mini-BR3 is a 26-residue core region of the BAFF-binding domain of BR3, i.e., the amino acid sequence: TPCVPAECFD LLVRHCVACG LLRTPR (SEQ ID NO:27)

"BR3 variant" means a BR3 polypeptide having at least about 80% amino acid sequence identity with the amino acid sequence of a native-sequence, full-length BR3 or BR3 ECD and binds a native-sequence BAFF polypeptide. Optionally, the BR3 variant includes a single cysteine-rich domain. Such BR3 variant polypeptides include, for instance, BR3 polypeptides wherein one or more amino acid residues are added, or deleted, at the N- and/or C-terminus, as well as within one or more internal domains, of the full-length amino acid sequence. Fragments of the BR3 ECD that bind a native sequence BAFF polypeptide are also contemplated. According to one embodiment, a BR3 variant polypeptide will have at least about 80% amino acid sequence identity, at least about 81% amino acid sequence identity, at least about 82% amino acid sequence identity, at least about 83% amino acid sequence identity, at least about 84% amino acid sequence identity, at least about 85% amino acid sequence identity, at least about 86% amino acid sequence identity, at least about 87% amino acid sequence identity, at least about 88% amino acid sequence identity, at least about 89% amino acid sequence identity, at least about 90% amino acid sequence identity, at least about 91% amino acid sequence identity, at least about 92% amino acid sequence identity, at least about 93% amino acid sequence identity, at least about 94% amino acid sequence identity, at least about 95% amino acid sequence identity, at least about 96% amino acid sequence identity, at least about 97% amino acid sequence identity, at least about 98% amino acid sequence identity or at least about 99% amino acid sequence identity with a human BR3 polypeptide or a specified fragment thereof (e.g., ECD). BR3 variant polypeptides do not encompass the native BR3 polypeptide sequence. According to another embodiment, BR3 variant polypeptides are at least about 10 amino acids in length, at least about 20 amino acids in length, at least about 30 amino acids in length, at least about 40 amino acids in length, at least about 50 amino acids in length, at least about 60 amino acids in length, or at least about 70 amino acids in length.

In one preferred embodiment, the BAFF antagonists herein are immunoadhesins comprising a portion of BR3, TACI or BCMA that binds BAFF, or variants thereof that bind BAFF. In other embodiments, the BAFF antagonist is a BAFF antibody. A "BAFF antibody" is an antibody that binds BAFF, and preferably binds BAFF within a region of human BAFF comprising residues 162-275 of the human BAFF sequence disclosed herein under the "BAFF" definition (SEQ ID NO:16). In another embodiment, the BAFF antagonist is BR3 antibody. A "BR3 antibody" is an antibody that binds BR3, and is preferably one that binds BR3 within a region of human BR3 comprising residues 23-38 of the human BR3 sequence disclosed herein under the "BR3" definition (SEQ ID NO:26). In general, the amino acid positions of human BAFF and human BR3 referred to herein are according to the sequence numbering under human BAFF and human BR3, SEQ ID NOS: 16 and 26, respectively, disclosed herein under the "BAFF" and "BR3" definitions.

Other examples of BAFF-binding polypeptides or BAFF antibodies can be found in, e.g., WO 2002/092620, WO 2003/014294, Gordon et al., *Biochemistry* 42(20):5977-5983 (2003), Kelley et al., *J. Biol. Chem.* 279 (16):16727-16735 (2004), WO 1998/18921, WO 2001/12812, WO 2000/68378 and WO 2000/40716.

A "package insert" is used to refer to instructions customarily included in commercial packages of therapeutic products, that contain information about the indications, usage, dosage, administration, contraindications, other therapeutic products to be combined with the packaged product, and/or warnings concerning the use of such therapeutic products, etc.

A "medicament" is an active drug to treat the joint damage or its symptoms or side effects.

II. Therapy

In one aspect, the present invention provides a method of treating joint damage in a subject such as a patient comprising administering an antagonist, preferably an antibody, that binds to a B-cell surface marker (more preferably a CD20 antibody) to the subject and assessing by radiographic x-ray if the subject has shown a reduction in joint damage upon treatment.

Thus, the invention contemplates a method for treating joint damage in a subject comprising administering an antagonist that binds to a B-cell surface marker to the subject and giving the subject, at least about one month after the administration, a radiographic test that measures a reduction in the joint damage as compared to baseline prior to the administration, wherein the amount of antagonist administered is effective in achieving a reduction in the joint damage, indicating that the subject has been successfully treated for the joint damage.

The invention also contemplates a method for treating joint damage in a subject comprising administering an antibody that binds to a B-cell surface marker to the subject and giving the subject, at least about one month after the administration, a radiographic test that measures a reduction in the joint damage as compared to baseline prior to the administration, wherein the amount of antibody administered is effective in achieving a reduction in the joint damage, indicating that the subject has been successfully treated for the joint damage.

The invention further contemplates a method for treating joint damage in a subject comprising administering a CD20 antibody to the subject and giving the subject, at least about one month after the administration, a radiographic test that measures a reduction in the joint damage as compared to baseline prior to the administration, wherein the amount of CD20 antibody administered is effective in achieving a reduction in the joint damage, indicating that the subject has been successfully treated for the joint damage.

In a preferred embodiment, the radiographic testing after administering the antagonist or antibody such as CD20 antibody occurs at least about two months, more preferably at least about 10 weeks, still more preferably at least about three months, further preferably at least about four months, still more preferably at least about five months, further more preferably at least about 24 weeks, or at least about six months, and most preferably at least about 52 weeks after administering the antagonist or antibody. In another preferred embodiment, the test measures a total modified Sharp score.

In another preferred embodiment, the subject is retreated in that the method further comprises administering to the subject an antagonist or antibody such as CD20 antibody in an amount effective to achieve a continued or maintained reduction in joint damage as compared to the effect of a prior administration of the antagonist or antibody such as CD20 antibody. Thus, the subject may be administered a second dosing of the antagonist or antibody and is evaluated by radiographic testing at least about one month (and preferably more than about two months, more preferably about 24 weeks or about 6 months) after such second dosing to determine if the second dosing is effective (i.e., an effective amount of the antagonist or antibody is administered) to maintain the effects of the first dosing or improve the reduction in joint damage as compared to the effect of the first dosing. This re-treatment regimen can be repeated as long as desired or necessary to achieve or maintain reduction in joint damage, which indicates successful treatment of the joint damage.

In another embodiment, the antagonist or antibody such as CD20 antibody is additionally (continued to be) administered to the subject even if there is not a clinical improvement in the subject at the time of the radiographic testing after a prior administration, such as the first administration of the antagonist or antibody. In the latter embodiment, preferably the clinical improvement is determined by assessing the number of tender or swollen joints, the Psoriasis Assessment Severity Index, a global clinical assessment of the subject, assessing erythrocyte sedimentation rate, or assessing the amount of C-reactive protein level.

For purposes of this invention, the second antagonist or antibody exposure for re-treatment is the next time the subject is treated with the antagonist or, for example, CD20 antibody after the initial antibody exposure, there being no intervening antagonist or, e.g., CD20 antibody treatment or exposure between the initial and second exposures. Such re-treatment may be scheduled or unscheduled, but is preferably a scheduled redosing, particularly to protect organs such as kidneys from damage. If an antibody, especially a CD20 antibody, is employed, preferably the second antibody exposure is about 0.5 to 4 grams, more preferably about 1.5 to 3.5 grams, still more preferably about 1.5 to 2.5 grams, the second exposure not being provided until from about 20 to 35 weeks (preferably about 23 to 30, more preferably about 23 to 28 weeks) from the initial exposure.

The method contemplates administering to the subject an effective amount of the antagonist or, for example, CD20 antibody to provide a third antagonist or antibody exposure (if antibody, more preferably CD20 antibody) preferably of about 0.5 to 4 grams, more preferably about 1.5 to 3.5 grams, still more preferably about 1.5 to 2.5 grams), the third exposure not being provided until from about 46 to 60 weeks (preferably about 46 to 55, more preferably about 46 to 52 weeks) from the initial exposure. Preferably, no further antagonist or antibody exposure is provided until at least about 70-75 weeks from the initial exposure, and still more preferably no further antagonist or antibody exposure is provided until about 74 to 80 weeks from the initial exposure.

Where an antibody is employed, any one or more of the antibody exposures herein may be provided to the subject as a single dose of antibody, or as separate doses, for example, about 1-4 separate doses of the antibody (e.g., constituting a first and second dose, or a first, second, and third dose, or a first, second, third, and fourth dose, etc). The particular number of doses (whether one, two or three or more) employed for each antibody exposure is dependent, for example, on the type of joint damage treated, the type of antibody employed, whether, what type, and how much and how many of a second medicament is employed as noted below, and the method and frequency of administration. Where separate doses are administered, the later dose (for example, second or third dose) is preferably administered from about 1 to 20 days, more preferably from about 6 to 16 days, and most preferably from about 14 to 16 days from the time the previous dose was administered. The separate doses are preferably administered within a total period of between about 1 day and 4 weeks, more preferably between about 1 and 20 days (e.g., within a period of 6-18 days). In one such aspect, the separate doses are administered about weekly, with the second dose being administered about one week from the first dose and any third or subsequent dose being administered about one week from the second dose. Each such separate dose of the antibody is preferably about 0.5 to 1.5 grams, more preferably about 0.75 to 1.3 grams.

In a most preferred embodiment, a method of treating joint damage in a subject is provided comprising administering an effective amount of an antibody that binds to a B-cell surface marker (e.g., a CD20 antibody) to the subject to provide an initial antibody exposure followed by a second antibody exposure, wherein the second exposure is not provided until from about 16 to 54 weeks from the initial exposure and each of the antibody exposures is provided to the subject as a single dose or as two or three separate doses of antibody. Preferably in such a method, the antibody exposures are of about 0.5 to 4 grams each, and most preferably the amounts given above.

In one embodiment, the subject is provided at least about three exposures of the antibody, for example, from about 3 to 60 exposures, and more particularly about 3 to 40 exposures, most particularly, about 3 to 20 exposures. Preferably, such exposures are administered at intervals each of 24 weeks. In one embodiment, each antibody exposure is provided as a single dose of the antibody. In an alternative embodiment, each antibody exposure is provided as separate doses of the antibody. However, not every antibody exposure need be provided as a single dose or as separate doses.

In one preferred embodiment, about 2-3 grams of the CD20 antibody is administered as the initial exposure. If about 3 grams are administered, then about 1 gram of the CD20 antibody is administered weekly for about three weeks as the initial exposure. If about 2 grams of the CD20 antibody is administered as the initial exposure, then about 1 gram of the CD20 antibody is administered followed in about two weeks by another about 1 gram of the antibody as the initial exposure. In a preferred aspect, the second exposure is at about 24 weeks or six months from the initial exposure and is administered in an amount of about 2 grams. In an alternative preferred aspect, the second exposure is at about 24 weeks or six months from the initial exposure and is administered as about 1 gram of the antibody followed in about two weeks by another about 1 gram of the antibody.

In a preferred embodiment of the multi-exposure method herein, the subject is in remission after the initial or any later antagonist or antibody exposures. More preferably, the multi-exposure method herein involves scheduled re-dosing or re-treating such that the subject is in remission when provided the second, and preferably all antagonist or antibody exposures. Such re-dosing is scheduled to prevent any relapse, recurrence, or organ damage, rather than to treat it therapeutically. Most preferably, the subject is in remission for at least about 24 weeks or six months, and still most preferably at least about nine months, and even still most preferably at least about 52 weeks or one year since the last antagonist or antibody exposure used in the re-treatment method.

In yet another embodiment, the subject is treated with the same antagonist or antibody, such as CD20 antibody, for at least two antagonist or antibody exposures, and preferably for each antagonist or antibody exposure. Thus, the initial and second antagonist or antibody exposures are preferably with the same antagonist or antibody, and more preferably all antagonist or antibody exposures are with the same antagonist or antibody, i.e., treatment for the first two exposures, and preferably all exposures, is with one type of antagonist or antibody that binds to a B-cell surface marker, such as CD20 antibody, e.g., all with rituximab or all with the same humanized 2H7.

In all the inventive methods set forth herein, the antagonist (such as CD20 or B-cell surface marker antibody) may be unconjugated, such as a naked antibody, or may be conjugated with another molecule for further effectiveness, such as, for example, to improve half-life. The preferred CD20 antibody herein is a chimeric, humanized, or human CD20 antibody, more preferably rituximab, a humanized 2H7 (e.g. comprising the variable domain sequences in SEQ ID Nos. 2 and 8, or is humanized 2H7 comprising the variable domain sequences in SEQ ID NOS:39 and 40, or comprising the variable domain sequences in SEQ ID NOS: 32 and 33, or comprising a variable heavy-chain domain with alteration N100A, or D56A and N100A, or D56A, N100Y, and S100aR in SEQ ID NO:8 and a variable light-chain domain with alteration M32L, or S92A, or M32L and S92A in SEQ ID NO:2), chimeric or humanized A20 antibody (Immunomedics), HUMAX-CD20™ human CD20 antibody (Genmab), or single-chain proteins binding to CD20 (Trubion Pharm Inc.). Still more preferred is rituximab or a humanized 2H7.

In a further embodiment of all the methods herein, the subject has never been previously treated with one or more drug(s), such as with an anti-TNF-alpha inhibitor, e.g., an anti-TNF-alpha or anti-TNF-alpha receptor antibody, to treat, for example, arthritis, or with immunosuppressive agent(s) to treat the joint damage or an underlying cause such as an autoimmune disorder, and/or has never been previously treated with an antagonist (for example, antibody) to a B-cell surface marker (e.g. never been previously treated with a CD20 antibody). In one such embodiment, the subject has never been previously treated with an anti-alpha 4 integrin antibody or co-stimulation modulator, a biologic agent, a DMARD other than MTX, except for azathioprine and/or leflunomide, a cell-depleting therapy, including investigational agents (e.g., CAMPATH, anti-CD4, anti-CD5, anti-CD3, anti-CD19, anti-CD11a, anti-CD22, or BLys/BAFF), a live/attenuated vaccine within 28 days prior to baseline, or intra-articular or parenteral glucocorticoids within 4 weeks prior to baseline.

In a still further aspect, the subject may have had a relapse with the joint damage or suffered organ damage such as kidney damage before being treated in any of the methods above, including after the initial or a later antagonist or antibody exposure. However, preferably, the subject has not relapsed with the joint damage and more preferably has not had such a relapse before at least the initial treatment.

In another embodiment, the antagonist (for example, CD20 antibody) is the only medicament administered to the subject to treat the joint damage. In another embodiment, the antagonist (e.g., CD20 antibody) is one of the medicaments used to treat the joint damage. In a further embodiment, the subject does not have a malignancy, including solid tumors, hematologic malignancies, or carcinoma in situ (except basal cell and squamous cell carcinoma of the skin that have been excised and cured). In a still further embodiment, the subject does not have rheumatoid arthritis (RA). In another aspect, the subject does not have rheumatic autoimmune disease other than RA, or significant systemic involvement secondary to RA (including but not limited to vasculitis, pulmonary fibrosis or Felty's syndrome). In another embodiment, the subject does have secondary Sjögren's syndrome or secondary limited cutaneous vasculitis. In another embodiment, the subject does not have functional class IV as defined by the ACR Classification of Functional Status in RA. In a further embodiment, the subject does not have inflammatory joint disease other than RA (including, but not limited to, gout, reactive arthritis, psoriatic arthritis, seronegative spondyloarthropathy, Lyme disease), or other systemic autoimmune disorder (including, but not limited to, systemic lupus erythematosus, inflammatory bowel disease, scleroderma, inflammatory myopathy, mixed connective tissue disease, or any overlap syndrome). In another embodiment, the subject does not have juvenile idiopathic arthritis (JIA) or juvenile RA (JRA) and/or RA before age 16. In another embodiment, the subject does not have significant and/or uncontrolled cardiac or pulmonary disease (including obstructive pulmonary disease), or significant concomitant disease, including but not limited to, nervous system, renal, hepatic, endocrine or gastrointestinal disorders, nor primary or secondary immunodeficiency (history of, or currently active), including known history of HIV infection. In another aspect, the subject does not have any neurological (congenital or acquired), vascular or systemic disorder which could affect any of the efficacy assessments, in particular, joint pain and swelling (e.g., Parkinson's disease, cerebral palsy, diabetic neuropathy). In a still further embodiment, the subject does not have multiple sclerosis. In a yet further embodiment, the subject does not have lupus or Sjögren's syndrome. In still another embodiment, the subject does not have an autoimmune disease. In yet another aspect of the invention, the joint damage is not associated with an autoimmune disease or with an autoimmune disease other than arthritis, or with a risk of developing an autoimmune disease or an autoimmune disease other than arthritis. For purposes of these lattermost statements, an "autoimmune disease" herein is a disease or disorder arising from and directed against an individual's own tissues or organs or a co-segregate or manifestation thereof or resulting condition therefrom. Without being limited to any one theory, B cells demonstrate a pathogenic effect in human autoimmune diseases through a multitude of mechanistic pathways, including autoantibody production, immune complex formation, dendritic and T-cell activation, cytokine synthesis, direct chemokine release, and providing a nidus for ectopic neo-lymphogenesis. Each of these pathways participates to different degrees in the pathology of autoimmune diseases.

In a preferred embodiment, the joint damage is caused by arthritis, aseptic joint loosening of orthopedic implants, non-union of a fracture, spondyloarthropathies, psoriasis, or Crohn's disease. More preferably, the joint damage is caused by arthritis, which is more preferably rheumatoid arthritis, osteoarthritis, ankylosing spondylitis, or psoriatic arthritis.

In still further embodiments, if the antagonist is an antibody, the antibody is administered intravenously or subcutaneously.

In further preferred aspects, if the antagonist is an antibody, the antibody is administered in a dose of about 0.4 to 4 grams, more preferably about 1.5 to 3.5 grams, still more preferably about 1.5 to 2.5 grams. In another aspect, the antibody is preferably administered in a dose of about 0.4 to 1.3 grams at a frequency of one to four doses within a period of about one month, more preferably about 500 mg to 1.2 grams, still more preferably about 500 mg or about 750 mg to about 1.1 grams, and more preferably the antibody is administered in two to three doses. Still more preferably, the antibody is administered within a period of about 2 to 3 weeks.

In another preferred aspect, the subject is rheumatoid factor negative. In another aspect, the subject is rheumatoid factor positive.

In another preferred aspect of the above-described method, the subject was administered methotrexate prior to the baseline or start of treatment. More preferably, the methotrexate was administered at a dose of about 10-25 mg/week. Also, preferably, the methotrexate was administered for at least about 12 weeks prior to the baseline, and still more preferably the methotrexate was administered at a stable dose the last four weeks prior to the baseline. In other embodiments, the methotrexate was administered perorally or parenterally.

In particularly preferred embodiments of the above-identified method, the joint damage is caused by rheumatoid arthritis and the subject has exhibited an inadequate response to one or more anti-tumor necrosis factor (TNF) inhibitors, and/or methotrexate is administered to the subject along with the antagonist, for example, CD20 antibody, and/or the antagonist is a CD20 antibody that is administered at a dose of about 1000 mg×2 on days 1 and 15 intravenously at the start of the treatment.

In still further embodiments, the invention provides a method of monitoring the treatment of joint damage in a subject comprising administering an effective amount of an antagonist to a B-cell surface marker (such as an antibody thereto, including a CD20 antibody) to the subject and measuring by radiography after at least about one month from the administration whether the joint damage has been reduced over baseline prior to the administration, wherein a decrease versus baseline in the subject after treatment indicates the antagonist or antibody such as CD20 antibody is having an effect on the joint damage. Preferably, the degree of reduction versus baseline is measured a second time after the administration of the antagonist or antibody such as CD20 antibody. Also, preferably the measurement is taken after at least about 24 weeks from the administration.

Also included herein is a method of monitoring the treatment of joint damage in a subject comprising administering an effective amount of an antagonist to a B-cell surface marker (such as an antibody thereto, including a CD20 antibody) to the subject and measuring by radiography after at least about 52 weeks from the administration whether the joint damage has been reduced over baseline prior to the administration, wherein a decrease versus baseline in the subject after treatment indicates the antagonist or antibody such as CD20 antibody is having an effect on the joint damage. Preferably, the degree of reduction versus baseline is measured a second time after the administration of the antagonist or antibody such as CD20 antibody.

In yet another aspect, the invention provides a method of determining whether to continue administering an antagonist to a B-cell surface marker (such as an antibody thereto, including a CD20 antibody) to a subject with joint damage comprising measuring by radiography reduction in joint damage in the subject after administration of the antagonist such as CD20 antibody a first time, measuring by radiography reduction in joint damage in the subject after administration of the antagonist such as CD20 antibody a second time, comparing the radiography scores in the subject at the first time and at the second time, and if the score is less at the second time than at the first time, continuing administration of the antagonist or antibody such as CD20 antibody.

In a still further embodiment, a step is included in the treatment method to test for the subject's response to treatment after the administration step to determine that the level of response is effective to treat the joint damage. For example, a step is included to test the radiographic score after administration and compare it to a baseline radiographic score obtained before administration to determine if treatment is effective by measuring if, and by how much, it has been changed. This test may be repeated at various scheduled or unscheduled time intervals after the administration to determine maintenance of any partial or complete remission. Alternatively, the methods herein comprise a step of testing the subject, before administration, to see if one or more biomarkers or symptoms are present for joint damage, as set forth above. In another method, a step may be included to check the subject's clinical history, as detailed above, for example, to rule out infections or malignancy as causes, for example, primary causes, of the subject's condition, prior to administering the antibody or antagonist to the subject. Preferably, the joint damage is primary (i.e., the leading disease), and is not secondary, such as secondary to infection or malignancy, whether solid or liquid tumors.

In one embodiment of all the methods herein, no other medicament than the antagonist such as CD20 antibody is administered to the subject to treat the joint damage.

In any of the methods herein, preferably one may administer to the subject along with the antagonist or antibody that binds a B-cell surface marker an effective amount of a second medicament (where the antagonist or antibody that binds a B-cell surface marker (e.g., the CD20 antibody) is a first medicament). The second medicament may be one or more medicaments, and include, for example, an immunosuppressive agent, cytokine antagonist such as a cytokine antibody, growth factor, hormone, integrin, integrin antagonist or antibody, or any combination thereof. The type of such second medicament depends on various factors, including the type of joint damage, the severity of the joint damage, the condition and age of the subject, the type and dose of first medicament employed, etc.

Examples of such additional medicaments include an interferon class drug such as interferon-alpha (e.g., from Amarillo Biosciences, Inc.), IFN-beta-1a (REBIF® and AVONEX®) or IFN-beta-1b (BETASERON®), an oligopeptide such as glatiramer acetate (COPAXONE®), an agent blocking CD4O-CD40 ligand, an immunosuppressive agent (such as mitoxantrone (NOVANTRONE®), methotrexate, cyclophosphamide, chlorambucil, leflunomide, and azathioprine), intravenous immunoglobulin (gamma globulin), lymphocyte-depleting therapy (e.g., mitoxantrone, cyclophosphamide, CAMPATH™ antibodies, anti-CD4, cladribine, a polypeptide construct with at least two domains comprising a de-immunized, autoreactive antigen or its fragment that is specifically recognized by the Ig receptors of autoreactive B-cells (WO 2003/68822), total body irradiation, bone marrow transplantation), integrin antagonist or antibody (e.g., an LFA-1 antibody such as efalizumab/RAPTIVA® commercially available from Genentech, or an alpha 4 integrin antibody such as natalizumab/ANTEGREN® available from Biogen, or others as noted above), drugs that treat symptoms secondary or related to joint damage such as those noted herein, steroid such as corticosteroid (e.g., prednisolone, methylprednisolone such as SOLU-MEDROL™ methylprednisolone sodium succinate for injection, prednisone such as low-dose prednisone, dexamethasone, or glucocorticoid, e.g., via joint injection, including systemic corticosteroid therapy), non-lymphocyte-depleting immunosuppressive therapy (e.g., MMF or cyclosporine), cholesterol-lowering drug of the "statin" class (which includes cerivastatin (BAYCOL™), fluvastatin (LESCOL™), atorvastatin (LIPITOR™), lovastatin (MEVACOR™), pravastatin (PRAVACHOL™), and simvastatin (ZOCOR™)), estradiol, testosterone (optionally at elevated dosages; Stuve et al. Neurology 8:290-301 (2002)), androgen, hormone-replacement therapy, a TNF inhibitor such as an antibody to TNF-alpha, DMARD, NSAID, plasmapheresis or plasma exchange, trimethoprim-sulfamethoxazole (BACTRIM™, SEPTRA™), mycophenolate mofetil, H2-blockers or proton-pump inhibitors (during the use of potentially ulcerogenic immunosuppressive therapy), levothyroxine, cyclosporin A (e.g. SANDIMMUNE®), somatastatin analogue, a DMARD or NSAID, cytokine antagonist such as antibody, anti-metabolite, immunosuppressive agent, rehabilitative surgery, radioiodine, thyroidectomy, BAFF antagonist such as BAFF or BR3 antibodies or immunoadhesins, anti-CD40 receptor or anti-CD40 ligand (CD154), anti-IL-6 receptor antagonist/antibody, another B-cell surface antagonist or antibody such as a humanized 2H7 or other humanized or human CD20 antibody with rituximab; IL-1 blockers, such as rHUIL-1Ra (Amgen-Synergen) and tiaprofenic acid I-1B inhibitor (Hoechst); and co-stimulatory modifiers, such as ORENCIA® (abatacept) (Bristol-Myers Squibb); enlimomab (anti-ICAM-1 monoclonal antibody); CDO-855 (humanized antibody, which binds specifically to a region of the Class II MHC complex, Celltech); CH-3298 (Chiroscience); acemetacin (Merck); GW353430 (anti-CD23 monoclonal antibody, Glaxo Wellcome); GR 252025 (COX02 inhibitor, Glaxo Wellcome); 4162W94 (anti-CD4 humanized antibody; Glaxo Wellcome); azathioprine (DMARD, Glaxo Welcome); penicilamine and fenoprofen (Eli Lilly); etc.

Preferred such medicaments are an antibiotic, anti-integrin, gamma globulin, a pain-control agent, an integrin antagonist, anti-CD4, cladribine, trimethoprimsulfamethoxazole, an H2-blocker, a proton-pump inhibitor, cyclosporine, cholesterol-lowering drug of the statin class, estradiol, testosterone, androgen, hormone-replacement drug, a TNF inhibitor such as a TNF-alpha inhibitor, DMARD, NSAID (to treat, for example, musculoskeletal symptoms), levothyroxine, cyclosporin A, somatastatin analogue, cytokine antagonist (including cytokine-receptor antagonist), antimetabolite, BAFF antagonist such as BAFF antibody or BR3 antibody, especially a BAFF antibody, immunosuppressive agent such as methotrexate or a corticosteroid, a bisphosphonate, a hormone, and another B-cell surface marker antibody, such as a combination of rituximab and a humanized 2H7 or other humanized CD20 antibody.

The more preferred such medicaments are an antibiotic, an immunosuppressive agent such as methotrexate or a corticosteroid, a DMARD, a pain-control agent, an integrin antagonist, a NSAID, a cytokine antagonist, a bisphosphonate, or a hormone, or a combination thereof.

In one particularly preferred embodiment, the second medicament is a DMARD, which is preferably selected from the group consisting of auranofin, chloroquine, D-penicilamine, injectable gold, oral gold, hydroxychloroquine, sulfasalazine, myocrisin and methotrexate.

In another such embodiment, the second medicament is a NSAID, which is preferably selected from the group consisting of: pentasa, mesalazine, asacol, codeine phosphate, benorylate, fenbufen, naprosyn, diclofenac, etodolac and indomethacin, aspirin and ibuprofen.

In another such embodiment, the second medicament is a pain-control agent, which is preferably selected from the group consisting of: paracetamol and dextropropoxyphene.

In a further such embodiment, the second medicament is an immunosuppressive agent, which is preferably selected from the group consisting of etanercept, infliximab, adalimumab, leflunomide, anakinra, azathioprine, methotrexate, and cyclophosphamide.

In other preferred embodiments, the second medicament is selected from the group consisting of OPG, etanercept, infliximab, etanercept, adalimumab, kinaret, raptiva, osteoprotegerin (OPG), RANKFc, anti-RANKL, pamidronate, alendronate, actonel, zolendronate, clodronate, methotrexate, azulfidine, hydroxychloroquine, doxycycline, leflunomide, sulfasalazine (SSZ), prednisolone, interleukin-1 receptor antagonist, prednisone and methylprednisolone.

In still preferred embodiments, the second medicament is selected from the group consisting of infliximab, an infliximab/methotrexate (MTX) combination, etanercept, a corticosteroid, cyclosporin A, azathioprine, auranofin, hydroxychloroquine (HCQ), combination of prednisolone, MTX, and SSZ, combinations of MTX, SSZ, and HCQ, the combination of cyclophosphamide, azathioprine, and HCQ, and the combination of adalimumab with MTX. If the second medicament is a corticosteroid, preferably it is prednisone, prednisolone, methylprednisolone, hydrocortisone, or dexamethasone. Also, preferably, the corticosteroid is administered in lower amounts than are used if the CD20 antibody is not administered to a subject treated with a corticosteroid. Most preferably, the second medicament is methotrexate.

All these second medicaments may be used in combination with each other or by themselves with the first medicament, so that the expression "second medicament" as used herein does not mean it is the only medicament besides the first medicament, respectively. Thus, the second medicament need not be one medicament, but may constitute or comprise more than one such drug.

These second medicaments as set forth herein are generally used in the same dosages and with administration routes as used hereinbefore or about from 1 to 99% of the heretofore-employed dosages. If such second medicaments are used at all, preferably, they are used in lower amounts than if the first medicament were not present, especially in subsequent dosings beyond the initial dosing with the first medicament, so as to eliminate or reduce side effects caused thereby.

For the re-treatment methods described herein, where a second medicament is administered in an effective amount with an antagonist or antibody exposure, it may be administered with any exposure, for example, only with one exposure, or with more than one exposure. In one embodiment, the second medicament is administered with the initial exposure. In another embodiment, the second medicament is administered with the initial and second exposures. In a still further embodiment, the second medicament is administered with all exposures. It is preferred that after the initial exposure, such as of steroid, the amount of such second medicament is reduced or eliminated so as to reduce the exposure of the subject to an agent with side effects such as prednisone, prednisolone, methylprednisolone, and cyclophosphamide.

The combined administration of a second medicament includes co-administration (concurrent administration), using separate formulations or a single pharmaceutical formulation, and consecutive administration in either order, wherein preferably there is a time period while both (or all) active agents (medicaments) simultaneously exert their biological activities.

The antibody or antagonist herein is administered by any suitable means, including parenteral, topical, subcutaneous, intraperitoneal, intrapulmonary, intranasal, and/or intralesional administration. Parenteral infusions include intramuscular, intravenous (i.v.), intraarterial, intraperitoneal, or subcutaneous administration. Intrathecal administration is also contemplated (see, e.g., US 2002/0009444, Grillo-Lopez, A concerning intrathecal delivery of a CD20 antibody). In addition, the antibody or antagonist may suitably be administered by pulse infusion, e.g., with declining doses of the antibody or antagonist. Preferably, the dosing is given intravenously or subcutaneously, and more preferably by intravenous infusion(s).

If multiple exposures of antibody are provided, each exposure may be provided using the same or a different administration means. In one embodiment, each exposure is by intravenous administration. In another embodiment, each exposure is given by subcutaneous administration. In yet another embodiment, the exposures are given by both intravenous and subcutaneous administration.

In one embodiment, the CD20 antibody is administered as a slow intravenous infusion rather than an intravenous push or bolus. For example, a steroid such as prednisolone or methylprednisolone (e.g., about 80-120 mg i.v., more specifically about 100 mg i.v.) is administered about 30 minutes prior to any infusion of the CD20 antibody. The CD20 antibody is, for example, infused through a dedicated line.

For the initial dose of a multi-dose exposure to CD20 antibody, or for the single dose if the exposure involves only one dose, such infusion is preferably commenced at a rate of about 50 mg/hour. This may be escalated, e.g., at a rate of about 50 mg/hour increments every about 30 minutes to a maximum of about 400 mg/hour. However, if the subject is experiencing an infusion-related reaction, the infusion rate is preferably reduced, e.g., to half the current rate, e.g., from 100 mg/hour to 50 mg/hour. Preferably, the infusion of such dose of CD20 antibody (e.g., an about 1000-mg total dose) is completed at about 255 minutes (4 hours 15 min.). Optionally, the subjects receive a prophylactic treatment of acetaminophen/paracetamol (e.g., about 1 g) and diphenhydramine HCl (e.g., about 50 mg or equivalent dose of similar agent) by mouth about 30 to 60 minutes prior to the start of an infusion.

If more than one infusion (dose) of CD20 antibody is given to achieve the total exposure, the second or subsequent CD20 antibody infusions in this infusion embodiment are preferably commenced at a higher rate than the initial infusion, e.g., at about 100 mg/hour. This rate may be escalated, e.g., at a rate of about 100 mg/hour increments every about 30 minutes to a maximum of about 400 mg/hour. Subjects who experience an infusion-related reaction preferably have the infusion rate reduced to half that rate, e.g., from 100 mg/hour to 50 mg/hour. Preferably, the infusion of such second or subsequent dose of CD20 antibody (e.g., an about 1000-mg total dose) is completed by about 195 minutes (3 hours 15 minutes).

In another embodiment, a method is provided for treating joint damage in a subject comprising administering an antagonist to a B-cell surface marker, such as an antibody thereto, for example, CD20 antibody, to the subject, and giving the subject, at least about 52 weeks after the administration, a radiographic test that measures a reduction in the joint damage as compared to baseline prior to the administration, wherein the amount of antagonist or antibody such as CD20 antibody administered is effective in achieving a reduction in the joint damage, indicating that the subject has been successfully treated.

In this method, preferably the test measures a total modified Sharp score. In another preferred embodiment, the antagonist is a CD20 antibody. More preferably, the CD20 antibody is rituximab or is humanized 2H7 comprising the variable domain sequences in SEQ ID Nos. 2 and 8, or is humanized 2H7 comprising the variable domain sequences in SEQ ID NOS:39 and 40, or is humanized 2H7 comprising the variable domain sequences in SEQ ID NOS:32 and 33, or is humanized 2H7 comprising a variable heavy-chain domain with alteration N100A, or D56A and N100A, or D56A, N100Y, and S100aR in SEQ ID NO:8 and a variable light-chain domain with alteration M32L, or S92A, or M32L and S92A in SEQ ID NO:2.

In another preferred embodiment, the joint damage is caused by arthritis, preferably RA, and more preferably early active RA. In another preferred embodiment, the subject has not been previously treated with an immunosuppressive agent before the administration of a first dose of antagonist or antibody such as CD20 antibody in the treatment method. In a preferred embodiment, the antagonist or antibody is administered in a dose of about 0.4 to 4 grams, and more preferably the antagonist or antibody is administered in a dose of about 0.4 to 1.3 grams at a frequency of one to four doses within a period of about one month. Still more preferably, the dose is about 500 mg to 1.2 grams, and in other embodiments is about 750 mg to 1.1 grams. In such aspects, the antagonist or antibody is preferably administered in two to three doses, and/or is administered within a period of about 2 to 3 weeks.

In another aspect, such method further comprises re-treating the subject by providing an additional administration to the subject of the antagonist such as a CD20 antibody in an amount effective to achieve a continued or maintained reduction in joint damage as compared to the effect of a prior administration of the antagonist or antibody such as CD20 antibody. In one aspect of this embodiment, the antagonist or antibody such as CD20 antibody is additionally administered to the subject even if there is no clinical improvement in the subject at the time of the radiographic testing after a prior administration. The re-treatment may be commenced at at least about 24 weeks after the first administration of the antagonist such as CD20 antibody, and one or more further re-treatments is optionally commenced. In another embodiment, the further re-treatment is commenced at at least about 24 weeks after the second administration of the antagonist such as CD20 antibody. In a further preferred aspect, joint damage has been reduced after the re-treatment as compared to the joint damage extent after the first radiographic assessment.

Preferably, in this method regarding the about 52-week assessment, a second medicament is administered in an effective amount, wherein the antagonist or antibody such as CD20 antibody is a first medicament. In one aspect, the second medicament is more than one medicament. In another aspect, the second medicament is an antibiotic, an immunosuppressive agent, a disease-modifying anti-rheumatic drug (DMARD), a pain-control agent, an integrin antagonist, a non-steroidal anti-inflammatory drug (NSAID), a cytokine antagonist, a bisphosphonate, or a hormone, or a combination thereof, most preferably methotrexate. The subject may be rheumatoid factor negative or positive. Also, preferably, the antagonist such as CD20 antibody is administered intravenously or subcutaneously, most preferably intravenously.

A discussion of methods of producing, modifying, and formulating such antibodies follows.

III. Production of Antibodies

The methods and articles of manufacture of the present invention use, or incorporate, an antibody that binds to a B-cell surface marker, especially one that binds to CD20. Accordingly, methods for generating such antibodies will be described here.

CD20 antigen to be used for production of, or screening for, antibody(ies) may be, e.g., a soluble form of CD20 or a portion thereof, containing the desired epitope. Alternatively, or additionally, cells expressing CD20 at their cell surface can be used to generate, or screen for, antibody(ies). Other forms of CD20 useful for generating antibodies will be apparent to those skilled in the art.

A description follows as to exemplary techniques for the production of the antibodies used in accordance with the present invention.

(i) Polyclonal Antibodies

Polyclonal antibodies are preferably raised in animals by multiple subcutaneous (s.c.) or intraperitoneal (i.p.) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal Antibodies

Monoclonal antibodies are obtained from a population of substantially homogeneous antibodies, i.e., the individual antibodies comprising the population are identical and/or bind the same epitope except for possible variants that arise during production of the monoclonal antibody, such variants generally being present in minor amounts. Thus, the modifier "monoclonal" indicates the character of the antibody as not being a mixture of discrete or polyclonal antibodies.

For example, the monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-SEPHAROSE™, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., *Curr.*

*Opinion in Immunol.*, 5:256-262 (1993) and Plückthun, *Immunol. Revs.*, 130:151-188 (1992).

In a further embodiment, antibodies or antibody fragments can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light chain constant domains in place of the homologous murine sequences (U.S. Pat. No. 4,816,567; Morrison, et al., *Proc. Natl Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

In addition, antibodies comprising a variant Fc region with high affinity for FcγR are useful for treating diseases where an enhanced efficacy of effector cell function is desired, such as autoimmune diseases, as set forth, for example, in US 2005/0037000 and WO 2004/63351 (Macrogenics, Inc. STAVENHAGEN et al.).

(iii) Humanized Antibodies

Methods for humanizing non-human antibodies have been described in the art. Preferably, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence that is closest to that of the rodent is then accepted as the human framework region (FR) for the humanized antibody (Sims et al., *J. Immunol.*, 151:2296 (1993); Chothia et al., *J. Mol. Biol.*, 196:901 (1987)). Another method uses a particular framework region derived from the consensus sequence of all human antibodies of a particular subgroup of light or heavy chain variable regions. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

(iv) Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993); and U.S. Pat. Nos. 5,591,669, 5,589,369 and 5,545,807.

Alternatively, phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson et al., *Current Opinion in Structural Biology* 3:564-571 (1993). Several sources of V-gene segments can be used for phage display. Clackson et al., *Nature*, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

Human antibodies may also be generated by in vitro activated B cells (see U.S. Pat. Nos. 5,567,610 and 5,229, 275).

(v) Antibody Fragments

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science*, 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. The antibody fragment may also be a "linear antibody", e.g., as described in U.S. Pat. No. 5,641,870 for example Such linear antibody fragments may be monospecific or bispecific.

(vi) Bispecific Antibodies

Bispecific antibodies are antibodies that have binding specificities for at least two different epitopes. Exemplary bispecific antibodies may bind to two different epitopes of the CD20 antigen. Other such antibodies may bind CD20 and further bind a second B-cell surface marker. Alternatively, an anti-CD20 binding arm may be combined with an arm that binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to the B cell. Bispecific antibodies may also be used to localize certain agents to the B cell. These antibodies possess a CD20-binding arm and an arm that binds the agent (e.g. methotrexate). Bispecific antibodies can be prepared as full-length antibodies or antibody fragments (e.g. F(ab')$_2$ bispecific antibodies).

Methods for making bispecific antibodies are known in the art. Traditional production of full length bispecific antibodies is based on the co-expression of two immunoglobulin heavy chain-light chain pairs, where the two chains have different specificities (Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy chain variable domain ($V_H$) connected to a light chain variable domain ($V_L$) by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al., *J. Immunol.* 147: 60 (1991).

IV. Conjugates and Other Modifications of the Antibody

Modifications of the antibody are contemplated herein. Thus, in one embodiment, the antibody may be conjugated to another molecule, for example, to increase half-life or stability or otherwise improve the pharmacokinetics of the antibody. For example, the antibody may be linked to one of a variety of non-proteinaceous polymers, e.g., polyethylene glycol (PEG), polypropylene glycol, polyoxyalkylenes, or copolymers of polyethylene glycol and polypropylene glycol. Antibody fragments, such as Fab', linked to one or more PEG molecules are an especially preferred embodiment of the invention.

The antibodies disclosed herein may also be formulated as liposomes. Liposomes containing the antibody are prepared by methods known in the art, such as described in Epstein et al., *Proc. Natl. Acad. Sci. USA*, 82:3688 (1985); Hwang et al., *Proc. Natl. Acad. Sci. USA*, 77:4030 (1980); U.S. Pat. Nos. 4,485,045 and 4,544,545; and WO 97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of an antibody of the present invention can be conjugated to the liposomes as described in Martin et al. *J. Biol. Chem.* 257: 286-288 (1982) via a disulfide interchange reaction.

Amino acid sequence modification(s) of protein or peptide antibodies described herein are contemplated. For example, it may be desirable to improve the binding affinity and/or other biological properties of the antibody Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

A useful method for identification of certain residues or regions of the antibody that are preferred locations for mutagenesis is called "alanine scanning mutagenesis" as described by Cunningham and Wells, *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a polypeptide or polymer. Other insertional variants of the antibody molecule include the fusion to the N- or C-terminus of the antibody of an enzyme, or a polypeptide that increases the serum half-life of the antibody.

Another type of variant is an amino acid substitution variant. These variants have at least one amino acid residue in the antibody molecule replaced by different residue. The sites of greatest interest for substitutional mutagenesis of antibodies include the hypervariable regions, but FR alterations are also contemplated. Conservative substitutions are shown in the table below under the heading of "preferred substitutions". If such substitutions result in a change in biological activity, then more substantial changes, denominated "exemplary substitutions" in the table below, or as further described below in reference to amino acid classes, may be introduced and the products screened.

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |

| Original Residue | Exemplary Substitutions | Preferred Substitutions |
|---|---|---|
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain Amino acids may be grouped according to similarities in the properties of their side chains (in A. L. Lehninger, in *Biochemistry*, second ed., pp. 73-75, Worth Publishers, New York (1975)):

(1) non-polar: Ala (A), Val (V), Leu (L), Ile (I), Pro (P), Phe (F), Trp (W), Met (M)

(2) uncharged polar: Gly (G), Ser (S), Thr (T), Cys (C), Tyr (Y), Asn (N), Gln (Q)

(3) acidic: Asp (D), Glu (E)

(4) basic: Lys (K), Arg (R), His (H)

Alternatively, naturally occurring residues may be divided into groups based on common side-chain properties:

(1) hydrophobic: Norleucine, Met, Ala, Val, Leu, Ile;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe.

Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody. Generally, the resulting variant(s) selected for further development will have improved biological properties relative to the parent antibody from which they are generated. A convenient way for generating such substitutional variants is affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or in additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. Such altering includes deleting one or more carbohydrate moieties found in the antibody, and/or adding one or more glycosylation sites that are not present in the antibody.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody are described in US Pat Appl No US 2003/0157108 (Presta, L.). See also US 2004/0093621 (Kyowa Hakko Kogyo Co., Ltd). Antibodies with a bisecting N-acetylglucosamine (GlcNAc) in the carbohydrate attached to an Fc region of the antibody are referenced in WO 2003/011878, Jean-Mairet et al. and U.S. Pat. No. 6,602,684, Umana et al. Antibodies with at least one galactose residue in the oligosaccharide attached to an Fc region of the antibody are reported in WO 1997/30087, Patel et al. See, also, WO 1998/58964 (Raju, S.) and WO 1999/22764 (Raju, S.) concerning antibodies with altered carbohydrate attached to the Fc region thereof. See also US 2005/0123546 (Umana et al.) on antigen-binding molecules with modified glycosylation.

The preferred glycosylation variant herein comprises an Fc region, wherein a carbohydrate structure attached to the Fc region lacks fucose. Such variants have improved ADCC function. Optionally, the Fc region further comprises one or more amino acid substitutions therein which further improve ADCC, for example, substitutions at positions 298, 333, and/or 334 of the Fc region (Eu numbering of residues).

Examples of publications related to "defucosylated" or "fucose-deficient" antibodies include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; Okazaki et al. *J. Mol. Biol.* 336:1239-1249 (2004); Yamane-Ohnuki et al. *Biotech. Bioeng.* 87: 614 (2004). Examples of cell lines producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (Yamane-Ohnuki et al. *Biotech. Bioeng.* 87: 614 (2004)).

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to modify the antibody of the invention with respect to effector function, e.g. so as to enhance ADCC and/or CDC of the antibody. This may be achieved by introducing one or more amino acid substitutions in an Fc region of an antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and ADCC. See Caron et al., *J. Exp Med.* 176:1191-1195 (1992) and Shopes, *J. Immunol.* 148:2918-2922 (1992). Homodimeric antibodies may also be prepared using heterobifunctional cross-linkers as described in Wolff et al. *Cancer Research* 53:2560-2565 (1993). Alternatively, an antibody can be engineered that has dual Fc regions and may thereby have enhanced complement lysis and ADCC capabilities. See Stevenson et al. *Anti-Cancer Drug Design* 3:219-230 (1989).

WO 00/42072 (Presta, L.) describes antibodies with improved ADCC function in the presence of human effector cells, where the antibodies comprise amino acid substitutions in the Fc region thereof. Preferably, the antibody with improved ADCC comprises substitutions at positions 298, 333, and/or 334 of the Fc region. Preferably the altered Fc region is a human IgG1 Fc region comprising or consisting of substitutions at one, two or three of these positions.

Antibodies with altered C1q binding and/or CDC are described in WO 99/51642, U.S. Pat. No. 6,194,551B1, U.S. Pat. No. 6,242,195B1, U.S. Pat. No. 6,528,624B1 and U.S. Pat. No. 6,538,124 (Idusogie et al.). The antibodies comprise an amino acid substitution at one or more of amino acid positions 270, 322, 326, 327, 329, 313, 333 and/or 334 of the Fc region thereof.

To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule. Antibodies with substitutions in an Fc region thereof and increased serum half-lives are also described in WO00/42072 (Presta, L.).

Engineered antibodies with three or more (preferably four) functional antigen binding sites are also contemplated (US Appln No. US 2002/0004587 A1, Miller et al.).

V. Pharmaceutical Formulations

Therapeutic formulations of the antibodies used in accordance with the present invention are prepared for storage by mixing an antibody having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Exemplary anti-CD20 antibody formulations are described in WO98/56418. This publication describes a liquid multidose formulation comprising 40 mg/mL rituximab, 25 mM acetate, 150 mM trehalose, 0.9% benzyl alcohol, 0.02% polysorbate 20 at pH 5.0 that has a minimum shelf life of two years storage at 2-8° C. Another anti-CD20 formulation of interest comprises 10 mg/mL rituximab in 9.0 mg/mL sodium chloride, 7.35 mg/mL sodium citrate dihydrate, 0.7 mg/mL polysorbate 80, and Sterile Water for Injection, pH 6.5.

Lyophilized formulations adapted for subcutaneous administration are described in U.S. Pat. No. 6,267,958 (Andya et al.). Such lyophilized formulations may be reconstituted with a suitable diluent to a high protein concentration and the reconstituted formulation may be administered subcutaneously to the mammal to be treated herein.

Crystallized forms of the antibody are also contemplated. See, for example, US 2002/0136719A1 (Shenoy et al.).

The formulation herein may also contain more than one active compound (a second medicament as noted above) as necessary, preferably those with complementary activities that do not adversely affect each other. The type and effective amounts of such medicaments depend, for example, on the amount of antibody present in the formulation, and clinical parameters of the subjects. The preferred such medicaments are noted above.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules)

or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semi-permeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

VI. Articles of Manufacture

In another embodiment of the invention, articles of manufacture containing materials useful for the treatment of joint damage described above are provided. The invention, in particular, provides an article of manufacture comprising: (a) a container comprising an antagonist such as an antibody that binds to a B-cell surface marker (e.g., a CD20 antibody) (preferably the container comprises the antibody and a pharmaceutically acceptable carrier or diluent within the container); and (b) a package insert with instructions for treating joint damage in a subject, wherein the instructions indicate that the subject is administered the antagonist or antibody (e.g., CD20 antibody) and is then subjected, at least about one month after the administration, to a radiographic test that measures a reduction in the joint damage as compared to baseline prior to the administration, wherein the amount of antagonist or antibody such as CD20 antibody administered is effective in achieving a reduction in the joint damage, indicating that the subject has been successfully treated.

In a preferred embodiment of this inventive aspect, the article of manufacture herein further comprises a container comprising a second medicament, wherein the antagonist or antibody is a first medicament, and which article further comprises instructions on the package insert for treating the subject with the second medicament, in an effective amount. The second medicament may be any of those set forth above, with an exemplary second medicament being those set forth above, including an antibiotic, an immunosuppressive agent, a disease-modifying anti-rheumatic drug (DMARD), a pain-control agent, an integrin antagonist, a non-steroidal anti-inflammatory drug (NSAID), a cytokine antagonist, bisphosphonate, or a hormone, or a combination thereof, more preferably a DMARD, NSAID, pain-control agent, or immunosuppressive agent. Most preferably, the second medicament is methotrexate.

In this aspect, the package insert is on or associated with the container. Suitable containers include, for example, bottles, vials, syringes, etc. The containers may be formed from a variety of materials such as glass or plastic. The container holds or contains a composition that is effective for treating the joint damage and may have a sterile access port (for example the container may be an intravenous solution bag or a vial having a stopper pierceable by a hypodermic injection needle). At least one active agent in the composition is the antagonist or antibody. The label or package insert indicates that the composition is used for treating joint damage in a subject eligible for treatment with specific guidance regarding dosing amounts and intervals of antagonist or antibody and any other medicament being provided. The article of manufacture may further comprise an additional container comprising a pharmaceutically acceptable diluent buffer, such as bacteriostatic water for injection (BWFI), phosphate-buffered saline, Ringer's solution, and/or dextrose solution. The article of manufacture may further include other materials desirable from a commercial and user standpoint, including other buffers, diluents, filters, needles, and syringes.

In more specific embodiments, an article of manufacture comprises: (a) a container comprising an antagonist such as an antibody that binds to a B-cell surface marker (e.g., a CD20 antibody) (preferably the container comprises the antibody and a pharmaceutically acceptable carrier or diluent within the container); and (b) a package insert with instructions for treating joint damage in a subject, wherein the instructions indicate that the subject is administered the antagonist or antibody (e.g., CD20 antibody) and is then subjected, at least about 52 weeks after the administration, to a radiographic test that measures a reduction in the joint damage as compared to baseline prior to the administration, wherein the amount of CD20 antibody administered is effective in achieving a reduction in the joint damage, indicating that the subject has been successfully treated. In a preferred embodiment, the article comprises a container comprising a second medicament, wherein the antagonist or antibody (such as CD20 antibody) is a first medicament, further comprising instructions on the package insert for treating the subject with the second medicament in an effective amount. Preferably, this second medicament is methotrexate.

Further details of the invention are illustrated by the following non-limiting Examples. The disclosures of all citations in the specification are expressly incorporated herein by reference.

Example 1

Efficacy and Safety of Rituximab in Patients with an Inadequate Response or Lack of Tolerance to Prior Anti-TNF Therapy This is a Phase III randomized, double-blind, parallel-group multicenter clinical trial, called: Randomised Evaluation of Long-term Efficacy of Rituximab in RA (REFLEX). The study design is shown in FIG. 1.

The objectives of this study were:
To determine the efficacy and safety of rituximab when used in combination with methotrexate (MTX) in 517 patients with active rheumatoid arthritis who have an inadequate response to one or more anti-TNF therapies.
To explore the pharmacokinetics and pharmacodynamics of rituximab in this patient population (e.g. extent of duration of B-cell depletion and effects on immunoglobulins and rheumatoid factor).

The outcomes of this study were:
Primary endpoint
The proportion of patients with an ACR20 response at Week 24.
Secondary Endpoints
Proportion of patients with ACR50 and ACR70 responses at Week 24.
Change in DAS28 from baseline to Week 24.

EULAR response at Week 24.
Changes from baseline in ACR core set.
Changes from baseline in SF-36.
Change in Genant-modified Sharp radiographic total at week 56.
Change in Genant-modified Sharp radiographic score at week 24 (exploratory);
Change in erosion score, and joint space narrowing score.

The key inclusion criteria of this study were:
Experienced an inadequate response to previous or current treatment with etanercept, infliximab or adalimumab because of toxicity or inadequate efficacy
Etanercept for ≥3 months at 25 mg twice a week
Infliximab at least 4 infusions of at ≥3 mg/kg
Adalimumab for ≥3 months at 40 mg every other week.
Must have received MTX at a dose 10-25 mg/week (peroral (p.o.) or parenteral) for at least 12 weeks, with the last 4 weeks prior to screening at a stable dose.
All other DMARDs/biological response modifiers withdrawn at least 4 weeks prior to randomization) 8 weeks for infliximab, leflunomide and adalimumab)
Prednisone equivalent ≤10 mg/day.
Swollen joint count (SJC) ≥8 (66 joint count), and tender joint count (TJC) ≥8 (68 joint count).
Either CRP ≥1.5 mg/dL (15 mg/L) or ESR ≥28 mm/h
Radiographic evidence of at least one joint with a definite erosion attributable to rheumatoid arthritis.

The study treatment of the study was:
Group A:
Rituximab two i.v. infusions of 1000 mg on days 1 and 15
Group B
Placebo i.v. infusions on days 1 and 15
Both Groups
100 mg i.v. methylprednisolone prior to each rituximab/placebo infusion
60 mg/d prednisone on days 2-7 and 30 mg/d on days 8-14

6-Month Results:

| Patient Populations: | | |
| --- | --- | --- |
| No of Pts | Placebo | Rituximab |
| Enrolled | 209 | 308 |
| ITT | 201 | 298 |
| Vial Breaks | 4 | 3 |
| Audited Site | 1 | 4 |
| Treated Prior Randomisation | 3 | 3 |
| ITT By Region | 201 | 298 |
| US | 116 (58%) | 172 (58%) |
| Non-US | 85 (42%) | 126 (42%) |
| ITT By RF | 201 | 298 |
| RF + ve | 160 (80%) | 234 (79%) |
| RF − ve | 41(20%) | 64 (21%) |
| Per Protocol | 161 | 259 |
| Exclusions | 48 (24%) | 49 (16%) |
| Safety | 209 | 308 |

ITT
  Randomised
  Received part of infusion
  Analysed as randomised
Per protocol
  As above but adhered to protocol
Safety
  Randomised
  Received part of infusion
  Analysed as received

| Patient Demographics: | | |
| --- | --- | --- |
| | Placebo (n = 201) | Rituximab 2 × 1000 mg (n = 298) |
| Sex | | |
| Female | 82% | 81% |
| Male | 18% | 19% |
| Age (Mean, Yrs) | 53 | 52 |
| Methotrexate dose (mg/wk) | 15 | 15 |
| Previous DMARDs (mean) | 2.5 | 2.6 |
| Number of prior anti-TNF therapies | 1.5 | 1.5 |
| Pts receiving concomitant Corticosteroids* | 78% | 74% |
| Pts receiving NSAIDs or COX2* | 75% | 67% |

| Patients' Baseline Disease Characteristics | | |
| --- | --- | --- |
| | Placebo (n = 201) | Rituximab 2 × 1000 mg (n = 298) |
| Disease Duration (yrs) | 11.7 | 12.2 |
| SJC (mean) | 23 | 23 |
| TJC (mean) | 33 | 34 |
| RF Positive | 80% | 79% |
| RF (mean, IU/L) | 320 | 328 |
| CRP (mean, mg/dL) | 3.8 | 3.8 |
| ESR (mean, mm/h) | 48 | 48 |
| DAS28 | 6.8 | 6.9 |

| Patient Disposition | | |
| --- | --- | --- |
| | Placebo | Rituximab 2 × 1000 mg |
| Randomised | 209 | 308 |
| Withdrawn | 97 (46%) | 54 (18%) |
| Adverse events | 1 (<1%) | 8 (3%) |
| Death | — | — |
| Insufficient response | 83 (40%) | 36 (12%) |
| Refused Treatment | 5 (2%) | 5 (2%) |
| Others | 8 (4%) | 5 (2%) |
| Completed 24 weeks | 112 (54%) | 254 (82%) |

The efficacy outcomes of the study are shown in FIGS. 1-12.

The radiographic outcomes of the study are shown in FIGS. 13-17.

Figures 18, 19:
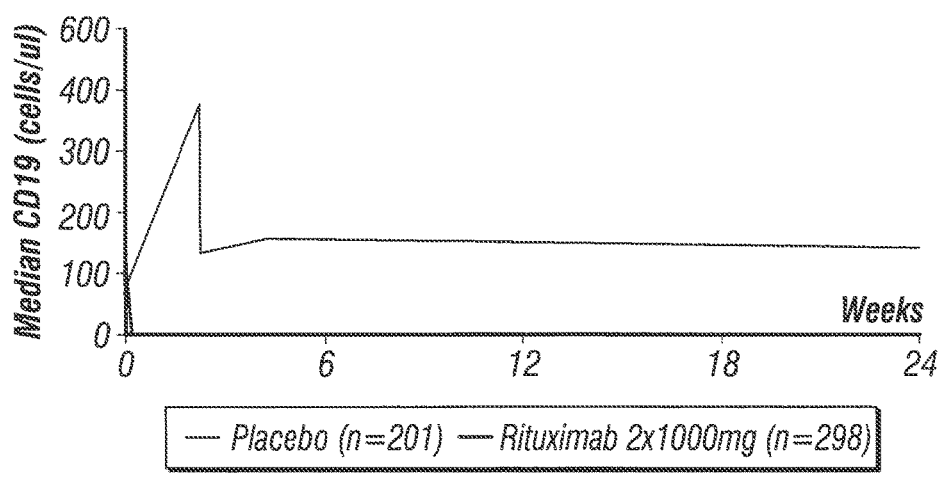
FIG. 18 shows mean percent change in ACR core set parameters at week 24 for RA patients treated with control or with rituximab (1000 mg×2) plus MTX.
FIG. 19 shows the median CD19 at six months of RA patients treated with control or with rituximab (1000 mg×2) plus MTX.
Figure 30:
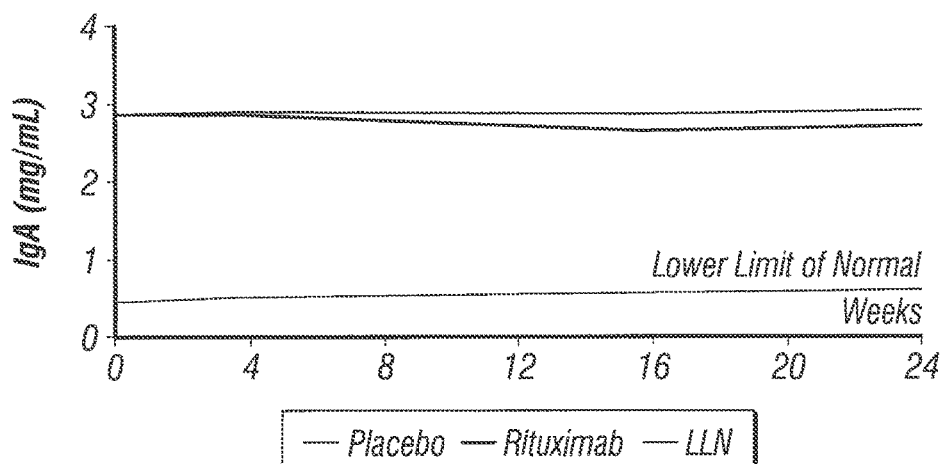
FIG. 30 shows IgA levels over six months in RA patients treated with control or with rituximab (1000 mg×2) plus MTX.
Figure 31:
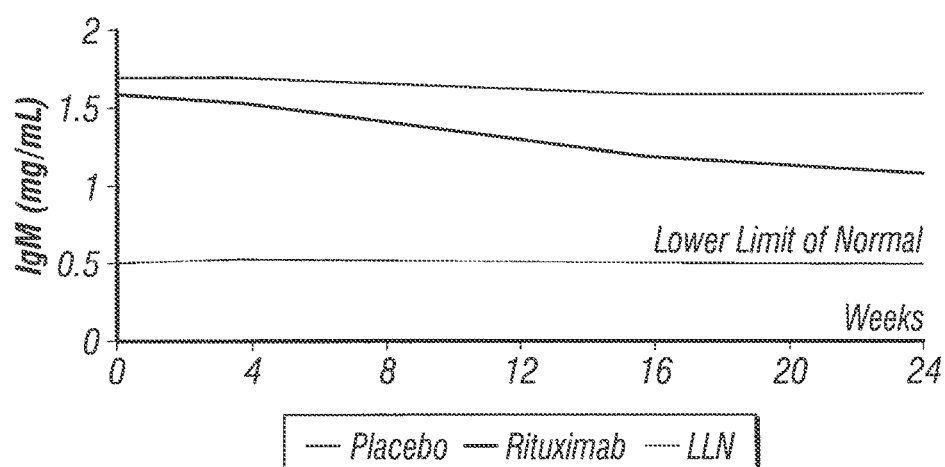
FIG. 31 shows IgM levels over six months in RA patients treated with control or with rituximab (1000 mg×2) plus MTX.

The mean change in ACR core set parameters is shown in FIG. 18.

The safety analysis of the study is shown in FIGS. 19-31.

The conclusions from REFLEX study were:
Rituximab was associated with a significant increase in ACR20 response rate over placebo (primary endpoint)
All secondary and exploratory endpoints (DAS, EULAR, ACR core set) supported primary analysis
The radiographic outcomes indicate that the treatment arm showed a lower Sharp-Genant total score over the 24 weeks versus the placebo arm (FIG. 13), a lower Sharp-Genant erosion score over the 24 weeks versus the placebo arm (FIG. 14), a lower Sharp-Genant JSN score over the 24 weeks versus the placebo arm (FIG. 15), a much larger proportion of patients with no change in erosion score at 24 weeks of the treatment versus the placebo arm (FIG. 16), with a summary of the radiographic endpoints at week 24 for placebo and treatment arms given in FIG. 17.

Rituximab was generally well tolerated.
Infusion related events
Rate of all infections comparable to placebo
Slight increase in rate/incidence of serious infections
No significant impact on immunoglobulins
Low HACA 56-Week Results:

|  | No. of patients (%)* | |
|---|---|---|
|  | Placebo (n = 186) | Rituximab (n = 277) |
| Completed 56 weeks | 141 (76) | 202 (73) |
| Withdrew | 46 (25) | 75 (27) |
| Withdrew and received treatment with TNF inhibitor | 12 (6.5) | 29 (10.5) |

* Patients with radiographic data available at 56 weeks.

Figure 41:
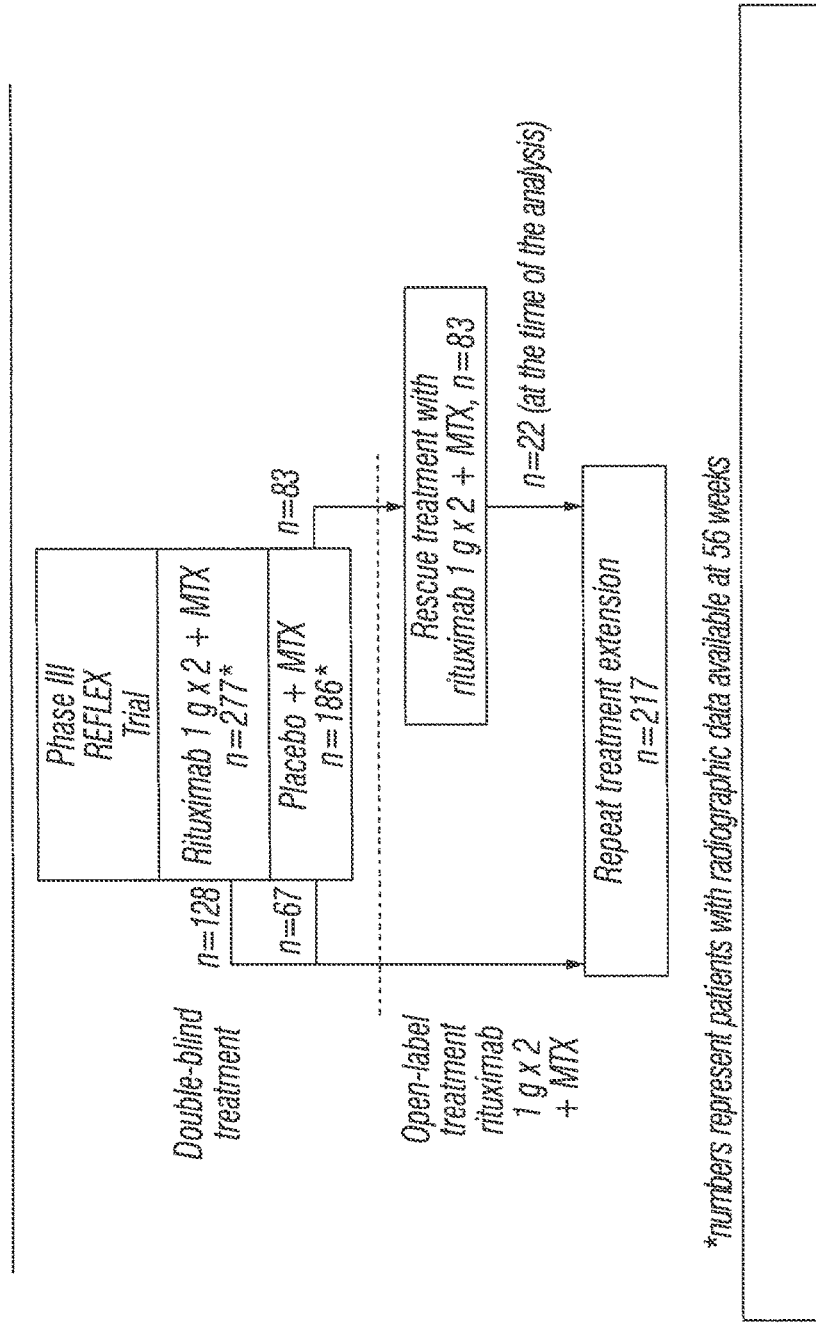
FIG. 41 illustrates the patient disposition of the REFLEX clinical trial at 56 weeks, including ongoing treatments of subgroups of patients selected from the treatment and placebo arms of the Phase III REFLEX clinical trial.

FIG. 41 further illustrates the patient disposition of the REFLEX clinical trial at 56 weeks, including ongoing treatments of subgroups of patients selected from the treatment and placebo arms of the Phase III REFLEX clinical trial.

Figure 42:
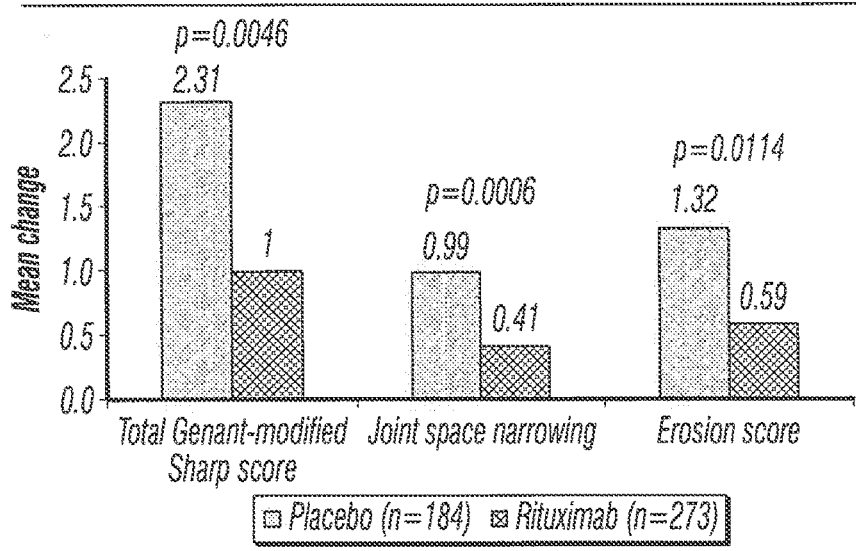
FIG. 42. Change in radiographic endpoints at week 56.

As shown in FIG. 42, at week 56 all of the mean change in total Genant-modified Sharp score (Genant, *Am. J. Med.*, 30: 35-47 (1983)), in joint space narrowing (JSN) and in erosion score showed a statistically significant improvement over placebo.

Figure 43:
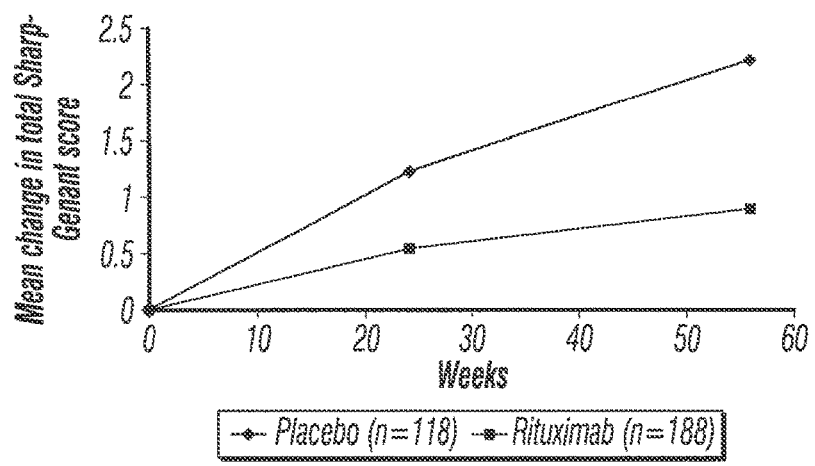
FIG. 43. Mean change in total Sharp-Genant score over time.

The efficacy of rituximab treatment is further illustrated by the mean change in total Sharp-Genant score over time. As shown in FIG. 43, the improvement has continued from week 24 to week 56.

Figures 44, 45:
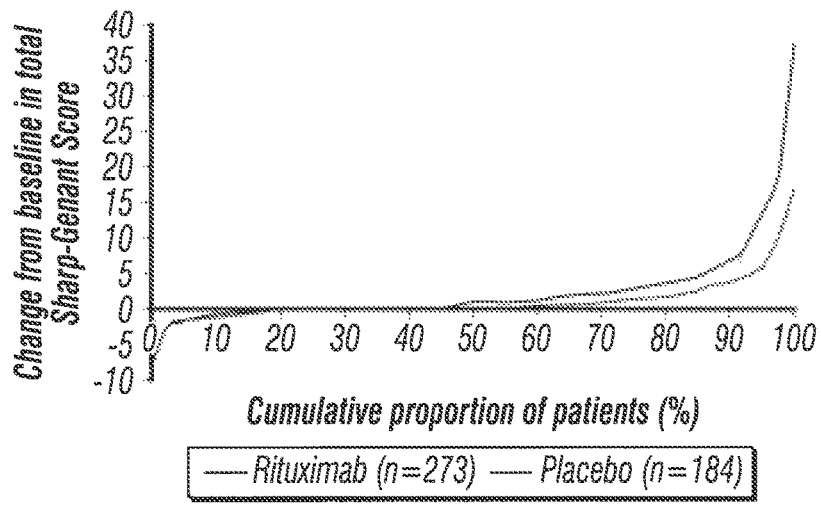
FIG. 44. Cumulative distribution of change in total Sharp-Genant score.
FIG. 45. Sesitivity analyses: vhange in total Sharp-Genant score.

FIG. 44 shows the cumulative distribution of change in total Sharp-Genant score.

FIG. 45 shows the results of sensitivity analyses, expressed by the change in total Sharp-Genant score. The rituximab+MTX treatment arm has been consistently superior over the placebo+MTX treatment arm.

Figure 46:
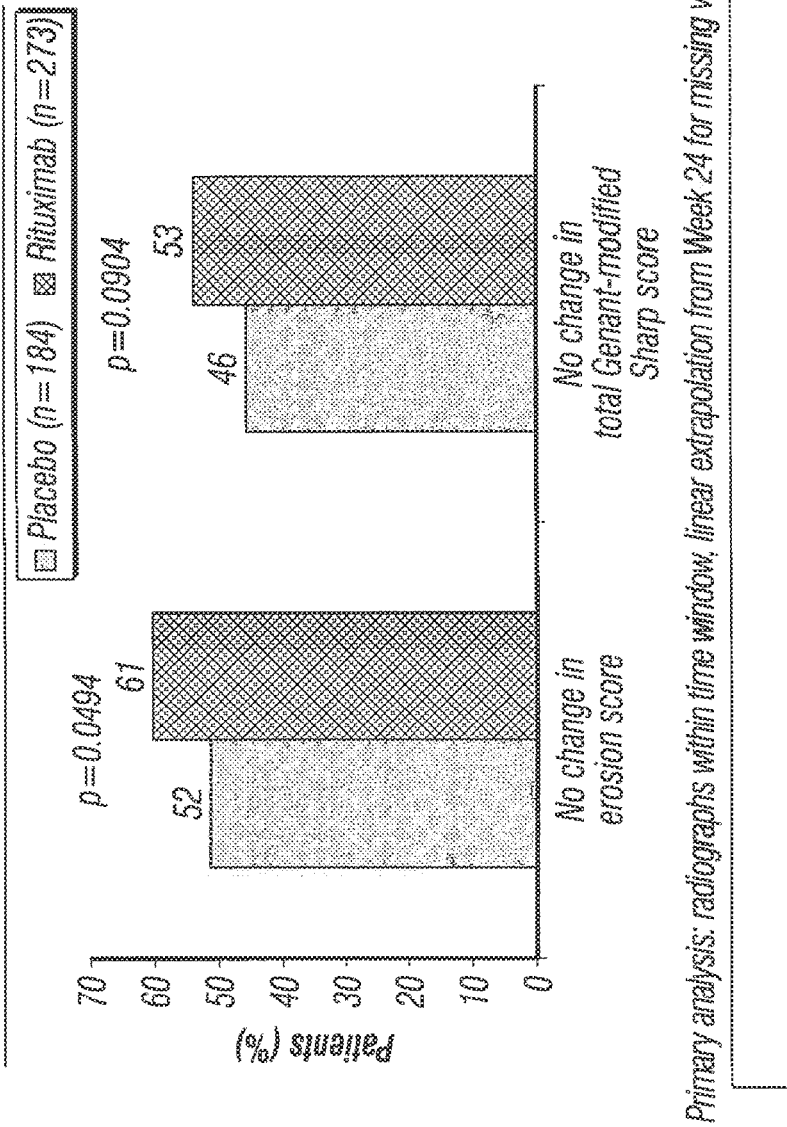
FIG. 46. Patients with no radiographic changes at week 56.

FIG. 46 shows the percentage of patients who showed no radiographic changes at the week 56 observation point in their joint condition, as measured by erosion score and Genant-modified Sharp score, respectively.

In conclusion, the results of this clinical trial show that rituximab significantly inhibits radiographic progression in rheumatoid arthritis (RA) patients with an inadequate response or intolerance to one or more TNF inhibitors. In addition, this study provides the first indication that a B cell-targeted therapy can inhibit radiographic progression.

Example 2

Rituximab in RA: Phase III Program

An important outcome to assess in RA includes the inhibition of progression of structural joint damage and the improvement in physical function. This outcome is particularly important for patients who have recently been diagnosed with RA, since early impact on these has potentially higher long-term benefit. Genovese et al., *Arthritis Rheum.* 46: 1443-1450 (2002). A population of early RA patients would therefore be an appropriate population to study for these important outcomes.

With regard to a suitable control treatment for these patients, the current gold standard therapy for early RA is MTX. Consequently, selecting a population of MTX-naïve patients and comparing rituximab plus MTX to MTX alone provides a comparison of this new treatment approach against the current gold standard for these patients.

This study is a randomized Phase III controlled soluble-blind, parallel-group multicenter study to evaluate the safety and efficacy of rituximab in combination with MTX compared to MTX alone, in MTX-naïve patients with active RA.

Primary Objectives:
1. To determine the efficacy of rituximab in the prevention of progression in structural joint damage and to evaluate the safety of rituximab in patients with active RA initiating treatment with MTX.
2. To evaluate the efficacy of rituximab in improving the patient's physical function and signs and symptoms of RA.
3. To investigate by a population analysis approach the pharmacokinetics (PK) of rituximab in the target RA patient population and the influence of covariates on the PK parameters.
4. To explore the long-term efficacy and safety of further courses of rituximab.

First Course—Study Design:
Group A: rituximab 500 mg i.v.×2 plus MTX (7.5 mg escalated to 20 mg p.o.)
Group B: rituximab 1000 mg i.v.×2 plus MTX (7.5 mg escalated to 20 mg p.o.)
Group C: Placebo rituximab i.v.×2 plus MTX (7.5 mg escalated to 20 mg p.o.)

For Group C patients, from week 104, re-treatment with courses of rituximab 500 mg i.v.×2 plus MTX will be available for eligible patients.

The following rules for re-treatment, in line with the above regimens, apply:

Second Course

A second course of rituximab plus MTX or placebo plus MTX will be administered as soon as feasibly possible when the following is achieved:
1. Minimum of 24 weeks has passed since the first infusion of the last course of study medication.
2. DAS28-ESR >2.6
3. Eligibility criteria for absolute neutrophil count (not below $1.5 \times 10^3$ µL), IgG (not below 5.0 mg/mL) and IgM (not below 0.40 mg/mL) were met at the last blood sample analysis.

In addition, the patient must meet the eligibility exclusion criteria 8, 10 and 11 as described below:
1. Significant cardiac or pulmonary disease (including obstructive pulmonary disease)
2. Primary or secondary immunodeficiency (history of, or currently active), including known history of HIV infection.
3. Known active infection of any kind (excluding fungal infections of nail beds), or any major episode of infection requiring hospitalization or treatment with i.v. anti-infectives within 4 weeks of infusion or completion of oral anti-infectives within 2 weeks prior to infusion.

Patients who do not meet the criteria for a second course of rituximab/placebo at week 24 will be followed every 4 to 8 weeks and will subsequently receive the second course at the time they become eligible based on the above criteria.

Further Courses:
From week 48 patients may become eligible to receive a third course of rituximab/placebo. The third course and beyond may only be administered to patients who have met the above criteria for the second course and in whom the investigator deems there has been a relevant clinical response following either the first or the second course of rituximab. Patients who have never had a clinical response should be withdrawn into safety follow-up (SFU).

Patients who are deemed to have had a clinical response, but do not currently meet the criteria for further courses of rituximab will be followed every 4 weeks from week 48 to week 56 and then every 8 weeks and will subsequently receive further courses at the time they become eligible based on the above criteria.

All patients will receive pre-medication with 100 mg i.v. methylprednisolone prior to each infusion. All patients will also receive a stable dose of folate (at least 5 mg/week) given as either a single dose or as a divided weekly dose.

All patients should continue to receive any background corticosteroid (at least 10 mg/day prednisone or equivalent) or oral nonsteroidal anti-inflammatory drugs (NSAIDs) at a stable dose. Randomization will be stratified by region (US or ROW) and rheumatoid factor (positive or negative) to ensure balanced allocation of patients across region and RF status between treatment arms.

Patients will attend the clinic once every 4 weeks for the first 24 weeks and every 8 weeks thereafter (except for weeks 48-56 where visits will be every 4 weeks) for efficacy, safety, immunology, and quality of life assessments. Radiographic assessments will be conducted at screening, week 24, and week 52. Radiographic assessments will also be conducted at 2 and 3 years after the first dose of study medication.

Evaluation of the primary endpoint (change in total modified Sharp score) will occur at 52 weeks. Secondary and exploratory endpoints will include further radiographic endpoints and signs and symptoms, physical function and remission endpoints.

At any time after radiographic assessment at week 52, patients who do not have a 20% improvement in both swollen and tender joint counts may receive rescue therapy with an increased dose of MTX or one non-biologic DMARD.

All patients who withdraw from the study or at any point or complete the total treatment period should return for SFU assessments at weeks 4, 12, 24, 36, and 48 after withdrawal or completion. This effectively follows the patient for one year after the patient withdraws from/completes the study. If a patient's peripheral B-cell count (CD19) has not returned to their baseline level or to within the normal range, whichever is lower, after one year, safety follow-up visits should continue to be performed at 12-week intervals until B-cell repletion occurs.

For all serious infectious adverse events reported CBC, differentials, platelets, quantitative Ig and CD19 counts should be determined within one week of the infectious adverse event becoming serious.

Patients withdrawing into SFU are to be strongly encouraged to return for all scheduled radiographic assessments (at weeks 24, 52, 104, and 152) irrespective of their point of withdrawal from the study. Radiographs for these patients are to be taken in line with the original schedule of assessments, relative to the original day of randomization.

Approximately 852 patients will be recruited into this study and will be randomized equally into three treatment groups. Patients will be stratified by region (US or Rest of World (ROW)) and RF status (positive RF at least 20 IU/mL or negative RF less than 20 IU/mL). The overall proportion of RF-negative patients will be limited to 20% of the total sample size. Recruitment will be competitive with no more than 70% and no less than 30% being enrolled in either region. There will be no replacement of patients should a patient's treatment be discontinued for any reason.

Target Population:

The target population for this study is patients with early active RA, who are naïve to MTX.

Inclusion Criteria:

Patients must meet the following criteria to be eligible for study entry:
1. Able and willing to give written informed consent and comply with the requirements of the study protocol.
2. Patients with RA diagnosed for at least 8 weeks, but no more than 4 years, according to the revised 1987 ACR criteria for the classification of RA.
3. Patients naïve to, and considered to be candidates for, treatment with MTX.
4. Swollen joint count (SJC) at least 8 (66 joint count), and tender joint count (TJC) at least 8 (68 joint count) at screening and baseline.
5. At screening CRP at least 1.2 mg/dL (12 mg/L).
6. Age 18-80 years.
7. Glucocorticoids at least 10 mg/day prednisolone or equivalent is permitted if stable for at least four weeks prior to baseline.
8. Use of NSAIDs is permitted if stable for at least two weeks prior to baseline.
9. For patients of reproductive potential (males and females), use of a reliable means of contraception (e.g., hormonal contraceptive, patch, intrauterine device, physical barrier) throughout study participation.
10. Must be willing to receive oral folate.
11. For RF-negative patients only, radiographic evidence of at least one joint with definite erosion attributable to RA.
12. Patients who are to receive, or who are current receiving, treatment on an outpatient basis.

Exclusion Criteria:

Exclusions Related to RA
1. Rheumatic autoimmune disease other than RA, or significant systemic involvement secondary to RA (including but not limited to vasculitis, pulmonary fibrosis or Felty's syndrome). Secondary Sjögren's syndrome or secondary limited cutaneous vasculitis with RA is permitted.
2. Functional class IV as defined by the ACR Classification of Functional Status in RA.
3. History of, or current, inflammatory joint disease other than RA (including, but not limited to, gout, reactive arthritis, psoriatic arthritis, seronegative spondyloarthropathy, Lyme disease), or other systemic autoimmune disorder (including, but not limited to, systemic lupus erythematosus, inflammatory bowel disease, scleroderma, inflammatory myopathy, mixed connective tissue disease, or any overlap syndrome).
4. Diagnosis of juvenile idiopathic arthritis (JIA) or juvenile RA (JRA) and/or RA before age 16.

Exclusions Related to General Health
5. Any surgical procedure, including bone/joint surgery/synovectomy (including joint fusion or replacement) within 12 weeks prior to baseline or planned during the study.
6. Lack of peripheral venous access.
7. Pregnancy or breast feeding.
8. Significant and/or uncontrolled cardiac or pulmonary disease (including obstructive pulmonary disease).

9. Evidence of significant concomitant disease, including but not limited to, nervous system, renal, hepatic, endocrine or gastrointestinal disorders which, in the investigator's opinion, would preclude patient participation.
10. Primary or secondary immunodeficiency (history of, or currently active), including known history of HIV infection.
11. Known active infection of any kind (excluding fungal infections of nail beds), or any major episode of infection requiring hospitalization or treatment with i.v. anti-infectives within 4 weeks of baseline or completion of oral anti-infectives within 2 weeks prior to baseline.
12. History of deep space/tissue infection (e.g. fasciitis, abscess, osteomyelitis) within 52 weeks prior to baseline.
13. History of serious recurrent or chronic infection (for screening for a chest infection a chest radiograph will be performed at screening if not performed within 12 weeks prior to screening).
14. History of cancer, including solid tumors, hematologic malignancies and carcinoma in situ (except basal cell and squamous cell carcinoma of the skin that have been excised and cured).
15. Any neurological (congenital or acquired), vascular or systemic disorder which could affect any of the efficacy assessments, in particular, joint pain and swelling (e.g., Parkinson's disease, cerebral palsy, diabetic neuropathy).
16. Currently active alcohol or drug abuse or history of alcohol or drug abuse within 24 weeks prior to baseline.

Exclusions Related to Medications

17. History of a severe allergic or anaphylactic reaction to a biologic agent or known hypersensitivity to any component of rituximab or to murine proteins.
18. Previous treatment with any approved or investigational biologic agent for RA.
19. Previous treatment with an anti-alpha 4 integrin antibody or co-stimulation modulator.
20. Concurrent treatment with any biologic agent or DMARD other than MTX. Treatment must be discontinued 14 days prior to baseline, except for the following: azathioprine for at least 28 days; leflunomide for at least 8 weeks (or at least 14 days after 11 days of standard cholestyramine or activated charcoal washout).
21. Previous treatment with any cell-depleting therapies, including investigational agents (e.g., CAMPATH, anti-CD4, anti-CD5, anti-CD3, anti-CD19, anti-CD11a, anti-CD22, BLys/BAFF, and anti-CD20).
22. Treatment with any investigational agent within 28 days of baseline or five half-lives of the investigational drug (whichever is the longer).
23. Receipt of a live/attenuated vaccine within 28 days prior to baseline (it is recommended that a patient's vaccination record and the need for immunization prior to receiving rituximab/placebo should be carefully investigated).
24. Intra-articular or parenteral glucocorticoids within 4 weeks prior to baseline.
25. Intolerance or contra-indications to i.v. glucocorticoids.

Exclusions Related to Laboratory Findings

26. Positive serum human chorionic gonadotropin (hCG) measured prior to the first rituximab infusion.
27. Positive tests for hepatitis B surface antigen (HBsAg), hepatitis B core antibody (HBsAb) or hepatitis C serology.
28. Hemoglobin less than 8.0 g/dL.
29. Concentrations of serum IgG and/or IgM below 5.0 and 0.40 mg/mL, respectively.
30. Absolute neutrophil count (ANC) less than $1.5 \times 10^3$/μL.
31. AST or ALT greater than 2.5 times upper limit of normal.

The end of treatment is defined as the 3-year time point, following which there will be an additional period of at least a year of SFU.

Rituximab (500 mg or 1000 mg) plus MTX or placebo plus MTX will be administered by IV infusion on days 1 and 15. Patients may be eligible for re-treatment (two doses 14 days apart) with a maximum frequency of one re-treatment every 24 weeks. Patients originally randomized to receive rituximab plus MTX will receive re-treatment at the same dose throughout the study. From week 104 patients originally randomized to placebo plus MTX may be eligible to receive rituximab (500 mg) plus MTX. Premedication with 100 mg i.v. methylprednisolone is to be administered prior to each infusion.

Methotrexate tablets (7.5 mg/week escalated to 20 mg/week) will be administered orally to all groups.

It is recommended that all patients should be pre-medicated with paracetamol/acetaminophen (1 gm p.o.) and diphenhydramine HCl (100 mg i.v. or oral equivalent antihistamine) 30 to 60 minutes prior to the start of an infusion to reduce the potential for infusion reactions.

Patients will receive folate or equivalent (at least 5 mg/week) given as either a single dose or as a divided weekly dose.

Patients may continue to receive any background glucocorticoid (at least 10 mg/day of prednisone or equivalent). Analgesics may be used for pain as required.

The primary endpoint is the change from screening in total modified Sharp score at week 52 using the modified intent-to-treat (ITT) population.

The radiographic secondary endpoints are:
1. a change in modified total Sharp score at Weeks 24 and 104
2. a change in modified Sharp erosion score at Week 52
3. a change in modified joint space narrowing score at Week 52
4. The proportion of patients without radiographic progression at Week 52 (defined as change in total modified Sharp score of less than or equal to 0). In addition, the proportion of patients without radiographic progression at Weeks 24 and 104 will be analyzed.

The radiographic exploratory endpoints are:
1. a change in modified Sharp scores will be presented over time.
2. Proportion of patients without radiographic progression at Weeks 24, 52, and 104 will be further presented in the following sub-categories:
   a. Proportion of patients with no change in modified Sharp erosion score from screening
   b. Proportion of patients with no change in modified joint space narrowing score from screening
   c. Proportion of patients with no newly eroded joints.

Radiographic assessments will be made as follows: separate radiographs of each hand posterior-anterior (PA) and each foot anterior-posterior (AP) will be taken as per schedule of assessments. At the screening visit the readability and quality of the radiographs (as can be found in a procedure manual for radiographic examinations of the hands, wrist and feet) must be confirmed before the patient leaves the site. Radiographs for RF-negative patients at the screening visit will be checked for radiographic evidence of at least one joint with a definite erosion attributable to RA by the central reading site. All radiographs will be assessed using the method according to Sharp, as modified by Genant, *Am. J. Med.*, 30: 35-47 (1983). The primary assessment will be the change from screening in the total modified Sharp score at week 52. The total modified Sharp score combines an erosion score and a joint space narrowing score of both hands and feet. The maximum total erosion score in the hands is 100 and in the feet 42, the maximum scores for joint space narrowing in the hands is 100 and in the feet 48. The maximum total modified Sharp score achievable is 290. The change in score at week 52 is to be calculated as: Change=week 52 score minus screening score.

Radiographs will be taken of the hands and feet to compute a total modified Sharp score. Before starting the trial all radiology departments will participate in training sessions to standardize radiographs. This will include standardization for validation procedures for equipment, films, cassettes, placement of hands/feet and procedures for obtaining consistent radiographs.

The change in total modified Sharp score is expected to be skewed and hence not normally distributed. Therefore, the change in total modified Sharp score at week 52 will be tested between treatment groups using a non-parametric test statistic stratifying for region and RF status. However, if the data are shown to be approximately normally distributed, the data will be analyzed using an analysis of variance (ANOVA) model with region, RF status, and treatment groups as exploratory terms in the model.

Closure principle will be used to adjust multiple comparisons in primary endpoint. The first comparison will be between each of the three treatment arms using a Kruskal-Wallis test statistic.

The three treatment arms will be considered different if there is sufficient statistical evidence to reject the following null hypothesis:

$H_o$: $\mu_1 = \mu_2 = \mu_3$ i.e., no evidence that there is any difference in the change in total modified Sharp score in any of the treatment arms and accept the alternative hypothesis:

$H_1$: $\mu_1$ does not equal $\mu_2$, or $\mu_1$ does not equal $\mu_3$, or $\mu_2$ does not equal $\mu_3$ i.e., there is a difference in the change in total modified Sharp score in at least one of the pairwise treatment comparisons.

If the test result is statistically significant at $\forall=0.05$ level, it is concluded that there is a difference in the change from baseline in total modified Sharp score at week 52, between the treatment arms.

Subsequently, each of the rituximab groups are compared with the placebo group, at the $\forall=0.05$ level, as described below. The primary comparisons will be considered to be the individual rituximab dose group vs. the placebo group, using the Van Elteren test statistic.

Each of the rituximab-treated arms will be considered superior to placebo if there is sufficient statistical evidence to reject the following null hypothesis:

$H_o$: $\mu_1 = \mu_2$ i.e., no evidence that the change in total modified Sharp score in the rituximab arm is superior to the placebo arm and accept the alternative hypothesis:

$H_1$: $\mu_1$ does not equal $\mu_2$ i.e., the change in total modified Sharp score in the rituximab arm is superior to the placebo arm.

If the test result is statistically significant at $\forall=0.05$ level, it will be concluded that the rituximab arm demonstrated a superior change from baseline in total modified Sharp score at week 52 when compared to the placebo arm.

Every effort will be made to ensure, wherever possible, that patients return for their radiographic visits, even if withdrawing from study drug. Missing week 52 data will be imputed using the following methods:

If week 52 radiographic data is missing, then week 24 radiographic data will be used to linearly extrapolate that patient's week 52 result. Those patients who withdraw prematurely from the study prior to week 52 will be included as part of the week 52 analysis of radiographic data. Any patient who has no post screening radiographic data will be excluded from the modified ITT population and hence from the primary endpoint analysis.

The influence of potential imbalances in treatment allocations within particular sites will be investigated. Sensitivity analyses will be performed to assess the impact of grossly imbalanced sites on the primary analysis.

As to the radiographic secondary endpoints, change in modified total Sharp score at weeks 24 and 104 will be analyzed in the same manner as specified for the primary endpoint. The change in modified Sharp erosion score at week 52 will be analyzed in the same manner as specified for the primary endpoint. In addition, change in modified Sharp erosion score at weeks 24 and 104 will be analyzed. Change in modified joint space narrowing score at week 52 will be analyzed in the same manner as specified for the primary endpoint. In addition, change in modified joint space narrowing score at weeks 24 and 104 will be analyzed. The proportion of patients without radiographic progression at week 52 (defined as a change in total modified Sharp score of less than or equal to 0) will be assessed as follows: The difference in the proportions will be tested using a Cochran-Mantel Haenszel (CMH) test statistic stratifying for region and RF status. In addition, the proportion of patients without radiographic progression at weeks 24 and 104 will be analyzed.

As to radiographic exploratory endpoints, the change in modified Sharp scores will be presented over time. The proportion of patients without radiographic progression at weeks 24, 52, and 104 will be further presented in the following sub-categories:

Proportion of patients with no change in modified Sharp erosion score from screening Proportion of patients with no change in modified joint space narrowing score from screening Proportion of patients with no newly eroded joints.

Details of the joints for radiographic assessment and grading scales (Genant, *Am. J. Med.*, 30: 35-47 (1983)) are as follows: Grading Scales:

1. Joint Space Narrowing (JSN)

Grade 0—Normal

Grade 0.5—Subtle JSN or equivocal findings.

Grade 1.0—Mild JSN (focal or minor).

Grade 1.5—Mild-to-moderate JSN.

Grade 2.0—Moderate JSN.

Grade 2.5—Moderate-to-severe JSN.

Grade 3.0—Severe JSN.

Grade 3.5—Severe JSN close to ankylosis.

Grade 4.0—Definite ankylosis.

2. Erosions (discrete interruption of cortical surface)
Grade 0—Normal
Grade 0.5—Subtle loss of cortical continuity or equivocal findings of bone erosion.
Grade 1.0—Mild. Definite but small erosions of one or both articular bones, usually at the bare areas involving less than 25% of the articular surfaces.
Grade 1.5—Mild-to-moderate. Small-medium erosions involving less than 25% of the articular surface of one or both articular bones.
Grade 2.0—Moderate. Medium-large erosions involving 26-50% of the articular surface of both articular bones.
Grade 2.5—Moderate-to-severe. Erosions of 51-75% of the articular surfaces.
Grade 3.0—Severe. Erosions of 76-90% of the articular surfaces.
Grade 3.5—Very severe. Erosions of 100% of the articular surfaces (total destruction of the articular surfaces).

Joint Evaluation:
1. Joint Space Narrowing in the hand (13 joints per hand)
   a. All proximal interphalangeal (PIP) joints on digits II-V.
   b. The interphalangeal joint on digit I.
   c. All metacarpophalangeal (MCP) joints.
   d. The carpometacarpal (CMC) joints of digits III-V as a single unit.
   e. The pericapitate (scaphoid-capitate and lunate-capitate combined) space.
   f. The radiocarpal joint.
2. Erosion Scores in the hand (14 joints per hand)
   a. All proximal interphalangeal (PIP) joints on digits II-V.
   b. The interphalangeal joint on digit I.
   c. All metacarpalphalangeal (MCP) joints
   d. The carpometacarpal (CMC) joints of digit I
   e. The scaphoid bone.
   f. The distal radius.
   g. The distal ulnar.

The scores will be summed separately (14×3.5 maximum per joint×2=98 for erosions and 13×4 maximum per joint×2 for JSN). Each sum will be normalized to a scale of 0-100. Both scores will be added to obtain a total score (scale 0-200).

3. Joint Space Narrowing and Erosions (6 joints per foot)
   a. All metatarsolphalangeal (MTP) joints.
   b. All interphalangeal joints on digit I.

The scores will be summed separately (6×3.5 maximum per joint×2=42 for erosions and 6×4 maximum per joint×2=48 for JSN. Both scores will be added to obtain a total score with a scale 0-90).

Original radiographs will be sent to the central reading site, where they will be quality controlled. Should the initial radiograph be of unacceptable quality, the center will be advised as to what amendments are needed and instructed to obtain a second radiograph.

All patients randomized in the study who have received at least part of a dose of rituximab (including those who have withdrawn into safety follow-up) will have radiographs of hands/wrists and feet taken at weeks 24, 52, 104, and 152. Patients are to be strongly encouraged to return for all radiographic assessments irrespective of their point of withdrawal from the study. Radiographs of these patients are to be taken in line with the original schedule of assessments, relative to the original day of randomization.

Additional secondary and exploratory endpoints will be for signs and symptoms, physical function, remission, and patient-reported outcomes.

The change in total modified Sharp score at week 52 will be tested between treatment groups using a non-parametric test statistic stratifying for region and RF status. However, if the data is shown to be approximately normally distributed, the data will be analyzed using an analysis of variance (ANOVA) model with region, RF status and treatment groups as exploratory terms in the model.

It is clearly desirable to maintain patients in a state of low disease activity by limiting disease flares and potentially limiting progression of structural damage. In the DANCER study referred to above (Emery et al., EULAR, supra, and Van Vollenhoven et al., EULAR, supra), at week 24, approximately 90% of patients treated with rituximab had not achieved EULAR (DAS28) remission. In the study that is the subject of this Example, such patients would be eligible to receive their first re-treatment of rituximab at week 24. Mandatory re-treatment based on DAS28-ESR provides objective information concerning a disease activity-based re-treatment paradigm. The minimum period of 24 weeks between courses is recommended based on the pharmacokinetics and pharmacodynamics of rituximab. Without being limited to any one theory, the pharmacokinetics and pharmacodynamics of rituximab appear to demonstrate that, at this time (week 24), drug levels are below the level of detection and there is evidence of returning peripheral CD19+ cells. This is paralleled by an apparent increase in disease activity after this time point, and therefore represents a reasonable point from which further courses could be given.

It is expected that rituximab (or a humanized 2H7 antibody substituted for rituximab) in combination with MTX will be efficacious in meeting the primary endpoint in the prevention of progression in structural joint damage as set forth in this Example, It is also expected that the regimen of this study will meet one or more of the secondary radiographic endpoints. Thus, it is expected that administration of a first dose of rituximab or humanized 2H7 (at 500 mg×2 or 100 mg×2) with methotrexate) will reduce joint damage from baseline (before first administration of CD20 antibody), as measured by the modified total Sharp score, at least about one month from baseline or start of treatment, preferably at least about 24 weeks from baseline, more preferably at least about 52 weeks from baseline, and at further time points up to 104 weeks from baseline. It is also expected that the patients can be efficaciously re-treated at 24 weeks or 52 weeks from baseline to maintain this prevention of progression of joint damage.

It is predicted and expected that administration of rituximab or a humanized 2H7 to the subject in the scheduled re-dosing protocol set forth above will be effective in preventing progression of structural joint damage at week 52 or later. These results are expected to be significantly better than those of the control.

It is also expected that at about week 48-54, another 1-g or 2-g dose of the CD20 antibody (e.g., rituximab or a humanized 2H7) given all at once or spread out over about 14-16 days in 0.5- or 1-gram amounts would be effective to treat joint damage for the entire second year, with or without one or more second medicaments such as immunosuppressive agents. Thus, the CD20 antibody would be administered initially within about the 2-week time period, followed by another treatment at about 4-8 months, followed by another treatment at about one year from initial treatment (measured from the time any one of the doses was given), followed by treatment at about two years from initial treatment, with expected success, in about one-half-gram or one-gram×2-4 dosing for each treatment, administered together, about weekly, or about every other week over about two to four weeks. The results of this treatment would be expected to be much better than those of the control with placebo. This re-treatment protocol is expected to be successfully used for several years with little or no adverse effects.

It is also contemplated that rituximab or another CD20 antibody will meet the primary endpoint as a monotherapy using the same regimen at the same dose or a higher dose without a second medicament such as MTX, and that re-treatment using the same regimen at the same dose or a higher dose would be successful as a monotherapy.

Example 3

Study of Efficacy of Retreatment with Rituximab in Patients with Rheumatoid Arthritis This example describes a phase III randomized double-blind, placebo-controlled multicenter study of retreatment with rituximab in subjects with RA receiving background methotrexate.

The primary objective of this study is to evaluate the efficacy of retreatment with rituximab in subjects with active RA who are receiving MTX and who have had an inadequate response to TNF inhibitors.

The secondary objectives of this study are as follows:
To evaluate the safety of retreatment with rituximab in subjects with active RA who are receiving MTX and who have had an inadequate response to TNF inhibitors
To evaluate the safety of rituximab in subjects with active RA who are receiving MTX and who have had an inadequate response to TNF inhibitors This is a Phase III, randomized, double-blind, placebo-controlled, multicenter study evaluating the efficacy of retreatment with rituximab in subjects with active RA who are receiving MTX. The study consists of four parts: screening, treatment period (open-label rituximab for first course and, for eligible subjects, double-blind, randomized retreatment), safety follow-up (SFU), and B-cell follow-up. Subjects must have had inadequate response to treatment with one or more TNF inhibitors because of toxicity or inadequate efficacy. Approximately 555 subjects will enter the treatment period at approximately 150 investigational sites in the United States. RF-positive and RF-negative subjects will be enrolled and will be allocated equally between treatment arms, with the overall proportion of RF-negative subjects limited to 20% of the total sample size.

Prior to Day 1, subjects will be discontinued from all DMARDs except MTX (for leflunomide, adalimumab, and infliximab for ≥8 weeks and etanercept for ≥4 weeks). All subjects will continue to receive MTX 10-25 mg/wk, at a stable dose for the study duration. The screening visit can occur up to 56 days prior to receiving the first dose of study treatment depending on washout requirements.

All subjects who meet eligibility criteria and are enrolled in the trial will receive rituximab for the first course of treatment. A course of rituximab is defined as two 1000 mg intravenous (IV) doses given 14 days apart, with pre-medication with methylprednisolone 100 mg IV prior to each dose of rituximab. All subjects will also receive a stable dose of folate (≥5 mg/wk). All subjects should continue to receive any background corticosteroids (≤10 mg/day prednisone or equivalent) or oral nonsteroidal anti-inflammatory drugs (NSAIDs) at a stable dose.

The first dose of rituximab should be given within 24 hours following baseline assessments. However, if necessary, up to 72 hours will be allowed between baseline assessments and the first dose of study drug.

During Weeks 24-40, subjects who have active disease based on a disease activity score in 28 joints (DAS 28-erythrocyte sedimentation rate [ESR]) of ≥2.6 will be considered eligible for retreatment and will be randomized in a 2:1 ratio to receive retreatment with one additional course of rituximab (Group A) or placebo (Group B). Subjects who do not meet the criteria for a second course of rituximab during Weeks 24-40 will continue to be followed for safety and efficacy. Subjects who meet the criteria for retreatment during Weeks 24-40 and refuse retreatment, for any reason, will be withdrawn from the treatment period and will enter into the SFU period.

Standard arthritis and safety assessments will be performed. Pharmacodynamic measures will include $CD19^+$ B cells, immunoglobulins, and autoantibodies. DAS 28-ESR scores will be calculated by the investigator at regularly scheduled visits (Prevoo et al. *Arthritis Rheum* 38:44-48 (1995); DAS-score.nl 2005 DAS-score.nl 2005: home of the DAS. Department of Rheumatology University Medical Center Nijmegan—the Netherlands. [cited 1 Sep. 2005]. Available from: http://www.das-score.nl/www.das-score.nl/index.html).

The treatment period is 72 weeks long (Day 1 to Week 72). All subjects who withdraw from the treatment period at any time or who receive retreatment with rituximab/placebo between Weeks 24-40 and complete the treatment period should return for SFU assessments at SFU Weeks 4, 12, 24, 36, and 48 after withdrawal or completion. All subjects will be followed for at least 48 weeks after their last dose of rituximab. All subjects who receive only one course of rituximab treatment (i.e., those that do not qualify for retreatment during the study) and complete the treatment period will not return for SFU.

Subjects whose peripheral B-cell counts have not recovered by the end of the treatment period or the SFU period will continue to be followed for laboratory evaluations and the occurrence of serious adverse events every 12 weeks until B-cell recovery. B-cell recovery is defined as peripheral B-cell counts that have returned to baseline values or the lower limit of normal (LLN), whichever is lower.

At or following 16 weeks after retreatment, subjects who have not achieved a 20% improvement in both tender joint counts (TJCs) and swollen joint counts (SJCs) compared with baseline may initiate rescue treatment with one non-biologic DMARD, the choice of which is at the discretion of their treating physician.

In a retreatment study of rituximab in RA, subjects achieved sustained American College of Rheumatology (ACR) 20, 50, and 70 responses (Pavelka et al. "Efficacy and safety following repeated courses of rituximab in patients with active rheumatoid arthritis." Abstract presented at EULAR 2005). However, because this study is an open-label study, there are no controlled data evaluating the efficacy and safety of retreatment with rituximab in RA. This present study is designed to evaluate the efficacy of retreatment in a placebo-controlled trial with a single additional course of rituximab in subjects with active RA. Subjects with active disease, as characterized by a DAS 28-ESR ≥2.6, will be treated with a second course of study drug (rituximab or placebo) during Weeks 24-40.

The purpose of retreatment with rituximab is to prevent flare, promote sustained control of disease, and potentially prevent disease progression. The criterion of DAS 28-ESR ≥2.6 for retreatment will ensure that subjects with clinically significant disease activity are retreated. The DAS 28-ESR will be calculated using the number of swollen and tender joints, the ESR, and the Patient's Global Assessment of Disease Activity (on a 100 mm visual analog scale [VAS]).

The primary endpoint of this study is the proportion of retreated subjects with an ACR20 at Week 48 relative to baseline (Day 1), not relative to time of retreatment. Baseline (Day 1), not time of retreatment, was chosen in order to evaluate the overall benefit of retreatment with rituximab in subjects with moderate to severe RA. Without being limited to any one theory, it is hypothesized that retreatment with RTX results in maintenance of effect to a slight improvement at Week 48 relative to Week 24, in comparison with a deterioration in placebo-treated subjects. Although there may be a clear treatment benefit in retreated subjects, ACR20 responses at Week 48 relative to a Week 24 baseline for both groups may be insignificant, Thus, this study is not designed to evaluate improvement from the time of retreatment.

Based on Week 24 data in the Phase III study (REFLEX, WA17042/U2646s/IDEC102-20), approximately 91% of subjects treated with rituximab would have met the retreatment criterion (DAS 28-ESR ≥2.6) at Week 24 of this protocol. Mandatory retreatment based on DAS 28-ESR will provide objective efficacy information using a disease activity-based retreatment paradigm. The minimum period of 24 weeks is based on the pharmacokinetics and pharmacodynamics of rituximab. This is paralleled by an apparent increase in disease activity after this timepoint and, therefore, represents a reasonable time to retreat.

The primary outcome measure is the proportion of retreated subjects with an ACR20 response at Week 48 relative to baseline (Day 1).

The secondary outcome measures are as follows:
Proportion of retreated subjects with an ACR50 and ACR70 response at Week 48 relative to baseline (Day 1).
Change in DAS 28-ESR at Week 48 compared with baseline (Day 1) for retreated subjects
Proportion of retreated subjects who achieve a European League Against Rheumatism (EULAR) response (good or moderate) at Week 48 relative to baseline (Day 1)
Change in ACR core set at Week 48 compared with baseline (Day 1) for retreated subjects (SJC, TJC, Health Assessment Questionnaire [HAQ], patient and physician global assessments, patient pain assessment, C-reactive protein [CRP], and ESR)
ACR-N at Week 48 in retreated subjects
Change in SF-36 subscale and summary scores from baseline (Day 1) to Week 48 in retreated subjects
Change in Functional Assessment of Chronic Illness Therapy-Fatigue (FACIT-F) assessment from baseline (Day 1) to Week 48 in retreated subjects
Proportion of ACR20, ACR50, and ACR70 response at Week 48 in all subjects The exploratory outcome measures are:
Proportion of all subjects who achieve an ACR20, ACR50, and ACR70 response at Week 72 compared with baseline
Proportion of subjects with DAS 28-ESR remission (DAS 28-ESR <2.6) at Week 48
Proportion of subjects with DAS 28-ESR low disease (DAS 28-ESR ≤3.2) at Week 48
Proportion of subjects with DAS 28-ESR remission (DAS 28-ESR <2.6) at Week 72
Proportion of subjects with DAS 28-ESR low disease (DAS 28-ESR ≤3.2) at Week 72

Eligible subjects who have active RF-positive (≥20 IU/mL) or RF-negative RA, are receiving MTX, and have had a previous or current inadequate response to one or more TNF inhibitors will be screened for study participation. RF-negative subjects will be limited to 20% of the total enrolled population.

Subjects must meet the following criteria to be eligible for study entry:
Signed informed consent form
Ability and willingness to comply with the requirements of the study protocol
Age 18-80
Diagnosis of RA for at least 6 months, according to the revised 1987 ACR criteria for the classification of RA (Hochberg et al. *Arthritis Rheum* 35:498-502 (1992)):
Class I
Complete functional capacity with ability to carry on all usual duties without handicaps
Class II
Functional capacity adequate to conduct normal activities despite handicap of discomfort or limited mobility of one or more joints
Class III
Functional capacity adequate to perform only few or none of the duties of usual occupation or self-care
Class IV
Largely or wholly incapacitated with subject bedridden or confined to wheel chair, permitting little or no self-care
Receiving treatment for RA on an outpatient basis
Documented moderate to severe active RA activity at screening as follows:
TJC ≥8 (68 joint count), and
SJC ≥8 (66 joint count), and
Abnormal CRP of ≥0.6 mg/dL, or ESR of ≥28 mm/hr
Documented inadequate response to previous or current treatment with one or more of the following: etanercept, infliximab, and/or adalimumab because of toxicity or inadequate efficacy
Inadequate efficacy consists of treatment with etanercept for ≥3 months at doses of 25 mg twice weekly or 50 mg weekly, at least four infusions of ≥3 mg/kg infliximab, or 40 mg adalimumab every other week for ≥3 months.
Use of MTX 10-25 mg/wk for ≥12 weeks prior to Day 1 at a stable dose for ≥4 weeks
Willingness to receive oral folic acid
If taking a background corticosteroid (≤10 mg/day prednisone or equivalent), use of the corticosteroid must be at a stable dose during the 4 weeks prior to Day 1
Use of one NSAID is permitted if the dose is stable for ≥2 weeks prior to Day 1
For men and women of reproductive potential, willingness to use a reliable means of contraception (e.g., hormonal contraceptive, intrauterine device, physical barrier) for ≥30 days prior to Day 1 and for the study duration or the duration that the subject's peripheral CD19+ B cells are depleted, whichever is longer Subjects who meet any of the following criteria will be excluded from study entry:
a. General
Rheumatic autoimmune disease other than RA or significant systemic involvement secondary to RA (e.g., vasculitis, pulmonary fibrosis, or Felty's syndrome)
Secondary Sjögren's syndrome with RA is permitted.
History of or current inflammatory joint disease other than RA (e.g., gout, reactive arthritis, psoriatic arthritis, seronegative spondyloarthropathy, or Lyme disease) or other systemic rheumatic disorder (e.g., systemic lupus erythematosus, inflammatory bowel disease, scleroderma, inflammatory myopathy, or overlap syndrome)

Functional Class IV, as defined by the ACR Classification of Functional Status in Rheumatoid Arthritis)

Any surgical procedure, including bone/joint surgery/synovectomy (including joint fusion or replacement), within 12 weeks prior to Day 1 or planned within 48 weeks after Day 1

Known hypersensitivity to any component of a humanized or murine monoclonal antibody Receipt of a live vaccination within 4 weeks prior to Day 1

Significant cardiac or pulmonary disease, including obstructive pulmonary disease Evidence of significant uncontrolled concomitant disease, such as, but not limited to nervous system, renal, hepatic, endocrine, or gastrointestinal disorders Known active bacterial, viral, fungal, mycobacterial, or other infection (including tuberculosis or atypical mycobacterial disease but excluding fungal infections of the nail beds) or any major episode of infection requiring hospitalization or treatment with IV antibiotics within 4 weeks of Day 1 or oral antibiotics within 2 weeks of Day 1

History of serious recurrent or chronic infection (for screening for a chest infection a chest radiograph will be performed at screening if not performed 12 weeks prior to screening)

History of or currently active primary or secondary immunodeficiency, including HIV infection History of cancer, including solid tumors and hematologic malignancies (except basal cell or squamous cell carcinoma of the skin that has been excised and cured)

History of significant cytopenias or other bone marrow disorders

History of alcohol, drug, or chemical abuse within 24 weeks prior to Day 1

Pregnancy or lactation

Neuropathies and neurovasculopathies that might interfere with pain evaluation

Poor peripheral venous access

Intolerance or contraindications to oral or IV corticosteroids b. Laboratory Exclusion Criteria Hemoglobin <8.0 g/dL Absolute neutrophil count <1.5×10³/µL IgM <0.40 mg/mL IgG <5.0 mg/mL A Aspartate aminotransferase (AST) or alanine aminotransferase (ALT) >2.5×the upper limit of normal Positive hepatitis B surface antigen or hepatitis C antibody serology For women of childbearing potential (including those who have had a tubal ligation), a positive serum pregnancy test at screening Excluded Previous or Concomitant Medications Current use of any DMARD other than MTX Concurrent treatment with any biologic agent Treatment must be discontinued at least 4 weeks prior to Day 1, except for the following: leflunomide for ≥8 weeks (or ≥14 days after 11 days of standard cholestyramine washout), infliximab ≥8 weeks, and adalimumab ≥8 weeks Treatment with any investigational agent within 4 weeks prior to Day 1 or five half-lives of the investigational drug (whichever is longer)

Any previous treatment with rituximab or other cell-depleting therapies, including CAMPATH, anti-CD4, anti-CD5, anti-CD3, anti-CD19, anti-CD11a, anti-CD22, BLys/BAFF, and other anti-CD20 agents Previous treatment with an anti-α 4 integrin agent, including natalizumab Previous treatment within 6 months of screening with IV γ globulin or the Prosorba® Column Upon completion of all screening evaluations and verification that the subject has met all inclusion and exclusion criteria, site personnel will contact the interactive voice response system (ivrs) to obtain the subject number and confirm subject enrollment for study drug inventory management. all enrolled subjects will receive rituximab as their initial course of treatment.

During Weeks 24-40, subjects who are eligible for retreatment will be randomized in a 2:1 ratio to either Group A (rituximab retreatment) or Group B (placebo; see Table 1). If a subject meets the eligibility criteria for retreatment during Weeks 24-40, site personnel will contact IVRS to initiate randomization of the subject and to obtain the study drug kit number.

An independent IVRS provider will conduct the randomization and hold the treatment assignment codes. Randomization will be stratified by study center, baseline RF status (RF positive, RF negative), and Week 24 improvements in tender and swollen joint count (≥20% improvement or <20% improvement). At the time of the unblinding, the treatment assignment codes and the kit treatment codes will be requested from the IVRS provider. Documentation of the transfer and the data included in the transfer will be kept on file.

TABLE 1

Study Treatment Groups

| Group A | Rituximab: | 1000 mg IV on Days 1 and 15 for the first course |
| --- | --- | --- |
| | | 1000 mg IV on Days 1 and 15 for the retreatment course for eligible subjects (DAS 28-ESR ≥ 2.6 and meets the retreatment criteria herein) during Weeks 24-40 |
| | Corticosteroids: | 100 mg IV methylprednisolone prior to each infusion |
| | MTX: | 10-25 mg/wk |
| | Folate: | ≥5 mg/wk |
| Group B | Rituximab: | 1000 mg IV on Days 1 and 15 for the first course |
| | | Placebo IV on Days 1 and 15 for the retreatment course for eligible subjects (DAS 28-ESR ≥ 2.6 and meets the retreatment criteria herein) during Weeks 24-40 |
| | Corticosteroids: | 100 mg IV methylprednisolone prior to each infusion |
| | MTX: | 10-25 mg/wk |
| | Folate: | ≥5 mg/wk |

During retreatment, treatment group assignment will be blinded to site personnel and Genentech. To prevent potential unblinding because of observed efficacy or laboratory changes during retreatment, a dual assessor approach will be used to evaluate efficacy and safety.

Peripheral CD19 B-cell counts will be blinded to site personnel and Genentech until the time of database lock for the primary endpoint at Week 48 for all subjects enrolled in the trial. Therefore, all subjects who have completed the treatment period and SFU prior to database lock will be assumed to be peripherally depleted and will remain in B-cell follow-up.

The Efficacy Assessor (or designee) should be a rheumatologist or skilled arthritis assessor. The Efficacy Assessor must not be the Principal Investigator. The Efficacy Assessor will only have access to efficacy data and will be responsible for completing the joint counts and Physician's Global Assessment of disease activity VAS only. To ensure consistent joint evaluation throughout the trial, individual subjects should be evaluated by the same joint assessor for all study visits. During a study visit, all subject-reported outcomes should be completed prior to all other assessments.

The Safety Assessor (or designee) should be a rheumatologist and will have access to both safety and efficacy data. The Safety Assessor may be the Principal Investigator. The Safety Assessor will have access to source documents, laboratory results, and Case Report Forms (CRFs) and will be responsible for calculating the DAS 28-ESR and making treatment decisions based on a subject's clinical response and laboratory parameters. The Safety Assessor will not complete any efficacy assessments or record the results of any efficacy assessments on behalf of the Efficacy Assessor.

Rituximab for use in this study is a sterile, clear, colorless, preservative-free liquid concentrate for IV administration. Rituximab is supplied at a concentration of 10 mg/mL in 500 mg (50 mL) single-use vials. The product is formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5.

All enrolled subjects will receive a course of rituximab (1000 mg rituximab by IV infusion on Days 1 and 15) as their initial treatment. During Weeks 24-40, subjects eligible for retreatment will be randomized to Group A to receive an additional course (two doses) of rituximab 1000 mg IV 14 days apart or to Group B to receive a course (two doses) of placebo 1000 mg IV 14 days apart.

Premedication with 1000 mg oral acetaminophen and 50 mg oral diphenhydramine is recommended for all subjects, and 100 mg IV methylprednisolone to be completed within 30-60 minutes prior to each rituximab/placebo infusion is required.

All subjects will continue to receive MTX at a stable dose of 10-25 mg/wk and receive a stable dose of folate ($\geq 5$ mg/week) given as either a single dose or as a divided weekly dose.

Rituximab/placebo infusions should be administered to subjects under the close supervision of the investigator or designee in a hospital or clinic where full resuscitation facilities are immediately available. Although rituximab may be administered on an outpatient basis, subjects may be hospitalized for observation at the discretion of the investigator. Rituximab/placebo should be administered as a slow IV infusion. Do not administer as an IV push or bolus. At the end of each infusion, the IV line should remain in place for at least 1 hour to allow administration of IV drugs if necessary. If no adverse event occurs during this time, the IV line may be removed.

Using appropriate aseptic technique, withdraw the necessary amount of rituximab/placebo and dilute to a final concentration of 4 mg/mL into an infusion bag containing either 0.9% Sodium Chloride, USP, or 5% Dextrose in Water, USP. Gently invert the bag to mix the solution. Rituximab vials are biologically and chemically stable at 2° C.-8° C. (36° F.-46° F.). Vials must not be used beyond the expiration date. Rituximab should be protected from exposure to direct sunlight.

Once reconstituted in IV bags, rituximab solutions for infusions may be stored at 2° C.–8° C. (36° F.-46° F.) for 24 hours. Rituximab solutions for infusion have been shown to be stable for an additional 24 hours at room temperature (23° C. or 73° F.). However, since rituximab solutions do not contain a preservative, diluted solutions should be refrigerated (2° C.-8° C.). No incompatibilities between rituximab and polyvinyl chloride or polyethylene bags have been observed.

As to retreatment, DAS 28-ESR will be calculated using the joint count and Patient's Global Assessment of Disease Activity (VAS) from the current visit and the ESR from the current or the previous visit only if the ESR from the current visit is unavailable. Subjects who meet the following criteria at any visit during Weeks 24-40 are eligible to receive retreatment with study drug (rituximab or placebo):

DAS 28-ESR $\geq 2.6$

Negative urine pregnancy test for women of childbearing potential (including those who have had a tubal ligation)

In addition, subjects who qualify for retreatment by DAS 28-ESR $\geq 2.6$ during Weeks 24-40 must also meet the following criteria in order to be retreated based on results from the previous visit if current results are unavailable:

Hemoglobin $\geq 8.0$ g/dL

Absolute neutrophil count $\geq 1.5\mu$ $10^3/\mu L$

IgM $\geq 0.40$ mg/mL

IgG $\geq 5.0$ mg/mL

No significant cardiac or pulmonary disease (including obstructive pulmonary disease)

No primary or secondary immunodeficiency, including known history of HIV infection No evidence of significant uncontrolled concomitant disease, such as, but not limited to nervous system, renal, hepatic, endocrine, or gastrointestinal disorders No active infection of any kind, (excluding fungal infections of nail beds), or any major episode of infection requiring hospitalization or treatment with IV antibiotics within 4 weeks of infusion or completion of oral antibiotics within 2 weeks prior to infusion Rituximab dose modification is not permitted during this study. In the event of an infusion-related reaction, the rate of infusion may be adjusted. If a subject experiences an infusion-related reaction requiring an interruption in the infusion and the investigator determines that the infusion should not be restarted, the subject should be withdrawn from the study treatment period and enrolled into the SFU.

All subjects will receive concomitant 10-25 mg/wk MTX, as prescribed by their treating physician. Subjects must have been treated with MTX for $\geq 12$ weeks prior to entering the study and must remain on a stable dose of MTX for $\geq 4$ weeks before Day 1 and during the study, unless modification is necessary for toxicity.

Certain adverse events that are commonly associated with MTX treatment may occur. In order to minimize MTX toxicity, all subjects treated with MTX will also receive a stable dose of folic acid ($\geq 5$ mg/week) given as either a single weekly dose or as a divided daily dose. The dosing regimen is at the investigator's discretion.

Daily treatment with $\leq 10$ mg prednisone or equivalent is allowed if the dose is stable for $\geq 4$ weeks prior to Day 1. The dose should remain stable throughout the study, unless modification is required for toxicity.

Use of one NSAID is allowed if the dose is stable for $\geq 2$ weeks prior to Day 1. The dose should remain stable throughout the study, unless modification is required for toxicity.

In addition, daily treatment with $\leq 325$ mg acetylsalicylic acid is allowed for cardiovascular prophylaxis.

Additional analgesics may be used for pain as required. However, subjects should not take analgesics within 12 hours prior to a visit where efficacy assessments will be performed. Adjustments to the analgesic regimen may be made, but the change must be documented in the appropriate CRFs.

Intra-articular injections of corticosteroid are discouraged, particularly during the first 48 weeks; however, they may be used on a limited basis to manage a subject's RA activity during the study. No more than one joint per 24-week period should be injected, and the same joint should not be injected more than once in any 48-week period. No single injection should exceed 40 mg triamcinolone (or equivalent), and the total dose of corticosteroid should not exceed 80 mg triamcinolone (or equivalent) during any 48-week period.

During the study, subjects may continue to receive a background corticosteroid with a dose of ≤10 mg/day of prednisone (or equivalent). In the case of a disease flare or non-RA condition, such as asthma, requiring treatment with oral corticosteroids, appropriate doses should be administered for a maximum of 2 weeks and should be tapered down to the previous level as rapidly as medically possible.

Increasing the dose of corticosteroids will be considered worsening of a subject's condition from baseline and should be recorded as an adverse event on the CRF.

IV or intramuscular corticosteroids are not permitted in the study, other than those specified in the protocol treatments.

Increasing the dose of corticosteroids will be considered worsening of a subject's condition from baseline and should be recorded as an adverse event on the CRF.

Subjects must remain on a stable dose of MTX for ≥4 weeks before Day 1 and during the study, unless modification is necessary for toxicity.

At or following 16 weeks after retreatment, subjects who have not achieved a 20% improvement in both TJCs and SJCs compared with baseline may initiate rescue treatment with one non-biologic DMARD, the choice of which is at the discretion of their treating physician. Subjects who receive rescue will not be withdrawn from the study.

Laboratory samples must be drawn prior to infusions of methylprednisolone IV and rituximab/placebo.

Subject-reported data (e.g., Patient's Global Assessment of Disease Activity, Patient's Assessment of Pain) may only be recorded by the study nurse/investigator on behalf of the subject if the subject has difficulty writing during the visit or is unable to read. This must be documented clearly in the subject notes.

To prevent potential unblinding, a dual assessor (Efficacy Assessor and Safety Assessor) approach will be used to evaluate efficacy and safety. It is essential that assessments completed by the subject and the Efficacy Assessor are made before those by the Safety Assessor.

The subject's overall assessment of his or her disease activity during the last 24 hours should be described using the 100-mm horizontal VAS where the left-hand extreme of the line represents no disease activity (symptom free and no arthritis symptoms) and the right-hand extreme represents maximum disease activity (maximum arthritis disease activity).

The subject's assessment of his or her level of pain during the last 24 hours should be described using the 100-mm horizontal VAS where the left-hand extreme of the line represents no pain and the right-hand extreme represents unbearable pain.

The Stanford HAQ disability index is a subject-reported questionnaire specific for RA. It consists of 20 questions referring to eight component sets: dressing/grooming, arising, eating, walking, hygiene, reach, grip, and activities. The questionnaire will be scored based on instructions from Stanford University Medical Center (Fries et al. *Arthritis Rheum* 23:137-145 (1980)).

The FACIT-F will be used to assess fatigue. It is a 13-item questionnaire in which subjects are requested to score each question on a 0-4 scale. The assessment was originally developed for chronic illnesses and is now validated for subjects with RA (Cella et al. *J Rheumatology* 32(5):811-819 (2005)).

The SF-36 is a generic health-related quality of life instrument that has been widely tested for its psychometric properties and is widely used in clinical and epidemiological studies (Ware et al. How to Score Version Two of the SF-36 Health Survey. Lincoln, R.I.: Qualitymetric Incorporated, 2000). The SF-36 (Version 2) is provided by the Medical Outcomes Trust (Boston, Mass., USA).

An evaluation of 66 joints for swelling and 68 joints for tenderness should be performed by a rheumatologist or skilled joint assessor. Joints will be evaluated and classified as swollen or not swollen and tender or not tender based on pressure and joint manipulation upon physical examination. Joints with total joint prosthesis or arthrodesis should not be evaluated; however, all other joints should be evaluated. The joints to be evaluated for swelling and tenderness are provided below:

Temporomandibular joint
Sternoclavicular joint
Acromioclavicular joint
Shoulders[a]
Elbows*
Wrists*
Interphalangeal on digit 1[a]
Distal interphalangeal joints on digits 2-5
Proximal interphalangeal joints on digits 2-5[a]
Metacarpophalangeal joints on digits 1-5[a]
Hips (tenderness only)
Knees[a]
Ankles
Metatarsals
Interphalangeal joints on toes 1-5
Metatarsophalangeal joints on toes 1-5

[a] Includes the 28 joints used to calculate the Disease Activity Score (DAS) 28.

Joints that have undergone a procedure should be evaluated as follows:

Surgery: Any joint that has been replaced or fused at any time prior to or during the study should be documented as nonevaluable (NE) for the duration of the study.

Any joint that has undergone synovectomy (including chemical and radiological synovectomy) should be documented as not done (ND) for 24 weeks following synovectomy. After this time, the joint may be evaluated again.

Intra-articular injection: Any joint that has received an intra-articular injection of a corticosteroid should be documented as ND for the following 12 weeks. After this time, the joint may be evaluated again.

Arthrocentesis: Any joint that undergoes synovial fluid aspiration will not be evaluated at the following scheduled visit and will be graded as ND. After this time, the joint may be evaluated again.

The physician's assessment of a subject's disease activity during the last 24 hours should be described using the 100-mm horizontal VAS where the left-hand extreme of the line represents no disease activity (symptom free and no arthritis symptoms) and the right-hand extreme represents maximum disease activity. This should be completed by the Efficacy Assessor who may or may not be a physician.

CRP will be analyzed at a central laboratory. ESR will be determined using the Westergren method at the local laboratory.

A DAS 28-ESR ≥2.6 has been selected as a threshold for retreatment in this trial. Subjects with a DAS 28-ESR ≥2.6 during Weeks 24-40 may be eligible to receive a second course of study drug (rituximab or placebo).

A general physical examination (including the cardiovascular, respiratory, gastrointestinal and neurological systems) should be performed at the times indicated in the Schedule of Assessments. Any persisting abnormalities should be stated each time the examination is performed. Diagnosis of new abnormalities should be recorded as an adverse event if appropriate.

Vital signs (heart rate, systolic and diastolic blood pressure, and temperature) will be taken at the times indicated in the Schedule of Assessments. Assessments should be taken after the subject has been in a semi-supine position for at least 5 minutes.

Twelve lead electrocardiograms (ECGs) should be performed at the times indicated in the Schedule of Assessments.

Posterior-anterior and lateral chest radiographs should be obtained at screening and reviewed by the investigator or designee. At screening, if chest radiographs have been taken within the past 12 weeks that show no clinically significant abnormality and there are no signs or symptoms suggestive of pulmonary disease that would exclude the subject from the trial, then chest radiograph does not need to be repeated.

Hematology, serology, chemistry, urinalysis, serum pregnancy test, flow cytometry, immunology, and CRP analyses will be performed by a central laboratory; pharmacokinetic and HACA analyses will be performed by Genentech; and urine pregnancy test and ESR assessments will be performed locally at the study sites. Instruction manuals and supply kits, including pharmacokinetic and HACA supplies, will be provided for all laboratory assessments. Laboratory assessments will include the following:

Hematology/CBC: Hemoglobin, hematocrit, red blood cells (RBC), white blood cells (WBC) with differential, and platelet counts.

Serology: Hepatitis B surface antigen (HBsAg) and hepatitis C virus (HCV) antibody.

Serum chemistries: AST/SGOT, ALT/SGPT, alkaline phosphatase, total protein, albumin, total bilirubin, blood urea nitrogen (BUN), uric acid, creatinine, random glucose, potassium, sodium, chloride, calcium, and phosphorous.

Urinalysis: Blood, protein, and glucose (microscopic examination, if abnormal and applicable).

Pregnancy test: All women of childbearing potential (including those who have had a tubal ligation) will have a serum pregnancy test at screening. In addition, regular urine pregnancy tests will be administered at all other visits. If a urine pregnancy test is positive, it must be confirmed by a serum pregnancy test.

Serum C3 and C4 complement levels.

Immunologic assessments: Quantitative immunoglobulins (Total Ig, IgG, IgA, and IgM), RF (total and isotype concentrations), and anti-cyclic-citrullinated peptide (CCP) antibody (IgG).

Expanded fluorescent-activated cell sorter (FACS) analysis: Cell populations assessed will include monocytes (CD14 and CD16); NK cells (CD56); T-cell subsets (CD3, CD4, CD8, CD45RO, and CD45RA); and B-cell subsets (CD19, CD27, CD38, and IgD). Activation markers may also be evaluated (CD25, CD69, CD40L, and CD80).

B cell FACS analysis: absolute B cells (CD19) only.

Analysis for HACA response will be performed using an ELISA for all enrolled subjects.

Pharmacokinetic assays: Serum samples will be obtained for pharmacokinetic assay at the visits indicated in the SOA and also at the same timepoints as HACA. Serum rituximab concentrations are required to accurately interpret HACA results.

Optional biomarker samples:

For subjects who consent separately, optional research samples (whole blood, serum) will be collected during the course of the study for exploratory biomarker assessments. Whole blood samples, collected using PAXgene™ RNA tubes, will be used for gene expression profiling. Serum sample assessments of markers related to RA or rituximab may include, but not be limited to, cytokine/chemokine measurements and quantitation of bone and cartilage turnover markers. All samples will be collected at the same timepoints for optimal data comparability.

It is anticipated that information from this analysis will promote and facilitate individualized health care via better understanding of rituximab's mode of action, related efficacy and safety, predictors for good response, and possibly determinants of RA (and other autoimmune) disease progression. These samples will be stored for up to 15 years after database closure.

All subjects must provide written informed consent before any study-specific procedures or assessments are performed, including changes to a subject's current treatment regimen. Screening evaluations may be performed during a 56-day period prior to the first infusion of rituximab on Day 1. Subject reported assessments should be performed prior to other clinical assessments.

If a subject fails a laboratory exclusion criterion at screening, the investigator may repeat the test up to twice within the screening period. If the subject fails the laboratory criterion a third time, they will be considered a screen failure. A blood sample or laboratory test will not be considered as re-tested if the sample was redrawn because of sample handling problems, breakage, or sample integrity. A subject who fails screening may be re-screened.

A subject may be re-screened if they did not meet all the eligibility criteria within 56 days of the original screening visit. A subject who undergoes re-screening must repeat the entire screening process and be re-consented prior to any study-specific procedures. Subjects may be re-screened only once.

a. Screening Visit (Day-56)

Written Informed Consent

Review of inclusion and exclusion criteria

Contact IVRS to obtain assignment of subject screening number

Demographic data (e.g., sex, age, race/ethnicity)

Complete medical history (including vaccination history)

Concomitant medications taken within 12 weeks before screening, including vaccines, all prior DMARDs, and biologic agents Vital signs (heart rate, blood pressure, and temperature)

Complete physical examination, including height and weight measurements
Joint evaluation
12-Lead ECG
Chest X-ray
  If a chest X-ray has been performed within 12 weeks before screening and showed no clinically significant abnormality, a chest X-ray is not required at screening.
Central laboratory assessments
  Hematology/CBC
  Hepatitis B surface antigen and hepatitis C antibody
  Serum pregnancy test for women of childbearing potential (including those who have had a tubal ligation)
  Serum chemistries
  Urinalysis
  CRP
  IgG and IgM
  Total RF
  ESR (local laboratory; Westergren method)

All assessments during the treatment period should be performed within the specified time window for each visit. Assessments and procedures scheduled on days when rituximab is administered should be performed prior to the rituximab infusion, unless otherwise indicated. For this study, Day 1 is the day of initial rituximab infusion. The Day 1 visit should be performed on a day that will allow subsequent visits (e.g., Day 15 visit) to occur without delay. Subject-reported assessments should be performed prior to other clinical assessments. For subjects eligible for retreatment, the visit at which the subject meets the eligibility criteria for retreatment is considered the qualifying visit.

a. Day 1
  All assessments will be performed 30 minutes pre-infusion unless otherwise specified.
  Review of inclusion and exclusion criteria
  Contact IVRS for subject enrollment number and study drug inventory
  Patient's Global Assessment of Disease Activity (VAS)
  Patient's Assessment of Pain (VAS)
  HAQ
    FACIT-F
    SF-36
  Vital signs (heart rate, blood pressure, and temperature): pre-infusion, during infusion (every 15 minutes for 1 hour, and then every 30 minutes until the end of infusion), and post-infusion (every minutes for 1 hour post-infusion)
  Physical examination, including measurement of body weight
  Joint evaluation
  Physician's Global Assessment of Disease Activity (VAS)
  Urine pregnancy test for women of childbearing potential (including those who have had a tubal ligation)
  Central laboratory assessments
    Hematology/CBC (within 30 minutes pre- and post-infusion)
    Serum chemistries
    Urinalysis
    Expanded FACS (within 30 minutes pre- and post-infusion)
    CD19 B cells (within 30 minutes pre- and post-infusion)
    CRP
    Immunoglobulins
    RF
    Anti-CCP antibody
    C3, C4
    Pharmacokinetic sample (30 minutes pre- and post-infusion)
    HACA sample
  ESR (local laboratory; Westergren method)
  Optional research biomarker samples (whole blood and serum samples)
  Methylprednisolone administration
  Rituximab administration
  Adverse events
  Concomitant medications b. Day 15 (±1 day)
  All assessments will be performed 30 minutes pre-infusion unless otherwise specified.
  Urine pregnancy test for women of childbearing potential (including those who have had a tubal ligation)
  Vital signs (heart rate, blood pressure, and temperature): pre-infusion, during infusion (every 15 minutes for 1 hour, and then every 30 minutes until end of infusion), and post-infusion (every 30 minutes for 1 hour post-infusion)
  Central laboratory assessments
    Hematology/CBC (within 30 minutes pre- and post-infusion of rituximab)
    Serum chemistries
    Urinalysis
    C3, C4
    Pharmacokinetic sample (30 minutes pre- and post-infusion)
  Methylprednisolone administration
  Rituximab administration
  Adverse events
  Concomitant medications c. Weeks 4, 12, and 20 (Days 28, 84, and 140, respectively; ±3 days)
  Patient's Global Assessment of Disease Activity (VAS)
  Patient's Assessment of Pain (VAS)
  HAQ
  FACIT-F (Week 12 only)
  Joint evaluation
  Physician's Global Assessment of Disease Activity (VAS)
  Urine pregnancy test for women of childbearing potential (including those who have had a tubal ligation)
  Central laboratory assessments
    Hematology/CBC
    Serum chemistries
    Urinalysis
    Expanded FACS (Week 12 only)
    CD19 B cells (Weeks 4 and 20 only)
    CRP
    C3, C4 (Week 4 only)
    Pharmacokinetic sample
    Immunoglobulins
  ESR (local laboratory; Westergren method)
  Optional research biomarker samples (whole blood and serum samples) (Week 12 only)
  Adverse events
  Concomitant medications d. Week 24 (Day 168 ±3 days)
  Patient's Global Assessment of Disease Activity (VAS)
  Patient's Assessment of Pain (VAS)
  HAQ
  FACIT-F
  SF-36
  Joint evaluation
  Physician's Global Assessment of Disease Activity (VAS)

Calculate DAS 28-ESR using the joint count and Patient's Global Assessment of Disease Activity (VAS) from this visit and the ESR from the previous visit, if ESR result is not available
 Evaluate subject's eligibility for retreatment based on the calculated DAS 28-ESR and laboratory results from the previous visit.
 If the subject is eligible for retreatment, proceed to Retreatment Day 1 and complete assessments as specified.
Urine pregnancy test for women of childbearing potential (including those who have had a tubal ligation)
Central laboratory assessments
 Hematology/CBC
 Serum chemistries
 Urinalysis
 Expanded FACS
 CRP
 Immunoglobulins
 RF
 Anti-CCP antibody
 Pharmacokinetic sample
 HACA sample
ESR (local laboratory; Westergren method)
Optional research biomarker samples (whole blood and serum samples)
Adverse events
Concomitant medications e. Week 28 (Day 196 ±3 days)
 Patient's Global Assessment of Disease Activity (VAS)
 Patient's Assessment of Pain (VAS)
 HAQ
 Joint evaluation
 Physician's Global Assessment of Disease Activity (VAS)
 Complete only if the subject has not been retreated. Calculate DAS 28-ESR using the joint count and Patient's Global Assessment of Disease Activity (VAS) from this visit and the ESR from the previous visit, if ESR result is not available.
  Evaluate subject's eligibility for retreatment based on the calculated DAS 28-ESR and laboratory results from the previous visit.
  If the subject is eligible for retreatment, proceed to Retreatment Day 1 and complete assessments as specified.
 Urine pregnancy test for women of childbearing potential (including those who have had a tubal ligation)
 Central laboratory assessment
  Hematology/CBC
  Serum chemistries
  Urinalysis
  CD19 B cells
  CRP
  Immunoglobulins
  Pharmacokinetic sample
 ESR (local laboratory; Westergren method)
 Adverse events
 Concomitant medications f. Weeks 32, 40, and 44 (Days 224, 280, and 308, respectively; ±3 days)
 Patient's Global Assessment of Disease Activity (VAS)
 Patient's Assessment of Pain (VAS)
 HAQ
 FACIT-F (Week 32 only)
 Joint evaluation
 Physician's Global Assessment of Disease Activity (VAS)
 Complete only if the subject has not been retreated. Calculate DAS 28-ESR using the joint count and Patient's Global Assessment of Disease Activity (VAS) from this visit and the ESR from the previous visit, if ESR result is not available (Weeks 32 and 40 only)
  Evaluate subject's eligibility for retreatment based on the calculated DAS 28-ESR and laboratory results from the previous visit.
  If the subject is eligible for retreatment, proceed to Retreatment Day 1 and complete assessments as specified.
 Urine pregnancy test for women of childbearing potential (including those who have had a tubal ligation)
 Central laboratory assessments
  Hematology/CBC
  Serum chemistries
  Urinalysis
  Expanded FACS (perform only if subject has not been retreated; Week 44 only)
  CD19 B cells
  Immunoglobulins
  CRP
  Pharmacokinetic sample
 ESR (local laboratory; Westergren method)
 Adverse events
 Concomitant medications g. Week 48 (Day 336 ±3 days)
 Patient's Global Assessment of Disease Activity (VAS)
 Patient's Assessment of Pain (VAS)
 HAQ
 FACIT-F
 SF-36
 Joint evaluation
 Physician's Global Assessment of Disease Activity (VAS)
 Urine pregnancy test for women of childbearing potential (including those who have had a tubal ligation)
 Central laboratory assessments
  Hematology/CBC
  Serum chemistries
  Urinalysis
  Expanded FACS
  CRP
  Immunoglobulins
  RF
  Anti-CCP antibody
  Pharmacokinetic sample
  HACA sample
 ESR (local laboratory; Westergren method)
 Optional research biomarker samples (whole blood and serum samples)
 Adverse Events
 Concomitant Medications h. Week 60 (Day 420 ±7 days)
 Patient's Global Assessment of Disease Activity (VAS)
 Patient's Assessment of Pain (VAS)
 HAQ
 FACIT-F
 Joint evaluation
 Physician's Global Assessment of Disease Activity (VAS)
 Urine pregnancy test for women of childbearing potential (including those who have had a tubal ligation)
 Central laboratory assessments
  Hematology/CBC
  Serum chemistries
  Urinalysis
  Expanded FACS
  CRP Immunoglobulins
Optional research biomarker sample (whole blood and serum samples)
ESR (local laboratory; Westergren method)
Adverse events
Concomitant medications i. Week 72 (Day 504 ±7 days)

Subjects whose peripheral B-cell (CD19$^+$) counts have not recovered at the completion of this visit will enter the B-cell follow-up period. B-cell recovery is defined as peripheral CD19$^+$ counts that have returned to baseline values or the LLN, whichever is lower.

Patient's Global Assessment of Disease Activity (VAS)
Patient's Assessment of Pain (VAS)
HAQ
FACIT-F
SF-36
Vital signs (heart rate, blood pressure, and temperature)
Physical examination, including weight
Joint evaluation
Physician's Global Assessment of Disease Activity (VAS)
12-Lead ECG
Urine pregnancy test for women of childbearing potential (including those who have had a tubal ligation)
Central laboratory assessments
  Hematology/CBC
  Serum chemistries
  Urinalysis
  Expanded FACS
  CRP
  Immunoglobulins
  RF
  Anti-CCP antibody
ESR (local laboratory; Westergren method)
Optional research biomarker samples (whole blood and serum samples)
Adverse events
Concomitant medications Subjects eligible for retreatment during Weeks 24-40 will be randomized to receive an additional course of study drug. Subjects should complete all Retreatment Day 1 assessments that have not been performed during the qualifying visit. Assessments performed from the qualifying visit do not need to be repeated.

If the infusion cannot be given on the same day as the qualifying visit, the subject should return for the infusion within 72 hours of the qualifying visit.

After the retreatment course (Retreatment Days 1 and 15), the subject should return to their next scheduled visit based on the schedule of assessments from the point at which the subject qualified for retreatment. For example, if a subject qualified for retreatment at the Week 32 visit, after the retreatment course (Retreatment Days 1 and 15), the subject's next scheduled visit should be the Week 40 visit.

a. Retreatment Day 1 (R1)

All assessments will be performed 30 minutes pre-infusion unless otherwise specified.

Randomization and assignment of study drug through IVRS
Patient's Global Assessment of Disease Activity (VAS)
Patient's Assessment of Pain (VAS)
HAQ
FACIT-F
SF-36
Vital signs (heart rate, blood pressure, and temperature): pre-infusion, during infusion (every 15 minutes for 1 hour, and then every 30 minutes until the end of infusion), and post-infusion (every 30 minutes for 1 hour post-infusion)
Physical examination, including measurement of body weight
Joint evaluation
Physician's Global Assessment of Disease Activity (VAS)
Urine pregnancy test for women of childbearing potential (including those who have had a tubal ligation)
Central laboratory assessments
  Hematology/CBC (within 30 minutes pre- and post-infusion)
  Serum chemistries
  Urinalysis
  CRP
  Expanded FACS (within 30 minutes pre- and post-infusion)
  CD19 B cells (within 30 minutes pre- and post-infusion)
  Immunoglobulins
  RF
  Anti-CCP antibody
  C3, C4
  Pharmacokinetic sample (30 minutes pre- and post-infusion)
  HACA sample
ESR (local laboratory; Westergren method)
Optional research biomarker samples (whole blood and serum samples)
Methylprednisolone administration
Study drug administration
Adverse events
Concomitant medications b. Retreatment Day 15 (R15; ±1 day)

All assessments will be performed 30 minutes pre-infusion unless otherwise specified.

Vital signs (heart rate, blood pressure, and temperature): pre-infusion, during infusion (every 15 minutes for 1 hour, and then every 30 minutes until the end of infusion), and post-infusion (every 30 minutes for 1 hour post-infusion)
Urine pregnancy test for women of childbearing potential (including those who have had a tubal ligation)
Central laboratory assessments
  Hematology/CBC (within 30 minutes pre- and post-infusion)
  Serum chemistries
  Urinalysis
  C3, C4
  Pharmacokinetic sample (30 minutes pre- and post-infusion)
  Methylprednisolone administration
  Study drug administration
  Adverse events
  Concomitant medications Subjects who withdraw early from the treatment period for any reason will be asked to return for an early treatment withdrawal visit (up to 14 days after withdrawal) and then to return at 4 weeks after the withdrawal visit and then every 12 weeks for at least 48 weeks from the time the subject withdraws. The following assessments will be performed at the early treatment withdrawal visit:

Patient's Global Assessment of Disease Activity (VAS)
Patient's Assessment of Pain (VAS)
HAQ
FACIT-F
SF-36

Vital signs (heart rate, blood pressure, and temperature)
Physical examination, including weight
Joint evaluation
Physician's Global Assessment of Disease Activity (VAS)
12-Lead ECG
Urine pregnancy test for women of childbearing potential (including those who have had a tubal ligation)
Central laboratory assessments
　Hematology/CBC
　Serum chemistries
　Urinalysis
　CRP
　CD19 B cells
　Immunoglobulins
　RF
　Anti-CCP antibody
　Pharmacokinetic sample
　HACA sample
Optional research biomarker sample (whole blood and serum samples)
　ESR (local laboratory; Westergren method)
Adverse events
Concomitant medications Safety follow up (SFU) assessments will be performed at SFU Weeks 4, 12, 24, 36, and 48 after early withdrawal or completion of the treatment period as defined for the following subjects:
　Subjects who were retreated during Weeks 24-40 and completed the treatment period (i.e., the Week 72 visit)
　Subjects who withdrew early from the treatment period
The following assessments will be performed at each SFU visit:
　All adverse events up to week 4
　Serious adverse events and infectious adverse events after week 4
　Concomitant medications used to treat these events
　Central laboratory assessments
　　Hematology/CBC
　　Immunoglobulins
　　Pharmacokinetic sample
　　HACA sample
　　CD19 B cells At the last SFU visit, subjects whose peripheral B-cell (CD19$^+$) counts have not recovered will enter the B-cell follow-up period. B-cell recovery is defined as peripheral CD19$^+$ counts that have returned to baseline values or the LLN, whichever is lower. For all serious infectious adverse events reported, CBC with differentials, quantitative Ig and CD19 counts should be determined within 1 week of onset.

Subjects whose peripheral B-cell (CD19$^+$) counts have not recovered at the last protocol defined visit (Week 72 or at end of SFU) will enter the B-Cell Follow-Up Period and return for study visits every 12 weeks from last visit until B-cell recovery. B-cell recovery is defined as peripheral CD19$^+$ counts that have returned to baseline values or the LLN, whichever is lower.

The following evaluations and procedures will be performed at each B-cell follow-up visit:
　Serious adverse events and infectious adverse events
　Concomitant medications used to treat these events
　Central laboratory assessments
　　Hematology/CBC
　　Immunoglobulins
　　Flow cytometry: B-cell (CD19$^+$) count
　　For all serious infectious adverse events reported, CBC with differentials, quantitative Ig and CD19 counts should be determined within 1 week of onset.

Blood, serum, and urine samples will be obtained at specified timepoints. Instructions for processing, storing, and shipping samples to Genentech and the central clinical laboratory will be provided in the laboratory manuals. Standard assays will be used for hematology, serology, chemistry, serum β-hCG, flow cytometry, immunology, and urinalysis.

Rituximab pharmacokinetic ELISA measures the rituximab levels in human serum samples. It uses affinity-purified polyclonal goat anti-rituximab as the capture reagent and goat antibody to mouse IgG F(ab)$_2$ conjugated to horseradish peroxidase (HRP) as the detection reagent.

The anti-rituximab HACA ELISA is a bridging assay, which uses rituximab as the capture reagent and biotinylated rituximab and streptavidin-HRP for detection. The assay uses a calibrator curve prepared with affinity-purified polyclonal goat antibodies to rituximab and is confirmed by immunodepletion with rituximab. Results from this assay will be reported relative to this polyclonal antibody in terms of relative units (RU)/mL.

Subjects may withdraw or be discontinued from the treatment period at any time, but should return to the study center within 14 days for an early treatment withdrawal visit, SFU and potentially B-cell follow-up. Subjects who have discontinued from the treatment period will be followed for safety assessments. Every effort should be made to obtain these assessments for subjects who discontinue early. The primary reason for early discontinuation must be recorded on the appropriate CRF page.

Reasons for subject discontinuation by the investigator include, but are not limited to, the following:
　Voluntary withdrawal of consent
　Any medical condition that may jeopardize the subject's safety if he or she continues in the study, as determined by the investigator
　Investigator determination that it is not in the subject's best interest to continue
　Subjects who have a positive urine or serum pregnancy test at any time during the study.

Subjects who withdraw early will not be replaced.
Genentech has the right to terminate this study at any time. Reasons for terminating the study may include, but are not limited to, the following:
　The incidence or severity of adverse events in this or other studies indicates a potential health hazard to subjects.
　Subject enrollment is unsatisfactory.
　Data recording is inaccurate or incomplete.

This study is designed to evaluate the efficacy of one course of retreatment with rituximab or placebo for eligible subjects and the safety of rituximab treatment in subjects with active RA who are receiving MTX and who had a previous or current inadequate response to one or more anti-TNF therapies. The eligibility of a subject for retreatment is based on the DAS 28-ESR remission criterion (DAS 28-ESR ≥2.6). Approximately 555 subjects will be enrolled. The study is open-label for the first course of treatment (with rituximab) and blinded for subjects eligible for a retreatment course (study drug). During Weeks 24-40, subjects who meet the retreatment criteria will be randomized to a 2:1 ratio to either rituximab or placebo.

Unless otherwise specified, all statistical tests are two sided and will be performed at the □=0.05 level of significance.

The primary endpoint is the proportion of subjects with an ACR20 response at Week 48 relative to baseline (Day 1). The analysis of unblinded data will commence once the Week 48 assessments from all subjects are in the database and the database is cleaned and frozen.

For the open-label treatment segment with rituximab (first 24 weeks of the study), the number of subjects enrolled will be tabulated by center. For subjects who discontinue from the open-label treatment segment, reasons for discontinuation will be summarized. Key eligibility criteria violations, other major protocol deviations, and the number of subjects who complete each scheduled dose will be summarized.

For the blinded retreatment segment with study drug, the number of subjects randomized will be tabulated by center and treatment group. The disposition of subjects will be summarized by treatment group with respect to subject randomization, treatment, and completion of the study. Key eligibility criteria violations, other major protocol deviations, and the number of subjects who complete each scheduled dose will be summarized by treatment group. For subjects who discontinue early from the placebo-controlled, retreatment segment, reasons for discontinuation will be summarized and listed by treatment group.

Baseline of the treatment groups will be assessed for comparability with respect to demographics (i.e., age, sex, race/ethnicity) and baseline characteristics (e.g., body weight, duration of RA, baseline RF status, baseline SJC/TJC, baseline DAS 28-ESR, and number of prior TNF therapies). The baseline value of any variable will be defined as the last available value prior to the first administration of rituximab (Day 1).

Safety will be assessed through the summary of adverse events, deaths, laboratory test results, vital signs, and HACAs. These summaries will be produced as overall summary for the open-label treatment segment and by treatment group for the placebo-controlled, retreatment segment. Safety analyses will be based on subjects who received any amount of study drug. Subjects will be analyzed according to the actual treatment received.

The following safety summaries will be included in the safety analyses.

Verbatim descriptions of treatment-emergent adverse events will be mapped to MedDRA thesaurus terms. Adverse events will be tabulated according to system organ class, treatment arm, and NCI CTCAE grade. Adverse event tabulations for serious adverse events, infection-related adverse events, rituximab-related infusion reactions, and adverse events leading to study drug discontinuation will be based on all treated subjects and tabulated following the first infusion of the initial rituximab course and the retreatment course.

In addition, serious adverse events will be summarized as incidence per 100 patient-years following the first infusion of the initial rituximab course and retreatment course as well as for the entire observation period.

Subject deaths and primary cause of death will be listed and/or summarized.

Descriptive summaries of laboratory values and changes from baseline throughout the study will be provided. The proportion of subjects experiencing treat-emergent laboratory abnormalities will be summarized.

Descriptive summaries of vital signs and changes from baseline throughout the study will be provided by treatment group.

The proportion of subjects with a measurable antibody response to rituximab will be summarized.

The intent-to-treat (ITT) population consists of all subjects who are randomized into the placebo-controlled retreatment segment and receive any study drug. The ITT population is the primary analysis population for the primary and secondary endpoints. Subjects will be analyzed according to their randomized treatment.

The primary endpoint is the proportion of retreated subjects with an ACR20 response at Week 48 compared with baseline (Day 1).

To achieve an ACR20 requires an ≥20% improvement compared with baseline in both TJCs and SJCs as well as an ≥20% improvement in three of five additional measurements as follows:

Physician's Global Assessment of disease activity
Patient's Global Assessment of Disease Activity (VAS)
Patient's Assessment of Pain (VAS)
HAQ
Acute phase reactant (CRP or ESR)

CRP will be used in the calculation of ACR20. If CRP is missing or not performed, ESR will be used.

The primary analysis of the difference in ACR20 response rates between placebo retreatment and rituximab retreatment arm will be presented using the Cochran-Mantel Haenszel test statistic, stratified by baseline RF status. Results will be summarized descriptively by treatment group and expressed as proportions, with the corresponding adjusted 95% confidence intervals (CIs) of the difference between response rates and p-values.

ACR20 response rates will also be analyzed using logistic regression and testing for an association between ACR20 response at Week 48 and treatment arm while controlling for baseline RF status using a logistic regression model. The parameter estimates from the model will be examined by tabulating the standard errors, Wald statistics, and odds ratios with the corresponding 95% CIs and p-values.

Sensitivity analyses will also be performed adjusting for potential explanatory terms for ACR20 response (e.g., baseline SJC).

The secondary endpoints will be analyzed as follows:
Proportion of subjects with ACR50 and ACR70 response at Week 48 will be analyzed in the same manner as specified for the primary endpoint.
Change in DAS 28-ESR from baseline to Week 48 will be assessed using an analysis of variance (ANOVA) model, with placebo/rituximab retreatment group and baseline RF status as explanatory terms in the model.
Ordered category of ACR response (ACR70 responders, ACR50-70 responders, ACR20-50 responders, and ACR20 non-responders) at Week 48 will be analyzed using the cumulative logits model, stratified by baseline RF status. The parameter estimates from the model will be examined by tabulating the standard errors, Wald statistics, and odds ratios with the corresponding 95% CIs and p-values.
EULAR response rates (good or moderate) at Week 48 will be analyzed in the same manner as specified for the primary endpoint.
Change in ACR core set (SJC, TJC, HAQ, patient's and physician's global assessments, pain, CRP, and ESR) from baseline to Week 48 will be analyzed in an ANOVA model, with placebo/rituximab retreatment group and baseline RF status as explanatory terms in the model.
Week 48 ACRn and AUC of ACRn at week 48 will be assessed using an analysis of variance (ANOVA) model, with placebo/rituximab retreatment group and baseline RF status as explanatory terms in the model.
Change in SF-36 subscale and summary scores from baseline to Week 48 will be reported for the eight domain scores and the mental and physical component scores using analyzed in an ANOVA model, with placebo/rituximab retreatment group and baseline RF status as explanatory terms in the model. In addition, the mental and physical component scores will be further categorized and analyzed.

Change in FACIT-F assessment from baseline to Week 48 will be analyzed using analyzed in an ANOVA model, with placebo/rituximab retreatment group and baseline RF status as explanatory terms in the model.

Proportion of subjects achieving DAS 28-ESR remission (DAS 28-ESR <2.6) at Week 48 will be analyzed in the same manner as specified for the primary endpoint.

Proportion of subjects achieving DAS 28-ESR low disease (DAS 28-ESR ≤3.2) at Week 48 will be analyzed in the same manner as specified for the primary endpoint.

Pharmacokinetic (PK) parameters derived from serum concentrations of rituximab, including maximum serum concentration ($C_{max}$), time of maximum serum concentration ($T_{max}$), area under the concentration-time curve (AUC), systemic clearance (CL), volume of distribution (V) and half-life ($t_{1/2}$), will be estimated for all subjects using population PK model. Due to the sparse sampling, the distribution phase may not be well characterized. PK data from this study will be combined with data from other studies for population PK analysis.

For the population PK analysis, overall mean PK parameters will be estimated for the entire study population along with estimates of intra- and inter-subject variance and an estimate of random error. Individual subject parameter estimates will be computed using post hoc analysis procedures. A prospective analysis plan will be prepared and the population PK analysis will be presented in a separate report from the clinical study report.

The population PK analyses will include an exploratory analysis to identify baseline covariates that affect the pharmacokinetics of rituximab in this patient population. Baseline covariates to be examined will include demographics and other subject characteristics, such as disease severity and selected laboratory measures.

Data will be summarized using descriptive statistics, including mean, standard deviation, geometric mean, coefficient of variation, median, and range.

Potential pharmacodynamic markers from blood samples, including B-cell counts, quantitative Ig levels, lymphocyte subtypes, and HACA concentration, will be summarized descriptively. For these analyses, the baseline values measured from the Day 1 predose sample will be used to calculate the change from baseline at each sampling timepoint.

Exploratory analyses will be performed to assess the possible relationship between pharmacodynamic markers, PK measures, and clinical response and will be specified in the Statistical Analysis Plan.

Approximately 555 subjects will be enrolled. Assuming a dropout rate of up to 25% during the open-label treatment segment and up to 10% subjects who achieve DAS 28-ESR remission at Week 24 and are not retreated, with a 2:1 randomization ratio, this sample size will have 80% power to detect a 16% difference in ACR20 response rates from baseline to Week 48 between the rituximab retreatment group (50% ACR20 responders) and placebo group (34% ACR20 responders) using Fisher's exact test.

Safety assessments will consist of monitoring and recording protocol-defined adverse events (AEs) and serious adverse events (SAEs); measurement of protocol-specified laboratory (hematology, clinical chemistry, and urinalysis) variables; measurement of protocol-specified vital signs; and other protocol-specified tests that are deemed critical to the safety evaluation of the study drug.

To monitor infusion-related reactions, vital signs will be obtained immediately pre-infusion, every 15 minutes for the first hour during the infusion, then every 30 minutes for the remainder of the infusion, and every 30 minutes for one hour post-infusion, on days of study drug administration. Additional readings may be obtained in the event of an infusion-related reaction (e.g., hypotension and/or fever).

An AE is any unfavorable and unintended sign, symptom, or disease temporally associated with the use of an investigational (medicinal) product or other protocol-imposed intervention, regardless of attribution.

This includes the following:
AEs not previously observed in the subject that emerge during the protocol-specified AE reporting period, including signs or symptoms associated with RA that were not present prior to the AE reporting period
Complications that occur as a result of protocol-mandated interventions (e.g., invasive procedures such as biopsies)
If applicable, AEs that occur prior to assignment of study treatment associated with medication washout, no treatment run-in, or other protocol-mandated intervention
Preexisting medical conditions (other than the condition being studied) judged by the investigator to have worsened in severity or frequency or changed in character during the protocol-specified AE reporting period An AE should be classified as an SAE if it meets the following criteria:
It results in death (i.e., the AE actually causes or leads to death).
It is life threatening (i.e., the AE, in the view of the investigator, places the subject at immediate risk of death. It does not include an AE that, had it occurred in a more severe form, might have caused death.).
It requires or prolongs inpatient hospitalization.
It results in persistent or significant disability/incapacity (i.e., the AE results in substantial disruption of the subject's ability to conduct normal life functions).
It results in a congenital anomaly/birth defect in a neonate/infant born to a mother exposed to the investigational product.
It is considered a significant medical event by the investigator based on medical judgment (e.g., may jeopardize the subject or may require medical/surgical intervention to prevent one of the outcomes listed above).

All AEs that do not meet any of the criteria for serious should be regarded as nonserious AEs.

The terms "severe" and "serious" are not synonymous. Severity (or intensity) refers to the grade of a specific AE, e.g., mild (Grade 1), moderate (Grade 2), or severe (Grade 3) myocardial infarction. "Serious" is a regulatory definition and is based on subject or event outcome or action criteria usually associated with events that pose a threat to a subject's life or functioning. Seriousness (not severity) serves as the guide for defining regulatory reporting obligations from the Sponsor to applicable regulatory authorities.

Severity and seriousness should be independently assessed when recording AEs and SAEs on the CRF.

Investigators will assess the occurrence of AEs and SAEs at all subject evaluation timepoints during the study. All AEs and SAEs whether volunteered by the subject, discovered by study personnel during questioning, or detected through physical examination, laboratory test, or other means will be recorded in the subject's medical record and on the appropriate AE or SAE CRF page.

Each recorded AE or SAE will be described by its duration (i.e., start and end dates), severity (see Table 2), regulatory seriousness criteria if applicable, suspected relationship to the investigational product (see following guidance), and actions taken.

The AE grading (severity) scale found in the NCI CTCAE, V3.0, will be used for AE reporting.

TABLE 2

Adverse Event Grading (Severity) Scale

| Grade | Severity | Alternate Description [a] |
|---|---|---|
| 1 | Mild (apply event-specific NCI CTCAE grading criteria) | Transient or mild discomfort (<48 hours); no interference with the subject's daily activities; no medical intervention/therapy required |
| 2 | Moderate (apply event-specific NCI CTCAE grading criteria) | Mild to moderate interference with the subject's daily activities; no or minimal medical intervention/therapy required |
| 3 | Severe (apply event-specific NCI CTCAE grading criteria) | Considerable interference with the subject's daily activities; medical intervention/therapy required; hospitalization possible |
| 4 | Very severe, life threatening, or disabling (apply event-specific NCI CTCAE grading criteria) | Extreme limitation in activity; significant medical intervention/therapy required, hospitalization probable |
| 5 | Death related to AE | |

Note: Regardless of severity, some events may also meet regulatory serious criteria. Refer to definitions of an SAE.
[a] Use these alternative definitions for Grade 1, 2, 3, and 4 events when the observed or reported AE is not in the NCI CTCAE listing.

To ensure consistency of AE and SAE causality assessments, investigators should apply the following general guideline:

Yes
  There is a plausible temporal relationship between the onset of the AE and administration of the investigational product, and the AE cannot be readily explained by the subject's clinical state, intercurrent illness, or concomitant therapies; and/or the AE follows a known pattern of response to the investigational product; and/or the AE abates or resolves upon discontinuation of the investigational product or dose reduction and, if applicable, reappears upon re-challenge.

No
  Evidence exists that the AE has an etiology other than the investigational product (e.g., preexisting medical condition, underlying disease, intercurrent illness, or concomitant medication); and/or the AE has no plausible temporal relationship to administration of the investigational product (e.g., cancer diagnosed 2 days after first dose of study drug).

Note: The investigator's assessment of causality for individual AE reports is part of the study documentation process. Regardless of the "Yes" or "No" causality assessment for individual AE reports, the Sponsor will promptly evaluate all reported SAEs against cumulative product experience to identify and expeditiously communicate possible new safety findings to investigators and applicable regulatory authorities.

RA should be recorded as an AE or SAE only if judged by the investigator to have unexpectedly worsened in severity and/or frequency or changed in nature any time during the study. When recording an unanticipated worsening of rheumatoid arthritis on an AE or SAE CRF page, it is important to convey the concept that the condition has changed by including applicable descriptors (e.g., "accelerated rheumatoid arthritis").

It is expected that re-treatment under the protocol herein (or with a different CD20 antibody) will be effective in preventing or slowing down the progression in structural joint damage and erosion caused by RA. It is contemplated that efficacious results would occur if MTX is not employed, i.e., monotherapy with the CD20 antibody is used.

Example 4

Study of Efficacy of Rituximab in Patients with Psoriatic Arthritis

The protocol in Example 2 is followed except that the patients are treated for joint damage caused by psoriatic arthritis. It is expected that similar results will be observed (using rituximab or a humanized 2H7 antibody) as for rheumatoid arthritis, i.e., that progression in structural joint damage will be prevented upon a first dose of CD20 antibody (with or without methotrexate depending on, e.g., dosages as can be adjusted appropriately) at at least about one month from baseline or start of treatment, preferably at least 24 weeks from baseline, more preferably at least 52 weeks from baseline, and at further time points up to 104 weeks from baseline.

These rituximab-based regimens challenge the current standard of care, and are expected to demonstrate improved net clinical benefit, with the primary objective to prevent progression in joint damage. These results are expected to be significantly better than those of the control arm.

It is predicted and expected that administration of rituximab or a humanized 2H7 to the subject in the scheduled re-dosing protocol set forth in Example 2 will be effective in preventing progression of structural joint damage at week 52 or later. These results are expected to be significantly better than those of the control.

It is also expected that at about week 48-54, another 1-g or 2-g dose of the CD20 antibody (e.g., rituximab or a humanized 2H7) given all at once or spread out over about 14-16 days in 0.5-gram or 1-gram amounts would be effective to treat joint damage for the entire second year, with or without one or more second medicaments such as immunosuppressive agents. Thus, the CD20 antibody would be administered initially within about the 2-week time period, followed by another treatment at about 4-8 months, followed by another treatment at about one year from initial treatment (measured from the time any one of the doses was given), followed by treatment at about two years from initial treatment, with expected success, in about one-half-gram or one-gram×2-4 dosing for each treatment, administered together, about weekly, or about every other week over about two to four weeks. The results of this treatment would be expected to be much better than those of the control with placebo. This re-treatment protocol is expected to be successfully used for several years with little or no adverse effects.

Example 5

Treatment Study of Efficacy of Rituximab in Patients with Osteoarthritis and Crohn's Disease It is expected that Example 2 results would be successful if the patients have joint damage as a result of osteoarthritis or Crohn's disease, whether rituximab or another CD20 antibody such as humanized 2H7 is used, and whether an immunosuppressive agent is used or not, with adjustment of doses as would be known to those skilled in the art. Further, if such patients are initially treated with CD20 antibody and then re-treated with such antibody about six months or about one year after first being treated, otherwise using the same dosing and other protocol of Example 2, it is expected that they will continue to experience prevention of progression of joint damage for an extended period of time.

It is also expected that rituximab or other CD20 antibody will be at least as effective as the conventional treatment regimen for induction and maintenance of joint damage remission, offering substantial advantages over standard therapy by virtue of its superior side-effect profile, e.g., much less toxic than steroids, and better at restoring tolerance.

It is expected that the patients in the treatment arm will tolerate rituximab infusions well and that their B cells will be depleted swiftly. Other than methotrexate, if needed, no additional immunosuppressive agents are expected to be necessary for induction of remission and maintenance of sustained remission (6 months or longer) in the CD20-antibody-treated patients.

What is claimed is:

1. A method for the treatment of joint damage caused by rheumatoid arthritis in a subject, wherein (a) the subject has exhibited an inadequate response to one or more antitumor necrosis factor (TNF) inhibitors; (b) the subject received a prior course of treatment with two 1000 mg intravenous (IV) doses of rituximab given 14 days apart and responded to the prior course of treatment and (c) the treatment comprises administering a further course of treatment with two 1000 mg IV doses of rituximab given 14 days apart and administered at weeks 24 to 40, wherein the subject to whom the further course of treatment is administered has active disease based on a disease activity score in 28 joints (DAS 28-erythrocyte sedimentation rate [ESR]) of ≥2.6, wherein the method slows or halts progression of structural joint damage for at least about 52 weeks in the subject.

2. The method of claim 1 wherein the further course is administered at about week 24.

3. The method of claim 1 further comprising administering methotrexate (MTX) to the subject.

4. The method of claim 3 further comprising administering corticosteroid to the subject prior to each rituximab administration.

5. A method for treating joint damage caused by rheumatoid arthritis in a subject who has exhibited an inadequate response to one or more anti-tumor necrosis factor (TNF) inhibitors comprising: (a) intravenously administering to the subject a first course of 1000 mg of rituximab on days 1 and 15 to which the subject responds; (b) re-treating the subject at weeks 24 to 40 with a further course of 1000 mg of rituximab administered on days 1 and 15 of the re-treatment, wherein the subject who is re-treated has active rheumatoid arthritis based on clinical assessment of disease activity score in 28 joints (DAS28-erythrocyte sedimentation rate [ESR]) of ≥2.6; and (c) giving the subject at least about 52 weeks after the administration in (a), a radiographic test that measures joint damage as compared to baseline prior to the administration, wherein the amount of rituximab administered is effective in treating the joint damage.

6. The method of claim 5 further comprising administering methotrexate (MTX) to the subject.

7. The method of claim 6 wherein the MTX is administered at a dose of about 10-25 mg/week.

8. The method of claim 6 further comprising administering corticosteroid to the subject.

9. The method of claim 8 comprising administering 100 mg IV methylprednisolone prior to each rituximab administration.

10. The method of claim 5 wherein the radiographic test measures a total modified Sharp score (TSS).

11. The method of claim 10 wherein the subject has no progression of structural damage compared to baseline as measured by TSS.

12. The method of claim 5 wherein the further course is administered at about week 24.

13. The method of claim 11 wherein the further course is administered at about week 24.

14. A method of slowing or halting progression of structural joint damage for at least about 52 weeks in a patient having rheumatoid arthritis which has exhibited an inadequate response to one or more anti-tumor necrosis factor (TNF) inhibitors comprising: (a) administering to the patient a first course of treatment with rituximab consisting of two 1000 mg intravenous (IV) doses of rituximab given 14 days apart, to which the patient responds; and (b) re-treating the patient with a further course of treatment with rituximab at weeks 24 to 40, wherein the further course consists of two 1000 mg intravenous (IV) doses of rituximab given 14 days apart and the patient has active disease based on a disease activity score in 28 joints (DAS 28-erythrocyte sedimentation rate [ESR]) of ≥2.6.

15. The method of claim 14 further comprising administering methotrexate (MTX) to the patient.

16. The method of claim 15 further comprising administering corticosteroid to the patient prior to each rituximab administration.

17. The method of claim 14 which halts progression of structural joint damage for at least 52 weeks in the patient.

18. The method of claim 14 wherein the further course is administered at about week 24.

* * * * *